US012799174B2

(12) United States Patent
Pei

(10) Patent No.: US 12,799,174 B2
(45) Date of Patent: Nov. 17, 2026

(54) STAPLED BETA-CATENIN LIGANDS

(71) Applicant: Ohio State Innovation Foundation, Columbus, OH (US)

(72) Inventor: Dehua Pei, Columbus, OH (US)

(73) Assignee: Ohio State Innovation Foundation, Columbus, OH (US)

( * ) Notice: Subject to any disclaimer, the term of this patent is extended or adjusted under 35 U.S.C. 154(b) by 1036 days.

(21) Appl. No.: 17/639,014

(22) PCT Filed: Aug. 28, 2020

(86) PCT No.: PCT/US2020/048523

§ 371 (c)(1),
(2) Date: Feb. 28, 2022

(87) PCT Pub. No.: WO2021/041895

PCT Pub. Date: Mar. 4, 2021

(65) Prior Publication Data

US 2022/0315631 A1 Oct. 6, 2022

Related U.S. Application Data

(60) Provisional application No. 62/894,195, filed on Aug. 30, 2019.

(51) Int. Cl.

| | |
|---|---|
| ***A61K 38/00*** | (2006.01) |
| ***A61K 38/02*** | (2006.01) |
| ***A61K 38/08*** | (2019.01) |
| ***A61K 38/10*** | (2006.01) |
| ***A61K 47/64*** | (2017.01) |
| ***C07K 14/47*** | (2006.01) |

(52) U.S. Cl.

CPC ........ *C07K 14/4702* (2013.01); *A61K 47/645* (2017.08)

(58) Field of Classification Search

CPC ... C07K 14/4702; A61K 47/645; A61K 38/00

See application file for complete search history.

(56) References Cited

U.S. PATENT DOCUMENTS

| | | | |
|---|---|---|---|
| 5,523,308 | A | 6/1996 | Costanzo et al. |
| 5,579,250 | A | 11/1996 | Balaji et al. |
| 5,595,756 | A | 1/1997 | Bally et al. |
| 5,612,895 | A | 3/1997 | Balaji et al. |
| 5,631,280 | A | 5/1997 | Ciccarone et al. |
| 5,804,558 | A | 9/1998 | Lehrer et al. |
| 5,965,536 | A | 10/1999 | Cohen et al. |
| 6,110,889 | A | 8/2000 | Miller et al. |
| 6,251,854 | B1 | 6/2001 | Montal et al. |
| 6,355,619 | B1 | 3/2002 | Miller et al. |
| 6,583,107 | B2 | 6/2003 | Laby et al. |
| 6,593,292 | B1 | 7/2003 | Rothbard et al. |
| 6,605,115 | B1 | 8/2003 | Cooke et al. |
| 6,649,587 | B1 | 11/2003 | Frydman et al. |
| 6,669,951 | B2 | 12/2003 | Rothbard et al. |
| 6,730,293 | B1 | 5/2004 | Rothbard et al. |
| 6,750,239 | B2 | 6/2004 | Hale et al. |
| 6,759,387 | B2 | 7/2004 | Rothbard et al. |
| 6,794,545 | B1 | 9/2004 | Frydman et al. |
| 6,809,176 | B2 | 10/2004 | Blokhin et al. |
| 6,864,355 | B1 | 3/2005 | May et al. |
| 6,960,648 | B2 | 11/2005 | Bonny |
| 6,982,351 | B2 | 1/2006 | Frydman et al. |
| 7,026,346 | B2 | 4/2006 | Chen et al. |
| 7,026,347 | B2 | 4/2006 | Frydman et al. |
| 7,084,241 | B2 | 8/2006 | Hogan et al. |
| 7,169,814 | B2 | 1/2007 | Rothbard et al. |
| 7,186,825 | B2 | 3/2007 | Frydman et al. |
| 7,229,961 | B2 | 6/2007 | Rothbard et al. |
| 7,253,207 | B2 | 8/2007 | Blokhin et al. |
| 7,279,502 | B2 | 10/2007 | Frydman et al. |
| 7,312,244 | B2 | 12/2007 | Frydman et al. |
| 7,468,418 | B2 | 12/2008 | Iversen et al. |
| 7,495,103 | B2 | 2/2009 | Hadida-Ruah et al. |
| 7,576,116 | B2 | 8/2009 | Chen |
| 7,585,834 | B2 | 9/2009 | Wender et al. |
| 7,687,481 | B2 | 3/2010 | McElroy et al. |
| 7,816,490 | B2 | 10/2010 | Hogan et al. |
| 7,850,949 | B2 | 12/2010 | Fang |
| 7,862,807 | B2 | 1/2011 | Goodman et al. |

(Continued)

FOREIGN PATENT DOCUMENTS

| | | |
|---|---|---|
| CA | 2455951 | 2/2003 |
| CA | 2949705 A1 | 11/2015 |

(Continued)

OTHER PUBLICATIONS

Drumm et al, Genetic Variation and Clinical Heterogeneity in Cystic Fibrosis, Annu. Rev. Pathol. Mech. Dis., 2012, 7, pp. 267-282 (Year: 2012).*

Yampolsky et al, The Exchangeability of Amino Acids in Proteins, Genetics, 2005, 170, pp. 1459-1472. (Year: 2005).*

He et al, "Peptide cojugates with small molecules designed to enhance efficacy and safety," Molecules, 24, 1855 (2019) (Year: 2019).*

Chen et al., Fusion protein linkers—property, design and functionality, Adv. Drug Deliv. Rev. 65:1357-1369 (2013) (Year: 2013).*

Lu et al, "linkers having a crucial role in antibody-drug conjugates," International Journal of Molecular Sciences 17:561, 1-22 (2016) (Year: 2016).*

Diderich, Philippe, et al., Phage Selection of Chemically Stabilized α-Helical Peptide Ligands, ACS Chemical Biology, vol. 11, No. 5, Mar. 11, 2016, pp. 1422-1427.

Borrelli, Antonella et al., Cell Penetrating Peptides as Molecular Carriers for Anti-Cancer Agents, MOLECULES, vol. 23, No. 2, Jan. 1, 2018.

(Continued)

*Primary Examiner* — Julie Ha
*Assistant Examiner* — Kristina M Hellman
(74) *Attorney, Agent, or Firm* — Meunier Carlin & Curfman LLC

(57) ABSTRACT

The present disclosure provides novel polypeptide conjugates. The polypeptide conjugates disclosed herein comprise a stapled peptidyl beta-catenin ligand and at least one staple which holds the peptidyl ligand in an α-helical confirmation, and a cell-penetrating peptide (CPP) conjugated, directly or indirectly, to the stapled peptide.

1 Claim, 25 Drawing Sheets

Specification includes a Sequence Listing.

(56) References Cited

U.S. PATENT DOCUMENTS

| | | | |
|---|---|---|---|
| 8,039,502 | B2 | 10/2011 | Chen et al. |
| 8,080,574 | B2 | 12/2011 | Chen |
| 8,084,467 | B2 | 12/2011 | Makriyannis et al. |
| 8,507,534 | B2 | 8/2013 | Keshavarz-Shokri et al. |
| 8,614,290 | B2 | 12/2013 | Wester et al. |
| 8,623,833 | B2 | 1/2014 | Rothbard et al. |
| 8,628,750 | B2 | 1/2014 | Wester et al. |
| 8,629,112 | B2 | 1/2014 | Gombert et al. |
| 8,754,224 | B2 | 6/2014 | Hurter et al. |
| 8,883,718 | B2 | 11/2014 | Warenius et al. |
| 8,901,071 | B2 | 12/2014 | O'Neil et al. |
| 8,999,919 | B2 | 4/2015 | Madden et al. |
| 9,139,530 | B2 | 9/2015 | Hurter et al. |
| 9,169,290 | B2 | 10/2015 | O'Neil |
| 9,216,969 | B2 | 12/2015 | Ruah et al. |
| 9,303,075 | B2 | 4/2016 | Brinkmann et al. |
| 9,868,767 | B2 | 1/2018 | Pei et al. |
| 10,501,496 | B2 | 12/2019 | Pei et al. |
| 10,626,147 | B2 | 4/2020 | Pei et al. |
| 10,738,093 | B2 | 8/2020 | Qian et al. |
| 10,815,276 | B2 | 10/2020 | Pei et al. |
| 10,913,773 | B2 | 2/2021 | Pei |
| 11,168,310 | B2 | 11/2021 | Sethuraman et al. |
| 11,225,506 | B2 | 1/2022 | Pei et al. |
| 11,339,192 | B2 | 5/2022 | Pei |
| 11,351,222 | B2 | 6/2022 | Pei et al. |
| 11,352,394 | B2 | 6/2022 | Pei et al. |
| 11,576,946 | B2 | 2/2023 | Pei et al. |
| 11,793,884 | B2 | 10/2023 | Pei et al. |
| 11,878,046 | B2 | 1/2024 | Pei et al. |
| 11,987,647 | B2 | 5/2024 | Pei |
| 11,987,812 | B2 | 5/2024 | Yonemitsu et al. |
| 11,987,821 | B2 | 5/2024 | Sethuraman et al. |
| 2002/0009491 | A1 | 1/2002 | Rothbard et al. |
| 2002/0035243 | A1 | 3/2002 | Imfeld et al. |
| 2002/0120100 | A1 | 8/2002 | Bonny |
| 2002/0127198 | A1 | 9/2002 | Rothbard et al. |
| 2003/0022831 | A1 | 1/2003 | Rothbard et al. |
| 2003/0032593 | A1 | 2/2003 | Wender et al. |
| 2003/0032594 | A1 | 2/2003 | Bonny |
| 2003/0072715 | A1 | 4/2003 | Frydman et al. |
| 2003/0130356 | A1 | 7/2003 | Frydman et al. |
| 2003/0138932 | A1 | 7/2003 | Moller et al. |
| 2003/0144337 | A1 | 7/2003 | Hale et al. |
| 2003/0167129 | A1 | 9/2003 | Nestor, Jr. et al. |
| 2003/0194745 | A1 | 10/2003 | McDowell et al. |
| 2004/0002117 | A1 | 1/2004 | Hogan et al. |
| 2004/0014669 | A1 | 1/2004 | Selsted et al. |
| 2004/0067983 | A1 | 4/2004 | Barrett et al. |
| 2004/0152687 | A1 | 8/2004 | Frydman et al. |
| 2004/0192665 | A1 | 9/2004 | Frydman et al. |
| 2004/0248783 | A1 | 12/2004 | Kawabe et al. |
| 2005/0107289 | A1 | 5/2005 | Ghadiri et al. |
| 2005/0192210 | A1 | 9/2005 | Rothbard et al. |
| 2006/0128614 | A1 | 6/2006 | Cheng et al. |
| 2006/0141514 | A1 | 6/2006 | Rozzelle et al. |
| 2006/0247210 | A1 | 11/2006 | Zhang et al. |
| 2007/0041904 | A1 | 2/2007 | Jiang et al. |
| 2007/0083334 | A1* | 4/2007 | Mintz .................... G16B 40/00 702/19 |
| 2007/0093427 | A1 | 4/2007 | Matsui et al. |
| 2008/0146815 | A1 | 6/2008 | Chen |
| 2008/0234183 | A1 | 9/2008 | Hallbrink et al. |
| 2008/0269309 | A1 | 10/2008 | Chen |
| 2009/0111799 | A1 | 4/2009 | Chen et al. |
| 2009/0186802 | A1 | 7/2009 | Alluis et al. |
| 2010/0168034 | A1 | 7/2010 | Lee et al. |
| 2010/0216767 | A1 | 8/2010 | Aikawa et al. |
| 2010/0221235 | A1 | 9/2010 | Arranz |
| 2010/0292148 | A1 | 11/2010 | Krippner et al. |
| 2011/0131679 | A2* | 6/2011 | La Rosa .............. C07K 14/415 800/278 |
| 2011/0269665 | A1 | 11/2011 | Kole |
| 2012/0016005 | A1 | 1/2012 | Samarsky et al. |
| 2012/0045393 | A1 | 2/2012 | Linder et al. |
| 2012/0071504 | A1 | 3/2012 | Yang et al. |
| 2012/0108823 | A1 | 5/2012 | Chen et al. |
| 2013/0085736 | A1 | 4/2013 | Reihsen et al. |
| 2014/0005118 | A1* | 1/2014 | Verdine .................. C07K 1/113 435/375 |
| 2014/0235557 | A1 | 8/2014 | De Waard |
| 2014/0294942 | A1 | 10/2014 | French et al. |
| 2014/0303071 | A1 | 10/2014 | O'Neil |
| 2014/0342992 | A1 | 11/2014 | Gait et al. |
| 2015/0038671 | A1 | 2/2015 | Parang et al. |
| 2015/0284437 | A1 | 10/2015 | Verdine et al. |
| 2015/0284455 | A1 | 10/2015 | Springer et al. |
| 2015/0297742 | A1 | 10/2015 | Strieker et al. |
| 2016/0031941 | A1 | 2/2016 | Eckert et al. |
| 2016/0115202 | A1 | 4/2016 | Pei et al. |
| 2016/0151512 | A1 | 6/2016 | Kim |
| 2016/0235807 | A1 | 8/2016 | Shailubhai |
| 2016/0271216 | A1 | 9/2016 | Kemper et al. |
| 2016/0317679 | A1 | 11/2016 | Baumhof et al. |
| 2017/0112896 | A1 | 4/2017 | Briesewitz |
| 2017/0152286 | A1* | 6/2017 | Li ............................ C07K 7/64 |
| 2017/0190743 | A1 | 7/2017 | Pei et al. |
| 2017/0281723 | A1 | 10/2017 | Pei et al. |
| 2017/0304383 | A1 | 10/2017 | Brieswewitz et al. |
| 2017/0355730 | A1 | 12/2017 | Pei et al. |
| 2018/0030094 | A1 | 2/2018 | Pei et al. |
| 2018/0030411 | A1 | 2/2018 | Kahvejian et al. |
| 2019/0216752 | A1 | 7/2019 | Im et al. |
| 2019/0282654 | A1 | 9/2019 | Pei et al. |
| 2019/0284239 | A1 | 9/2019 | Pei et al. |
| 2019/0284240 | A1 | 9/2019 | Pei et al. |
| 2019/0309020 | A1 | 10/2019 | Pei et al. |
| 2019/0365911 | A1 | 12/2019 | Liu et al. |
| 2020/0276323 | A1 | 9/2020 | Pei |
| 2020/0291070 | A1 | 9/2020 | Pei et al. |
| 2020/0353092 | A1 | 11/2020 | Foster et al. |
| 2020/0354697 | A1 | 11/2020 | Sethuraman et al. |
| 2020/0385427 | A1 | 12/2020 | Pei et al. |
| 2021/0038737 | A1 | 2/2021 | Pei et al. |
| 2021/0070806 | A1 | 3/2021 | Pei |
| 2021/0115088 | A1 | 4/2021 | Pei |
| 2021/0169966 | A1 | 6/2021 | Pei et al. |
| 2021/0244824 | A1 | 8/2021 | Pei et al. |
| 2021/0261500 | A1 | 8/2021 | Pei et al. |
| 2022/0160819 | A1 | 5/2022 | Pei et al. |
| 2022/0177523 | A1 | 6/2022 | Pei et al. |
| 2022/0281920 | A1 | 9/2022 | Pei |
| 2022/0306693 | A1 | 9/2022 | Pei et al. |
| 2023/0020092 | A1 | 1/2023 | Qian et al. |
| 2023/0106131 | A1 | 4/2023 | Pei |
| 2023/0212235 | A1 | 7/2023 | Pei |
| 2023/0312653 | A1 | 10/2023 | Dougherty et al. |
| 2023/0322859 | A1 | 10/2023 | Pei |
| 2024/0173423 | A1 | 5/2024 | Pei et al. |

FOREIGN PATENT DOCUMENTS

| | | | |
|---|---|---|---|
| CA | 3092062 | A1 | 8/2019 |
| CA | 2417064 | | 2/2022 |
| CN | 1889949 | A | 1/2007 |
| CN | 105440105 | | 3/2016 |
| CN | 106852146 | B | 8/2021 |
| CN | 113861268 | A | 12/2021 |
| EP | 1185493 | A1 | 3/2002 |
| EP | 1185493 | | 7/2005 |
| EP | 1574507 | | 9/2005 |
| EP | 1797901 | | 6/2007 |
| EP | 2420255 | | 2/2012 |
| EP | 2426203 | A2 | 3/2012 |
| EP | 3149025 | A2 | 4/2017 |
| EP | 3149025 | B1 | 6/2019 |
| EP | 3544623 | A1 | 10/2019 |
| EP | 3613426 | A1 | 2/2020 |
| EP | 3790890 | A1 | 3/2021 |
| GB | 965160 | A | 7/1964 |
| HK | 40019383 | | 10/2020 |
| JP | 3791981 | | 6/2006 |
| JP | 2009527251 | A | 7/2009 |
| JP | 2010526091 | | 7/2010 |

(56) References Cited

FOREIGN PATENT DOCUMENTS

| | | | |
|---|---|---|---|
| JP | 2012131743 | A | 7/2012 |
| JP | 5909611 | B2 | 4/2016 |
| JP | 2016065018 | | 4/2016 |
| JP | 2017519041 | A | 7/2017 |
| JP | 2020169170 | A | 10/2020 |
| JP | 6807831 | B2 | 1/2021 |
| JP | 7175887 | B2 | 11/2022 |
| TW | 201825510 | A | 7/2018 |
| WO | 9921877 | | 5/1999 |
| WO | 0011022 | | 3/2000 |
| WO | 0113957 | | 3/2001 |
| WO | 0152875 | | 7/2001 |
| WO | 0231109 | | 4/2002 |
| WO | 02057313 | | 7/2002 |
| WO | 02064091 | | 8/2002 |
| WO | 02067917 | | 9/2002 |
| WO | 02090503 | | 11/2002 |
| WO | WO-2002092617 | A1 | 11/2002 |
| WO | 03059942 | | 7/2003 |
| WO | 03070755 | | 8/2003 |
| WO | 03092631 | | 11/2003 |
| WO | 03092632 | | 11/2003 |
| WO | 2004050685 | | 6/2004 |
| WO | 2006041805 | | 4/2006 |
| WO | 2006058436 | | 6/2006 |
| WO | 2006086773 | | 8/2006 |
| WO | 2007040535 | | 4/2007 |
| WO | 2007055578 | | 5/2007 |
| WO | 2007070372 | | 6/2007 |
| WO | 2007072037 | | 6/2007 |
| WO | WO-2007071396 | A2 | 6/2007 |
| WO | 2007096662 | | 8/2007 |
| WO | WO-2007097561 | A1 | 8/2007 |
| WO | 2007106554 | | 9/2007 |
| WO | 2007108749 | | 9/2007 |
| WO | 2007111993 | | 10/2007 |
| WO | 2008077194 | | 7/2008 |
| WO | 2008134761 | | 11/2008 |
| WO | WO-2009005793 | A2 | 1/2009 |
| WO | 2009027706 | | 3/2009 |
| WO | 2009092062 | | 7/2009 |
| WO | 2009098450 | | 8/2009 |
| WO | 2010045335 | | 4/2010 |
| WO | WO-2010039088 | A1 | 4/2010 |
| WO | 2010072406 | | 7/2010 |
| WO | 2010107832 | | 9/2010 |
| WO | 2011095218 | | 8/2011 |
| WO | 2011095607 | | 8/2011 |
| WO | WO-2011126010 | A1 | 10/2011 |
| WO | 2013123266 | | 8/2013 |
| WO | 2013142184 | | 9/2013 |
| WO | 2013150338 | | 10/2013 |
| WO | 2014053629 | | 4/2014 |
| WO | 2014053882 | | 4/2014 |
| WO | WO-2014052276 | A1 | 4/2014 |
| WO | 2014086835 | | 6/2014 |
| WO | 2014190257 | | 11/2014 |
| WO | 2014190313 | | 11/2014 |
| WO | 2015051030 | | 4/2015 |
| WO | 2015148620 | | 10/2015 |
| WO | 2015153761 | | 10/2015 |
| WO | 2015179434 | | 11/2015 |
| WO | 2015179691 | | 11/2015 |
| WO | WO-2015179741 | A1 | 11/2015 |
| WO | 2016033368 | | 3/2016 |
| WO | 2016044683 | | 3/2016 |
| WO | 2016054510 | | 4/2016 |
| WO | 2016177898 | | 11/2016 |
| WO | WO-2016173214 | A1 | 11/2016 |
| WO | WO-2017044855 | A2 | 3/2017 |
| WO | WO-2017048466 | A1 | 3/2017 |
| WO | WO-2017050836 | A1 | 3/2017 |
| WO | WO-2017083637 | A1 | 5/2017 |
| WO | 2017109076 | | 6/2017 |
| WO | WO-2017097901 | A1 | 6/2017 |
| WO | 2017114440 | | 7/2017 |
| WO | 2017147283 | | 8/2017 |
| WO | WO-2018056530 | A1 | 3/2018 |
| WO | 2018089648 | | 5/2018 |
| WO | 2018098226 | | 5/2018 |
| WO | 2018098231 | | 5/2018 |
| WO | 2018098282 | | 5/2018 |
| WO | WO-2019018898 | A1 | 1/2019 |
| WO | 2019051327 | | 3/2019 |
| WO | 2019070962 | | 4/2019 |
| WO | 2019/084528 | A1 | 5/2019 |
| WO | 2019148194 | | 8/2019 |
| WO | WO-2019148195 | A2 | 8/2019 |
| WO | WO-2019165183 | A1 | 8/2019 |
| WO | 2019217682 | | 11/2019 |
| WO | WO-2019213662 | A1 | 11/2019 |
| WO | 2020010103 | | 1/2020 |
| WO | WO-2020028254 | A1 | 2/2020 |
| WO | WO-2020030927 | A1 | 2/2020 |
| WO | WO-2020102630 | A1 | 5/2020 |
| WO | WO-2020198151 | A1 | 10/2020 |
| WO | WO-2020227194 | A1 | 11/2020 |
| WO | WO-2021041895 | A1 | 3/2021 |
| WO | WO-2021127650 | A1 | 6/2021 |
| WO | WO-2021138397 | A1 | 7/2021 |
| WO | WO-2022125987 | A1 | 6/2022 |
| WO | 2022178379 | | 8/2022 |
| WO | WO-2022213118 | A1 | 10/2022 |
| WO | WO-2022240757 | A1 | 11/2022 |
| WO | WO-2022251415 | A1 | 12/2022 |
| WO | WO-2022271810 | A2 | 12/2022 |

OTHER PUBLICATIONS

Ali, Ameena et al., ed Peptides Inhibitors: A New Window for Target Drug Discovery, Computational and Structural Biotechnology Journal, vol. 17, Jan. 1, 2019, pp. 263-281.

Dougherty, Patrick et al., Enhancing the Cell Permeability of Stapled Peptides with a Cyclic Cell-Penetrating Peptide, Journal of Medicinal Chemistry, vol. 62, No. 22, Oct. 28, 2019, pp. 10098-10107.

Extended European Search Report for EP Application 20857054.9 dated Sep. 7, 2023, 13 pages.

International Search Report and Written Opinion, issued by the International Searching Authority (ISA/US) in PCT Application No. PCT/US2020/048523 on Nov. 30, 2020. 9 pages.

Dietrich, Laura, et al. "Cell permeable stapled peptide inhibitor of Wnt signaling that targets β-catenin protein-protein Interactions." Cell chemical biology 24.8 (2017): 958-968.

Ali, Syed Ausaf et al. "A review of methods available to estimate solvent-accessible surface areas of soluble proteins in the folded and unfolded states." Current Protein and Peptide Science 15.5 (2014): 456-476.

Alhakamy, N. A., Nigatu, A. S., Berkland, C. J., and Ramsey, J. D. (2013) Noncovalently associated cell-penetrating peptides for gene delivery applications. Ther. Deliv. 4, 741-757.

Almarsson, Örn, and ZAWOROTKO, Michael J. "Crystal engineering of the composition of pharmaceutical phases. Do pharmaceutical co-crystals represent a new path to improved medicines?" Chemical communications 17 (2004): 1889-1896.

Alonso, A et al., Protein tyrosine phosphates in the human genome, Cell, Jun. 2004, 117(6): 699-711.

Altschul, Stephen F., et al. "Gapped BLAST and PSI-BLAST: a new generation of protein database search programs." Nucleic acids research 25.17 (1997): 3389-3402.

Altschul, Stephen F., et al., "Basic local alignment search tool." Journal of molecular biology 215.3 (1990): 403-410.

Alzani, R. et al. "Suramin induces deoligomerization of human tumor necrosis factor alpha." J. Biol. Chem. 268, (1993): 12526-12529.

Andaloussi, S. E. L. et al., "Design of a peptide-based vector, PepFect6, for efficient delivery of siRNA in cell culture and systemically in vivo," Noucleic Acids Research, May 2011, 39(9):3972-3987.

(56) References Cited

OTHER PUBLICATIONS

Ander, J. et al., "Chemical modification allows phallotoxins and amatoxins to be used as tools in cell biology," Beilstein Journal of Organic Chemistry, 2012, 8(233):2072-2084.
Angelini, Alessandro, et al. "Bicyclic peptide inhibitor reveals large contact interface with a protease target." ACS chemical biology 7.5 (2012): 817-821.
Appelbaum, Jacob S., et al. "Arginine topology controls escape of minimally cationic proteins from early endosomes to the cytoplasm." Chemistry & biology 19.7 (2012): 819-830.
Ardi, V. C., et al., "Macrocycles that inhibit the binding between heat shock protein 90 and TPR-containing proteins." ACS Chem. Biol. 6, (2011): 1357-1366.
Aramburu, J.; et al., "Selective inhibition of NFAT activation by a peptide spanning the calcineurin targeting site of NFAT." Mol. Cell 1998, 1, 627-637.
Aramburu, J.; et al., "Affinity-driven peptide selection of an NFAT inhibitor more selective than cyclosporine A." Science 1999, 285, 2129-2133.
Arthanari, Y et al., (2010) Delivery of therapeutic shRNA and siRNA by Tat fusion peptide targeting bcr-abl fusion gene in Chronic Myeloid Leukemia cells. J. Controlled Release 145, 272-280.
Baud, Véronique, and Karin, Michael. "Is NF-κB a good target for cancer therapy? Hopes and pitfalls." Nature reviews Drug discovery 8.1 (2009): 33.
Bedewy, W., et al., "Generation of a cell-permeable cycloheptapeptidyl inhibitor against the pepitidyl-prolyl somerase Pin1." Organic & biomolecular chemistry 15.21 (2017): 4540-4543.
Beste, G. et al. "Small antibody-like proteins with prescribed ligand specificities derivedfrom the lipocalin fold." Proc. Natl. Acad. Sci. USA 96, (1999): 1898-1903.
Beutler, B et al. "Purification of cachectin, a lipoprotein-lipase suppressing hormone secreted by endotoxin-induced RAW 264.7 cells." J. Exp. Med. 161, (1985): 984-995.
Bird, Gregory H., et al. "Biophysical determinants for cellular uptake of hydrocarbon-stapled peptide helices." Nature chemical biology 12.10 (2016): 845-852.
Birts, C. N. et al. "A cyclic peptide inhibitor of C-terminal binding protein dimerization links metabolism with mitotic fidelity in breast cancer cells." Chem. Sci., 4, (2013): 3046-3057.
Bold, G.; et al., "New aza-dipeptide analogues as potent and orally absorbed HIV-1 protease inhibitors: candidates for clinical development." J. Med. Chem. 1998, 41, 3387-3401.
Bolte, S. et al., A guided tour into subcellular colocalization analysis in light microscopy, J. Microsc., Dec. 2006, 224(Pt. 3), 213-232.
Bruno PA et al., "A synthetic loop replacement peptide blocks canonical NF-κB signaling", Agnew. Chem. Int. Ed. 2016, 55, 14997-15001.
Buller, F., et al. "Discovery of TNF inhibitors from a DNA-encoded chemical library based on Diels-Alder cycloaddition." Chem. Biol. 16, (2009): 1075-1086.
Burke, T.R. Jr. et al., "Potent Inhibition of Insulin Receptor Dephosphorylation by a Hexamer Peptide Containing the Phosphotyrosyl Mimetic F2Pmp," Biochem. Biophys. Res. Commun., Oct. 1994, 204(1):129-134.
Cardote, T. et al., "Cyclic and macrocyclic peptides as chemical tools to recognise protein surfaces and probe protein-protein interactions." ChemMedChem 11.8 (2016): 787-794.
Carpenter, A E. et al., "CellProfiler: image analysis software for identifying and quantifying cell phenotypes," Genome Biology, 2006, 7:R100, 11 pages.
Cascales, L. et al., "Identification and Characterization of a New Family of Cell-Penetrating Peptides," J. Biol. Chem., Oct. 2011, 286(42):36932-36943.
Chan, D. S. et al. "Structure-based discovery of natural-product-like TNF-alpha inhibitors." Angew. Chem. Int. Ed. Engl. 49, (2010): 2860-2864.
Chapman, J. R. "Chronic calcineurin inhibitor nephrotoxicity-lest we forget." Am. J. Transplant 2011, 11, 693-697.
Chatterjee, Jayanta, et al. "N-methylation of peptides: a new perspective in medicinal chemistry." Accounts of chemical research 41.10 (2008): 1331-1342.
Chen, Ying, et al. "Inhibition of the nuclear export receptor XPO1 as a therapeutic target for platinum-resistant ovarian cancer." Clinical Cancer Research 23.6 (2017): 1552-1563.
Chen et al. "Bicyclic Peptide Ligands Pulled out of Cysteine-Rich Peptide Libraries," JACS, 135(17), (2013): 6562-6569.
Chen, G. & Goeddel, D. V. "TNF-R1 signaling: a beautiful pathway." Science 296, (2002): 1634-1635.
Chen, S., et al., "Structurally diverse cyclization linkers impose different backbone conformations in bicyclic peptides." ChemBioChem. 13, (2012): 1032-1038.
Chen, S. et al., "Dithiol amino acids can structurally shape and enhance the ligand-binding properties of polypeptides." Nature chemistry 6.11 (2014): 1009-1016.
Chen, X., et al., "On-bead screening of combinatorial libraries: Reduction of nonspecific binding by decreasing surface ligand density." J. Comb. Chem. 11, (2009): 604-611.
Cheng, Seng H., et al. "Defective intracellular transport and processing of CFTR is the molecular basis of most cystic fibrosis." Cell 63.4 (1990): 827-834.
Chierici, S.; et al., "A case study of 2,2-dimethylthiazolidine as locked cis proline amide bond: synthesis, NMR and molecular modeling studies of a-conotoxin EVIA peptide analog." Org. Biomol. Chem. 2004, 2, 2436-2441.
Chistiakov, Dimitry A., and Chistiakova, Emma I. "T-cell protein tyrosine phosphatase: A role in inflammation and autoimmunity." International Journal of Diabetes Mellitus 2.2 (2010): 114-118.
Choi et al., "Cell permeable NFAT inhibitory peptide Sim-2-VIVIT inhibits sT-cell activation and alleviates allergic airways inflammation and hyper-responsiveness", 2012, Immunology Letters 143:2 pp. 170-176.
Choi, H., et al., "Discovery of the inhibitors of tumor necrosis factor alpha with structure-based virtual screening." Bioorg. Med. Chem. Lett. 20, (2010): 6195-6198.
Choi, Hee-Jung, et al., "Thermodynamics of β-catenin-ligand interactions: the roles of the N-and C-terminal tails in modulating binding affinity." Journal of Biological Chemistry 281.2 (2006): 1027-1038.
Chu, Qian, et al. "Towards understanding cell penetration by stapled peptides." MedChemComm 6.1 (2015): 111-119.
Cildir, Gökhan, et al., "Noncanonical NF-κB signaling in health and disease." Trends in molecular medicine 22.5 (2016): 414-429.
Cochran, Andrea G., et al., "Tryptophan zippers: Stable, monomeric β-hairpins." Proceedings of the National Academy of Sciences 98.10 (2001): 5578-5583.
Collins, M., and Thrasher, A. (2015) Gene therapy: progress and predictions. Proc. R. Soc. B 282, 20143003.
Cooley, Christina B., et al. "Oligocarbonate molecular transporters: oligomerization-based syntheses and cell-penetrating studies." Journal of the American Chemical Society 131.45 (2009): 16401-16403.
Crabtree, G. R. "Generic signals and specific outcomes: signaling through Ca2+, calcineurin, and NF-AT." Cell 1999, 96, 611-614.
Craik, David J., et al. "The future of peptide-based drugs." Chemical biology & drug design 81.1 (2013): 136-147.
Cushing, Patrick R., et al. "A Stabilizing Influence: CAL PDZ Inhibition Extends the Half-Life of ΔF508-CFTR." Angewandte Chemie International Edition 49.51 (2010): 9907-9911.
Cushing, P. R. et al., "The Relative Binding Affinities of PDZ Partners for CFTR: A Biochemical Basis for Efficient Endocytic Recycling," Biochemistry, 2008, 47(38): 10084-10098.
Dai, Simon, et al. "The IKB kinase (IKK) inhibitor, NEMO-binding domain peptide, blocks osteoclastogenesis and bone erosion in inflammatory arthritis." Journal of Biological Chemistry 279.36 (2004): 37219-37222.
Davé, Shaival H., et al. "Amelioration of chronic murine colitis by peptide-mediated transduction of the IκB kinase inhibitor NEMO binding domain peptide." The Journal of Immunology 179.11 (2007): 7852-7859.
Davies, S. J.; et al., "Structure-activity relationships of the peptide deformylase inhibitor BB-3497: modification of the P2' and P3' side chains." Bioorg. Med. Chem. Lett. 2003, 13, 2715-2718.

(56) References Cited

OTHER PUBLICATIONS

Delfín, Dawn A., et al. "Improvement of cardiac contractile function by peptide-based inhibition of NF-κB in the utrophin/dystrophin-deficient murine model of muscular dystrophy." Journal of translational medicine 9.1 (2011): 68.
Depaul, A. J.; et al., "Equilibrium conformational dynamics in an RNA tetraloop from massively parallel molecular dynamics." Nucleic Acids Res. 2010, 38, 4856-4867.
Deshayes, Sebastien, et al. "Cell-penetrating peptides: tools for intracellular delivery of therapeutics." Cellular and Molecular Life Sciences CMLS 62.16 (2005): 1839-1849.
Desimmie, B. A. et al. "Phage Display-directed Discovery of LEDGF/p75 Binding Cyclic Peptide Inhibitors of HIV Replication." Mol. Therapy 20, (2012): 2064-2075.
Dewan, V. et al. "Cyclic peptide inhibitors of HIV-I capsid-human lysy1-tRNA synthetase interaction." ACS Chem. Biol. 7, (2012):761-769.
Do, H. et al., "Di-fatty acyl-conjugated linear and cyclic peptides for siRNA delivery." ACS omega 2.10 (2017): 6939-6957.
Dong et al., A Photocontrolled B-Hairpin Peptide. Chemistry—A European Journal. 2006, 12 (4): 1114-1120.
Doran, Todd M., et al. "Role of amino acid hydrophobicity, aromaticity, and molecular vol. on IAPP (20-29) amyloid self-assembly." Proteins: Structure, Function, and Bioinformatics 80.4 (2012): 1053-1065.
Dougherty, Patrick G. et al., "Macrocycles as protein-protein interaction inhibitors." Biochemical Journal 474.7 (2017): 1109-1125.
Dowdy, S. F. (2017) Overcoming cellular barriers for RNA therapeutics. Nat. Biotechnol. 35, 222-229.
Doyle, D. A et al., "Crystal Structures of a Complexed and Peptide-Free Membrane Protein-Binding Domain: Molecular Basis of Peptide Recognition by PDZ," Cell, Jun. 1996, 85(7):1067-1076.
Driggers, E. M et al., "The exploration of macrocycles for drug discovery—an underexploited structural class," Nat. Rev. Drug Discov., Jul. 2008, 7:608-624.
D'Souza et al., Structural parameters modulating the cellular uptake of disulfide-rich cyclic cell-penetrating peptides: MCoT1-II and SFT1-1, European Journal of Medicinal Chemistry, vol. 88, 99 10-18, 2014.
Duchardt, Falk, et al. "A comprehensive model for the cellular uptake of cationic cell-penetrating peptides." Traffic 8.7 (2007): 848-866.
Duchardt, F. et al., "A Cell-penetrating Peptide Derived from Human Lactoferrin with Conformation-dependent Uptake Efficiency," J. Biol. Chem., Dec. 2009, 284(52):36099-36108.
Dumy, P.; et al., "Pseudo-prolines as a molecular hinge: reversible induction of cis amide bonds into peptide backbones." J. Am. Chem. Soc. 1997, 119, 918-925.
Eguchi, Akiko, et al. "Protein transduction domain of HIV-1 Tat protein promotes efficient delivery of DNA into mammalian cells." Journal of Biological Chemistry 276.28 (2001): 26204-26210.
Eichler, J. et al., "Novel a-glucosidase inhibitors identified using multiple cyclic peptide combinatorial libraries," Molecular Diversity, Aug. 1996, 1(4):233-240.
Eisenberg, David, et al., "The hydrophobic moment detects periodicity in protein hydrophobicity." Proceedings of the National Academy of Sciences 81.1 (1984): 140-144.
El Andaloussi, Samir, et al. "Design of a peptide-based vector, PepFect6, for efficient delivery of siRNA in cell culture and systemically in vivo." Nucleic acids research 39.9 (2011): 3972-3987.
Elchebly, Mounib, et al. "Increased insulin sensitivity and obesity resistance in mice lacking the protein tyrosine phosphatase-1B gene." Science 283.5407 (1999): 1544-1548.
El-Sayed, Ayman, et al., "Delivery of macromolecules using arginine-rich cell-penetrating peptides: ways to overcome endosomal entrapment." The AAPS journal 11.1 (2009): 13-22.
Engelman, D. M., et al., "Identifying nonpolar transbilayer helices in amino acid sequences of membrane proteins." Annual review of biophysics and biophysical chemistry 15.1 (1986): 321-353.
Esposito, E. & Cuzzocrea, S. "TNF-alpha as a therapeutic target in inflammatory diseases, ischemia-reperfusion injury and trauma." Curr. Med. Chem. 16, (2009): 3152-3167.
Fernandez-Lopez, S et al., "Antibacterial agents based on the cyclic D,L- alpha-peptide architecture," Nature, Jul. 2001, 412:452-455 and Correction page, Nature, Nov. 2001, 414:329.
Ferrari, Aldo, et al. "Caveolae-mediated internalization of extracellular HIV-1 tat fusion proteins visualized in real time." Molecular therapy 8.2 (2003): 284-294.
Fittipaldi, Antonio, et al. "Cell membrane lipid rafts mediate caveolar endocytosis of HIV-1 Tat fusion proteins." Journal of Biological Chemistry 278.36 (2003): 34141-34149.
Fosgerau, Keld and Hoffmann, Torsten. "Peptide therapeutics: current status and future directions." Drug discovery today 20.1 (2015): 122-128.
Frackenpohl, J. et al., "The Outstanding Biological Stability of- and y-Peptides toward Proteolytic Enzymes: An In Vitro Investigation with Fifteen Peptidases," Chembiochem, Jun. 2001, 2(6):445-455.
Frankel, Alan D., and Pabo, Carl O. "Cellular uptake of the tat protein from human immunodeficiency virus." Cell 55.6 (1988): 1189-1193.
Frost, J. R. et al., "Macrocyclization of Organo-Peptide Hybrids through a Dual Bio-orthogonal Ligation: Insights from Structure-Reactivity Studies," ChemBioChem, Jan. 2013, 14(1): 147-160.
Furka, A., et al. "General method for rapid synthesis of multicomponent peptide mixtures." Int. J. Pep. Prat. Res. 37, (1991): 487-493.
Futaki, Shiroh. "Membrane-permeable arginine-rich peptides and the translocation mechanisms." Advanced drug delivery reviews 57.4 (2005): 547-558.
Futaki, S. et al., "Arginine-rich peptides. An abundant source of membrane-permeable peptides having potential as carriers for intracellular protein delivery." The Journal of Biological Chemistry, 2001, 276(8):5836-5840.
Gaj, T., et al., C. F. (2013) ZFN, TALEN, and CRISPR/Cas-based methods for genome engineering. Trends Biotechnol. 31, 397-405.
Gaurnier-Hausser, Anita, et al. "NEMO-binding domain peptide inhibits constitutive NF-κB activity and reduces tumor burden in a canine model of relapsed, refractory diffuse large B-cell lymphoma." Clinical Cancer Research 17.14 (2011): 4661-4671.
GenBank: AEV23320.1. "Beta-fibrinogen, partial [Boana albopunctata]." Feb. 13, 2012. https://www.ncbi.nlm.nih.gov/protein/AEV23320.1?report=genbank&log$-protalign&blast_rank=3&RID=FMTADBYS014. 1 page.
Giacca, M., and Zacchigna, S. (2012) Virus-mediated gene delivery for human gene therapy. J. Controlled Release 161, 377-388.
Giebel, L. B. et al., "Screening of cyclic peptide phage libraries identifies ligands that bind streptavidin with high affinities," Biochemistry, 1995, 34(47):15430-15435.
Gobbo, M. et al., "Synthesis and biological activity of some linear and cyclic kinin analogues," International Journal of Peptide & Protein Research, Jul. 1994, 44(1):1-9.
Godwin, Peter, et al. "Targeting nuclear factor-kappa B to overcome resistance to chemotherapy." Frontiers in oncology 3 (2013): 120.
Goncalves, E. et al., "Binding of Oligoarginine to Membrane Lipids and Heparan Sulfate: Structural and Thermodynamic Characterization of a Cell-Penetrating Peptide," Biochemistry, 2005, 44(7):2692-2702.
Gotoh, Yusuke, et al. "A homogeneous time-resolved fluorescence-based high-throughput screening system for discovery of inhibitors of IKKβ-NEMO interaction." Analytical biochemistry 405.1 (2010): 19-27.
Goun, Elena A., et al. "Molecular transporters: synthesis of oligoguanidinium transporters and their application to drug delivery and real-time imaging." Chem Bio Chem 7.10 (2006): 1497-1515.
Green, Maurice and Loewenstein, Paul M. "Autonomous functional domains of chemically synthesized human immunodeficiency virus tat trans-activator protein." Cell 55.6 (1988): 1179-1188.
Grigoriu, S.; et al., "The molecular mechanism of substrate engagement and immunosuppressant inhibition of calcineurin." PLoS Biol. 2013, 11, e1001492.
Guo, Bingqian, et al. "Protein engineering of the N-terminus of NEMO: structure stabilization and rescue of IKKβ binding." Biochemistry 53.43 (2014): 6776-6785.

(56) References Cited

OTHER PUBLICATIONS

Gupta, Bhawna, et al., "Intracellular delivery of large molecules and small particles by cell-penetrating proteins and peptides." Advanced drug delivery reviews 57.4 (2005): 637-651.
Gupta, Subash C., et al. "Inhibiting NF-κB activation by small molecules as a therapeutic strategy." Biochimica et Biophysica Acta (BBA)-Gene Regulatory Mechanisms 1799.10-12 (2010): 775-787.
Gwack, Y.; et al., "A genome-wide Drosophila RNAi screen identifies DYRK-family kinases as regulators of NFAT." Nature 2006, 441, 646-650.
Hamill, K. M. et al., "Polymyxins facilitate entry into mammalian cells" Chem. Sci., 2016, 7:5059-5068.
Hancock R., et al., Peptide inhibitors of the Keap1-Nrf2 protein-protein interaction. Free Radic. Biol. Med. 52, (2012):444-451.
Hardee, C., et al., (2017) Advances in Non-Viral DNA Vectors for Gene Therapy. Genes 8, 65.
Hariton-Gazal, E. et al., "Functional Analysis of Backbone Cyclic Peptides Bearing the Arm Domain of the HIV-1 Rev Protein: Characterization of the Karyophilic Properties and Inhibition of Rev-Induced Gene Expression," Biochemistry, 2005, 44(34): 11555-11566.
He, M. M. et al. "Small-molecule inhibition of TNF-a." Science 310, (2005): 1022-1025.
He, R et al., "Recent Advances in PTP1B Inhibitor Development for the Treatment of Type 2 Diabetes and Obesity," Chapter 6 In: New Therapeutic Strategies for Type 2 Diabetes: Small Molecule Approaches, Jones, R. M. (ed.), RSC Drug Discovery Series No. 27, The Royal Society of Chemistry, 2012, pp. 142-176.
Heinis, C., et al., "Phage-encoded combinatorial chemical libraries based on bicyclic peptides." Nat. Chem. Biol. 5, (2009): 502-507.
Herce, H. D., et al. "Arginine-rich peptides destabilize the plasma membrane, consistent with a pore formation translocation mechanism of cell-penetrating peptides." Biophysical journal 97.7 (2009): 1917-1925.
Herce, Henry D., and Garcia, Angel E. "Molecular dynamics simulations suggest a mechanism for translocation of the HIV-1 Tat peptide across lipid membranes." Proceedings of the National Academy of Sciences 104.52 (2007): 20805-20810.
Herndon, Thomas M., et al. "US Food and Drug Administration approval: carfilzomib for the treatment of multiple myeloma." Clinical cancer research 19.17 (2013): 4559-4563.
Herrington, Felicity D., et al., "Modulation of NF-κB signaling as a therapeutic target in autoimmunity." Journal of biomolecular screening 21.3 (2016): 223-242.
Hernandez, Lídia, et al. "Activation of NF-κB signaling by inhibitor of NF-κB kinase β increases aggressiveness of ovarian cancer." Cancer research 70.10 (2010): 4005-4014.
Hili, R. et al., "Macrocyclization of Linear Peptides Enabled by Amphoteric Molecules," J. Am. Chem. Soc., 2010, 132(9):2889-2891.
Hintersteiner, M. et al. "Single bead labeling method for combining confocal fluorescence on-bead screening and solution validation of tagged one-bead one-compound libraries." Chem. Biol. 16, (2009): 724-735.
Hirose, Hisaaki, et al. "Transient focal membrane deformation induced by arginine-rich peptides leads to their direct penetration into cells." Molecular Therapy 20.5 (2012): 984-993.
Hojo, M.; et al., "Cyclosporine induces cancer progression by a cell-autonomous mechanism." Nature 1999, 397, 530-534.
Holub, J. M. et al., "Improved assays for determining the cytosolic access of peptides, proteins, and their mimetics," Biochemistry, Dec. 2013, 52(50):9036-9046.
Hopp, Thomas P. and WOODS, Kenneth R. "Prediction of protein antigenic determinants from amino acid sequences." Proceedings of the National Academy of Sciences 78.6 (1981): 3824-3828.
Horn, M. et al., "Tuning the properties of a novel short cell-penetrating peptide by intramolecular cyclization with a triazole bridge," Chem. Commun. 2016, 52:2261-2264.
Houghten, R. A et al. "Generation and use of synthetic peptide combinatorial libraries for basic research and drug discovery." Nature 354, (1991): 84-86.
Hoyer, J. A. N. and Neundorf, Ines. "Peptide vectors for the nonviral delivery of nucleic acids." Accounts of chemical research 45.7 (2012): 1048-1056.
Hu, B. et al., "Method for screening and MALDI-TOF MS sequencing of encoded combinatorial libraries." Anal. Chem. 79, (2007): 7275-7285.
Huang, H-C., et al., "Regulation of the antioxidant response element by protein kinase C-mediated phosphorylation of NF-E2-related factor 2." Proceedings of the National Academy of Sciences 97.23 (2000): 12475-12480.
Humphrey, W.; et al., "VMD: visual molecular dynamics." J. Mol. Graphics 1996, 14, 33-38.
Ianaro, Angela, et al. "NEMO-binding domain peptide inhibits proliferation of human melanoma cells." Cancer letters 274.2 (2009): 331-336.
Illsley, N. P. et al., "Membrane chloride transport measured using a chloride- sensitive fluorescent probe," Biochemistry, 1987, 26(5):1215-1219.
Inoyama, Daigo, et al. "Optimization of fluorescently labeled Nrf2 peptide probes and the development of a fluorescence polarization assay for the discovery of inhibitors of Keap1-Nrf2 interaction." Journal of biomolecular screening 17.4 (2012): 435-447.
Ishii, Tetsuro, et al. "Transcription factor Nrf2 coordinately regulates a group of oxidative stress-inducible genes in macrophages." Journal of Biological Chemistry 275.21 (2000): 16023-16029.
Jang, S. et al., "Cell-Penetrating, Dimeric a-Helical Peptides: Nanomolar Inhibitors of HIV-1 Transcription", Angew. Chem. Int. Ed. 2014, 53, 10086-10089.
Janin, J. O. E. L. "Surface and inside vols. in globular proteins." Nature 277.5696 (1979): 491-492.
Jeong, Ji Hoon, et al. "siRNA conjugate delivery systems." Bioconjugate chemistry 20.1 (2008): 5-14.
Jha, D. et al., "CyLoP-1: A Novel Cysteine-Rich Cell-Penetrating Peptide for Cytosolic Delivery of Cargoes," Bioconj. Chem., 2011, 22(3) :319-328.
Jiang, Bisheng, and PEI, Dehua. "A selective, cell-permeable nonphosphorylated bicyclic peptidyl inhibitor against peptidyl-prolyl isomerase Pin1." Journal of medicinal chemistry 58.15 (2015): 6306-6312.
Jimi, Eijiro, et al. "Selective inhibition of NF-κB blocks osteoclastogenesis and prevents inflammatory bone destruction in vivo." Nature medicine 10.6 (2004): 617.
Johnson, Mark L. and Rajamannan, Nalini. "Diseases of Wnt signaling." Reviews in Endocrine and Metabolic Disorders 7 (2006): 41-49.
Jójárt, B.; et al., "Performance of the general amber force field in modeling aqueous POPC membrane bilayers." J. Comput. Chem. 2007, 28, 2051-2058.
Joo, S. H., et al., "High-throughput sequence determination of cyclic peptide library members by partial Edman degradation/mass spectrometry." J. Am. Chem. Soc. 128, (2006): 13000-13009.
Joo, Sang Hoon. "Cyclic peptides as therapeutic agents and biochemical tools." Biomolecules & therapeutics 20.1 (2012): 19-26.
Jorgensen, W. L.; et al., "Solvation and Conformation of Methanol in Water." J. Am. Chem. Soc. 1983, 105, 1407-1413.
Josephson, Lee, et al. "High-efficiency intracellular magnetic labeling with novel superparamagnetic-Tat peptide conjugates." Bioconjugate chemistry 10.2 (1999): 186-191.
Joy, Stephen T., and Arora, Paramjit S. "An optimal hydrogen-bond surrogate for α-helices." Chemical Communications 52.33 (2016): 5738-5741.
Juliano, R. L. (2016) The delivery of therapeutic oligonucleotides. Nucleic Acids Res. 44(14): 6518-6548.
Junkes, Christof, et al. "Cyclic antimicrobial R-, W-rich peptides: the role of peptide structure and *E. coli* outer and inner membranes in activity and the mode of action." European Biophysics Journal 40.4 (2011): 515-528.
Kaduk, C.; et al., "Synthesis of Fmoc-amino acid fluorides via DAST, an alternative fluoridation agent." Lett. Pep. Sci. 1995, 2, 285-288.

(56) References Cited

OTHER PUBLICATIONS

Kang, S.; et al., "Inhibition of the calcineurin-NFAT interaction by small organic molecules reflects binding at an allosteric site." J. Biol. Chem. 2005, 280, 37698-37706.
Kansanen, Emilia, et al. "The Keap1-Nrf2 pathway: mechanisms of activation and dysregulation in cancer." Redox biology 1.1 (2013): 45-49.
Kaplan, Ian M., et al., "Cationic TAT peptide transduction domain enters cells by macropinocytosis." Journal of Controlled Release 102.1 (2005): 247-253.
Karin, Michael. "Nuclear factor-κB in cancer development and progression." Nature 441.7092 (2006): 431-436.
Karpurapu et al., "Inhibition of nuclear factor of activated T cells (NFAT) c3 activation attenuates acute lung injury and pulmonary edema in murine models of sepsis", Oncotarget 9(12), pp. 10606-10620.
Kawakami, T. et al., "In Vitro Selection of Multiple Libraries Created by Genetic Code Reprogramming to Discover Macrocyclic Peptides That Antagonize VEGFR2 Activity in Living Cells," ACS Chem. Biol., Apr. 2013, 8(6):1205-1214.
Kawakami, M., & Cerami, A. Studies of endotoxin-induced decrease in lipoprotein-lipase activity. J. Exp. Med. 154, (1981): 631-639.
Kerem, Bat-sheva, et al. "Identification of the cystic fibrosis gene: genetic analysis." Science 245.4922 (1989): 1073-1080.
Khabar, K.S.A. et al., "WEHI-13V AR: a stable and sensitive variant of WEHI 164 clone 13 fibrosarcoma for tumor necrosis factor bioassay." Immunol. Lett. 46, (1995): 107-110.
Khakshoor, Omid, and NOWICK, James S. "Artificial β-sheets: chemical models of β-sheets." Current opinion in chemical biology 12.6 (2008): 722-729.
Kiani, A.; et al., "Manipulating immune responses with immunosuppressive agents the target NFAT." Immunity 2000, 12, 359-372.
Kimber, Matthew S., et al. "Structural basis for specificity switching of the Src SH2 domain." Molecular cell 5.6 (2000): 1043-1049.
Kodadek, T. & Bachhawat-Sikder, K. "Optimized protocols for the isolation of specific protein-binding peptides or peptoids from combinatorial libraries displayed on beads." Mol. BioSyst. 2, (2006): 25-35.
Kohli, R. M. et al., "Biomimetic synthesis and optimization of cyclic peptide antibiotics," Nature, Aug. 2002, 418:658-661.
Koide, A. et al. "The fibronectin type III domain as a scaffold for novel binding proteins." J. Mol. Biol. 284, (1998): 1141-1151.
Kornegay, Joe N., et al. "NBD delivery improves the disease phenotype of the golden retriever model of Duchenne muscular dystrophy." Skeletal muscle 4.1 (2014): 18.
Kriegler, M et al. "A Novel Form of TNF/cachectin Is a Cell Surface Cytotoxic Transmembrane Protein: Ramifications for the Complex Physiology of TNF." Cell 53, (1988): 45-53.
Kritzer, J. A et al., "Rapid selection of cyclic peptides that reduce a-synuclein toxicity in yeast and animal models," Nature Chemical Biology, Sep. 2009, 5(9):655-663.
Kundu, R et al., "Hybrid Organic-Inorganic Inhibitors of a PDZ Interaction that Regulates the Endocytic Fate of CFTR," Angew. Chem. Int. Ed., Jul. 2012, 51(29):7217-7220.
Kwon, Y-U et al., "Quantitative Comparison of the Relative Cell Permeability of Cyclic and Linear Peptides," Chemistry & Biology, Jun. 2007, 14(6):671-677.
Kyte, Jack, and Doolittle, Russell F. "A simple method for displaying the hydropathic character of a protein." Journal of molecular biology 157.1 (1982): 105-132.
Lächelt, U., and Wagner., E. (2015) Nucleic Acid Therapeutics Using Polyplexes: A Journey of 50 Years (and Beyond). Chem. Rev. 115, 11043-11078.
Lai, Jonathan R., et al. "Design of non-cysteine-containing antimicrobial β-hairpins: Structure-activity relationship studies with linear protegrin-1 analogues." Biochemistry 41.42 (2002): 12835-12842.
Lalonde, M.S et al., "Inhibition of Both HIV-1 Reverse Transcription and Gene Expression by a Cyclic Peptide that Binds the Tat-Transactivating Response Element (TAR) RNA", PLoS Pathogenes May 2011, 7(5) e1002038.
Lam, K. S. et al. "A new type of synthetic peptide library for identifying ligand-binding activity." Nature 354, (1991): 82-84.
Lamontagne, K. R. Jr. et al., "Protein tyrosine phosphatase PTPIB suppresses p210 bcr-abl-induced transformation of Rat-1 fibroblasts and promotes differentiation of K562 cells," Proc. Natl. Acad. Sci. U. S. A., Nov. 1998, 95(24):14094-14099.
Langham, Allison A., et al., "Comparison of interactions between beta-hairpin decapeptides and SDS/DPC micelles from experimental and simulation data." BMC biochemistry 8.1 (2007): 1-13.
Larochelle, Jonathan R., et al. "Fluorescence correlation spectroscopy reveals highly efficient cytosolic delivery of certain penta-arg proteins and stapled peptides." Journal of the American Chemical Society 137.7 (2015): 2536-2541.
Lättig-Tünnemann, Gisela, et al. "Backbone rigidity and static presentation of guanidinium groups increases cellular uptake of arginine-rich cell-penetrating peptides." Nature communications 2 (2011): 453.
Lau, Yu Heng, et al. "Peptide stapling techniques based on different macrocyclisation chemistries." *Chemical Society Reviews* 44.1 (2015): 91-102.
Law, M., et al., (2008) Physicochemical characterization of siRNA-peptide complexes. Biotechnol Prog, 24, 957-963.
Leduc, A. M. et al. "Helix-stabilized cyclic peptides as selective inhibitors of steroid receptor-coactivator interactions." Proc. Natl. Acad. Sci. USA 100, (2003): 11273-11278.
Lee, H. J. et al., "PDZ domains and their binding partners: structure, specificity, and modification," Cell Communication and Signaling, 2010, 8:8, 18 pages.
Lee, J. et al., "Using marine natural products to discover a protease that catalyzes peptide macrocyclization of diverse substrates," J. Am. Chem. Soc., Feb. 2009, 131(6):2122-2124.
Lee et al. Identification and Characterization of a Novel Integrin-Linked Kinase Inhibitor, Journal of Medicinal Chemistry, 2011, vol. 54, Iss. 18, p. 6364-6374, Publish Online Aug. 8, 2011.
Lessard, L. et al., "The two faces of PTPIB in cancer," Biochim. Biophys. Acta, Mar. 2010, 1804(3):613-619.
Leung, C. H. et al. "Structure-based repurposing of FDA-approved drugs as TNF-a inhibitors." ChemMedChem 6, (2011): 765-768.
Lewis, Kaitlyn N., et al. "Nrf2, a guardian of healthspan and gatekeeper of species longevity." Integrative and comparative biology 50.5 (2010): 829-843.
Li, H.; et al., "Interaction of calcineurin with substrates and targeting proteins." Trends Cell Biol. 2011, 21, 91-103.
Li, H.; et al., "Structural delineation of the calcineurin-NFAT interaction and its parallels to PP1 targeting interactions." J. Mol. Biol. 2004, 342, 1659-1674.
Li, H.; et al., "Structure of calcineurin in complex with PVIVIT peptide: portrait of a low-affinity signaling interaction." J. Mol. Biol. 2007, 369, 1296-1306.
Li, S. et al., "Photolithographic synthesis of cyclic peptide arrays using a differential deprotection strategy," Chem. Commun., 2005, 5:581-583.
Li, S. et al., "Fluoride enhances the activity of fungicides that destabilize cell membranes," Bioorganic & Medicinal Chemistry Letters, 2012, 22(9):3317-3322.
Liao et al., Cell-permeable bicyclic peptidyl inhibitors against T-cell protein tyrosine phosphates from a combinatorial library, Organic & Biomolecular Chemistry, vol. 15, pp. 9595-9598, 2017.
Lian, Wenlong, et al. "Cell-permeable bicyclic peptide inhibitors against intracellular proteins." Journal of the American Chemical Society 136.28 (2014): 9830-9833.
Lian, Wenlong, et al. "Screening bicyclic peptide libraries for protein-protein interaction inhibitors: discovery of a tumor necrosis factor-a antagonist." Journal of the American Chemical Society 135.32 (2013): 11990-11995.
Lightfoot, H. et al., "Endogenous polyamine function—the RNA perspective." Nucleic acids research 42.18 (2014): 11275-11290.
Lin, K-J, et al., "QSAR studies of antimicrobial alpha, beta-polypeptides," Pharmaceutical Biotechnology, 2003, 10(5):299-303 (with English Abstract).
Lindgren M. et al., "Classes and Prediction of Cell-Penetrating Peptides," Chapter 1 In: Cell-Penetrating Peptides: Methods and

(56) References Cited

OTHER PUBLICATIONS

Protocols, Methods in Molecular Biology, vol. 683, pp. 3-19, Springer Science+Business Media, LLC 2011.
Liu, T. et al., "Membrane permeable cyclic peptidyl inhibitors against human Peptidylprolyl Isomerase Pin1." Journal of medicinal chemistry 53.6 (2010): 2494-2501.
Liu, Jianquan, et al. "Nanostructured materials designed for cell binding and transduction." Biomacromolecules 2.2 (2001): 362-368.
Liu, R., et al., "A novel peptide-based encoding system for "one-bead one-compound" peptidomimetic and small molecule combinatorial libraries." J. Am. Chem. Soc. 124, (2002): 7678-7680.
Liu, T. et al. "Synthesis and screening of a cyclic peptide library: Discovery of small-molecule ligands against human prolactin receptor." Bioorg. Med. Chem. 17, (2009): 1026-1033.
Liu, T., et al., "High-throughput screening of one-bead-one compound libraries: identification of cyclic peptidyl inhibitors against calcineurin/NF AT interaction." ACS Comb. Sci. 13, (2011): 537-546.
Liu, X., Chen, C. & Hop, C. E. "Do we need to optimize plasma protein and tissue binding in drug discovery?" Curr. Top. Med. Chem. 11, (2011):450-466.
Liu, Y et al., "Multifunctional Tandem Peptide Modified Paclitaxel-Loaded Liposomes for the Treatment of Vasculogenic Mimicry and Cancer Stem Cells in Malignant Glioma," ACS Applied Materials & Interfaces, 2015, 7(30):16792-16801.
Liu, J.; et al., "Calcineurin is a common target of cyclophilin-cyclosporine A and FKBP-FK506 complexes." Cell 1991, 66, 807-815.
Llinas-Brunet, M.; et al., "A systematic approach to the optimization of substrate-based inhibitors of the hepatitis C virus NS3 protease: discovery of potent and specific tripeptide inhibitors." J. Med. Chem. 2004, 47, 6584-6594.
Lo, Shih-Ching, et al. "Structure of the Keap1: Nrf2 interface provides mechanistic insight into Nrf2 signaling." The EMBO journal 25.15 (2006): 3605-3617.
Lu, K. P. et al., "The prolyl isomerase PIN1: a pivotal new twist in phosphorylation signaling and disease," Nat. Rev. Mol. Cell Biol., Nov. 2007, 8:904-916.
Luechapanichkul, R.; et al., "Specificity profiling of dual specificity phosphatase vaccinia VH1-related (VHR) reveals two distinct substrate binding modes." J. Biol. Chem. 2013, 288, 6498-6510.
Luzi et al. Subunit disassembly and inhibition of TNFalpha by a semi-synthetic bicyclic peptide, Protein Engineering, Design, & Selection 28(2), (2015): 45-52.
Ma, Bing, et al. "Total synthesis of the antimitotic bicyclic peptide celogentin c." Journal of the American Chemical Society 132.3 (2009): 1159-1171.
Ma, L. et al. "A Novel Small-Molecule Tumor Necrosis Factor α Inhibitor Attenuates Inflammation in a Hepatitis Mouse Model." J. Biol. Chem. 289, (2014): 12457-12466.
Ma, Yan, et al. "Direct cytosolic delivery of cargoes in vivo by a chimera consisting of D- and L-arginine residues." Journal of controlled release 162.2 (2012): 286-294.
Magzoub, M. et al., "Conformational states of the cell-penetrating peptide penetratin when interacting with phospholipid vesicles: effects of surface charge and peptide concentration," Biochim. Biophys. Acta, Jun. 2002, 1563(1-2):53-63.
Maiolo, et al. "Effects of cargo molecules on the cellular uptake of arginine-rich cell-penetrating peptides." Biochimica et Biophysica Acta (BBA)-Biomembranes 1712.2 (2005): 161-172.
Majer et al., Structure-based substitute specificity mapping of human cathespin D using statine-based inhibitors, Protein Science, vol. 6, pp. 1458-1466, 1997.
Maly, D. J. et al., "Combinatorial Strategies for Targeting Protein Families: Application to the Proteases," Chembiochem, Jan. 2002, 3(1):16-37.
Maly, D. J. et al., "Expedient Solid-Phase Synthesis of Fluorogenic Protease Substrates Using the 7-Amino-4-carbamoylmethylcoumarin (ACC) Fluorophore," J. Org. Chem., 2002, 67(3):910-915.
Mancini, F. et al., Inhibition of tumor necrosis factor-a (TNF-a )-TNF-a receptor binding by structural analogues of suramin. Biochem. Pharmocol. 58, (1999): 851-859.
Mandal, Deendayal, et al., "Cell-penetrating homochiral cyclic peptides as nuclear-targeting molecular transporters." Angewandte Chemie International Edition 50.41 (2011): 9633-9637.
Marsault, E. et al., "Macrocycles Are Great Cycles: Applications, Opportunities, and Challenges of Synthetic Macrocycles in Drug Discovery," J. Med. Chem., 2011, 54(7): 1961-2004.
Martin, T. L. et al., The light side of horseradish peroxidase histochemistry. J. Histochem. Cytochem. 32, (1984):793.
May, Michael J., et al. "Selective inhibition of NF-κB activation by a peptide that blocks the interaction of NEMO with the IκB kinase complex." Science 289.5484 (2000): 1550-1554.
Meutermans, W. D. F. et al., "Synthesis of Difficult Cyclic Peptides by Inclusion of a Novel Photolabile Auxiliary in a Ring Contraction Strategy," J. Am. Chem. Soc., 1999, 121(42):9790-9796. Published Online: Oct. 8, 1999.
Meyer, Daniel, et al. "Aromatic interactions with naphthylalanine in a β-hairpin peptide." Journal of Peptide Science 19.5 (2013): 277-282.
Millward, S.W., et al., "Design of cyclic peptides that bind protein surfaces with antibody-like affinity." ACS Chem. Biol. 2, (2007): 625-634.
Millward, S. W. et al., "A General Route for Post-Translational Cyclization of mRNA Display Libraries," J. Am. Chem. Soc., 2005, 127(41):14142-14143. Published Online: Sep. 27, 2005.
Ming, Z. et al., "Synthesis of RGD containing peptides and their vasodilation effect," Preparative Biochemistry Biotechnology, 2000, 30(3):247-256.
Miranda, E. et al. "A Cyclic Peptide Inhibitor of HIF-1 Heterodimerization That Inhibits Hypoxia Signaling in Cancer Cells." J. Am. Chem. Soc. 135, (2013): 10418-10425.
Mishra, Abhijit, et al. "Translocation of HIV TAT peptide and analogues induced by multiplexed membrane and cytoskeletal interactions." Proceedings of the National Academy of Sciences 108.41 (2011): 16883-16888.
Miskolzie, M. et al., "An NMR conformational analysis of cyclic bradykinin mimics. Evidence for a-turn," Journal of Biomolecular Structure & Dynamics, 2000, 17(6):947-955.
Mitra, Sayantan, and Barrios, Amy M. "Highly sensitive peptide-based probes for protein tyrosine phosphatase activity utilizing a fluorogenic mimic of phosphotyrosine." Bioorganic & medicinal chemistry letters 15.23 (2005): 5142-5145.
Moore, J. D. et al., "Pin1 inhibitors: Pitfalls, progress and cellular pharmacology," Bioorg. Med. Chem. Lett., Aug. 2013, 23(15):4283-4291.
Morais Cabral, J. H. et al., "Crystal structure of a PDZ domain," Nature, Aug. 1996, 382:649-652.
Morrison, et al., "Combinatorial alanine-scanning." Current opinion in chemical biology 5.3 (2001): 302-307.
Mosmann, T., "Rapid colorimetric assay for cellular growth and survival: Application to proliferation and cytotoxicity assays," J. Immunol. Methods, Dec. 1983, 65(1-2):55-63.
Mueller, Judith, et al. "Comparison of cellular uptake using 22 CPPs in 4 different cell lines." Bioconjugate chemistry 19.12 (2008): 2363-2374.
Muratovska, Aleksandra, and Eccles, Michael R. "Conjugate for efficient delivery of short interfering RNA (siRNA) into mammalian cells." FEBS letters 558.1-3 (2004): 63-68.
Nakase, Ikuhiko, et al. "Efficient intracellular delivery of nucleic acid pharmaceuticals using cell-penetrating peptides." Accounts of chemical research 45.7 (2011): 1132-1139.
Nakase, Ikuhiko, et al. "Interaction of arginine-rich peptides with membrane-associated proteoglycans is crucial for induction of actin organization and macropinocytosis." Biochemistry 46.2 (2007): 492-501.
Ndikuyeze, Georges Habineza, et al. "A phase I clinical trial of systemically delivered NEMO binding domain peptide in dogs with spontaneous activated B-cell like diffuse large B-cell lymphoma." PloS one 9.5 (2014): e95404.

(56) References Cited

OTHER PUBLICATIONS

Needleman, Saul B., and Wunsch, Christian D. "A general method applicable to the search for similarities in the amino acid sequence of two proteins." Journal of molecular biology 48.3 (1970): 443-453.

Nevola, Laura, and Giralt, Ernest. "Modulating protein-protein interactions: the potential of peptides." Chemical Communications 51.16 (2015): 3302-3315.

Ngu-Schwemlein, M. et al., "In vitro synergy between some cationic amphipathic cyclooctapeptides and antibiotics," Australian Journal of Chemistry, 2015, 68(2):218-223.

Nguyen, Leonard T., et al. "Serum stabilities of short tryptophan- and arginine-rich antimicrobial peptide analogs." PloS one 5.9 (2010): e12684.

Nischan, N. et al., "Covalent Attachment of Cyclic TAT Peptides to GFP Results in Protein Delivery into Live Cells with Immediate Bioavailability," Angew. Chem. Int. Ed., 2015, 54:1950-1953, with Supporting Information pp. S1-S26.

Noguchi, H.; et al., "A new cell-permeable peptide allows successful allogeneic islet transplantation in mice." Nat. Med. 2004, 10, 305-309.

Nori, Aparna, et al. "Tat-conjugated synthetic macromolecules facilitate cytoplasmic drug delivery to human ovarian carcinoma cells." Bioconjugate chemistry 14.1 (2003): 44-50.

Ocampo-Garcia, B. E. et al., "Design and biological evaluation of 99mTc-N2S2-Tat(49-57)-c(RGDyK): A hybrid radiopharmaceutical for tumors expressing a(v)(3) integrins," Nuclear Medicine and Biology (2013), 40(4):481-487.

Oeckinghaus, Andrea, and GHOSH, Sankar. "The NF-κB family of transcription factors and its regulation." Cold Spring Harbor perspectives in biology 1.4 (2009): a000034.

Oh, D. et al., "Antibacterial activities of amphiphilic cyclic cell-penetrating peptides against multidrug-resistant pathogens," Molecular Pharmaceutics, 2014, 11(10):3528-3536.

Oh, D. et al., "Amphiphilic Bicyclic Peptides as Cellular Delivery Agents," ChemMedChem, 2014, 9(11):2449-2453.

Oh, D. et al., "Enhanced cellular uptake of short polyarginine peptides through fatty acylation and cyclization." Molecular pharmaceuticals 11.8 (2014): 2845-2854.

Okamoto, H. et al., "Conformational transitions of cyclic D,L-Peptides," Journal of Computational Chemistry, 2009, 30(6):962-973.

Orange et al. "Cell penetrating peptide inhibitors of Nuclear Factor-kappa B," Cell Mol Life Sci, 2008, 62(22), 3564-3591.

Palm-Apergi, Caroline, et al. "The membrane repair response masks membrane disturbances caused by cell-penetrating peptide uptake." The FASEB Journal 23.1 (2009): 214-223.

Pande et al., Synthesis and Antibacterial Evaluation of Carboxamide Derivatives of Amino Acids (Pharmaceutical Chemistry Journal, vol. 48, No. 1, Apr. 2014).

Passioura, Toby, et al. "Selection-based discovery of druglike macrocyclic peptides." Annual review of biochemistry 83 (2014): 727-752.

Pawson, T. et al., "Assembly of Cell Regulatory Systems Through Protein Interaction Domains," Science, Apr. 2003, 300(5618) :445-452.

Pelay-Gimeno, Marta, et al. "Structure-based design of inhibitors of protein-protein interactions: mimicking peptide binding epitopes." Angewandte Chemie International Edition 54.31 (2015): 8896-8927.

Pelay-Gimeno, Marta, et al. "Strukturbasierte Entwicklung von Protein-Protein-Interaktionsinhibitoren: Stabilisierung und Nachahmung von Peptidliganden." Angewandte Chemie 127.31 (2015): 9022-9054.

Peng, Q., et al., (2008) Disulfide Cross-Linked Polyethylenimines (PEI) Prepared via Thiolation of Low Molecular Weight PEI as Highly Efficient Gene Vectors. Bioconjugate Chem. 19, 499-506.

Pennica, D. et al. "Human Tumour Necrosis Factor: Precursor Structure, Expression and Homology to Lymphotoxin." Nature 312, (1984):724-729.

Perni, R. B.; et al., "Preclinical profile of VX-950, a potent, selective, and orally bioavailable inhibitor of hepatitis C Virus NS3-4A serine protease." Antimicrob. Agents Chemother. 2006, 50, 899-909.

Peterson, Jennifer M., et al. "Peptide-based inhibition of NF-κB rescues diaphragm muscle contractile dysfunction in a murine model of Duchenne muscular dystrophy." Molecular medicine 17.5-6 (2011): 508-515.

Pettersen, E. F.; et al., "UCSF Chimera—a visualization system for exploratory research and analysis." J. Comput. Chem. 2004, 13, 1605-1612.

Pham, Wellington, et al. "Enhancing membrane permeability by fatty acylation of oligoarginine peptides." Chembiochem 5.8 (2004): 1148-1151.

Platz, K. P.; et al., "Nephrotoxicity following orthotopic liver transplantation. A comparison between cyclosporine and FK506." Transplantation 1994, 58, 170-178.

Pomilio, A B. et al., "Naturally-Occurring Cyclopeptides: Structures and Bioactivity," Current Organic Chemistry, Nov. 2006, 10(16):2075-2121.

Pooga, Margus, et al. "Cellular translocation of proteins by transportan." The FASEB Journal 15.8 (2001).

Pritz, S. et al., "Synthesis of Biologically Active Peptide Nucleic Acid-Peptide Conjugates by Sortase-Mediated Ligation," Journal of Organic Chemistry, 2007, 72(10):3909-3912.

Qian et al. "Enhancing the Cell Permeability and Metabolic Stability of Peptidyl Drugs by Reversible Bicylcization," Angew Chem Int Ed English 56(6) (2016): 1525-1529.

Qian, Ziqing, et al. "Discovery and mechanism of highly efficient cyclic cell-penetrating peptides." Biochemistry 55.18 (2016): 2601-2612.

Qian, Ziqing, et al. "Efficient delivery of cyclic peptides into mammalian cells with short sequence motifs." ACS chemical biology 8.2 (2012): 423-431.

Qian, Ziqing, et al. "Intracellular delivery of peptidyl ligands by reversible cyclization: discovery of a PDZ domain inhibitor that rescues CFTR activity." Angewandte Chemie International Edition 54.20 (2015): 5874-5878. Angew. Chem. 2015, 127, 5972.

Qian, Ziqing, et al. "Monitoring the cytosolic entry of cell-penetrating peptides using a pH-sensitive fluorophore." Chemical Communications 51.11 (2015): 2162-2165.

Qian, Ziqing, et al. "Early endosomal escape of a cyclic cell-penetrating peptide allows effective cytosolic cargo delivery." Biochemistry 53.24 (2014): 4034-4046.

Qian et al., "Structure-Based Optimization of a Peptidyl Inhibitor against Calcineurin-Nuclear Factor of Activated T Cell (NFAT) Interaction." J. Med. Chem. 2014, 57, 7792-7797.

Qin, C. et al., "Optimization of Antibacterial Cyclic Decapeptides," J. Comb. Chem., 2004, 6(3):398-406.

R-Group_SASA_and LogP_as Hydrophobicity Measure Claims 97 and 100; generated in ChemOffice Excel 2010 (Year 2022).

Rajendran, Peramaiyan, et al. "Antioxidants and human diseases." Clinica chimica acta 436 (2014): 332-347.

Rao, A .; et al., "Transcription factors of the NFAT family: regulation and function." Annu. Rev. Immunol. 1997, 15, 707-747.

Reay, Daniel P., et al. "Systemic delivery of NEMO binding domain/IKKγ inhibitory peptide to young mdx mice improves dystrophic skeletal muscle histopathology." Neurobiology of disease 43.3 (2011): 598-608.

Ren, L. et al., "Substrate Specificity of Protein Tyrosine Phosphatases 1B, RPTPα, SHP-1, and SHP-2," Biochemistry, 2011, 50(12):2339-2356.

Rezai, Taha, et al. "Conformational flexibility, internal hydrogen bonding, and passive membrane permeability: successful in silico prediction of the relative permeabilities of cyclic peptides." Journal of the American Chemical Society 128.43 (2006): 14073-14080.

Rezai, T. et al., "Testing the Conformational Hypothesis of Passive Membrane Permeability Using Synthetic Cyclic Peptide Diastereomers," J. Am. Chem. Soc., 2006, 128(8):2510-2511.

Rice, Peter, et al., "EMBOSS: the European molecular biology open software suite." *Trends in genetics* 16.6 (2000): 276-277.

(56) References Cited

OTHER PUBLICATIONS

Richard, Jean Philippe, et al. "Cellular uptake of unconjugated TAT peptide involves clathrin-dependent endocytosis and heparan sulfate receptors." Journal of Biological Chemistry 280.15 (2005): 15300-15306.
Ricouart, A. et al., "Design of potent protein kinases inhibitors using the bisubstrate approach," Journal of Medicinal Chemistry, 1991, 34(1):73-78.
Riedl, S. J. et al., "Molecular mechanisms of caspase regulation during apoptosis," Nat. Rev. Mol. Cell Biol., Nov. 2004, 5:897-907.
Roberts, K. D. et al., "Efficient synthesis of thioether-based cyclic peptide libraries," Tetrahedron Letters, Nov. 1998, 39(45):8357-8360.
Roberts, K. E. et al., "Computational Design of a PDZ Domain Peptide Inhibitor that Rescues CFTR Activity," Plos Computational Biology, Apr. 2012, 8(4): e1002477, 12 pages.
Robinson, John A. "β-Hairpin peptidomimetics: design, structures and biological activities." Accounts of chemical research 41.10 (2008): 1278-1288.
Rothbard, Jonathan B., et al. "Conjugation of arginine oligomers to cyclosporin A facilitates topical delivery and inhibition of inflammation." Nature medicine 6.11 (2000): 1253.
Rothwarf, David M., et al. "IKK-γ is an essential regulatory subunit of the IκB kinase complex." Nature 395.6699 (1998): 297.
Rotstein, B. H. et al., "Solvatochromic Reagents for Multicomponent Reactions and their Utility in the Development of Cell-Permeable Macrocyclic Peptide Vectors," 2011, Chem. Eur. J., 17:12257-12261.
Roy, J.; et al., "Cracking the phosphatase code: Docking interactions determine substrate specificity." Sci. Signal. 2009, 2, re9, 1-7.
Rueping, Magnus, et al. "Cellular uptake studies with β-peptides." ChemBioChem 3.2-3 (2002): 257-259.
Rushe, Mia, et al. "Structure of a NEMO/IKK-associating domain reveals architecture of the interaction site." Structure 16.5 (2008): 798-808.
Rusnati, M. et al., "Multiple Interactions of HIV-I Tat Protein with Size-defined Heparin Oligosaccharides," J. Biol. Chem., Oct. 1999, 274(40):28198-28205.
Rutledge, S.E., et al., "Molecular recognition of protein surfaces: high affinity ligands for the CBPKIX domain." J. Am. Chem. Soc. 125, (2003): 14336-14347.
Saar, Külliki, et al. "Cell-penetrating peptides: a comparative membrane toxicity study." Analytical biochemistry 345.1 (2005): 55-65.
Sahin, U., et al., (2014) mRNA-based therapeutics—developing a new class of drugs. Nat. Rev. Drug Discov. 13, 759-780.
Saito, H. et al. "A tumor necrosis factor receptor loop peptide mimic inhibits bone destruction to the same extent as anti-tumor necrosis factor monoclonal antibody in murine collagen-induced arthritis." Arthritis Rheum. 56, (2007):1164-1174.
Sako, Y., et al., "Ribosomal synthesis of bicyclic peptides via two orthogonal inter-side-chain reactions." J. Am. Chem. Soc. 130, (2008): 7232-7234.
Salvado, I. et al., "Membrane-disrupting iridium(III) oligocationic organometallopeptides," Chemical Communications, 2016, 52(73): 11008-11011.
Sandberg, Mats, et al. "NRF2-regulation in brain health and disease: implication of cerebral inflammation." Neuropharmacology 79 (2014): 298-306.
Schafmeister, C. E et al., "An All-Hydrocarbon Cross-Linking System for Enhancing the Helicity and Metabolic Stability of Peptides," J. Am. Chem. Soc., 2000, 122(24):5891-5892.
Schmidt, Nathan, et al. "Arginine-rich cell-penetrating peptides." FEBS letters 584.9 (2010): 1806-1813.
Scholl, Markus, et al., "Dendritic and hyperbranched polyamides." Progress in Polymer Science 34.1 (2009): 24-61.
Schwarze, Steven R., et al. "In vivo protein transduction: delivery of a biologically active protein into the mouse." Science 285.5433 (1999): 1569-1572.
Scott, C. P et al., "Production of cyclic peptides and proteins in vivo," Proc. Natl. Acad. Sci. U. S. A., Nov. 1999, 96(24):13638-13643.
Shen, Q. et al., "De novo design of helical peptides to inhibit tumor necrosis factor-a by disrupting its trimer formation." Med. Chem. Commun. 7, (2016): 725-729.
Shepherd, Nicholas E., et al. "Single turn peptide alpha helices with exceptional stability in water." Journal of the American Chemical Society 127.9 (2005): 2974-2983.
Shi, B. et al. (2011) Biodistribution of Small Interfering RNA at the Organ and Cellular Levels after Lipid Nanoparticle-mediated Delivery. J Histochem Cytochem. 59(8): 727-740.
Shibata, W. et al., "Cutting edge: the IkB kinase (IKK) inhibitor, NEMO-binding domain peptide, blocks inflammatory injury in murine colitis." The Journal of Immunology 179.5 (2007): 2681-2685.
Shirazi, A. N. et al., "Cysteine and arginine-rich peptides as molecular carriers," Bioorg. Med. Chem. Lett., 2016, 26:656-661.
Shirazi, A. N. et al., "Cyclic Peptide-Capped Gold Nanoparticles as Drug Delivery Systems," Molecular Pharmaceutics, 2013, 11:500-511.
Shirazi, A. N. et al., "Design and Biological Evaluation of Cell-Penetrating Peptide-Doxorubicin Conjugates as Prodrugs," Molecular Pharmaceutics, 2013, 10:488-499.
Shirazi, A. N. et al., "Cyclic peptides containing tryptophan and arginine as Src kinase inhibitors", Bioorganic & Medicinal Chemistry Letters 23 (2013) 3230-3234.
Shrake, Andrew, and Rupley, John A. "Environment and exposure to solvent of protein atoms. Lysozyme and insulin." Journal of molecular biology 79.2 (1973): 351-371.
Sieber, M.; et al., "Novel inhibitors of the calcineurin/NFATc hub—alternatives to CsA and FK506?" Cell Commun. Signal. 2009, 7, 25.
Sigal, N. H.; et al., "Is cyclophilin involved in the immunosuppressive and nephrotoxic mechanism of action of cyclosporine A?" J. Exp. Med. 1991, 173, 619-628.
Sigman, M. S.; et al., "Schiff base catalysts for the asymmetric Strecker reaction identified and optimized from parallel synthetic libraries." J. Am. Chem. Soc. 1998, 120, 4901-4902.
Skelton, Nicholas J., et al. "β-hairpin polypeptides by design and selection." Journal of Spectroscopy 17.2-3 (2003): 213-230.
Slee, E. A et al., "Benzyloxycarbonyl-Val-Ala-Asp (OMe) fluoromethylketone (Z-VAD.FMK) inhibits apoptosis by blocking the processing of CPP32," Biochemical Journal, Apr. 1996, 315(1):21-24.
Songyang, Z et al., "Recognition of Unique Carboxyl-Terminal Motifs by Distinct PDZ Domains," Science, Jan. 1997, 275(5296):73-77.
Sorin, E. J.; et al., "Exploring the helix-coil transition via all-atom equilibrium ensemble simulations." Biophys. J. 2005, 88, 2472-2493.
Sousa Da Silva, A. W.; et al., "ACPYPE-AnteChamberPYthon Parser interfacE." BMC Res. Notes 2012, 5, 367.
Sporn et al., "Chemoprevention of Cancer," Carcinogenesis, vol. 21 (2000), 525-530.
Srinivas, et al., Biaryl amino acid templates in place of D-Pro-L-Pro in cyclic beta-hairpin cationic antimicrobial peptidemimetics, Organic and Biomolecular Chemistry vol. 5, pp. 3100-3105, 2007.
Stanford, Stephanie M., et al. "High-throughput screen using a single-cell tyrosine phosphatase assay reveals biologically active inhibitors of tyrosine phosphatase CD45." Proceedings of the National Academy of Sciences 109.35 (2012): 13972-13977.
Steiner, D., Forrer, P. & Plueckthun, A. "Efficient selection of DARPins with subnanomolar affinities using SRP phage display." J. Mol. Biol. 382, (2008):1211-1227.
Stewart, Kelly M. et al., "Cell-penetrating peptides as delivery vehicles for biology and medicine." Organic & biomolecular chemistry 6.13 (2008): 2242-2255.
Stewart, J. M. et al., "Bradykinin antagonists: Anti-cancer drugs for the new millennium?" Peptides for the New Millennium, Proceedings of the American Peptide Symposium, 16th, Minneapolis, MN,

(56) References Cited

OTHER PUBLICATIONS

United States, Jun. 26-Jul. 1, 1999 (2000), Meeting Date 1999, 219-221. Fields, G. B et al., (eds.), Kluwer Academic Publishers, Dordrecht, Neth.
Suhorutsenko, Julia, et al. "Cell-penetrating peptides, PepFects, show no evidence of toxicity and immunogenicity in vitro and in vivo." Bioconjugate chemistry 22.11 (2011): 2255-2262.
Sun, Shao-Cong, et al., "Regulation of nuclear factor-κB in autoimmunity." Trends in immunology 34.6 (2013): 282-289.
Sun, Y. et al., "A thioester ligation approach to amphipathic bicyclic peptide library." Org. Lett. 3, (2001): 1681-1684.
Sweeney, M. C et al. "Decoding protein-protein interactions through combinatorial chemistry: sequence specificity of SHP-1, SHP-2, and Ship SH2 domains." Biochemistry 44, (2005): 14932-14947.
Taguchi, Keiko, et al., "Molecular mechanisms of the Keap1-Nrf2 pathway in stress response and cancer evolution." Genes to cells 16.2 (2011): 123-140.
Tai, Z., et al., (2015) Biodegradable Stearylated Peptide with Internal Disulfide Bonds for Efficient Delivery of siRNA In Vitro and In Vivo. Biomacromolecules 16, 1119-1130.
Takada, Y. et al. "Evodiamine Abolishes Constitutive and Inducible NF-κB Activation by Inhibiting IκBα Kinase Activation, Thereby Suppressing NF-κB-regulated Antiapoptotic and Metastatic Gene Expression, Up-regulating Apoptosis, and Inhibiting Invasion." J. Biol. Chem. 280, (2005): 17203-17212.
Takasaki, W. et al., "Structure-based design and characterization of exocyclic peptidomimetics that inhibit TNF alpha binding to its receptor." Nat. Biotechnol. 15, (1997): 1266-1270.
Takeuchi, K.; et al., "Structure of the calcineurin-NFAT complex: defining a T cell activation switch using solution NMR and crystal coordinates." Structure 2007, 15, 587-597.
Tam, J. P. et al., "Disulfide bond formation in peptides by dimethyl sulfoxide. Scope and applications," J. Am. Chem. Soc., 1991, 113(17):6657-6662.
Tang, P. et al. "Human pro-Tumor Necrosis Factor Is a Homotrimer." Biochemistry (Mosc.) 35, (1995): 8216-8225.
Tavassoli, A., et al., "Inhibition of HIV budding by a genetically selected cyclic peptide targeting the Gag-TSG 101 interaction." ACS Chem. Biol. 3, (2008): 757-764.
Thakkar, A. et al., "Global analysis of peptide cyclization efficiency." ACS Comb. Sci. 15, (2013): 120-129.
Thakkar, A. et al., "Traceless capping agent for peptide sequencing by partial Edman degradation and mass spectrometry." Anal. Chem. 78, (2006): 5935-5939.
Thornberry, N. A. et al., "A Combinatorial Approach Defines Specificities of Members of the Caspase Family and Granzyme B. Functional Relationships Established for Key Mediators of Apoptosis," J. Biol. Chem., Jul. 1997, 272(29):17907-17911.
Tien, Matthew Z., et al. "Maximum allowed solvent accessibilities of residues in proteins." PloS one 8.11 (2013): e80635.
Timmerman, P. et al. "A combinatorial approach for the design of complementarity determining region-derived peptidomimetics with in vitro anti-tumoral activity." J. Biol. Chem. 284, (2009): 34126-34134.
Tong, Kit I., et al. "Different electrostatic potentials define ETGE and DLG motifs as hinge and latch in oxidative stress response." Molecular and cellular biology 27.21 (2007): 7511-7521.
Tong, Kit I., et al. "Keapl recruits Neh2 through binding to ETGE and DLG motifs: characterization of the two-site molecular recognition model." Molecular and cellular biology 26.8 (2006): 2887-2900.
Traboulsi, H. et al., "Macrocyclic Cell Penetrating Peptides: A Study of Structure-Penetration Properties," Bioconjugate Chemistry, 2015, 26:405-411.
Trinh, Thi B., et al. "Discovery of a direct Ras inhibitor by screening a combinatorial library of cell-permeable bicyclic peptides." ACS combinatorial science 18.1 (2015): 75-85.
Tse, B. N et al., "Translation of DNA into a Library of 13 000 Synthetic Small-Molecule Macrocycles Suitable for in Vitro Selection," J. Am. Chem. Soc., 2008, 130(46):15611-15626.
Turner, R. A. et al., "Click chemistry as a macrocyclization tool in the solid- phase synthesis of small cyclic peptides," Org. Lett., Nov. 2007, 9(24): 5011-5014. Epub Oct. 23, 2007.
Tyagi, M. et al., "Internalization of HIV-1 Tat requires cell surface heparan sulfate proteoglycans," J. Biol. Chem., Feb. 2001, 276(5):3254-3261. Epub Oct. 6, 2000.
Upadhyaya, et al. "Direct Ras inhibitors identified from a structurally ridigified bicyclic peptide library." Tetrahedron, 2014, 70(42), 7714-7720.
Upadhyaya, Punit, et al. "Inhibition of Ras signaling by blocking Ras-effector interactions with cyclic peptides." Angewandte Chemie International Edition 54.26 (2015): 7602-7606. Angew. Chem. 127, (2015): 7712.
Varkouhi, Amir K., et al. "Endosomal escape pathways for delivery of biologicals." Journal of Controlled Release 151.3 (2011): 220-228.
Van Goor, F et al., "Correction of the F508del-CFTR protein processing defect in vitro by the investigational drug VX-809," Proc. Natl. Acad. Sci. U. S. A., Nov. 2011, 108(46):18843-18848.
Varland, Sylvia, et al., "N-terminal modifications of cellular proteins: The enzymes involved, their substrate specificities and biological effects." *Proteomics* 15.14 (2015): 2385-2401.
Verdine, Gregory L. and Hilinski, Gerard J. "Stapled peptides for intracellular drug targets." *Methods in enzymology.* vol. 503. Academic Press, 2012. 3-33.
Verma, Udit N., et al. "Nuclear role of IκB kinase-γ/NF-κB essential modulator (IKKγ/NEMO) in NF-κB-dependent gene expression." Journal of Biological Chemistry 279.5 (2004): 3509-3515.
Virta, P. & Lonnberg, H. J. "Solid-supported synthesis of cryptand-like macrobicyclic peptides." J. Org. Chem. 68, (2003): 8534.
Vriens, Kim, et al., "Antifungal plant defensins: mechanisms of action and production." Molecules 19.8 (2014): 12280-12303.
Wadia, Jehangir S. and Dowdy, Steven F. "Transmembrane delivery of protein and peptide drugs by TAT-mediated transduction in the treatment of cancer." Advanced drug delivery reviews 57.4 (2005): 579-596.
Wajant, H. et al. "Tumor Necrosis Factor Signaling." Cell Death Differ 10, (2003): 45-65.
Walensky, Loren D., and Bird, Gregory H. "Hydrocarbon-stapled peptides: principles, practice, and progress: miniperspective." *Journal of medicinal chemistry* 57.15 (2014): 6275-6288.
Wallbrecher, R. et al., "Exploration of the Design Principles of a Cell-Penetrating Bicylic Peptide Scaffold," Bioconjugate Chemistry, 2014, 25(5):955-964. Published Online: Apr. 3, 2014.
Wang, C-W. et al., "Increased potency of a novel D-beta-naphthylalanine-substituted antimicrobial peptide against fluconazole-resistant fungal pathogens," FEMS Yeast Research, 2009, 9(6):967-970.
Wang, J.; et al., "Automatic atom type and bond type perception in molecular mechanical calculations." J. Mol. Graphic. Model. 2006, 25, 247-260.
Wang, J.; et al., "Development and testing of a general AMBER force field." J. Comput. Chem. 2004, 25, 1157-1174.
Wedemeyer, W. J.; et al., "Proline cis-trans isomerization and protein folding." Biochemistry 2002, 41, 14637-14644.
Wender, P. A. et al., "The design, synthesis, and evaluation of molecules that enable or enhance cellular uptake: Peptoid molecular transporters," Proc. Natl. Acad. Sci. U. S. A., Nov. 2000, 97(24):13003-13008.
Wells, James A. and Mcclendon, Christopher L. "Reaching for high-hanging fruit in drug discovery at protein-protein interfaces." Nature 450.7172 (2007): 1001.
White, Tina R., et al. "On-resin N-methylation of cyclic peptides for discovery of orally bioavailable scaffolds." Nature chemical biology 7.11 (2011): 810.
Wohr, T.; et al., "Pseudo-prolines as a solubilizing, structure-disrupting protection technique in peptide synthesis." J. Am. Chem. Soc. 1996, 118, 9218-9227.
Wolde, Michael, et al. "Targeting CAL as a negative regulator of AF508-CFTR cell-surface expression an RNA interference and structure-based mutagenetic approach." Journal of Biological Chemistry 282.11 (2007): 8099-8109.

(56) References Cited

OTHER PUBLICATIONS

Wu, G. et al., "Structural basis of IAP recognition by Smac/DIABLO," Nature, Dec. 2000, 408(6815):1008-1012.
Wu, X., et al., "Inhibition of Ras-effector interactions by cyclic peptides." Med. Chem. Commun. 4, (2013): 378-382.
Xie, L. et al., "Cellular Effects of Small Molecule PTP1B Inhibitors on Insulin Signaling," Biochemistry, 2003, 42(44):12792-12804.
Xu, L.H. et al. "Directed evolution of high-affinity antibody mimics using mRNA display." Chem. Biol. 9, (2002):933-942.
Yamagishi, Y. et al. "Natural product-like macrocyclic N-methyl-peptide inhibitors against a ubiquitin ligase uncovered from a ribosome-expressed de novo library." Chem. Biol. 18, (2011):1562-1570.
Yamaoka, Shoji, et al. "Complementation cloning of NEMO, a component of the IκB kinase complex essential for NF-κB activation." Cell 93.7 (1998): 1231-1240.
Yin, J. et al. "Genetically encoded short peptide tag for versatile protein labeling by Sfp phosphopantetheinyl transferase." Proc. Natl. Acad. Sci. USA 102 (2005): 15815-15820.
Yoo, J. et al., (2017) Bioreducible branched poly(modified nona-arginine) cell-penetrating peptide as a novel gene delivery platform. J. Controlled Release 246, 142-154.
Yu, H., "Therapeutic potential of VIVIT, a selective peptide inhibitor of nuclear factor of activated T cells, in cardiovascular disorders." Cardiovasc Drug Rev. 2007 Summer;25(2):175-87.
Yu, H. et al., "Selective modulation of nuclear factor of activated T-cell function in restenosis by a potent bipartite peptide inhibitor." Circulation research 110.2 (2012): 200-210.
Zabolotny, J. M. et al., "PTP1B regulates leptin signal transduction in vivo," Dev. Cell, Apr. 2002, 2(4):489-495.
Zhang, Donna D., et al. "Distinct cysteine residues in Keap1 are required for Keap1-dependent ubiquitination of Nrf2 and for stabilization of Nrf2 by chemopreventive agents and oxidative stress." Molecular and cellular biology 23.22 (2003): 8137-8151.
Zhang, Meijuan, et al. "Emerging roles of Nrf2 and phase II antioxidant enzymes in neuroprotection." Progress in neurobiology 100 (2013): 30-47.
Zhang, Zhong-Yin. "Drugging the undruggable: therapeutic potential of targeting protein tyrosine phosphatases." Accounts of chemical research 50.1 (2017): 122-129.
Zhao, Bingchuan, et al. "A Thioether-Stabilized d-Proline-1-Proline-Induced β-Hairpin Peptide of Defensin Segment Increases Its Anti-Candida albicans Ability." ChemBioChem 17.15 (2016): 1416-1420.
Zhao, Kun, et al. "Enhanced activity of cyclic transporter sequences driven by phase behavior of peptide-lipid complexes." Soft Matter 8.24 (2012): 6430-6433.
Zhao, Hui, et al. "Crosslinked aspartic acids as helix-nucleating templates." Angewandte Chemie 128.39 (2016): 12267-12272.
Zhou, H. et al. "Structure-based design of high-affinity macrocyclic peptidomimetics to block the menin-mixed lineage leukemia 1 (MLLI) protein-protein interaction." J. Med. Chem. (2013) 56, 1113-1123.
Ziegler, A. et al., "Interaction of the protein transduction domain of HIV-1 TAT with heparan sulfate: binding mechanism and thermodynamic parameters," Biophys. J., Jan. 2004, 86(1):254-263.
Ziegler, A., "Thermodynamic studies and binding mechanisms of cell-penetrating peptides with lipids and glycosaminoglycans," Advanced Drug Delivery Reviews, Mar. 2008, 60(4-5):580-597. Epub Oct. 22, 2007.
Zugazagoitia et al., Current Challenges in Cancer Treatment, Clinical Therapies, vol. 38, (2016), pp. 1551-156.
International Preliminary Report on Patentability issued for Application No. PCT/US2017/062951 on Jun. 6, 2019.
International Search Report and Written Opinion issued for Application No. PCT/US2017/062951 on Apr. 30, 2018.
International Search Report and Written Opinion issued for Application No. PCT/US2017/060881 on Apr. 26, 2018.
International Preliminary Report on Patentability issued for Application No. PCT/US17/60881, dated May 23, 2019.
International Preliminary Report on Patentability issued for Application No. PCT/US2017/063020 dated Jun. 6, 2019.
International Search Report and Written Opinion issued for Application No. PCT/US2017/063020 dated May 4, 2018.
International Search Report and Written Opinion issued for Application No. PCT/US2019/031522, dated Sep. 27, 2019.
International Preliminary Report on Patentability issued for Application No. PCT/US2019/031522, dated Nov. 19, 2020.
International Search Report and Written Opinion issued for Application No. PCT/US2014/039332, dated Dec. 3, 2014,.
International Preliminary Report on Patentability issued for Application No. PCT/US2014/039332, dated Dec. 3, 2015.
International Search Report and Written Opinion issued for Application No. PCT/US2017/062945, dated Feb. 16, 2018.
International Preliminary Report on Patentability issued for Application No. PCT/US2017/062945, dated Jun. 6, 2019.
International Search Report and Written Opinion for International Application No. PCT/US2015/032043, mailed Jan. 14, 2016.
International Preliminary Report on Patentability for International Application No. PCT/US2015/032043, dated Nov. 22, 2016.
International Search Report and Written Opinion issued in International Application No. PCT/US2015/47267, Dated Dec. 7, 2015.
International Preliminary Report on Patentability issued in International Application No. PCT/US2015/47267 dated Mar. 9, 2017.
International Search Report and Written Opinion issued in International Application No. PCT/US2019/015695 on Jul. 25, 2019.
International Preliminary Report on Patentability issued for Application No. PCT/US2019/015695, dated Aug. 13, 2020.
International Preliminary Report on Patentability issued for International Application No. PCT/US2018/054345 dated Apr. 16, 2020.
International Search Report and Written Opinion issued for International Application No. PCT/US2018/054345 dated Mar. 4, 2019.
International Search Report and Written Opinion issued for International Application No. PCT/US2019/040335 on Nov. 6, 2019, 15 pages.
International Preliminary Report on Patentability issued for International Application No. PCT/US2019/040335 dated Jan. 14, 2021.
International Preliminary Report on Patentability issued for International Application No. PCT/US2020/048523 on Mar. 10, 2022.
English translation of Office Action for Chinese Application No. 201780069098.8 dated Nov. 28, 2022.
English translation of Office Action for Chinese Application No. 201780069098.8 dated Aug. 3, 2023.
Extended European Search Report issued Nov. 17, 2016, in European Application No. 14800563.
Communication pursuant to Article 94(3) EPC issued Jul. 13, 2017, in European Application No. 14800563.
Communication under Rule 71(3) EPC issued Dec. 14, 2017, in European Application No. 14800563.
Communication under Rule 71(3) EPC issued May 18, 2018, in European Application No. 14800563.
Decision to Grant a European Patent pursuant to Art 97(1) EPC issued Oct. 5, 2018, in European Application No. 14800563.
Extended European Search Report issued for Application No. 15796259.8, dated Jan. 22, 2018, 6 pages.
Extended European Search Report issued in EP 17870556.2, mailed Sep. 8, 2020.
Communication pursuant to Article 94(3) EPC for European Application No. 17870556.2 dated Sep. 1, 2022, 5 pages.
Extended European Search Report issued for Application No. 15835788.9, dated Jun. 1, 2018.
Communication Pursuant to Rule 164(1) EPC, issued for Application No. 17874485, dated Feb. 3, 2021.
Extended European Search Report for EP Application No. 19799961.8 dated Feb. 2, 2022.
Extended European Search Report for EP Application No. 17874485.0 dated November May 10, 2021.
Office Action for EP Application No. 17874485.0 dated Nov. 16, 2022, 5 pages.
Extended European Search Report issued for European Application No. 19743545.6 dated Dec. 13, 2021, 9 pages.
English translation of Office Action for Taiwanese Application No. 106140322 dated Jan. 6, 2022.

(56) References Cited

OTHER PUBLICATIONS

English translation of Office Action for Taiwanese Application No. 106140322 dated Aug. 4, 2022.
English translation of Office Action for Taiwanese Application No. 106138809 dated Nov. 5, 2021.
Office Action with English translation for Japanese Application No. 2019-524067 dated Oct. 5, 2021.
Office Action with English translation for Japanese Application No. 2019-524067 dated May 10, 2022.
English translation of Decision to Grant for Japanese Application No. 2019-524067 dated Oct. 11, 2022.
Office Action with English translation for Japanese Application No. 2022-179784 dated Nov. 7, 2023, 5 pages.
Restriction Requirement for U.S. Appl. No. 17/136,578 dated Dec. 16, 2022, 8 pages.
Office Action for U.S. Appl. No. 17/136,578 dated Mar. 15, 2023, 13 pages.
Notice of Allowance for U.S. Appl. No. 17/136,578 dated Aug. 25, 2023, 8 pages.
Restriction Requirement for U.S. Appl. No. 16/348,706 dated May 14, 2020, 6 pages.
Office Action issued in U.S. Appl. No. 16/348,706, dated Nov. 16, 2020, 11 pages.
Office Action for U.S. Appl. No. 16/348,706 dated Mar. 1, 2021, 12 pages.
Notice of Allowance for U.S. Appl. No. 16/348,706 dated Aug. 30, 2021, 14 pages.
Notice of Allowance for U.S. Appl. No. 16/348,706 dated Apr. 15, 2022, 5 pages.
Restriction Requirement issued in U.S. Appl. No. 14/893,203 mailed Jun. 20, 2016, 10 pages.
Office Action issued in U.S. Appl. No. 14/893,203 mailed Dec. 6, 2016, 8 pages.
Notice of Allowance issued in U.S. Appl. No. 14/893,203 mailed May 9, 2017, 10 pages.
Restriction Requirement issued in U.S. Appl. No. 15/672,617 mailed Oct. 3, 2018, 8 pages.
Office Action issued in U.S. Appl. No. 15/672,617 mailed Mar. 1, 2019, 8 pages.
Notice of Allowance issued in U.S. Appl. No. 15/672,617 mailed Jul. 22, 2019, 11 pages.
Office Action issued in U.S. Appl. No. 16/462,914 dated Apr. 17, 2020, 10 pages.
Notice of Allowance issued in U.S. Appl. No. 16/462,914 mailed Sep. 29, 2020, 10 pages.
Restriction Requirement issued in U.S. Appl. No. 16/462,920, mailed Apr. 13, 2020, 8 pages.
Office Action issued in U.S. Appl. No. 16/462,920, mailed Aug. 18, 2020, 27 pages.
Office Action issued in U.S. Appl. No. 16/462,920, mailed Feb. 16, 2021, 15 pages.
Office Action issued in U.S. Appl. No. 16/462,920, mailed Jul. 6, 2021, 8 pages.
Notice of Allowance for U.S. Appl. No. 16/462,920 dated Feb. 2, 2022, 8 pages.
Restriction Requirement issued for U.S. Appl. No. 16/462,922 dated Dec. 14, 2020, 8 pages.
Office Action issued for U.S. Appl. No. 16/462,922 dated Sep. 13, 2021, 21 pages.
Office Action for U.S. Appl. No. 16/462,922 dated Jan. 31, 2022, 9 pages.
Office Action for U.S. Appl. No. 16/462,922 dated May 10, 2022, 11 pages.
Office Action for U.S. Appl. No. 16/462,922 dated Dec. 22, 2022, 11 pages.
Advisory Action for U.S. Appl. No. 16/462,922 dated Mar. 30, 2023, 5 pages.
Office Action for U.S. Appl. No. 16/462,922 dated Jul. 7, 2023, 10 pages.
Restriction Requirement for U.S. Appl. No. 16/965,718 dated Oct. 7, 2021, 9 pages.
Office Action for U.S. Appl. No. 16/965,718 dated Jan. 27, 2022, 18 pages.
Notice of Allowance for U.S. Appl. No. 16/965,718 dated May 17, 2022, 6 pages.
Notice of Allowance for U.S. Appl. No. 16/965,718 dated Oct. 5, 2022, 6 pages.
Restriction Requirement for U.S. Appl. No. 17/053,684 dated Aug. 6, 2021, 9 pages.
Office Action for U.S. Appl. No. 17/053,684 dated Apr. 1, 2022, 12 pages.
Office Action for U.S. Appl. No. 17/053,684 dated Aug. 5, 2022, 14 pages.
Advisory Action for U.S. Appl. No. 17/053,684 dated Nov. 2, 2022, 4 pages.
Office Action for U.S. Appl. No. 17/053,684 dated Jan. 20, 2023, 10 pages.
Office Action for U.S. Appl. No. 17/053,684 dated May 11, 2023, 7 pages.
Office Action for U.S. Appl. No. 17/053,684 dated Sep. 8, 2023, 8 pages.
Restriction Requirement for U.S. Appl. No. 17/538,330 dated Oct. 14, 2022, 8 pages.
Office Action for U.S. Appl. No. 17/538,330 dated Mar. 16, 2023, 11 pages.
Notice of Allowance for U.S. Appl. No. 17/538,330 dated Sep. 7, 2023, 7 pages.
Restriction Requirement for U.S. Appl. No. 17/257,224 dated Sep. 27, 2023, 7 pages.
Restriction Requirement for U.S. Appl. No. 16/753,681 dated Nov. 18, 2020, 6 pages.
Office Action for U.S. Appl. No. 16/753,681 dated Mar. 10, 2021, 10 pages.
Notice of Allowance for U.S. Appl. No. 16/753,681 dated Feb. 16, 2022, 7 pages.
Office Action for U.S. Appl. No. 17/750,966 dated Oct. 24, 2022, 12 pages.
Notice of Allowance for U.S. Appl. No. 17/750,966 dated Mar. 2, 2023, 7 pages.
Advisory Action for U.S. Appl. No. 16/965,713, dated Aug. 11, 2022, 4 Pages.
Advisory Action for U.S. Appl. No. 17/052,935, dated Feb. 1, 2023, 3 Pages.
Amendment After Notice of Allowance for U.S. Appl. No. 15/360,719, dated Aug. 10, 2020, 05 Pages.
Amendment/Response filed on Apr. 21, 2021, to Non Final Office Action dated Jan. 25, 2021 for U.S. Appl. No. 16/852,615, 16 Pages.
Applicant Initiated Interview Summary for U.S. Appl. No. 15/312,878, dated Oct. 30, 2019, 04 Pages.
Applicant Initiated Interview Summary for U.S. Appl. No. 15/360,719, dated Oct. 30, 2019, 04 Pages.
Applicant's Summary of Examiner Interview for U.S. Appl. No. 15/360,719, dated Jun. 3, 2020, 01 Page.
Assem N., et al., "Acetone-Linked Peptides: A Convergent Approach for Peptide Macrocyclization and Labeling," Angewandte Chemie International Edition, 2015, vol. 54, pp. 8665-8668.
Barford D., et al., "Crystal Structure of Human Protein Tyrosine Phosphatase 1B," Science, Mar. 11, 1994, vol. 263, No. 5152, pp. 1397-1404.
Biswas G., et al., "Synthesis of Ibuprofen Conjugated Molecular Transporter Capable of Enhanced Brain Penetration," Hindawi Journal of Chemistry, Jan. 16, 2017, vol. 2017, Article ID. 4746158, pp. 1-10 (11 Pages).
Bockus A.T., et al., "Going Out on a Limb: Delineating The Effects of (Beta)-Branching, N- Methylation, and Side Chain Size on the Passive Permeability, Solubility, and Flexibility of Sanguinamide A Analogues," Journal of Medicinal Chemistry, Aug. 26, 2015, vol. 58, pp. 7409-7418.
Bottcher T., et al., "Synthesis and Activity of Biomimetic Biofilm Disruptors," Journal of the American Chemical Society, Feb. 13, 2013, vol. 135, No. 8, pp. 2927-2930.

(56) References Cited

OTHER PUBLICATIONS

Bowie J.U., et al., "Deciphering the Message in Protein Sequences: Tolerance to Amino acid Substitutions," Science, Mar. 16, 1990, vol. 247, pp. 1306-1310.
Burgess W.H., et al., "Possible Dissociation of the Heparin-Binding and Mitogenic Activities of Heparin-Binding (Acidic Fibroblast) Growth Factor-1 from its Receptor-Binding Activities by Site-Directed Mutagenesis of a Single Lysine Residue," Journal of Cell Biology, Nov. 1, 1990, vol. 111, pp. 2129-2138.
Buyanova M., et al., "Discovery of a Bicyclic Peptidyl Pan-Ras Inhibitor," Journal of Medicinal Chemistry, Sep. 9, 2021, vol. 64, No. 17, pp. 13038-13053 (36 Pages).
Calvo S.E., et al., "The Mitochondrial Proteome and Human Disease," Annual Review of Genomics and Human Genetics, 2010, vol. 11, pp. 25-44 (25 Pages).
Cerrato C.P., et al., "Novel Cell-Penetrating Peptide Targeting Mitochondria," The FASEB Journal, Nov. 2015, vol. 29, No. 11, pp. 4589-4599 (11 Pages).
Chen K., et al., "Engineering Cell-permeable Proteins Through Insertion of Cell- Penetrating Motifs Into Surface Loops," ACS Chemical Biology, Aug. 3, 2020, vol. 15, No. 9, pp. 2568-2576 (10 Pages), DOI: 10.1021/acschembio.0c00593, XP055837925.
Chinnery P.F., et al., "Peptide Nucleic Acid Delivery to Human Mitochondria," Gene Therapy, 1999, vol. 6, No. 12, pp. 1919-1928.
clinicaltrials.gov: "ALRN-6924 in Patients With Advanced Solid Tumors or Lymphomas," ClinicalTrials.gov Identifier: NCT02264613, Oct. 15, 2014, pp. 1-8.
Communication Pursuant to Article 94(3) EPC for European Application No. 19182012.5, dated Dec. 5, 2022, 04 Pages.
Communication Pursuant to Article 94(3) EPC for European Application No. 19182012.5, dated May 27, 2021, 07 Pages.
Communication Pursuant to Article 94(3) EPC for European Application No. 19182012.5, dated Sep. 29, 2021, 07 Pages.
Communication Pursuant to Article 94(3) EPC for European Application No. 19743545.6, dated Jun. 26, 2024, 06 Pages.
Communication Pursuant to Article 94(3) EPC for European Application No. 19799961.8, dated Jul. 5, 2024, 5 Pages.
Communication Pursuant to Article 94(3) EPC, issued for European Application No. 17870556.2, dated Jul. 16, 2025.
Communication Pursuant to Article 94(3) EPC issued for European Application No. 17874485.0, dated Jul. 16, 2025, 6 pages.
Communication pursuant to Rule 164(1) EPC for Application No. 19831072.4, dated Jul. 29, 2022, 13 Pages.
Communication Pursuant to Rules 161 and 162 EPC for European Application No. 20903078.2, dated Sep. 5, 2022, 21 Pages.
Communication Pursuant to Rules 70(2) and 70a(2) EPC for European Application No. 19831072.4, dated Nov. 22, 2022, 18 Pages.
Corrected Notice of Allowability for U.S. Appl. No. 16/852,615, dated Dec. 7, 2021, 02 Pages.
CROMM p. H., et al., "Orthogonal Ring-closing Alkyne and Olefin Metathesis for the Synthesis of Small GTPase-targeting Bicyclic Peptides," Nature Communications, Apr. 14, 2016, vol. 7 (11300), pp. 1-7, DOI: 10.1038/ncomms11300.
CROMM P.M., et al., "Hydrocarbon Stapled Peptides as Modulators of Biological Function," ACS Chemical Biology, 2015, vol. 10, No. 6, pp. 1362-1375.
Dash S., et al., "Deficiency of the RNA Binding Protein Caprin2 Causes Lens Defects and Features of Peters Anomaly," Developmental Dynamics, Wiley-Liss INC New York , NY, US, Oct. 2015, vol. 244, Np. 10, pp. 1313-1327 (27 Pages), XP071971264.
Dastpeyman M., et al., "Endosomal Escape Cell-penetrating Peptides Significantly Enhance Pharmacological Effectiveness and CNS Activity of Systemically Administered Antisense Oligonucleotides," International Journal of Pharmaceutics, 2021, vol. 599, No. 120398, pp. 1-10.
Decision of Refusal for Japanese Application No. 2017-513613, dated Dec. 26, 2019, 13 Pages.
Decision of Refusal for Japanese Application No. 2020-072542, dated Apr. 20, 2022, 05 Pages.
Decision of Refusal for Japanese Application No. 2020-543254, dated Mar. 14, 2023, 06 Pages.
Decision to Grant a European Patent Pursuant to Article 97(1) EPC for European Application No. 15796259.8, dated May 31, 2019, 02 Pages.
Decision to Grant a Patent (PatentsApplication2022-179784) for Japanese Application No. 2022-17978, Apr. 16, 2024, 7 Pages.
Drysdale M.J., et al., "Targeting Hsp90 for the Treatment of Cancer," Current Opinion in Drug Discovery and Development, Jun. 30, 2006, vol. 9, No. 4, pp. 483-495 (1 Page).
Eisenbergweiss., Proceedings of the National Academy of Sciences of the United States of America, 1984, vol. 81, No. 1, pp. 140-144.
Eke, et al., Public Library of Science ONE, 2009, vol. 4, p. E6434.
Engel M., et al., "Regiospecific Synthesis of 3,5-Bis(Bromomethyl)Benzoic Acid, A Cysteine Crosslinking Agent," Tetrahedron, 1993, vol. 49, No. 39, pp. 8761-8770.
Ernster L., et al., "Mitochondria: A Historical Review," The Journal of Cell Biology, Dec. 1981, vol. 91, No. 3, Part. 2, pp. 227s-255s.
Examiner Initiated Interview Summary for U.S. Appl. No. 15/360,719, dated May 13, 2020, 03 Pages.
Examiner Interview Summary for U.S. Appl. No. 16/852,615, dated Aug. 4, 2021, 02 Pages.
Extended European Search Report for European Application No. 11843945.4, dated Apr. 2, 2015, 5 Pages.
Extended European Search Report for European Application No. 18870802.8, dated Jun. 22, 2021, 08 Pages.
Extended European Search Report for European Application No. 19182012.5, dated Jan. 27, 2020, 07 Pages.
Extended European Search Report for European Application No. 19743190.1, dated Apr. 22, 2022, 16 Pages.
Extended European Search Report for European Application No. 19796864.7, dated May 18, 2022, 09 Pages.
Extended European Search Report for European Application No. 19831072.4, dated Nov. 3, 2022, 13 Pages.
Fadzen C.M., et al., "Chimeras of Cell-penetrating Peptides Demonstrate Synergistic Improvement in Antisense Efficacy," Biochemistry, Aug. 2019, vol. 58, No. 38, pp. 3980-3989, (30 Pages).
Fang S., et al., "Mdm2 is a RING Finger-Dependent Ubiquitin Protein Ligase for Itself and p53," Journal of Biological Chemistry, Mar. 24, 2000, vol. 275, No. 12, pp. 8945-8951.
Fernandez-Carneado J., et al., "Highly Efficient, Nonpeptidic Oligoguanidinium Vectors that Selectively Internalize into Mitochondria," Journal of the American Chemical Society, 2005, vol. 127, No. 3, pp. 869-874.
Final Office Action for U.S. Appl. No. 15/312,878, dated Sep. 9, 2019, 13 Pages.
Final Office Action for U.S. Appl. No. 15/360,719, dated Feb. 11, 2020, 06 Pages.
Final Office Action for U.S. Appl. No. 15/506,877, dated Nov. 2, 2018, 13 Pages.
Final Office Action for U.S. Appl. No. 15/506,877, dated Apr. 19, 2019, 16 Pages.
Final Office Action for U.S. Appl. No. 16/462,922, dated Mar. 26, 2024, 23 Pages.
Final Office Action for U.S. Appl. No. 16/759,600, dated Nov. 12, 2021, 20 Pages.
Final Office Action for U.S. Appl. No. 16/965,713, dated Mar. 23, 2023, 08 Pages.
Final Office Action for U.S. Appl. No. 16/965,713, dated May 26, 2022, 10 Pages.
Final Office Action for U.S. Appl. No. 17/052,935, dated Dec. 6, 2022, 08 Pages.
Final Office Action for U.S. Appl. No. 17/832,107, mailed Apr. 25, 2025, 9 pages.
Final Office Action for U.S. Appl. No. 18/644,750, mailed Jul. 2, 2025, 7 pages.
Final Office Action for U.S. Appl. No. 16/852,615, dated Jun. 29, 2021, 17 Pages.
First Examination Report for Indian Application No. 201617042520, dated Aug. 29, 2019, 5 Pages.
First Office Action for Chinese Application No. 201580034608.9, dated Jan. 6, 2020, 17 Pages.

(56) References Cited

OTHER PUBLICATIONS

First Office Action for Chinese Application No. 201880070271.0, dated Mar. 6, 2023, 18 Pages.
Furumai R., et al., "Potent Histone Deacetylase Inhibitors Built From Trichostatin A and Cyclic Tetrapeptide Antibiotics Including Trapoxin," Proceedings of the National Academy of Sciences of the United States of America, Jan. 2, 2001, vol. 98, No. 1, pp. 87-92.
Greene T.W., et al., "Protective Groups in Organic Synthesis," John Wiley & Sons Inc., Third Edition, 1999, 20 Pages.
Gu, Shanshan, et al. "PROTACs: an emerging targeting technique for protein degradation in drug discovery." Bio Essays 40.4 (2018): 1700247, 11 pages.
Hicks A.N., et al., "A Novel EEV-Conjugated PMO, ENTR-701, Reduces Nuclear Foci and Corrects Aberrant Splicing in Myotonic Dystrophy Type 1 Preclinical Models," New Directions in Biology and Disease of Skeletal Muscle Conference, Jun. 20, 2022, 01 Page.
Horton K.L., et al., "Mitochondria-Penetrating Peptides," Chemistry and Biology, Apr. 2008, vol. 15, No. 4, pp. 375-382.
Hoye A.T., et al., "Targeting Mitochondria," Accounts of Chemical Research, Jan. 2008, vol. 41, No. 1, pp. 87-97.
Hu B., et al., "Efficient p53 Activation and Apoptosis by Simultaneous Disruption of Binding to MDM2 and MDMX," Cancer Research, Sep. 15, 2007, vol. 67, No. 18, pp. 8810-8817.
Huang X., et al., "Slipping Synthesis of Cucurbit[7]Uril-based [2]Rotaxane in Organic Environment," Tetrahedron Letters, Nov. 21, 2012, vol. 53, No. 47, pp. 6414-6417 (5 Pages).
Intention to Grant for European Application No. 15796259.8, dated Dec. 12, 2018, 145 Pages.
Intention to Grant for European Application No. 15796259.8, dated Jul. 31, 2018, 143 Pages.
International Preliminary Report on Patentability for International Application No. PCT/US2011/061613, dated Jun. 6, 2013, 7 Pages.
International Preliminary Report on Patentability for International Application No. PCT/US2018/057894, dated May 7, 2020, 06 Pages.
International Preliminary Report on Patentability for International Application No. PCT/US2019/015697, dated Aug. 13, 2020, 07 Pages.
International Preliminary Report on Patentability for International Application No. PCT/US2019/030915, dated Nov. 19, 2020, 06 Pages.
International Preliminary Report on Patentability for International Application No. PCT/US2020/066459, dated Jun. 30, 2022, 07 Pages.
International Preliminary Report on Patentability for International Application No. PCT/US2020/067427, dated Jul. 14, 2022, 9 Pages.
International Preliminary Report on Patentability for International Application No. PCT/US2022/017211, dated Aug. 22, 2023, 07 Pages.
International Preliminary Report on Patentability for International Application No. PCT/US2022/034507, dated Jan. 4, 2024, 9 Pages.
International Preliminary Report on Patentability for International Application No. PCT/US2022/071489, dated May 26, 2023, 09 Pages.
International Search Report and Written Opinion for International Application No. PCT/US2011/061613, dated Apr. 2, 2012, 8 Pages.
International Search Report and Written Opinion for International Application No. PCT/US2018/057894, dated Jan. 15, 2019, 10 Pages.
International Search Report and Written Opinion for International Application No. PCT/US2019/015697, dated Jul. 19, 2019, 11 Pages.
International Search Report and Written Opinion for International Application No. PCT/US2019/030915, dated Jul. 15, 2019, 8 Pages.
International Search Report and Written Opinion for International Application No. PCT/US2020/067427, dated May 6, 2021, 14 Pages.
International Search Report and Written Opinion for International Application No. PCT/US2022/017211, dated Jul. 7, 2022, 12 Pages.
International Search Report and Written Opinion for International Application No. PCT/US2022/034507, dated Jan. 25, 2023, 15 Pages.
International Search Report for International Application No. PCT/US2020/066459, dated Apr. 6, 2021, 05 Pages.
International Search Report for International Application No. PCT/US2022/071489, dated Aug. 5, 2022, 05 Pages.
Invitation to Pay Additional Fees and, where Applicable, Protest Fee for International Application No. PCT/US2022/017211, dated May 10, 2022, 2 Pages.
Invitation to Pay Additional Fees and Where Applicable Protest Fee for PCT Application No. PCT/US2020/067427, dated Mar. 11, 2021, 3 Pages.
Invitation to Pay Additional Fees for International Application No. PCT/US2015/032043, dated Sep. 8, 2015, 2 Pages.
Invitation to Pay Additional Fees for International Application No. PCT/US2020/066459, dated Sep. 8, 2015, 02 Pages.
Isidro-Llobet A., et al., "Amino Acid-Protecting Groups," Chemical Reviews, 2009, vol. 109, No. 6, pp. 2455-2504 (51 Pages).
Jean S.R., et al., "Peptide-Mediated Delivery of Chemical Probes and Therapeutics to Mitochondria," Accounts of Chemical Research, 2016, vol. 49, No. 9, pp. 1893-1902 (10 Pages).
Jin, Jinmei, et al. "The peptide PROTAC modality: a novel strategy for targeted protein ubiquitination." Theranostics 10.22 (2020): 10141.
Jirka, Silvana MG, et al. "Cyclic peptides to improve delivery and exon skipping of antisense oligonucleotides in a mouse model for duchenne muscular dystrophy." Molecular Therapy 26.1 (2018): 132-147.
Jo H., et al., "Development of (Alpha)-Helical Calpain Probes by Mimicking a Natural Protein-Protein Interaction," Journal of the American Chemical Society, Sep. 22, 2012, vol. 134, No. 42, pp. 17704-17713.
Kalafatovic, Daniela, and Ernest Giralt. "Cell-penetrating peptides: Design strategies beyond primary structure and amphipathicity." Molecules 22.11 (2017): 1929.
Kalra, et al., Breast Cancer Research, 2009, vol. 11, p. R25.
Kang B.H., et al., "Combinatorial Drug Design Targeting Multiple Cancer Signaling Networks Controlled by Mitochondrial Hsp90," The Journal of Clinical Investigation, Mar. 2009, vol. 119, No. 3, pp. 454-464.
Kessler, Horst. "Conformation and biological activity of cyclic peptides." Angewandte Chemie International Edition in English 21.7 (1982): 512-523.
Kim W-J., et al., "Protein Tyrosine Phosphatase Conjugated With a Novel Transdermal Delivery Peptide, Astrotactin 1-derived Peptide Recombinant Protein Tyrosine Phosphatase (AP-rPTP), Alleviates Both Atopic Dermatitis-like and Psoriasis-like Dermatitis," Journal of Allergy and Clinical Immunology, Jan. 2018, vol. 141, No. 1, pp. 137-151.
Kim Y-W., et al., "Synthesis of All-hydrocarbon Stapled (Alpha)-helical Peptides by Ring-closing Olefin Metathesis," Nature Protocols, 2011, vol. 6, No. 6, pp. 761-772 (11 Pages).
Kyte J., et al., Journal of Molecular Biology, 1982, vol. 157, No. 1, pp. 105-132.
Lazar E., et al., "Transforming Growth Factor (Alpha): Mutation of Aspartic Acid 47 and Leucine 48 Results in Different Biological Activities," Molecular and Cellular Biology, Mar. 1988, vol. 8, No. 3, pp. 1247-1252.
Lee D.L., et al., "Effects of Single d-Amino Acid Substitutions on Disruption of β-sheet Structure and Hydrophobicity in Cyclic 14-Residue Antimicrobial Peptide Analogs Related to Gramicidin S," The Journal of Peptide Research, Feb. 2004, vol. 63, No. 2, pp. 69-84 (27 Pages).
Li, Qian, et al. "Arginine-rich membrane-permeable peptides are seriously toxic." Pharmacology research & perspectives 5.5 (2017): e00334, 5 pgs.
Madden M.M., et al., "Synthesis of Cell-permeable Stapled Peptide Dual Inhibitors of the p53-Mdm2/Mdmx Interactions via Photoinduced Cycloaddition," Bioorganic & Medicinal Chemistry Letters, 2011, vol. 21, No. 5, pp. 1472-1475.
Maiti K.K., et al., "Guanidine-Containing Molecular Transporters: Sorbitol-Based Transporters Show High Intracellular Selectivity

(56) References Cited

OTHER PUBLICATIONS

Toward Mitochondria," Angewandte Chemie International Edition, 2007, vol. 46, No. 31, pp. 5880-5884 (5 Pages).
Malty R.H., et al., "Mitochondrial Targets for Pharmacological Intervention in Human Disease," Journal of Proteome Research, 2015, vol. 14, No. 1, pp. 5-21.
Markovac A., et al., "Antimalarials. 12. Preparation of Carbon Isosteres of Selected 4- Pyridinemethanols as Suppressive Antimalarials," Journal of Medicinal Chemistry, 1980, vol. 23, No. 11, pp. 1198-1201.
Martinez-Rodriguez S., et al., "Natural Occurrence and Industrial Applications of D-Amino Acids: An Overview," Chemistry & Biodiversity, 2010, vol. 7, No. 6, pp. 1531-1548.
Matsson P., et al., "Cell Permeability Beyond the Rule of 5," Advanced Drug Delivery Reviews, 2016, vol. 101, pp. 1-52.
May M.J., et al., Selective Inhibition of NF-(Kappa)B Activation by a Peptide That Blocks the Interaction of NEMO With the I(Kappa)B Kinase Complex, Science, Sep. 1, 2000, vol. 289, No. 5484, pp. 1550-1554 (6 Pages).
Murphy M.P., "Targeting Lipophilic Cations to Mitochondria," Biochimica et Biophysica Acta, Bioenergetics, 2008, vol. 1777, pp. 1028-1031.
Nair J.B., et al., "A Dual-Targeting Octaguanidine-Doxorubicin Conjugate Transporter for Inducing Caspase-Mediated Apoptosis on Folate-Expressing Cancer Cells," ChemMedChem, 702, Supporting Information, 2016, vol. 11, No. 7, pp. 1-11 (12 Pages).
Non-Final Office Action for U.S. Appl. No. 15/312,878, dated Apr. 8, 2019, 14 Pages.
Non-Final Office Action for U.S. Appl. No. 15/360,719, dated Aug. 23, 2019, 15 Pages.
Non-Final Office Action for U.S. Appl. No. 15/506,877, dated Apr. 6, 2018, 12 Pages.
Non-Final Office Action for U.S. Appl. No. 16/759,600, dated Mar. 29, 2021, 18 Pages.
Non-Final Office Action for U.S. Appl. No. 16/762,914, dated Apr. 17, 2020, 10 Pages.
Non-Final Office Action for U.S. Appl. No. 16/852,615, dated Jan. 25, 2021, 22 Pages.
Non-Final Office Action for U.S. Appl. No. 16/965,713, dated Nov. 22, 2021, 11 Pages.
Non-Final Office Action for U.S. Appl. No. 16/965,713, dated Sep. 29, 2022, 11 Pages.
Non-Final Office Action for U.S. Appl. No. 17/052,935, dated Apr. 14, 2022, 11 Pages.
Non-Final Office Action for U.S. Appl. No. 17/052,935, dated Mar. 16, 2023, 14 Pages.
Non-Final Office Action for U.S. Appl. No. 17/257,224, dated Jun. 20, 2024, 24 Pages.
Non-Final Office Action for U.S. Appl. No. 17/257,224, dated Dec. 22, 2023, 06 Pages.
Non-Final Office Action for U.S. Appl. No. 17/817,836, dated Jan. 18, 2024, 10 Pages.
Non-Final Office Action for U.S. Appl. No. 17/832,107, dated Oct. 15, 2024, 78 Pages.
Non-Final Office Action for U.S. Appl. No. 18/104,643, dated Sep. 3, 2024, 40 Pages.
Non-Final Office Action for U.S. Appl. No. 18/333,516, dated Mar. 26, 2024, 9 Pages.
Non-Final Office Action for U.S. Appl. No. 18/644,750, dated Apr. 10, 2025, 10 Pages.
Notice of Allowance for Taiwan Application No. 106140322, dated May 27, 2024, 1 Page.
Notice of Allowance for U.S. Appl. No. 15/312,878, dated Nov. 25, 2019, 08 Pages.
Notice of Allowance for U.S. Appl. No. 15/360,719, dated May 19, 2020, 09 Pages.
Notice of Allowance for U.S. Appl. No. 15/506,877, dated Jun. 25, 2019, 11 Pages.
Notice of Allowance for U.S. Appl. No. 16/759,600, dated May 6, 2022, 10 Pages.
Notice of Allowance for U.S. Appl. No. 16/759,600, dated Oct. 28, 2022, 03 Pages.
Notice of Allowance for U.S. Appl. No. 16/852,615, dated Sep. 22, 2021, 10 Pages.
Notice of Allowance for U.S. Appl. No. 16/965,713, dated Jun. 14, 2023, 08 Pages.
Notice of Allowance for U.S. Appl. No. 17/052,935, dated Jul. 6, 2023, 09 Pages.
Notice of Allowance for U.S. Appl. No. 17/053,684, dated Mar. 18, 2024, 07 Pages.
Notice of Allowance for U.S. Appl. No. 17/257,224, dated Oct. 9, 2024, 5 Pages.
Notice of Allowance for U.S. Appl. No. 17/832,107, mailed Jul. 2, 2025, 8 pages.
Notice of Allowance for U.S. Appl. No. 18/104,643, dated Feb. 6, 2025, 13 Pages.
Notice of Allowance for U.S. Appl. No. 18/333,516, dated Sep. 11, 2024, 5 Pages.
Notice of Allowance for U.S. Appl. No. 18/333,516, dated Jan. 21, 2025, 6 Pages.
Notice of Reason for Refusal for Japanese Application No. 2020-543254, dated Sep. 13, 2022, 3 Pages.
Notice of Reasons for Refusal for Japanese Application No. 2017-513613, dated Apr. 18, 2019, 11 Pages.
Notice of Reasons for Refusal for Japanese Application No. 2020-072542, dated Jun. 30, 2021, 10 Pages.
Notice of Termination of Reconsideration by Examiners before Appeal Proceedings for Japanese Application No. 2020-072542, dated Nov. 22, 2022, 02 Pages.
Notification on Grant of Patent Right for Invention for Chinese Application No. 201780069098.8, dated Oct. 25, 2023, 4 Pages.
Office Action for Canadian Application No. 2,949,705, dated Apr. 22, 2021, 03 Pages.
Office Action for Canadian Application No. 2,949,705, dated Feb. 25, 2022, 04 Pages.
Office Action for Canadian Application No. 3,043,464, dated Mar. 6, 2024, 05 Pages.
Office Action for Canadian Application No. 2,949,705, dated Feb. 8, 2023, 04 Pages.
Office Action for Japanese Application No. 2019-524067, dated Nov. 7, 2023, 7 Pages.
Office Action for Japanese Application No. 2020072542, dated Aug. 29, 2022, 06 Pages.
Office Action for Taiwanese Application No. 106140322, dated Feb. 5, 2024, 2 Pages.
Office Action issued in U.S. Appl. No. 17/639,014, dated Aug. 7, 2025.
Partial Supplementary European Search Report for European Application No. 19743190.1, dated Jan. 19, 2022, 17 Pages.
Pathak R.K., et al., "Targeted Nanoparticles in Mitochondrial Medicine," Wiley Interdisciplinary Reviews: Nanomedicine and Nanobiotechnology, May 2015, vol. 7, No. 3, pp. 315-329 (29 Pages).
Phan J., et al., "Structure-based Design of High Affinity Peptides Inhibiting the Interaction of p53 with MDM2 and MDMX," The Journal of Biological Chemistry, Jan. 15, 2010, vol. 285, No. 3, pp. 2174-2183.
Preliminary Amendment for International U.S. Appl. No. 17/053,684, dated Nov. 6, 2020, 8 Pages.
Preliminary Amendment for U.S. Appl. No. 15/312,878, dated Nov. 21, 2016, 09 Pages.
Preliminary Amendment for U.S. Appl. No. 15/360,719, dated Feb. 6, 2017, 04 Pages.
Preliminary Amendment for U.S. Appl. No. 17/530,664, dated Feb. 24, 2022, 07 Pages.
Preliminary Amendment for U.S. Appl. No. 17/757,421, dated Jun. 15, 2022, 11 Pages.
Preliminary Amendment for U.S. Appl. No. 16/852,615, dated Aug. 21, 2020, 04 Pages.
Reineke E.L., et al., "Degradation of the Tumor Suppressor PML by Pin1 Contributes to the Cancer Phenotype of Breast Cancer MDA-MB-231 Cells," Molecular and Cellular Biology, Feb. 2008, vol. 28, No. 3, pp. 997-1006.

(56) References Cited

OTHER PUBLICATIONS

Reissmann, Siegmund. "Cell penetration: scope and limitations by the application of cellpenetrating peptides." Journal of Peptide Science 20.10 (2014): 760-784.
Replacement Preliminary Amendment for U.S. Appl. No. 17/757,421, dated Nov. 18, 2022, 13 Pages.
Response filed on Feb. 4, 2022, to Restriction Requirement dated Aug. 6, 2021 for U.S. Appl. No. 17/053,684, 08 Pages.
Response filed on Jan. 4, 2020, to First Examination Report dated Aug. 29, 2019, for Indian Application No. 201617042520, 12 Pages.
Response filed on Jan. 5, 2024, to Non Final Office Action dated Sep. 8, 2023 ,for U.S. Appl. No. 17/053,684, 4 Pages.
Response filed on Aug. 8, 2019, to Notice of Reasons for Refusal dated Apr. 18, 2019 for Japanese Application 2017-513613, 29 Pages.
Response filed on Jul. 8, 2019, to Non Final Office Action dated Apr. 8, 2019 for U.S. Appl. No. 15/312,878, 20 Pages.
Response filed on Mar. 8, 2023, to Communication Pursuant to Article 94(3) EPC, dated Nov. 16, 2022 for European Application No. 17874485.0, 9 Pages.
Response filed on Mar. 9, 2023, to Restriction Requirement dated Jan. 12, 2023 for U.S. Appl. No. 17/530,664, 06 Pages.
Response filed on Oct. 9, 2023, to Non Final Office Action dated Jul. 7, 2023 for U.S. Appl. No. 16/462,922, 13 Pages.
Response filed on Apr. 14, 2020, to Decision of Refusal dated Dec. 26, 2019 for Japanese Application No. 2017-513613, 35 Pages.
Response filed on May 14, 2020, to Office Action dated Jan. 6, 2020 for Chinese Application No. 201580034608.9, 12 Pages.
Response filed on Nov. 14, 2019, to Final Office Action dated Sep. 9, 2019 for U.S. Appl. No. 15/312,878, 22 Pages.
Response filed on Dec. 15, 2021, to Notice of Reasons For Rejection dated Jun. 30, 2021 for Japanese Application No. 2020-072542, 13 Pages.
Response filed on Aug. 19, 2021, to Office Action dated Apr. 22, 2021 for Canadian Application No. 2,949,705, 59 Pages.
Response filed on May 21, 2021, to Communication Pursuant to Rules 161(1) and 162 EPC, for European Application No. 19799961.8, 8 Pages.
Response filed on Jun. 23, 2022, to Non Final Office Action dated Feb. 25, 2022 for Canadian Application No. 2,949,705, 64 Pages.
Response filed on Aug. 24, 2020, to Extended European Search Report dated Jan. 27, 2020 for European Application No. 19182012.5, 03 Pages.
Response filed on Nov. 25, 2019, to Non Final Office Action dated Aug. 23, 2019 for U.S. Appl. No. 15/360,719, 18 Pages.
Response filed on Nov. 25, 2021, to Extended European Search Report, dated May 10, 2021 for European Application No. 17874485.0, 13 Pages.
Response filed on Oct. 25, 2022, to Final Office Action dated Aug. 5, 2022 for U.S. Appl. No. 17/053,684, 9 Pages.
Response filed on Aug. 27, 2021, to Final Office Action dated Jun. 29, 2021 for U.S. Appl. No. 16/852,615, 14 Pages.
Response filed on Apr. 28, 2020, to Final Office Action dated Feb. 11, 2020 for U.S. Appl. No. 15/360,719, 11 Pages.
Response filed on Oct. 29, 2018 to Intended to Grant Mailed on Jul. 31, 2018 for European Application No. 15796259.8, 24 Pages.
Response filed on Nov. 30, 2023 to Restriction Requirement dated Sep. 27, 2023, for U.S. Appl. No. 17/257,224, 11 Pages.
Response filed on Aug. 31, 2022, to Extended European Search Report, dated Feb. 2, 2022 for European Application No. 19799961.8, 14 Pages.
Response for European Application No. 19831072.4, dated Jun. 2, 2023 to Communication dated 03November 2022, 16 Pages.
Response to Communication Pursuant to Rules 161(1) and 162 EPC for European Application Serial No. 17874485.0, dated Jan. 13, 2020, 21 Pages.
Response to Notice to File Corrected Application Papers for U.S. Appl. No. 15/360,719, dated Sep. 28, 2020, 04 Pages.
Response to Restriction Requirement for U.S. Appl. No. 15/312,878, dated Jan. 23, 2019, 16 Pages.
Response to Restriction Requirement for U.S. Appl. No. 15/360,719, dated Jan. 23, 2019, 12 Pages.
Response to Rule 312 Communication for U.S. Appl. No. 15/360,719, dated Aug. 26, 2020, 02 Pages.
Response With English Translation of Claims filed on Nov. 3, 2022 , to Office Action, dated Aug. 2, 2022 for Taiwanese Application No. 106140322, 16 Pages.
Response With English Translation of Claims filed on Jul. 5, 2022 , to Office Action, dated Jan. 6, 2022 for Taiwanese Application No. 106140322, 14 Pages.
Restriction Requirement for U.S. Appl. No. 15/312,878, dated Nov. 23, 2018, 09 Pages.
Restriction Requirement for U.S. Appl. No. 15/360,719, dated Dec. 5, 2018, 07 Pages.
Restriction Requirement for U.S. Appl. No. 15/506,877, dated Nov. 15, 2017, 10 Pages.
Restriction Requirement for U.S. Appl. No. 16/965,713, dated Jul. 13, 2021, 06 Pages.
Restriction Requirement for U.S. Appl. No. 17/052,935, dated Feb. 18, 2022, 08 Pages.
Restriction Requirement for U.S. Appl. No. 17/530,664, dated Jan. 12, 2023, 09 Pages.
Restriction Requirement for U.S. Appl. No. 17/817,836, dated Sep. 7, 2023, 10 Pages.
Restriction Requirement for U.S. Appl. No. 18/644,750, dated Dec. 23, 2024, 09 Pages.
Restriction Requirement U.S. Appl. No. 17/832,107, dated Jun. 21, 2024, 5 Pages.
Rhodes, Curran A., et al. "Cell-permeable bicyclic peptidyl inhibitors against NEMO-IkB kinase interaction directly from a combinatorial library." Journal of the American Chemical Society 140.38 (2018): 12102-12110.
Rizo J., et al., "Constrained Peptides: Models of Bioactive Peptides and Protein Substructures," Annual Review of Biochemistry, 1992, vol. 61, pp. 387-418.
Rresponse to Notice to File Corrected Application Papers for U.S. Appl. No. 15/312,878, dated Feb. 12, 2020, 04 Pages.
Sahni A., et al., "Cell-Penetrating Peptides Escape the Endosome by Inducing Vesicle budding and Collapse," ACS Chemical Biology, Sep. 18, 2020, vol. 15, No. 9, pp. 2485-2492 (17 Pages).
Sajid, Muhammad Imran, et al. "Applications of amphipathic and cationic cyclic cellpenetrating peptides: Significant therapeutic delivery tool." Peptides 141 (2021): 170542.
Sakamoto K., et al., "Generation of KS-58 as the First K-Ras(G12D)-Inhibitory Peptide Presenting Anti-cancer Activity in Vivo," Scientific Reports, Dec. 10, 2020, vol. 10, No. 1, Publication. 21671, 16 Pages, DOI: 10.1038/$41598-020-78712-5, XP055935156.
Search Report for Chinese Application No. 201880070271.0 dated Mar. 6, 2023, 3 pages.
Second Office Action for Chinese Application No. 201580034608.9, dated Sep. 9, 2020, 10 Pages.
Second Office Action for Chinese Application No. 201780069098.8, dated Aug. 3, 2023, 7 Pages.
Seia, Michael, and Einat Zisman. "Different roles of D-amino acids in immune phenomena." The FASEB journal 11.6(1997): 449-456.
Seisel Q., et al., "Optimization of the Process of Inverted Peptides (PIPEPLUS) to Screen PDZ Domain Ligands," Bioorganic & Medicinal Chemistry Letters, 2017, vol. 27, No. 14, pp. 3111-3116.
Shair M.D., "A Closer View of an Oncoprotein-tumor Suppressor Interaction," Chemistry & Biology, Nov. 1997, vol. 4, No. 11, pp. 791-794.
Shi Z-D., et al., "Macrocyclization in the Design of Non-Phosphorus-Containing Grb2 SH2 Domain-Binding Ligands," Journal of Medicinal Chemistry, 2004, vol. 47, No. 8, pp. 2166-2169.
Stebbins C.E., et al., "Crystal Structure of an Hsp90-Geldanamycin Complex: Targeting of a Protein Chaperone by an Antitumor Agent," Cell, Apr. 18, 1997, vol. 89, No. 2, pp. 239-250.
Sun Y., et al., "Establishment of MicroRNA Delivery System by PP7 Bacteriophage-Like Particles Carrying Cell-Penetrating Peptide," Journal of Bioscience and Bioengineering, Aug. 31, 2017, vol. 124, No. 2, pp. 242-249, DOI: 10.1016/j.jbiosc.2017.03.012, XP085114983.
Supplemental Response filed on Nov. 17, 2022, to Final Office Action dated Aug. 5, 2022 for U.S. Appl. No. 17/053,684, 3 Pages.

(56) References Cited

OTHER PUBLICATIONS

Tan X., et al., "Closing the Loop: Constraining TAT Peptide by (Gamma)PNA Hairpin for Enhanced Cellular Delivery of Biomolecules," Bioconjugate Chemistry, 2018, vol. 29, No. 9, pp. 2892-2898.
Tan Y.S., et al., "Stapled Peptide Design: Principles and Roles of Computation," Drug Discovery Today, Jun. 2016, vol. 21, No. 10, pp. 1642-1653.
Tian Y., et al., "Achieving Enhanced Cell Penetration of Short Conformationally Constrained Peptides through Amphiphilicity Tuning," Chemical Science, 2017, vol. 8, No. 11, pp. 7576-7581 (6 Pages).
Toogood P.L., "Mitochondrial Drugs," Current Opinion in Chemical Biology, 2008, vol. 12, No. 4, pp. 457-463.
Toro A., et al., "TAT-mediated Intracellular Delivery of Purine Nucleoside Phosphorylase Corrects Its Deficiency in Mice," The Journal of Clinical Investigation, Oct. 2006, vol. 116, No. 10, pp. 2717-2726.
Vassilev L.T., et al., "In Vivo Activation of the p53 Pathway by Small-Molecule Antagonists of MDM2," Science, Feb. 6, 2004, vol. 303, No. 5659, pp. 844-848 (6 Pages).
Verdine G.L., et al., "The Challenge of Drugging Undruggable Targets in Cancer: Lessons Learned from Targeting BCL-2 Family Members," Clinical Cancer Research, Dec. 15, 2007, vol. 13, No. 24, pp. 7264-7270.
Verdurmen et al., "Preferential Uptake of L-versus D-Amino Acid Cell-Penetrating Peptides in a Cell Type-Dependent Manner," Chemistry & Biology, 2011, vol. 18, p. 1000-1010.
Voluntary Amendment for Canadian Application No. 2,949,705, dated Nov. 18, 2016, 06 Pages.
Wade M., et al., "MDM2, MDMX and p53 in Oncogenesis and Cancer Therapy," Nature Reviews Cancer, 2013, vol. 13, No. 2, pp. 83-96.
Walensky L.D., et al., "Activation of Apoptosis in Vivo by a Hydrocarbon-Stapled BH3 Helix," Science, Sep. 3, 2004, vol. 305, No. 5689, pp. 1466-1470.
Walensky L.D., et al., "Hydrocarbon-stapled Peptides: Principles, Practice, and Progress: Miniperspective," Journal of Medicinal Chemistry, Feb. 19, 2019, vol. 57, No. 15, pp. 6275-6288.
Weissig V., et al., "DQAsome/DNA Complexes Release DNA Upon Contact with Isolated Mouse Liver Mitochondria," Journal of Controlled Release, 2001, vol. 75, No. 3, pp. 401-408.
Wipf P., et al., "Mitochondrial Targeting of Selective Electron Scavengers: Synthesis and Biological Analysis of Hemigramicidin-TEMPO Conjugates," Journal of the American Chemical Society, 2005, vol. 127, No. 36, pp. 12460-12461.
Wolfe, Justin M., et al. "Machine learning to predict cell-penetrating peptides for antisense delivery." ACS central science 4.4 (2018): 512-520.
Wolfe, Justin M., et al. "Perfluoroaryl bicyclic cell-penetrating peptides for delivery of antisense oligonucleotides." Angewandte Chemie 130.17 (2018): 4846-4849.
Written Amendment for Japanese Application No. 2017-513613, dated Aug. 14, 2020, 02 Pages.
Written Amendment for Japanese Application No. 2017-513613, dated Jan. 26, 2017, 11 Pages.
Written Amendment for Japanese Application No. 2020-072542, dated May 12, 2020, 13 Pages.
Written Amendment for Japanese Application No. 2020-072542, dated Sep. 22, 2022, 06 Pages.
Wu B., et al., "Octa-Guanidine Morpholino Restores Dystrophin Expression in Cardiac and Skeletal Muscles and Ameliorates Pathology in Dystrophic mdx Mice," Molecular Therapy, May 2009, vol. 17, No. 5, pp. 864-871.
Xie, Jing, et al. "Cell-penetrating peptides in diagnosis and treatment of human diseases: from preclinical research to clinical application." Frontiers in pharmacology 11 (2020): 697.
Yamada Y., et al., "Delivery of Bioactive Molecules to the Mitochondrial Genome Using a Membrane-Fusing, Liposome-Based Carrier, DF-MITO-Porter," Biomaterials, Feb. 2012, vol. 33, No. 5, pp. 1589-1595.
Yin H., et al., "Non-viral Vectors for Gene-based Therapy," Nature Reviews Genetics, Aug. 2014, vol. 15, pp. 541-555.
Zhang S., et al., "Acquisition of a Potent and Selective TC-PTP Inhibitor via a Stepwise Fluorophore-Tagged Combinatorial Synthesis and Screening Strategy," Journal of the American Chemical Society, 2009, vol. 131, No. 36, pp. 13072-13079.
Zhang Y., et al., "Cyclic Peptidyl Inhibitors of Grb2 and Tensin SH2 Domains Identified From Combinatorial Libraries," Journal of Combinatorial Chemistry, 2008, vol. 10, No. 2, pp. 247-255.
Zhang Z., et al., "GTP-state-selective Cyclic Peptide Ligands of KRas(G12D) Block Its Interaction With Raf," ACS Central Science, Sep. 23, 2020, vol. 6, pp. 1753-1761.
Zhao K., et al., "Cell-Permeable Peptide Antioxidants Targeted to Inner Mitochondrial Membrane Inhibit Mitochondrial Swelling, Oxidative Cell Death, and Reperfusion Injury," The Journal of Biological Chemistry, Aug. 13, 2004, vol. 279, No. 33, pp. 34682-34690.
Zhou X.Z., et al., "The Isomerase PIN1 Controls Numerous Cancer-driving Pathways and is a Unique Drug Target," Nature Reviews Cancer, 2016, vol. 16, No. 463, pp. 1-16.
Non-Final Office Action for U.S. Appl. No. 18/644,750, mailed Dec. 3, 2025, 7 pages.
Communication Pursuant to Article 94(3) EPC for European Application No. 17874485.0, dated Dec. 11, 2025, 5 Pages.
Communication Pursuant to Article 94(3) EPC for European Application No. 17874485.0, dated Feb. 17, 2026, 5 Pages.
Kawczynski., "Synthesis of Conjugates of Enzyme Inhibitors With Amino Acid Structure and Penetrating Peptides as Potential Compounds Antifungal (With English Translation)," Doctoral Dissertation, 2016, pp. 1-238.
Non-Final Office Action for U.S. Appl. No. 18/644,750, mailed Mar. 9, 2026, 6 pages.
Non-Final Office Action for U.S. Appl. No. 18/755,185, mailed May 29, 2026, 33 pages.
Qian Z., et al., "Developments and Applications of Cyclic Cell Penetrating Peptides," Ohio State University, 2014, 183 pages.
Quian et al., "Efficient Delivery of Cyclic Peptides into Mammalian Cells with Short Sequence Motifs," ACS Chem Biol, Feb. 15, 2013, vol. 8, No. 2, pp. 423-431.
Re-Examination Office Action and Search Report for Taiwanese Application No. 113132218, mailed Jan. 21, 2026, 10 pages.
Restriction Requirement for U.S. Appl. No. 18/541,815, mailed Apr. 10, 2026, 8 pages.
Restriction Requirement for U.S. Appl. No. 18/755,185, mailed Mar. 11, 2026, 7 pages.

* cited by examiner

SEQUENCE LISTING

```
<160> NUMBER OF SEQ ID NOS: 158

<210> SEQ ID NO 1
<211> LENGTH: 17
<212> TYPE: PRT
<213> ORGANISM: Artificial Sequence
<220> FEATURE:
<223> OTHER INFORMATION: synthetic construct

<400> SEQUENCE: 1

Gly Gly Tyr Pro Glu Asp Ile Leu Asp Lys His Leu Gln Arg Val Ile
1               5                   10                  15

Leu


<210> SEQ ID NO 2
<211> LENGTH: 17
<212> TYPE: PRT
<213> ORGANISM: Artificial Sequence
<220> FEATURE:
<223> OTHER INFORMATION: synthetic construct
<220> FEATURE:
<221> NAME/KEY: MOD_RES
<222> LOCATION: (1)..(1)
<223> OTHER INFORMATION: ACETYLATION

<400> SEQUENCE: 2

Gly Gly Tyr Pro Glu Asp Ile Leu Asp Lys His Leu Gln Arg Val Ile
1               5                   10                  15

Leu
```

<210> SEQ ID NO 3
<211> LENGTH: 24
<212> TYPE: PRT
<213> ORGANISM: Artificial Sequence
<220> FEATURE:
<223> OTHER INFORMATION: synthetic construct

<400> SEQUENCE: 3

Leu Ser Gln Glu Gln Leu Glu His Arg Glu Arg Ser Leu Gln Thr Leu
1 5 10 15

Arg Ile Asp Gln Arg Met Leu Phe
20

<210> SEQ ID NO 4
<211> LENGTH: 24
<212> TYPE: PRT
<213> ORGANISM: Artificial Sequence
<220> FEATURE:
<223> OTHER INFORMATION: synthetic construct
<220> FEATURE:
<221> NAME/KEY: MISC_FEATURE
<222> LOCATION: (10)..(10)
<223> OTHER INFORMATION: Xaa is any amino acid which can be utilized to form a staple
<220> FEATURE:
<221> NAME/KEY: MISC_FEATURE
<222> LOCATION: (14)..(14)
<223> OTHER INFORMATION: Xaa is any amino acid which can be utilized to form a staple

<400> SEQUENCE: 4

Leu Ser Gln Glu Gln Leu Glu His Arg Xaa Arg Ser Leu Xaa Thr Leu
1 5 10 15

Arg Asp Ile Gln Arg Met Leu Phe
20

<210> SEQ ID NO 5
<211> LENGTH: 24
<212> TYPE: PRT
<213> ORGANISM: Artificial Sequence
<220> FEATURE:
<223> OTHER INFORMATION: synthetic construct

<400> SEQUENCE: 5

Leu Ser Gln Glu Gln Leu Glu His Arg Glu Arg Ser Leu Gln Thr Leu
1 5 10 15

Arg Asp Ile Gln Arg Leu Leu Phe
20

<210> SEQ ID NO 6
<211> LENGTH: 17
<212> TYPE: PRT
<213> ORGANISM: Artificial Sequence
<220> FEATURE:
<223> OTHER INFORMATION: synthetic construct
<220> FEATURE:
<221> NAME/KEY: MISC_FEATURE
<222> LOCATION: (6)..(6)
<223> OTHER INFORMATION: Xaa is any amino acid which can be utilized to form a staple
<220> FEATURE:
<221> NAME/KEY: MISC_FEATURE
<222> LOCATION: (10)..(10)
<223> OTHER INFORMATION: Xaa is any amino acid which can be utilized to form a staple

<400> SEQUENCE: 6

-continued

Arg Arg Trp Pro Arg Xaa Ile Leu Asp Xaa His Val Arg Arg Val Trp
1 5 10 15

Arg

<210> SEQ ID NO 7
<211> LENGTH: 6
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(6)
<223> OTHER INFORMATION: forms a cyclic peptide
<220> FEATURE:
<221> NAME/KEY: MISC_FEATURE
<222> LOCATION: (2)..(2)
<223> OTHER INFORMATION: L-napthylalanine

<400> SEQUENCE: 7

Phe Xaa Arg Arg Arg Gln
1 5

<210> SEQ ID NO 8
<211> LENGTH: 6
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(6)
<223> OTHER INFORMATION: forms a cyclic peptide
<220> FEATURE:
<221> NAME/KEY: MISC_FEATURE
<222> LOCATION: (2)..(2)
<223> OTHER INFORMATION: L-napthylalanine

<400> SEQUENCE: 8

Phe Xaa Arg Arg Arg Cys
1 5

<210> SEQ ID NO 9
<211> LENGTH: 6
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(6)
<223> OTHER INFORMATION: forms a cyclic peptide
<220> FEATURE:
<221> NAME/KEY: MISC_FEATURE
<222> LOCATION: (2)..(2)
<223> OTHER INFORMATION: L-napthylalanine
<220> FEATURE:
<221> NAME/KEY: MISC_FEATURE
<222> LOCATION: (6)..(6)
<223> OTHER INFORMATION: selenocysteine

<400> SEQUENCE: 9

Phe Xaa Arg Arg Arg Xaa
1 5

<210> SEQ ID NO 10
<211> LENGTH: 6
<212> TYPE: PRT
<213> ORGANISM: Artificial Sequence
<220> FEATURE:
<223> OTHER INFORMATION: Synthetic Construct -continued

```
<220> FEATURE:
<221> NAME/KEY: MISC_FEATURE
<222> LOCATION: (1)..(6)
<223> OTHER INFORMATION: forms a cyclic peptide
<220> FEATURE:
<221> NAME/KEY: MISC_FEATURE
<222> LOCATION: (4)..(4)
<223> OTHER INFORMATION: L-napthylalanine

<400> SEQUENCE: 10

Arg Arg Arg Xaa Phe Gln
1               5


<210> SEQ ID NO 11
<211> LENGTH: 6
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(6)
<223> OTHER INFORMATION: forms a cyclic peptide
<220> FEATURE:
<221> NAME/KEY: MISC_FEATURE
<222> LOCATION: (5)..(5)
<223> OTHER INFORMATION: L-napthylalanine

<400> SEQUENCE: 11

Arg Arg Arg Arg Xaa Phe
1               5


<210> SEQ ID NO 12
<211> LENGTH: 6
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(6)
<223> OTHER INFORMATION: forms a cyclic peptide
<220> FEATURE:
<221> NAME/KEY: MISC_FEATURE
<222> LOCATION: (2)..(2)
<223> OTHER INFORMATION: L-napthylalanine

<400> SEQUENCE: 12

Phe Xaa Arg Arg Arg Arg
1               5


<210> SEQ ID NO 13
<211> LENGTH: 7
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(7)
<223> OTHER INFORMATION: forms a cyclic peptide
<220> FEATURE:
<221> NAME/KEY: MISC_FEATURE
<222> LOCATION: (2)..(2)
<223> OTHER INFORMATION: D-napthylalanine
<220> FEATURE:
<221> NAME/KEY: MISC_FEATURE
<222> LOCATION: (3)..(3)
<223> OTHER INFORMATION: Xaa is D-arginine
<220> FEATURE:
<221> NAME/KEY: MISC_FEATURE
<222> LOCATION: (5)..(5)
<223> OTHER INFORMATION: Xaa is D-arginine
```

<220> FEATURE:
<221> NAME/KEY: MISC_FEATURE
<222> LOCATION: (5)..(5)
<223> OTHER INFORMATION: Xaa is D-glutamine
<220> FEATURE:
<221> NAME/KEY: MISC_FEATURE
<222> LOCATION: (7)..(7)
<223> OTHER INFORMATION: Xaa can be any naturally occurring amino acid

<400> SEQUENCE: 13

Phe Xaa Xaa Arg Xaa Arg Xaa
1               5

<210> SEQ ID NO 14
<211> LENGTH: 7
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(7)
<223> OTHER INFORMATION: forms a cyclic peptide
<220> FEATURE:
<221> NAME/KEY: MISC_FEATURE
<222> LOCATION: (2)..(2)
<223> OTHER INFORMATION: D-napthylalanine
<220> FEATURE:
<221> NAME/KEY: MISC_FEATURE
<222> LOCATION: (3)..(3)
<223> OTHER INFORMATION: Xaa is D-arginine
<220> FEATURE:
<221> NAME/KEY: MISC_FEATURE
<222> LOCATION: (5)..(5)
<223> OTHER INFORMATION: Xaa is D-arginine

<400> SEQUENCE: 14

Phe Xaa Xaa Arg Xaa Arg Gln
1               5

<210> SEQ ID NO 15
<211> LENGTH: 7
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(7)
<223> OTHER INFORMATION: forms a cyclic peptide
<220> FEATURE:
<221> NAME/KEY: MISC_FEATURE
<222> LOCATION: (2)..(2)
<223> OTHER INFORMATION: L-napthylalanine

<400> SEQUENCE: 15

Phe Xaa Arg Arg Arg Arg Gln
1               5

<210> SEQ ID NO 16
<211> LENGTH: 7
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(7)
<223> OTHER INFORMATION: forms a cyclic peptide
<220> FEATURE:
<221> NAME/KEY: MISC_FEATURE
<222> LOCATION: (1)..(1)
<223> OTHER INFORMATION: Xaa is D-phenylalanine
<220> FEATURE:
<221> NAME/KEY: MISC_FEATURE
<222> LOCATION: (2)..(2)
<223> OTHER INFORMATION: L-napthylalanine
<220> FEATURE:
<221> NAME/KEY: MISC_FEATURE
<222> LOCATION: (4)..(4)
<223> OTHER INFORMATION: Xaa is D-arginine
<220> FEATURE:
<221> NAME/KEY: MISC_FEATURE
<222> LOCATION: (6)..(6)
<223> OTHER INFORMATION: Xaa is D-arginine

<400> SEQUENCE: 16

Xaa Xaa Arg Xaa Arg Xaa Gln
1               5

<210> SEQ ID NO 17
<211> LENGTH: 7
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(7)
<223> OTHER INFORMATION: forms a cyclic peptide
<220> FEATURE:
<221> NAME/KEY: MISC_FEATURE
<222> LOCATION: (5)..(5)
<223> OTHER INFORMATION: L-napthylalanine

<400> SEQUENCE: 17

Arg Arg Phe Arg Xaa Arg Gln
1               5

<210> SEQ ID NO 18
<211> LENGTH: 7
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(7)
<223> OTHER INFORMATION: forms a cyclic peptide
<220> FEATURE:
<221> NAME/KEY: MISC_FEATURE
<222> LOCATION: (6)..(6)
<223> OTHER INFORMATION: L-napthylalanine

<400> SEQUENCE: 18

Phe Arg Arg Arg Arg Xaa Gln
1               5

<210> SEQ ID NO 19
<211> LENGTH: 7
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(7)
<223> OTHER INFORMATION: forms a cyclic peptide
<220> FEATURE:
<221> NAME/KEY: MISC_FEATURE
<222> LOCATION: (1)..(1)
<223> OTHER INFORMATION: Xaa is D-arginine
<220> FEATURE:
<221> NAME/KEY: MISC_FEATURE
<222> LOCATION: (5)..(5)
<223> OTHER INFORMATION: L-napthylalanine

```
<400> SEQUENCE: 19

Xaa Arg Phe Arg Xaa Arg Gln
1               5


<210> SEQ ID NO 20
<211> LENGTH: 7
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(7)
<223> OTHER INFORMATION: forms a cyclic peptide
<220> FEATURE:
<221> NAME/KEY: MISC_FEATURE
<222> LOCATION: (3)..(3)
<223> OTHER INFORMATION: L-napthylalanine

<400> SEQUENCE: 20

Arg Arg Xaa Phe Arg Arg Gln
1               5


<210> SEQ ID NO 21
<211> LENGTH: 8
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(8)
<223> OTHER INFORMATION: forms a cyclic peptide

<400> SEQUENCE: 21

Cys Arg Arg Arg Arg Phe Trp Gln
1               5


<210> SEQ ID NO 22
<211> LENGTH: 8
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(8)
<223> OTHER INFORMATION: forms a cyclic peptide
<220> FEATURE:
<221> NAME/KEY: MISC_FEATURE
<222> LOCATION: (2)..(2)
<223> OTHER INFORMATION: Xaa is D-phenylalanine
<220> FEATURE:
<221> NAME/KEY: MISC_FEATURE
<222> LOCATION: (3)..(3)
<223> OTHER INFORMATION: L-napthylalanine
<220> FEATURE:
<221> NAME/KEY: MISC_FEATURE
<222> LOCATION: (5)..(5)
<223> OTHER INFORMATION: Xaa is D-arginine
<220> FEATURE:
<221> NAME/KEY: MISC_FEATURE
<222> LOCATION: (7)..(7)
<223> OTHER INFORMATION: Xaa is D-arginine

<400> SEQUENCE: 22

Phe Xaa Xaa Arg Xaa Arg Xaa Gln
1               5


<210> SEQ ID NO 23
```

<211> LENGTH: 8
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(8)
<223> OTHER INFORMATION: forms a cyclic peptide
<220> FEATURE:
<221> NAME/KEY: MISC_FEATURE
<222> LOCATION: (3)..(3)
<223> OTHER INFORMATION: L-napthylalanine

<400> SEQUENCE: 23

Phe Phe Xaa Arg Arg Arg Arg Gln
1               5

<210> SEQ ID NO 24
<211> LENGTH: 8
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(8)
<223> OTHER INFORMATION: forms a cyclic peptide
<220> FEATURE:
<221> NAME/KEY: MISC_FEATURE
<222> LOCATION: (6)..(6)
<223> OTHER INFORMATION: L-napthylalanine

<400> SEQUENCE: 24

Arg Phe Arg Phe Arg Xaa Arg Gln
1               5

<210> SEQ ID NO 25
<211> LENGTH: 8
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(8)
<223> OTHER INFORMATION: forms a cyclic peptide
<220> FEATURE:
<221> NAME/KEY: MISC_FEATURE
<222> LOCATION: (1)..(1)
<223> OTHER INFORMATION: selenocysteine

<400> SEQUENCE: 25

Xaa Arg Arg Arg Arg Phe Trp Gln
1               5

<210> SEQ ID NO 26
<211> LENGTH: 8
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(8)
<223> OTHER INFORMATION: forms a cyclic peptide
<220> FEATURE:
<221> NAME/KEY: MISC_FEATURE
<222> LOCATION: (2)..(2)
<223> OTHER INFORMATION: L-napthylalanine

<400> SEQUENCE: 26

-continued

```
Phe Xaa Arg Arg Arg Arg Gln Lys
1               5


<210> SEQ ID NO 27
<211> LENGTH: 8
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(8)
<223> OTHER INFORMATION: forms a cyclic peptide
<220> FEATURE:
<221> NAME/KEY: MISC_FEATURE
<222> LOCATION: (2)..(2)
<223> OTHER INFORMATION: L-napthylalanine

<400> SEQUENCE: 27

Phe Xaa Arg Arg Arg Arg Gln Cys
1               5


<210> SEQ ID NO 28
<211> LENGTH: 8
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(8)
<223> OTHER INFORMATION: forms a cyclic peptide
<220> FEATURE:
<221> NAME/KEY: MISC_FEATURE
<222> LOCATION: (1)..(1)
<223> OTHER INFORMATION: Xaa is D-phenylalanine
<220> FEATURE:
<221> NAME/KEY: MISC_FEATURE
<222> LOCATION: (2)..(2)
<223> OTHER INFORMATION: L-napthylalanine
<220> FEATURE:
<221> NAME/KEY: MISC_FEATURE
<222> LOCATION: (4)..(4)
<223> OTHER INFORMATION: Xaa is D-arginine
<220> FEATURE:
<221> NAME/KEY: MISC_FEATURE
<222> LOCATION: (6)..(6)
<223> OTHER INFORMATION: Xaa is D-arginine

<400> SEQUENCE: 28

Xaa Xaa Arg Xaa Arg Xaa Arg Gln
1               5


<210> SEQ ID NO 29
<211> LENGTH: 8
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(8)
<223> OTHER INFORMATION: forms a cyclic peptide
<220> FEATURE:
<221> NAME/KEY: MISC_FEATURE
<222> LOCATION: (2)..(2)
<223> OTHER INFORMATION: L-napthylalanine

<400> SEQUENCE: 29

Phe Xaa Arg Arg Arg Arg Arg Gln
1               5
```

-continued

<210> SEQ ID NO 30
<211> LENGTH: 9
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(9)
<223> OTHER INFORMATION: forms a cyclic peptide
<220> FEATURE:
<221> NAME/KEY: MISC_FEATURE
<222> LOCATION: (5)..(5)
<223> OTHER INFORMATION: L-napthylalanine
<220> FEATURE:
<221> NAME/KEY: MISC_FEATURE
<222> LOCATION: (8)..(8)
<223> OTHER INFORMATION: L-norleucine

<400> SEQUENCE: 30

Arg Arg Arg Arg Xaa Phe Asp Xaa Cys
1               5

<210> SEQ ID NO 31
<211> LENGTH: 5
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(5)
<223> OTHER INFORMATION: forms a cyclic peptide
<220> FEATURE:
<221> NAME/KEY: MISC_FEATURE
<222> LOCATION: (2)..(2)
<223> OTHER INFORMATION: L-napthylalanine

<400> SEQUENCE: 31

Phe Xaa Arg Arg Arg
1               5

<210> SEQ ID NO 32
<211> LENGTH: 5
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(5)
<223> OTHER INFORMATION: forms a cyclic peptide

<400> SEQUENCE: 32

Phe Trp Arg Arg Arg
1               5

<210> SEQ ID NO 33
<211> LENGTH: 5
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(5)
<223> OTHER INFORMATION: forms a cyclic peptide
<220> FEATURE:
<221> NAME/KEY: MISC_FEATURE
<222> LOCATION: (4)..(4)
<223> OTHER INFORMATION: L-napthylalanine

<400> SEQUENCE: 33

-continued

Arg Arg Arg Xaa Phe
1               5

<210> SEQ ID NO 34
<211> LENGTH: 5
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(5)
<223> OTHER INFORMATION: forms a cyclic peptide

<400> SEQUENCE: 34

Arg Arg Arg Trp Phe
1               5

<210> SEQ ID NO 35
<211> LENGTH: 6
<212> TYPE: PRT
<213> ORGANISM: Artificial Sequence
<220> FEATURE:
<223> OTHER INFORMATION: synthetic construct
<220> FEATURE:
<221> NAME/KEY: MISC_FEATURE
<222> LOCATION: (1)..(6)
<223> OTHER INFORMATION: forms a cyclic peptide

<400> SEQUENCE: 35

Phe Phe Arg Arg Arg Gln
1               5

<210> SEQ ID NO 36
<211> LENGTH: 6
<212> TYPE: PRT
<213> ORGANISM: Artificial Sequence
<220> FEATURE:
<223> OTHER INFORMATION: synthetic construct
<220> FEATURE:
<221> NAME/KEY: MISC_FEATURE
<222> LOCATION: (1)..(6)
<223> OTHER INFORMATION: forms a cyclic peptide
<220> FEATURE:
<221> NAME/KEY: MISC_FEATURE
<222> LOCATION: (3)..(3)
<223> OTHER INFORMATION: Xaa is D-arginine
<220> FEATURE:
<221> NAME/KEY: MISC_FEATURE
<222> LOCATION: (5)..(5)
<223> OTHER INFORMATION: Xaa is D-arginine

<400> SEQUENCE: 36

Phe Phe Xaa Arg Xaa Gln
1               5

<210> SEQ ID NO 37
<211> LENGTH: 6
<212> TYPE: PRT
<213> ORGANISM: Artificial Sequence
<220> FEATURE:
<223> OTHER INFORMATION: synthetic construct
<220> FEATURE:
<221> NAME/KEY: MISC_FEATURE
<222> LOCATION: (1)..(6)
<223> OTHER INFORMATION: forms a cyclic peptide
<220> FEATURE:
<221> NAME/KEY: MISC_FEATURE
<222> LOCATION: (4)..(4)
<223> OTHER INFORMATION: Xaa is D-arginine -continued

<400> SEQUENCE: 37

Phe Phe Arg Xaa Arg Gln
1               5

<210> SEQ ID NO 38
<211> LENGTH: 6
<212> TYPE: PRT
<213> ORGANISM: Artificial Sequence
<220> FEATURE:
<223> OTHER INFORMATION: synthetic construct
<220> FEATURE:
<221> NAME/KEY: MISC_FEATURE
<222> LOCATION: (1)..(6)
<223> OTHER INFORMATION: forms a cyclic peptide

<400> SEQUENCE: 38

Phe Arg Phe Arg Arg Gln
1               5

<210> SEQ ID NO 39
<211> LENGTH: 6
<212> TYPE: PRT
<213> ORGANISM: Artificial Sequence
<220> FEATURE:
<223> OTHER INFORMATION: synthetic construct
<220> FEATURE:
<221> NAME/KEY: MISC_FEATURE
<222> LOCATION: (1)..(6)
<223> OTHER INFORMATION: forms a cyclic peptide

<400> SEQUENCE: 39

Phe Arg Arg Phe Arg Gln
1               5

<210> SEQ ID NO 40
<211> LENGTH: 6
<212> TYPE: PRT
<213> ORGANISM: Artificial Sequence
<220> FEATURE:
<223> OTHER INFORMATION: synthetic construct
<220> FEATURE:
<221> NAME/KEY: MISC_FEATURE
<222> LOCATION: (1)..(6)
<223> OTHER INFORMATION: forms a cyclic peptide

<400> SEQUENCE: 40

Phe Arg Arg Arg Phe Gln
1               5

<210> SEQ ID NO 41
<211> LENGTH: 6
<212> TYPE: PRT
<213> ORGANISM: Artificial Sequence
<220> FEATURE:
<223> OTHER INFORMATION: synthetic construct
<220> FEATURE:
<221> NAME/KEY: MISC_FEATURE
<222> LOCATION: (1)..(6)
<223> OTHER INFORMATION: forms a cyclic peptide
<220> FEATURE:
<221> NAME/KEY: MISC_FEATURE
<222> LOCATION: (2)..(2)
<223> OTHER INFORMATION: Xaa is L-naphthylalanine

<400> SEQUENCE: 41

Gly Xaa Arg Arg Arg Gln
1               5

<210> SEQ ID NO 42

```
<211> LENGTH: 6
<212> TYPE: PRT
<213> ORGANISM: Artificial Sequence
<220> FEATURE:
<223> OTHER INFORMATION: synthetic construct
<220> FEATURE:
<221> NAME/KEY: MISC_FEATURE
<222> LOCATION: (1)..(6)
<223> OTHER INFORMATION: forms a cyclic peptide

<400> SEQUENCE: 42

Phe Phe Phe Arg Ala Gln
1               5


<210> SEQ ID NO 43
<211> LENGTH: 6
<212> TYPE: PRT
<213> ORGANISM: Artificial Sequence
<220> FEATURE:
<223> OTHER INFORMATION: synthetic construct
<220> FEATURE:
<221> NAME/KEY: MISC_FEATURE
<222> LOCATION: (1)..(6)
<223> OTHER INFORMATION: forms a cyclic peptide

<400> SEQUENCE: 43

Phe Phe Phe Arg Arg Gln
1               5


<210> SEQ ID NO 44
<211> LENGTH: 7
<212> TYPE: PRT
<213> ORGANISM: Artificial Sequence
<220> FEATURE:
<223> OTHER INFORMATION: synthetic construct
<220> FEATURE:
<221> NAME/KEY: MISC_FEATURE
<222> LOCATION: (1)..(7)
<223> OTHER INFORMATION: forms a cyclic peptide

<400> SEQUENCE: 44

Phe Phe Arg Arg Arg Arg Gln
1               5


<210> SEQ ID NO 45
<211> LENGTH: 7
<212> TYPE: PRT
<213> ORGANISM: Artificial Sequence
<220> FEATURE:
<223> OTHER INFORMATION: synthetic construct
<220> FEATURE:
<221> NAME/KEY: MISC_FEATURE
<222> LOCATION: (1)..(7)
<223> OTHER INFORMATION: forms a cyclic peptide

<400> SEQUENCE: 45

Phe Arg Arg Phe Arg Arg Gln
1               5


<210> SEQ ID NO 46
<211> LENGTH: 7
<212> TYPE: PRT
<213> ORGANISM: Artificial Sequence
<220> FEATURE:
<223> OTHER INFORMATION: synthetic construct
<220> FEATURE:
<221> NAME/KEY: MISC_FEATURE
<222> LOCATION: (1)..(7)
<223> OTHER INFORMATION: forms a cyclic peptide

<400> SEQUENCE: 46
```

Phe Arg Arg Arg Phe Arg Gln
1 5

<210> SEQ ID NO 47
<211> LENGTH: 7
<212> TYPE: PRT
<213> ORGANISM: Artificial Sequence
<220> FEATURE:
<223> OTHER INFORMATION: synthetic construct
<220> FEATURE:
<221> NAME/KEY: MISC_FEATURE
<222> LOCATION: (1)..(7)
<223> OTHER INFORMATION: forms a cyclic peptide

<400> SEQUENCE: 47

Arg Phe Phe Arg Arg Arg Gln
1 5

<210> SEQ ID NO 48
<211> LENGTH: 7
<212> TYPE: PRT
<213> ORGANISM: Artificial Sequence
<220> FEATURE:
<223> OTHER INFORMATION: synthetic construct
<220> FEATURE:
<221> NAME/KEY: MISC_FEATURE
<222> LOCATION: (1)..(7)
<223> OTHER INFORMATION: forms a cyclic peptide

<400> SEQUENCE: 48

Arg Phe Arg Arg Phe Arg Gln
1 5

<210> SEQ ID NO 49
<211> LENGTH: 7
<212> TYPE: PRT
<213> ORGANISM: Artificial Sequence
<220> FEATURE:
<223> OTHER INFORMATION: synthetic construct
<220> FEATURE:
<221> NAME/KEY: MISC_FEATURE
<222> LOCATION: (1)..(7)
<223> OTHER INFORMATION: forms a cyclic peptide

<400> SEQUENCE: 49

Phe Arg Phe Arg Arg Arg Gln
1 5

<210> SEQ ID NO 50
<211> LENGTH: 7
<212> TYPE: PRT
<213> ORGANISM: Artificial Sequence
<220> FEATURE:
<223> OTHER INFORMATION: synthetic construct
<220> FEATURE:
<221> NAME/KEY: MISC_FEATURE
<222> LOCATION: (1)..(7)
<223> OTHER INFORMATION: forms a cyclic peptide

<400> SEQUENCE: 50

Phe Phe Phe Arg Arg Arg Gln
1 5

<210> SEQ ID NO 51
<211> LENGTH: 7
<212> TYPE: PRT
<213> ORGANISM: Artificial Sequence
<220> FEATURE:
<223> OTHER INFORMATION: synthetic construct

```
<220> FEATURE:
<221> NAME/KEY: MISC_FEATURE
<222> LOCATION: (1)..(7)
<223> OTHER INFORMATION: forms a cyclic peptide

<400> SEQUENCE: 51

Phe Phe Arg Arg Arg Phe Gln
1               5


<210> SEQ ID NO 52
<211> LENGTH: 7
<212> TYPE: PRT
<213> ORGANISM: Artificial Sequence
<220> FEATURE:
<223> OTHER INFORMATION: synthetic construct
<220> FEATURE:
<221> NAME/KEY: MISC_FEATURE
<222> LOCATION: (1)..(7)
<223> OTHER INFORMATION: forms a cyclic peptide

<400> SEQUENCE: 52

Phe Arg Phe Phe Arg Arg Gln
1               5


<210> SEQ ID NO 53
<211> LENGTH: 7
<212> TYPE: PRT
<213> ORGANISM: Artificial Sequence
<220> FEATURE:
<223> OTHER INFORMATION: synthetic construct
<220> FEATURE:
<221> NAME/KEY: MISC_FEATURE
<222> LOCATION: (1)..(7)
<223> OTHER INFORMATION: forms a cyclic peptide

<400> SEQUENCE: 53

Arg Arg Phe Phe Phe Arg Gln
1               5


<210> SEQ ID NO 54
<211> LENGTH: 7
<212> TYPE: PRT
<213> ORGANISM: Artificial Sequence
<220> FEATURE:
<223> OTHER INFORMATION: synthetic construct
<220> FEATURE:
<221> NAME/KEY: MISC_FEATURE
<222> LOCATION: (1)..(7)
<223> OTHER INFORMATION: forms a cyclic peptide

<400> SEQUENCE: 54

Phe Phe Arg Phe Arg Arg Gln
1               5


<210> SEQ ID NO 55
<211> LENGTH: 7
<212> TYPE: PRT
<213> ORGANISM: Artificial Sequence
<220> FEATURE:
<223> OTHER INFORMATION: synthetic construct
<220> FEATURE:
<221> NAME/KEY: MISC_FEATURE
<222> LOCATION: (1)..(7)
<223> OTHER INFORMATION: forms a cyclic peptide

<400> SEQUENCE: 55

Phe Phe Arg Arg Phe Arg Gln
1               5
```

<210> SEQ ID NO 56
<211> LENGTH: 7
<212> TYPE: PRT
<213> ORGANISM: Artificial Sequence
<220> FEATURE:
<223> OTHER INFORMATION: synthetic construct
<220> FEATURE:
<221> NAME/KEY: MISC_FEATURE
<222> LOCATION: (1)..(7)
<223> OTHER INFORMATION: forms a cyclic peptide

<400> SEQUENCE: 56

Phe Arg Arg Phe Phe Arg Gln
1 5

<210> SEQ ID NO 57
<211> LENGTH: 7
<212> TYPE: PRT
<213> ORGANISM: Artificial Sequence
<220> FEATURE:
<223> OTHER INFORMATION: synthetic construct
<220> FEATURE:
<221> NAME/KEY: MISC_FEATURE
<222> LOCATION: (1)..(7)
<223> OTHER INFORMATION: forms a cyclic peptide

<400> SEQUENCE: 57

Phe Arg Arg Phe Arg Phe Gln
1 5

<210> SEQ ID NO 58
<211> LENGTH: 7
<212> TYPE: PRT
<213> ORGANISM: Artificial Sequence
<220> FEATURE:
<223> OTHER INFORMATION: synthetic construct
<220> FEATURE:
<221> NAME/KEY: MISC_FEATURE
<222> LOCATION: (1)..(7)
<223> OTHER INFORMATION: forms a cyclic peptide

<400> SEQUENCE: 58

Phe Arg Phe Arg Phe Arg Gln
1 5

<210> SEQ ID NO 59
<211> LENGTH: 7
<212> TYPE: PRT
<213> ORGANISM: Artificial Sequence
<220> FEATURE:
<223> OTHER INFORMATION: synthetic construct
<220> FEATURE:
<221> NAME/KEY: MISC_FEATURE
<222> LOCATION: (1)..(7)
<223> OTHER INFORMATION: forms a cyclic peptide

<400> SEQUENCE: 59

Arg Phe Phe Arg Phe Arg Gln
1 5

<210> SEQ ID NO 60
<211> LENGTH: 7
<212> TYPE: PRT
<213> ORGANISM: Artificial Sequence
<220> FEATURE:
<223> OTHER INFORMATION: synthetic construct
<220> FEATURE:
<221> NAME/KEY: MISC_FEATURE
<222> LOCATION: (1)..(7)
<223> OTHER INFORMATION: forms a cyclic peptide
<220> FEATURE:

<221> NAME/KEY: MISC_FEATURE
<222> LOCATION: (2)..(2)
<223> OTHER INFORMATION: Xaa is L-naphthylalanine

<400> SEQUENCE: 60

Gly Xaa Arg Arg Arg Arg Gln
1               5

<210> SEQ ID NO 61
<211> LENGTH: 8
<212> TYPE: PRT
<213> ORGANISM: Artificial Sequence
<220> FEATURE:
<223> OTHER INFORMATION: synthetic construct
<220> FEATURE:
<221> NAME/KEY: MISC_FEATURE
<222> LOCATION: (1)..(8)
<223> OTHER INFORMATION: forms a cyclic peptide

<400> SEQUENCE: 61

Phe Phe Phe Arg Arg Arg Arg Gln
1               5

<210> SEQ ID NO 62
<211> LENGTH: 8
<212> TYPE: PRT
<213> ORGANISM: Artificial Sequence
<220> FEATURE:
<223> OTHER INFORMATION: synthetic construct
<220> FEATURE:
<221> NAME/KEY: MISC_FEATURE
<222> LOCATION: (1)..(8)
<223> OTHER INFORMATION: forms a cyclic peptide

<400> SEQUENCE: 62

Arg Phe Phe Arg Arg Arg Arg Gln
1               5

<210> SEQ ID NO 63
<211> LENGTH: 8
<212> TYPE: PRT
<213> ORGANISM: Artificial Sequence
<220> FEATURE:
<223> OTHER INFORMATION: synthetic construct
<220> FEATURE:
<221> NAME/KEY: MISC_FEATURE
<222> LOCATION: (1)..(8)
<223> OTHER INFORMATION: forms a cyclic peptide

<400> SEQUENCE: 63

Arg Arg Phe Phe Arg Arg Arg Gln
1               5

<210> SEQ ID NO 64
<211> LENGTH: 8
<212> TYPE: PRT
<213> ORGANISM: Artificial Sequence
<220> FEATURE:
<223> OTHER INFORMATION: synthetic construct
<220> FEATURE:
<221> NAME/KEY: MISC_FEATURE
<222> LOCATION: (1)..(8)
<223> OTHER INFORMATION: forms a cyclic peptide

<400> SEQUENCE: 64

Arg Phe Phe Phe Arg Arg Arg Gln
1               5

<210> SEQ ID NO 65

<211> LENGTH: 8
<212> TYPE: PRT
<213> ORGANISM: Artificial Sequence
<220> FEATURE:
<223> OTHER INFORMATION: synthetic construct
<220> FEATURE:
<221> NAME/KEY: MISC_FEATURE
<222> LOCATION: (1)..(8)
<223> OTHER INFORMATION: forms a cyclic peptide

<400> SEQUENCE: 65

Arg Arg Phe Phe Phe Arg Arg Gln
1               5

<210> SEQ ID NO 66
<211> LENGTH: 8
<212> TYPE: PRT
<213> ORGANISM: Artificial Sequence
<220> FEATURE:
<223> OTHER INFORMATION: synthetic construct
<220> FEATURE:
<221> NAME/KEY: MISC_FEATURE
<222> LOCATION: (1)..(8)
<223> OTHER INFORMATION: forms a cyclic peptide

<400> SEQUENCE: 66

Phe Phe Arg Arg Phe Arg Arg Gln
1               5

<210> SEQ ID NO 67
<211> LENGTH: 8
<212> TYPE: PRT
<213> ORGANISM: Artificial Sequence
<220> FEATURE:
<223> OTHER INFORMATION: synthetic construct
<220> FEATURE:
<221> NAME/KEY: MISC_FEATURE
<222> LOCATION: (1)..(8)
<223> OTHER INFORMATION: forms a cyclic peptide

<400> SEQUENCE: 67

Phe Phe Arg Arg Arg Arg Phe Gln
1               5

<210> SEQ ID NO 68
<211> LENGTH: 8
<212> TYPE: PRT
<213> ORGANISM: Artificial Sequence
<220> FEATURE:
<223> OTHER INFORMATION: synthetic construct
<220> FEATURE:
<221> NAME/KEY: MISC_FEATURE
<222> LOCATION: (1)..(8)
<223> OTHER INFORMATION: forms a cyclic peptide

<400> SEQUENCE: 68

Phe Arg Arg Phe Phe Arg Arg Gln
1               5

<210> SEQ ID NO 69
<211> LENGTH: 9
<212> TYPE: PRT
<213> ORGANISM: Artificial Sequence
<220> FEATURE:
<223> OTHER INFORMATION: synthetic construct
<220> FEATURE:
<221> NAME/KEY: MISC_FEATURE
<222> LOCATION: (1)..(9)
<223> OTHER INFORMATION: forms a cyclic peptide

<400> SEQUENCE: 69

Phe Phe Phe Arg Arg Arg Arg Arg Gln
1 5

<210> SEQ ID NO 70
<211> LENGTH: 10
<212> TYPE: PRT
<213> ORGANISM: Artificial Sequence
<220> FEATURE:
<223> OTHER INFORMATION: synthetic construct
<220> FEATURE:
<221> NAME/KEY: MISC_FEATURE
<222> LOCATION: (1)..(10)
<223> OTHER INFORMATION: forms a cyclic peptide

<400> SEQUENCE: 70

Phe Phe Phe Arg Arg Arg Arg Arg Arg Gln
1 5 10

<210> SEQ ID NO 71
<211> LENGTH: 7
<212> TYPE: PRT
<213> ORGANISM: Artificial Sequence
<220> FEATURE:
<223> OTHER INFORMATION: synthetic construct
<220> FEATURE:
<221> NAME/KEY: MISC_FEATURE
<222> LOCATION: (1)..(7)
<223> OTHER INFORMATION: forms a cyclic peptide
<220> FEATURE:
<221> NAME/KEY: MISC_FEATURE
<222> LOCATION: (2)..(2)
<223> OTHER INFORMATION: Xaa is L-naphthylalanine
<220> FEATURE:
<221> NAME/KEY: MISC_FEATURE
<222> LOCATION: (4)..(4)
<223> OTHER INFORMATION: Xaa is D-arginine
<220> FEATURE:
<221> NAME/KEY: MISC_FEATURE
<222> LOCATION: (6)..(6)
<223> OTHER INFORMATION: Xaa is D-arginine

<400> SEQUENCE: 71

Phe Xaa Arg Xaa Arg Xaa Gln
1 5

<210> SEQ ID NO 72
<211> LENGTH: 7
<212> TYPE: PRT
<213> ORGANISM: Artificial Sequence
<220> FEATURE:
<223> OTHER INFORMATION: synthetic construct
<220> FEATURE:
<221> NAME/KEY: MISC_FEATURE
<222> LOCATION: (1)..(7)
<223> OTHER INFORMATION: forms a cyclic peptide
<220> FEATURE:
<221> NAME/KEY: MISC_FEATURE
<222> LOCATION: (1)..(2)
<223> OTHER INFORMATION: Xaa can be any naturally occurring amino acid

<400> SEQUENCE: 72

Xaa Xaa Arg Arg Arg Arg Gln
1 5

<210> SEQ ID NO 73
<211> LENGTH: 7
<212> TYPE: PRT
<213> ORGANISM: Artificial Sequence
<220> FEATURE:
<223> OTHER INFORMATION: synthetic construct
<220> FEATURE:

<221> NAME/KEY: MISC_FEATURE
<222> LOCATION: (1)..(7)
<223> OTHER INFORMATION: forms a cyclic peptide
<220> FEATURE:
<221> NAME/KEY: MISC_FEATURE
<222> LOCATION: (2)..(2)
<223> OTHER INFORMATION: Xaa is D-phenylalanine
<220> FEATURE:
<221> NAME/KEY: MISC_FEATURE
<222> LOCATION: (5)..(5)
<223> OTHER INFORMATION: Xaa is D-arginine

<400> SEQUENCE: 73

Phe Xaa Phe Arg Xaa Arg Gln
1               5

<210> SEQ ID NO 74
<211> LENGTH: 7
<212> TYPE: PRT
<213> ORGANISM: Artificial Sequence
<220> FEATURE:
<223> OTHER INFORMATION: synthetic construct
<220> FEATURE:
<221> NAME/KEY: MISC_FEATURE
<222> LOCATION: (1)..(7)
<223> OTHER INFORMATION: forms a cyclic peptide
<220> FEATURE:
<221> NAME/KEY: MISC_FEATURE
<222> LOCATION: (1)..(1)
<223> OTHER INFORMATION: Xaa is D-phenylalanine
<220> FEATURE:
<221> NAME/KEY: MISC_FEATURE
<222> LOCATION: (3)..(3)
<223> OTHER INFORMATION: Xaa is D-phenylalanine
<220> FEATURE:
<221> NAME/KEY: MISC_FEATURE
<222> LOCATION: (4)..(4)
<223> OTHER INFORMATION: Xaa is D-arginine
<220> FEATURE:
<221> NAME/KEY: MISC_FEATURE
<222> LOCATION: (6)..(6)
<223> OTHER INFORMATION: Xaa is D-arginine

<400> SEQUENCE: 74

Xaa Phe Xaa Xaa Arg Xaa Gln
1               5

<210> SEQ ID NO 75
<211> LENGTH: 7
<212> TYPE: PRT
<213> ORGANISM: Artificial Sequence
<220> FEATURE:
<223> OTHER INFORMATION: synthetic construct
<220> FEATURE:
<221> NAME/KEY: MISC_FEATURE
<222> LOCATION: (1)..(7)
<223> OTHER INFORMATION: forms a cyclic peptide
<220> FEATURE:
<221> NAME/KEY: MISC_FEATURE
<222> LOCATION: (1)..(1)
<223> OTHER INFORMATION: Xaa is D-phenylalanine
<220> FEATURE:
<221> NAME/KEY: MISC_FEATURE
<222> LOCATION: (3)..(3)
<223> OTHER INFORMATION: Xaa is D-phenylalanine
<220> FEATURE:
<221> NAME/KEY: MISC_FEATURE
<222> LOCATION: (5)..(5)
<223> OTHER INFORMATION: Xaa is D-arginine

<400> SEQUENCE: 75

Xaa Phe Xaa Arg Xaa Arg Gln
1               5

<210> SEQ ID NO 76
<211> LENGTH: 7
<212> TYPE: PRT
<213> ORGANISM: Artificial Sequence
<220> FEATURE:
<223> OTHER INFORMATION: synthetic construct
<220> FEATURE:
<221> NAME/KEY: MISC_FEATURE
<222> LOCATION: (1)..(7)
<223> OTHER INFORMATION: forms a cyclic peptide
<220> FEATURE:
<221> NAME/KEY: MISC_FEATURE
<222> LOCATION: (2)..(2)
<223> OTHER INFORMATION: Xaa is D-phenylalanine
<220> FEATURE:
<221> NAME/KEY: MISC_FEATURE
<222> LOCATION: (4)..(4)
<223> OTHER INFORMATION: Xaa is D-arginine
<220> FEATURE:
<221> NAME/KEY: MISC_FEATURE
<222> LOCATION: (6)..(6)
<223> OTHER INFORMATION: Xaa is D-arginine

<400> SEQUENCE: 76

Phe Xaa Phe Xaa Arg Xaa Gln
1               5

<210> SEQ ID NO 77
<211> LENGTH: 7
<212> TYPE: PRT
<213> ORGANISM: Artificial Sequence
<220> FEATURE:
<223> OTHER INFORMATION: synthetic construct
<220> FEATURE:
<221> NAME/KEY: MISC_FEATURE
<222> LOCATION: (1)..(7)
<223> OTHER INFORMATION: forms a cyclic peptide
<220> FEATURE:
<221> NAME/KEY: MISC_FEATURE
<222> LOCATION: (1)..(1)
<223> OTHER INFORMATION: Xaa is D-phenylalanine
<220> FEATURE:
<221> NAME/KEY: MISC_FEATURE
<222> LOCATION: (3)..(3)
<223> OTHER INFORMATION: Xaa is L-naphthylalanine
<220> FEATURE:
<221> NAME/KEY: MISC_FEATURE
<222> LOCATION: (4)..(4)
<223> OTHER INFORMATION: Xaa is D-arginine
<220> FEATURE:
<221> NAME/KEY: MISC_FEATURE
<222> LOCATION: (6)..(6)
<223> OTHER INFORMATION: Xaa is D-arginine

<400> SEQUENCE: 77

Xaa Phe Xaa Xaa Arg Xaa Gln
1               5

<210> SEQ ID NO 78
<211> LENGTH: 7
<212> TYPE: PRT
<213> ORGANISM: Artificial Sequence
<220> FEATURE:
<223> OTHER INFORMATION: synthetic construct
<220> FEATURE:
<221> NAME/KEY: MISC_FEATURE
<222> LOCATION: (1)..(7)
<223> OTHER INFORMATION: forms a cyclic peptide
<220> FEATURE:
<221> NAME/KEY: MISC_FEATURE
<222> LOCATION: (1)..(1)
<223> OTHER INFORMATION: Xaa is D-phenylalanine
<220> FEATURE:
<221> NAME/KEY: MISC_FEATURE -continued
<222> LOCATION: (2)..(2)
<223> OTHER INFORMATION: Xaa is L-naphthylalanine
<220> FEATURE:
<221> NAME/KEY: MISC_FEATURE
<222> LOCATION: (3)..(3)
<223> OTHER INFORMATION: Xaa is D-phenylalanine
<220> FEATURE:
<221> NAME/KEY: MISC_FEATURE
<222> LOCATION: (4)..(4)
<223> OTHER INFORMATION: Xaa is D-arginine
<220> FEATURE:
<221> NAME/KEY: MISC_FEATURE
<222> LOCATION: (6)..(6)
<223> OTHER INFORMATION: Xaa is D-arginine

<400> SEQUENCE: 78

Xaa Xaa Xaa Xaa Arg Xaa Gln
1               5

<210> SEQ ID NO 79
<211> LENGTH: 7
<212> TYPE: PRT
<213> ORGANISM: Artificial Sequence
<220> FEATURE:
<223> OTHER INFORMATION: synthetic construct
<220> FEATURE:
<221> NAME/KEY: MISC_FEATURE
<222> LOCATION: (1)..(7)
<223> OTHER INFORMATION: forms a cyclic peptide
<220> FEATURE:
<221> NAME/KEY: MISC_FEATURE
<222> LOCATION: (1)..(1)
<223> OTHER INFORMATION: Xaa is L-naphthylalanine
<220> FEATURE:
<221> NAME/KEY: MISC_FEATURE
<222> LOCATION: (3)..(3)
<223> OTHER INFORMATION: Xaa is D-phenylalanine
<220> FEATURE:
<221> NAME/KEY: MISC_FEATURE
<222> LOCATION: (4)..(4)
<223> OTHER INFORMATION: Xaa is D-arginine
<220> FEATURE:
<221> NAME/KEY: MISC_FEATURE
<222> LOCATION: (6)..(6)
<223> OTHER INFORMATION: Xaa is D-arginine

<400> SEQUENCE: 79

Xaa Phe Xaa Xaa Arg Xaa Gln
1               5

<210> SEQ ID NO 80
<211> LENGTH: 6
<212> TYPE: PRT
<213> ORGANISM: Artificial Sequence
<220> FEATURE:
<223> OTHER INFORMATION: synthetic construct
<220> FEATURE:
<221> NAME/KEY: MISC_FEATURE
<222> LOCATION: (1)..(6)
<223> OTHER INFORMATION: forms a cyclic peptide
<220> FEATURE:
<221> NAME/KEY: MISC_FEATURE
<222> LOCATION: (2)..(2)
<223> OTHER INFORMATION: Xaa is L-naphthylalanine
<220> FEATURE:
<221> NAME/KEY: MISC_FEATURE
<222> LOCATION: (3)..(3)
<223> OTHER INFORMATION: Xaa is D-arginine
<220> FEATURE:
<221> NAME/KEY: MISC_FEATURE
<222> LOCATION: (5)..(5)
<223> OTHER INFORMATION: Xaa is D-arginine

<400> SEQUENCE: 80

-continued

Phe Xaa Xaa Arg Xaa Gln
1               5

<210> SEQ ID NO 81
<211> LENGTH: 6
<212> TYPE: PRT
<213> ORGANISM: Artificial Sequence
<220> FEATURE:
<223> OTHER INFORMATION: synthetic construct
<220> FEATURE:
<221> NAME/KEY: MISC_FEATURE
<222> LOCATION: (1)..(6)
<223> OTHER INFORMATION: forms a cyclic peptide
<220> FEATURE:
<221> NAME/KEY: MISC_FEATURE
<222> LOCATION: (1)..(1)
<223> OTHER INFORMATION: Xaa is D-phenylalanine
<220> FEATURE:
<221> NAME/KEY: MISC_FEATURE
<222> LOCATION: (2)..(2)
<223> OTHER INFORMATION: Xaa is L-naphthylalanine
<220> FEATURE:
<221> NAME/KEY: MISC_FEATURE
<222> LOCATION: (3)..(3)
<223> OTHER INFORMATION: Xaa is D-arginine
<220> FEATURE:
<221> NAME/KEY: MISC_FEATURE
<222> LOCATION: (5)..(5)
<223> OTHER INFORMATION: Xaa is D-arginine

<400> SEQUENCE: 81

Xaa Xaa Xaa Arg Xaa Gln
1               5

<210> SEQ ID NO 82
<211> LENGTH: 8
<212> TYPE: PRT
<213> ORGANISM: Artificial Sequence
<220> FEATURE:
<223> OTHER INFORMATION: synthetic construct
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (2)..(2)
<223> OTHER INFORMATION: Xaa is D-phenylalanine
<220> FEATURE:
<221> NAME/KEY: MISC_FEATURE
<222> LOCATION: (5)..(5)
<223> OTHER INFORMATION: Xaa is D-arginine
<220> FEATURE:
<221> NAME/KEY: MISC_FEATURE
<222> LOCATION: (7)..(7)
<223> OTHER INFORMATION: Xaa is D-arginine

<400> SEQUENCE: 82

Lys Xaa Phe Arg Xaa Arg Xaa Asp
1               5

<210> SEQ ID NO 83
<211> LENGTH: 8
<212> TYPE: PRT
<213> ORGANISM: Artificial Sequence
<220> FEATURE:
<223> OTHER INFORMATION: synthetic construct
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (1)..(1)

<223> OTHER INFORMATION: Xaa is L-2,3-diaminopropionic acid
<220> FEATURE:
<221> NAME/KEY: MISC_FEATURE
<222> LOCATION: (2)..(2)
<223> OTHER INFORMATION: Xaa is D-phenylalanine
<220> FEATURE:
<221> NAME/KEY: MISC_FEATURE
<222> LOCATION: (5)..(5)
<223> OTHER INFORMATION: Xaa is D-arginine
<220> FEATURE:
<221> NAME/KEY: MISC_FEATURE
<222> LOCATION: (7)..(7)
<223> OTHER INFORMATION: Xaa is D-arginine

<400> SEQUENCE: 83

Xaa Xaa Phe Arg Xaa Arg Xaa Asp
1               5

<210> SEQ ID NO 84
<211> LENGTH: 8
<212> TYPE: PRT
<213> ORGANISM: Artificial Sequence
<220> FEATURE:
<223> OTHER INFORMATION: synthetic construct
<220> FEATURE:
<221> NAME/KEY: DISULFID
<222> LOCATION: (1)..(8)
<223> OTHER INFORMATION: Cys residues jopined by disulfide bond

<400> SEQUENCE: 84

Cys Trp Trp Arg Arg Arg Arg Cys
1               5

<210> SEQ ID NO 85
<211> LENGTH: 9
<212> TYPE: PRT
<213> ORGANISM: Artificial Sequence
<220> FEATURE:
<223> OTHER INFORMATION: synthetic construct
<220> FEATURE:
<221> NAME/KEY: DISULFID
<222> LOCATION: (1)..(9)
<223> OTHER INFORMATION: Cys residues jopined by disulfide bond

<400> SEQUENCE: 85

Cys Trp Trp Val Arg Arg Arg Arg Cys
1               5

<210> SEQ ID NO 86
<211> LENGTH: 8
<212> TYPE: PRT
<213> ORGANISM: Artificial Sequence
<220> FEATURE:
<223> OTHER INFORMATION: synthetic construct
<220> FEATURE:
<221> NAME/KEY: DISULFID
<222> LOCATION: (1)..(8)
<223> OTHER INFORMATION: Cys residues jopined by disulfide bond

<400> SEQUENCE: 86

Cys Phe Trp Arg Arg Arg Arg Cys
1               5

<210> SEQ ID NO 87
<211> LENGTH: 8
<212> TYPE: PRT
<213> ORGANISM: Artificial Sequence
<220> FEATURE:
<223> OTHER INFORMATION: synthetic construct
<220> FEATURE:
<221> NAME/KEY: DISULFID
<222> LOCATION: (1)..(8)
<223> OTHER INFORMATION: Cys residues jopined by disulfide bond

<400> SEQUENCE: 87

Cys Trp Trp Trp Arg Arg Arg Cys
1               5

<210> SEQ ID NO 88
<211> LENGTH: 7
<212> TYPE: PRT
<213> ORGANISM: Artificial Sequence
<220> FEATURE:
<223> OTHER INFORMATION: synthetic construct
<220> FEATURE:
<221> NAME/KEY: MISC_FEATURE
<222> LOCATION: (1)..(7)
<223> OTHER INFORMATION: forms a cyclic peptide
<220> FEATURE:
<221> NAME/KEY: MISC_FEATURE
<222> LOCATION: (1)..(1)
<223> OTHER INFORMATION: Xaa is L-homeoproline
<220> FEATURE:
<221> NAME/KEY: MISC_FEATURE
<222> LOCATION: (2)..(2)
<223> OTHER INFORMATION: Xaa is L-napthylalanine
<220> FEATURE:
<221> NAME/KEY: MISC_FEATURE
<222> LOCATION: (5)..(6)
<223> OTHER INFORMATION: Xaa is D-arginine
<220> FEATURE:
<221> NAME/KEY: MISC_FEATURE
<222> LOCATION: (7)..(7)
<223> OTHER INFORMATION: Xaa is D-glutamate

<400> SEQUENCE: 88

Xaa Xaa Arg Glu Xaa Xaa Xaa
1               5

<210> SEQ ID NO 89
<211> LENGTH: 7
<212> TYPE: PRT
<213> ORGANISM: Artificial Sequence
<220> FEATURE:
<223> OTHER INFORMATION: synthetic construct
<220> FEATURE:
<221> NAME/KEY: MISC_FEATURE
<222> LOCATION: (1)..(7)
<223> OTHER INFORMATION: forms a cyclic peptide
<220> FEATURE:
<221> NAME/KEY: MISC_FEATURE
<222> LOCATION: (1)..(1)
<223> OTHER INFORMATION: Xaa is L-homeoproline
<220> FEATURE:
<221> NAME/KEY: MISC_FEATURE
<222> LOCATION: (2)..(2)
<223> OTHER INFORMATION: Xaa is L-napthylalanine
<220> FEATURE:
<221> NAME/KEY: MISC_FEATURE
<222> LOCATION: (5)..(6)
<223> OTHER INFORMATION: Xaa is D-arginine
<220> FEATURE:
<221> NAME/KEY: MISC_FEATURE
<222> LOCATION: (7)..(7)
<223> OTHER INFORMATION: Xaa is D-glutamate

<400> SEQUENCE: 89

Xaa Xaa Arg Arg Xaa Xaa Xaa
1               5

<210> SEQ ID NO 90
<211> LENGTH: 7
<212> TYPE: PRT
<213> ORGANISM: Artificial Sequence -continued
<220> FEATURE:
<223> OTHER INFORMATION: synthetic construct
<220> FEATURE:
<221> NAME/KEY: MISC_FEATURE
<222> LOCATION: (1)..(7)
<223> OTHER INFORMATION: forms a cyclic peptide
<220> FEATURE:
<221> NAME/KEY: MISC_FEATURE
<222> LOCATION: (1)..(1)
<223> OTHER INFORMATION: Xaa is L-homeoproline
<220> FEATURE:
<221> NAME/KEY: MISC_FEATURE
<222> LOCATION: (2)..(3)
<223> OTHER INFORMATION: Xaa is L-napthylalanine
<220> FEATURE:
<221> NAME/KEY: MISC_FEATURE
<222> LOCATION: (5)..(6)
<223> OTHER INFORMATION: Xaa is D-arginine
<220> FEATURE:
<221> NAME/KEY: MISC_FEATURE
<222> LOCATION: (7)..(7)
<223> OTHER INFORMATION: Xaa is D-glutamate

<400> SEQUENCE: 90

Xaa Xaa Xaa Arg Xaa Xaa Xaa
1               5

<210> SEQ ID NO 91
<211> LENGTH: 7
<212> TYPE: PRT
<213> ORGANISM: Artificial Sequence
<220> FEATURE:
<223> OTHER INFORMATION: synthetic construct
<220> FEATURE:
<221> NAME/KEY: MISC_FEATURE
<222> LOCATION: (1)..(7)
<223> OTHER INFORMATION: forms a cyclic peptide
<220> FEATURE:
<221> NAME/KEY: MISC_FEATURE
<222> LOCATION: (1)..(1)
<223> OTHER INFORMATION: Xaa is L-homeoproline
<220> FEATURE:
<221> NAME/KEY: MISC_FEATURE
<222> LOCATION: (2)..(3)
<223> OTHER INFORMATION: Xaa is L-napthylalanine
<220> FEATURE:
<221> NAME/KEY: MISC_FEATURE
<222> LOCATION: (5)..(6)
<223> OTHER INFORMATION: Xaa is D-arginine

<400> SEQUENCE: 91

Xaa Xaa Xaa Arg Xaa Xaa Glu
1               5

<210> SEQ ID NO 92
<211> LENGTH: 7
<212> TYPE: PRT
<213> ORGANISM: Artificial Sequence
<220> FEATURE:
<223> OTHER INFORMATION: synthetic construct
<220> FEATURE:
<221> NAME/KEY: MISC_FEATURE
<222> LOCATION: (1)..(7)
<223> OTHER INFORMATION: forms a cyclic peptide
<220> FEATURE:
<221> NAME/KEY: MISC_FEATURE
<222> LOCATION: (1)..(1)
<223> OTHER INFORMATION: Xaa is L-homeoproline
<220> FEATURE:
<221> NAME/KEY: MISC_FEATURE
<222> LOCATION: (2)..(2)
<223> OTHER INFORMATION: Xaa is L-napthylalanine
<220> FEATURE:
<221> NAME/KEY: MISC_FEATURE
<222> LOCATION: (5)..(6)

<223> OTHER INFORMATION: Xaa is D-arginine
<220> FEATURE:
<221> NAME/KEY: MISC_FEATURE
<222> LOCATION: (7)..(7)
<223> OTHER INFORMATION: Xaa is D-glutamate

<400> SEQUENCE: 92

Xaa Xaa Phe Arg Xaa Xaa Xaa
1               5

<210> SEQ ID NO 93
<211> LENGTH: 7
<212> TYPE: PRT
<213> ORGANISM: Artificial Sequence
<220> FEATURE:
<223> OTHER INFORMATION: synthetic construct
<220> FEATURE:
<221> NAME/KEY: MISC_FEATURE
<222> LOCATION: (1)..(7)
<223> OTHER INFORMATION: forms a cyclic peptide
<220> FEATURE:
<221> NAME/KEY: MISC_FEATURE
<222> LOCATION: (1)..(1)
<223> OTHER INFORMATION: Xaa is L-homeoproline
<220> FEATURE:
<221> NAME/KEY: MISC_FEATURE
<222> LOCATION: (2)..(2)
<223> OTHER INFORMATION: Xaa is L-napthylalanine
<220> FEATURE:
<221> NAME/KEY: MISC_FEATURE
<222> LOCATION: (5)..(6)
<223> OTHER INFORMATION: Xaa is D-arginine

<400> SEQUENCE: 93

Xaa Xaa Phe Arg Xaa Xaa Glu
1               5

<210> SEQ ID NO 94
<211> LENGTH: 7
<212> TYPE: PRT
<213> ORGANISM: Artificial Sequence
<220> FEATURE:
<223> OTHER INFORMATION: synthetic construct
<220> FEATURE:
<221> NAME/KEY: MISC_FEATURE
<222> LOCATION: (1)..(7)
<223> OTHER INFORMATION: forms a cyclic peptide
<220> FEATURE:
<221> NAME/KEY: MISC_FEATURE
<222> LOCATION: (1)..(1)
<223> OTHER INFORMATION: Xaa is L-homeoproline
<220> FEATURE:
<221> NAME/KEY: MISC_FEATURE
<222> LOCATION: (2)..(2)
<223> OTHER INFORMATION: Xaa is L-napthylalanine
<220> FEATURE:
<221> NAME/KEY: MISC_FEATURE
<222> LOCATION: (3)..(3)
<223> OTHER INFORMATION: Xaa is D-phenylalanine
<220> FEATURE:
<221> NAME/KEY: MISC_FEATURE
<222> LOCATION: (5)..(6)
<223> OTHER INFORMATION: Xaa is D-arginine
<220> FEATURE:
<221> NAME/KEY: MISC_FEATURE
<222> LOCATION: (7)..(7)
<223> OTHER INFORMATION: Xaa is D-glutamate

<400> SEQUENCE: 94

Xaa Xaa Xaa Arg Xaa Xaa Xaa
1               5

<210> SEQ ID NO 95

<211> LENGTH: 7
<212> TYPE: PRT
<213> ORGANISM: Artificial Sequence
<220> FEATURE:
<223> OTHER INFORMATION: synthetic construct
<220> FEATURE:
<221> NAME/KEY: MISC_FEATURE
<222> LOCATION: (1)..(7)
<223> OTHER INFORMATION: forms a cyclic peptide
<220> FEATURE:
<221> NAME/KEY: MISC_FEATURE
<222> LOCATION: (1)..(1)
<223> OTHER INFORMATION: Xaa is L-homeoproline
<220> FEATURE:
<221> NAME/KEY: MISC_FEATURE
<222> LOCATION: (2)..(2)
<223> OTHER INFORMATION: Xaa is L-napthylalanine
<220> FEATURE:
<221> NAME/KEY: MISC_FEATURE
<222> LOCATION: (3)..(3)
<223> OTHER INFORMATION: Xaa is D-phenylalanine
<220> FEATURE:
<221> NAME/KEY: MISC_FEATURE
<222> LOCATION: (5)..(6)
<223> OTHER INFORMATION: Xaa is D-arginine

<400> SEQUENCE: 95

Xaa Xaa Xaa Arg Xaa Xaa Glu
1               5

<210> SEQ ID NO 96
<211> LENGTH: 7
<212> TYPE: PRT
<213> ORGANISM: Artificial Sequence
<220> FEATURE:
<223> OTHER INFORMATION: synthetic construct
<220> FEATURE:
<221> NAME/KEY: MISC_FEATURE
<222> LOCATION: (1)..(7)
<223> OTHER INFORMATION: forms a cyclic peptide
<220> FEATURE:
<221> NAME/KEY: MISC_FEATURE
<222> LOCATION: (1)..(1)
<223> OTHER INFORMATION: Xaa is L-homeoproline
<220> FEATURE:
<221> NAME/KEY: MISC_FEATURE
<222> LOCATION: (2)..(2)
<223> OTHER INFORMATION: Xaa is L-napthylalanine
<220> FEATURE:
<221> NAME/KEY: MISC_FEATURE
<222> LOCATION: (3)..(3)
<223> OTHER INFORMATION: Xaa is D-napthylalanine
<220> FEATURE:
<221> NAME/KEY: MISC_FEATURE
<222> LOCATION: (5)..(6)
<223> OTHER INFORMATION: Xaa is D-arginine

<400> SEQUENCE: 96

Xaa Xaa Xaa Arg Xaa Xaa Glu
1               5

<210> SEQ ID NO 97
<211> LENGTH: 7
<212> TYPE: PRT
<213> ORGANISM: Artificial Sequence
<220> FEATURE:
<223> OTHER INFORMATION: synthetic construct
<220> FEATURE:
<221> NAME/KEY: MISC_FEATURE
<222> LOCATION: (1)..(7)
<223> OTHER INFORMATION: forms a cyclic peptide
<220> FEATURE:
<221> NAME/KEY: MISC_FEATURE
<222> LOCATION: (1)..(1)
<223> OTHER INFORMATION: Xaa is L-homeoproline -continued

```
<220> FEATURE:
<221> NAME/KEY: MISC_FEATURE
<222> LOCATION: (2)..(2)
<223> OTHER INFORMATION: Xaa is L-napthylalanine
<220> FEATURE:
<221> NAME/KEY: MISC_FEATURE
<222> LOCATION: (3)..(3)
<223> OTHER INFORMATION: Xaa is D-napthylalanine
<220> FEATURE:
<221> NAME/KEY: MISC_FEATURE
<222> LOCATION: (5)..(6)
<223> OTHER INFORMATION: Xaa is D-arginine
<220> FEATURE:
<221> NAME/KEY: MISC_FEATURE
<222> LOCATION: (7)..(7)
<223> OTHER INFORMATION: Xaa is D-glutamate

<400> SEQUENCE: 97

Xaa Xaa Xaa Arg Xaa Xaa Xaa
1               5


<210> SEQ ID NO 98
<211> LENGTH: 8
<212> TYPE: PRT
<213> ORGANISM: Artificial Sequence
<220> FEATURE:
<223> OTHER INFORMATION: synthetic construct
<220> FEATURE:
<221> NAME/KEY: MISC_FEATURE
<222> LOCATION: (1)..(1)
<223> OTHER INFORMATION: Arg is modified with pimelic acid
<220> FEATURE:
<221> NAME/KEY: MISC_FEATURE
<222> LOCATION: (1)..(4)
<223> OTHER INFORMATION: Cyclization between Arg is modified with
      pimelic acid and Arg is modified with lysine peptoid residue
<220> FEATURE:
<221> NAME/KEY: MISC_FEATURE
<222> LOCATION: (4)..(4)
<223> OTHER INFORMATION: Arg is modified with lysine peptoid residue

<400> SEQUENCE: 98

Arg Gln Arg Arg Gly Arg Arg Arg
1               5


<210> SEQ ID NO 99
<211> LENGTH: 19
<212> TYPE: PRT
<213> ORGANISM: Artificial Sequence
<220> FEATURE:
<223> OTHER INFORMATION: synthetic construct
<220> FEATURE:
<221> NAME/KEY: DISULFID
<222> LOCATION: (2)..(19)
<223> OTHER INFORMATION: Cys residues jopined by disulfide bond

<400> SEQUENCE: 99

Lys Cys Phe Gln Trp Gln Arg Asn Met Arg Lys Val Arg Gly Pro Pro
1               5                   10                  15

Val Ser Cys


<210> SEQ ID NO 100
<211> LENGTH: 11
<212> TYPE: PRT
<213> ORGANISM: Artificial Sequence
<220> FEATURE:
<223> OTHER INFORMATION: synthetic construct
<220> FEATURE:
<221> NAME/KEY: MISC_FEATURE
<222> LOCATION: (1)..(11)
<223> OTHER INFORMATION: Cyclization between Lys and Glu
<220> FEATURE:
```

<221> NAME/KEY: MISC_FEATURE
<222> LOCATION: (2)..(2)
<223> OTHER INFORMATION: Xaa is D-arginine
<220> FEATURE:
<221> NAME/KEY: MISC_FEATURE
<222> LOCATION: (4)..(4)
<223> OTHER INFORMATION: Xaa is D-arginine
<220> FEATURE:
<221> NAME/KEY: MISC_FEATURE
<222> LOCATION: (6)..(6)
<223> OTHER INFORMATION: Xaa is D-arginine
<220> FEATURE:
<221> NAME/KEY: MISC_FEATURE
<222> LOCATION: (8)..(8)
<223> OTHER INFORMATION: Xaa is D-lysine
<220> FEATURE:
<221> NAME/KEY: MISC_FEATURE
<222> LOCATION: (10)..(10)
<223> OTHER INFORMATION: Xaa is D-arginine

<400> SEQUENCE: 100

Lys Xaa Arg Xaa Gly Xaa Lys Xaa Arg Xaa Glu
1               5                   10

<210> SEQ ID NO 101
<211> LENGTH: 12
<212> TYPE: PRT
<213> ORGANISM: Artificial Sequence
<220> FEATURE:
<223> OTHER INFORMATION: synthetic construct
<220> FEATURE:
<221> NAME/KEY: MISC_FEATURE
<222> LOCATION: (1)..(12)
<223> OTHER INFORMATION: Cyclization between Lys and Glu
<220> FEATURE:
<221> NAME/KEY: MISC_FEATURE
<222> LOCATION: (2)..(2)
<223> OTHER INFORMATION: Xaa is D-arginine
<220> FEATURE:
<221> NAME/KEY: MISC_FEATURE
<222> LOCATION: (4)..(4)
<223> OTHER INFORMATION: Xaa is D-arginine
<220> FEATURE:
<221> NAME/KEY: MISC_FEATURE
<222> LOCATION: (6)..(6)
<223> OTHER INFORMATION: Xaa is D-arginine
<220> FEATURE:
<221> NAME/KEY: MISC_FEATURE
<222> LOCATION: (8)..(8)
<223> OTHER INFORMATION: Xaa is D-arginine
<220> FEATURE:
<221> NAME/KEY: MISC_FEATURE
<222> LOCATION: (10)..(10)
<223> OTHER INFORMATION: Xaa is D-arginine

<400> SEQUENCE: 101

Lys Xaa Arg Xaa Arg Xaa Arg Xaa Arg Xaa Arg Glu
1               5                   10

<210> SEQ ID NO 102
<211> LENGTH: 14
<212> TYPE: PRT
<213> ORGANISM: Artificial Sequence
<220> FEATURE:
<223> OTHER INFORMATION: synthetic construct
<220> FEATURE:
<221> NAME/KEY: MISC_FEATURE
<222> LOCATION: (13)..(13)
<223> OTHER INFORMATION: Xaa is D-proline

<400> SEQUENCE: 102

Arg Val Arg Thr Arg Gly Lys Arg Arg Ile Arg Arg Xaa Pro
1               5                   10

<210> SEQ ID NO 103
<211> LENGTH: 14
<212> TYPE: PRT
<213> ORGANISM: Artificial Sequence
<220> FEATURE:
<223> OTHER INFORMATION: synthetic construct
<220> FEATURE:
<221> NAME/KEY: MISC_FEATURE
<222> LOCATION: (13)..(13)
<223> OTHER INFORMATION: Xaa is D-proline

<400> SEQUENCE: 103

Arg Thr Arg Thr Arg Gly Lys Arg Arg Ile Arg Val Xaa Pro
1               5                   10

<210> SEQ ID NO 104
<211> LENGTH: 8
<212> TYPE: PRT
<213> ORGANISM: Artificial Sequence
<220> FEATURE:
<223> OTHER INFORMATION: synthetic construct

<400> SEQUENCE: 104

Trp Arg Trp Arg Trp Arg Trp Arg
1               5

<210> SEQ ID NO 105
<211> LENGTH: 34
<212> TYPE: PRT
<213> ORGANISM: Artificial Sequence
<220> FEATURE:
<223> OTHER INFORMATION: synthetic construct
<220> FEATURE:
<221> NAME/KEY: DISULFID
<222> LOCATION: (4)..(21)
<223> OTHER INFORMATION: Cys residues jopined by disulfide bond
<220> FEATURE:
<221> NAME/KEY: DISULFID
<222> LOCATION: (11)..(23)
<223> OTHER INFORMATION: Cys residues jopined by disulfide bond
<220> FEATURE:
<221> NAME/KEY: DISULFID
<222> LOCATION: (17)..(29)
<223> OTHER INFORMATION: Cys residues jopined by disulfide bond

<400> SEQUENCE: 105

Gly Gly Val Cys Pro Lys Ile Leu Lys Lys Cys Arg Arg Asp Ser Asp
1               5                   10                  15

Cys Pro Gly Ala Cys Ile Cys Arg Gly Asn Gly Tyr Cys Gly Ser Gly
            20                  25                  30

Ser Asp

<210> SEQ ID NO 106
<211> LENGTH: 10
<212> TYPE: PRT
<213> ORGANISM: Artificial Sequence
<220> FEATURE:
<223> OTHER INFORMATION: synthetic construct
<220> FEATURE:
<221> NAME/KEY: MISC_FEATURE
<222> LOCATION: (1)..(10)
<223> OTHER INFORMATION: Macrocyclization by multicomponent reaction
      with aziridine aldehyde and isocyanide
<220> FEATURE:
<221> NAME/KEY: MISC_FEATURE
<222> LOCATION: (2)..(2)
<223> OTHER INFORMATION: Xaa is L-3-cyclohexyl-alanine
<220> FEATURE:
<221> NAME/KEY: MISC_FEATURE
<222> LOCATION: (3)..(3)

-continued

<223> OTHER INFORMATION: Xaa is D-arginine
<220> FEATURE:
<221> NAME/KEY: MISC_FEATURE
<222> LOCATION: (4)..(4)
<223> OTHER INFORMATION: Xaa is L-cyclohexylalanine
<220> FEATURE:
<221> NAME/KEY: MISC_FEATURE
<222> LOCATION: (5)..(5)
<223> OTHER INFORMATION: Xaa is D-arginine
<220> FEATURE:
<221> NAME/KEY: MISC_FEATURE
<222> LOCATION: (6)..(6)
<223> OTHER INFORMATION: Xaa is L-cyclohexylalanine
<220> FEATURE:
<221> NAME/KEY: MISC_FEATURE
<222> LOCATION: (7)..(7)
<223> OTHER INFORMATION: Xaa is D-arginine
<220> FEATURE:
<221> NAME/KEY: MISC_FEATURE
<222> LOCATION: (8)..(8)
<223> OTHER INFORMATION: Xaa is L-cyclohexylalanine
<220> FEATURE:
<221> NAME/KEY: MISC_FEATURE
<222> LOCATION: (9)..(9)
<223> OTHER INFORMATION: Xaa is D-arginine

<400> SEQUENCE: 106

Pro Xaa Xaa Xaa Xaa Xaa Xaa Xaa Xaa Gly
1               5                   10

<210> SEQ ID NO 107
<211> LENGTH: 13
<212> TYPE: PRT
<213> ORGANISM: Artificial Sequence
<220> FEATURE:
<223> OTHER INFORMATION: synthetic construct
<220> FEATURE:
<221> NAME/KEY: MISC_FEATURE
<222> LOCATION: (1)..(1)
<223> OTHER INFORMATION: Ser is modified with trimesic acid
<220> FEATURE:
<221> NAME/KEY: MISC_FEATURE
<222> LOCATION: (1)..(13)
<223> OTHER INFORMATION: N-terminal amine and side chains of two
      L-2,3-diaminopropionic acid residues bicyclized with trimesic acid
<220> FEATURE:
<221> NAME/KEY: MISC_FEATURE
<222> LOCATION: (2)..(2)
<223> OTHER INFORMATION: Xaa is D-valine
<220> FEATURE:
<221> NAME/KEY: MISC_FEATURE
<222> LOCATION: (4)..(4)
<223> OTHER INFORMATION: Xaa is L-4-(phosphonodifluoromethyl)
      phenylalanine
<220> FEATURE:
<221> NAME/KEY: MISC_FEATURE
<222> LOCATION: (6)..(6)
<223> OTHER INFORMATION: Xaa is L-2,3-diaminopropionic acid
<220> FEATURE:
<221> NAME/KEY: MISC_FEATURE
<222> LOCATION: (8)..(8)
<223> OTHER INFORMATION: Xaa is L-naphthylalanine
<220> FEATURE:
<221> NAME/KEY: MISC_FEATURE
<222> LOCATION: (13)..(13)
<223> OTHER INFORMATION: Xaa is L-2,3-diaminopropionic acid

<400> SEQUENCE: 107

Ser Xaa Pro Xaa His Xaa Phe Xaa Arg Arg Arg Arg Xaa
1               5                   10

<210> SEQ ID NO 108
<211> LENGTH: 17
<212> TYPE: PRT
<213> ORGANISM: Artificial Sequence
<220> FEATURE:
<223> OTHER INFORMATION: synthetic construct
<220> FEATURE:
<221> NAME/KEY: MISC_FEATURE
<222> LOCATION: (1)..(1)
<223> OTHER INFORMATION: D-alanine is modified with trimesic acid
<220> FEATURE:
<221> NAME/KEY: MISC_FEATURE
<222> LOCATION: (1)..(1)
<223> OTHER INFORMATION: Xaa is D-alanine
<220> FEATURE:
<221> NAME/KEY: MISC_FEATURE
<222> LOCATION: (1)..(17)
<223> OTHER INFORMATION: N-terminal amine and side chains of two
L-2,3-diaminopropionic acid residues bicyclized with trimesic acid
<220> FEATURE:
<221> NAME/KEY: MISC_FEATURE
<222> LOCATION: (2)..(2)
<223> OTHER INFORMATION: Xaa is sarcosine
<220> FEATURE:
<221> NAME/KEY: MISC_FEATURE
<222> LOCATION: (4)..(4)
<223> OTHER INFORMATION: Xaa is D-phosphothreonine
<220> FEATURE:
<221> NAME/KEY: MISC_FEATURE
<222> LOCATION: (5)..(5)
<223> OTHER INFORMATION: Xaa is L-homoproline
<220> FEATURE:
<221> NAME/KEY: MISC_FEATURE
<222> LOCATION: (6)..(6)
<223> OTHER INFORMATION: Xaa is L-naphthylalanine
<220> FEATURE:
<221> NAME/KEY: MISC_FEATURE
<222> LOCATION: (9)..(9)
<223> OTHER INFORMATION: Xaa is D-alanine
<220> FEATURE:
<221> NAME/KEY: MISC_FEATURE
<222> LOCATION: (10)..(10)
<223> OTHER INFORMATION: Xaa is L-2,3-diaminopropionic acid
<220> FEATURE:
<221> NAME/KEY: MISC_FEATURE
<222> LOCATION: (12)..(12)
<223> OTHER INFORMATION: Xaa is L-naphthylalanine
<220> FEATURE:
<221> NAME/KEY: MISC_FEATURE
<222> LOCATION: (17)..(17)
<223> OTHER INFORMATION: Xaa is L-2,3-diaminopropionic acid

<400> SEQUENCE: 108

Xaa Xaa Asp Xaa Xaa Xaa Arg Ala Xaa Xaa Phe Xaa Arg Arg Arg Arg
1               5                   10                  15

Xaa

<210> SEQ ID NO 109
<211> LENGTH: 16
<212> TYPE: PRT
<213> ORGANISM: Artificial Sequence
<220> FEATURE:
<223> OTHER INFORMATION: synthetic construct
<220> FEATURE:
<221> NAME/KEY: MISC_FEATURE
<222> LOCATION: (1)..(15)
<223> OTHER INFORMATION: Three Cys side chains bicyclized with tris
(bromomethyl)benzene

<400> SEQUENCE: 109

Cys Arg Arg Ser Arg Arg Gly Cys Gly Arg Arg Ser Arg Arg Cys Gly
1               5                   10                  15

<210> SEQ ID NO 110
<211> LENGTH: 5
<212> TYPE: PRT
<213> ORGANISM: Artificial Sequence
<220> FEATURE:

-continued

<223> OTHER INFORMATION: synthetic construct
<220> FEATURE:
<221> NAME/KEY: MISC_FEATURE
<222> LOCATION: (1)..(2)
<223> OTHER INFORMATION: linked by dodecanoyl moiety

<400> SEQUENCE: 110

Lys Arg Arg Arg Arg
1 5

<210> SEQ ID NO 111
<211> LENGTH: 16
<212> TYPE: PRT
<213> ORGANISM: Artificial Sequence
<220> FEATURE:
<223> OTHER INFORMATION: synthetic construct

<400> SEQUENCE: 111

Leu Lys Lys Leu Cys Lys Leu Leu Lys Lys Leu Cys Lys Leu Ala Gly
1 5 10 15

<210> SEQ ID NO 112
<211> LENGTH: 9
<212> TYPE: PRT
<213> ORGANISM: Artificial Sequence
<220> FEATURE:
<223> OTHER INFORMATION: synthetic construct
<220> FEATURE:
<221> NAME/KEY: MISC_FEATURE
<222> LOCATION: (5)..(9)
<223> OTHER INFORMATION: Cyclization between Lys and Glu

<400> SEQUENCE: 112

Arg Arg Arg Arg Lys Arg Arg Arg Glu
1 5

<210> SEQ ID NO 113
<211> LENGTH: 9
<212> TYPE: PRT
<213> ORGANISM: Artificial Sequence
<220> FEATURE:
<223> OTHER INFORMATION: synthetic construct
<220> FEATURE:
<221> NAME/KEY: MISC_FEATURE
<222> LOCATION: (4)..(9)
<223> OTHER INFORMATION: Cyclization between Lys and Glu

<400> SEQUENCE: 113

Arg Arg Arg Lys Arg Arg Arg Arg Glu
1 5

<210> SEQ ID NO 114
<211> LENGTH: 9
<212> TYPE: PRT
<213> ORGANISM: Artificial Sequence
<220> FEATURE:
<223> OTHER INFORMATION: synthetic construct
<220> FEATURE:
<221> NAME/KEY: MISC_FEATURE
<222> LOCATION: (3)..(9)
<223> OTHER INFORMATION: Cyclization between Lys and Glu

<400> SEQUENCE: 114

Arg Arg Lys Arg Arg Arg Arg Arg Glu
1 5

<210> SEQ ID NO 115
<211> LENGTH: 9
<212> TYPE: PRT

<213> ORGANISM: Artificial Sequence
<220> FEATURE:
<223> OTHER INFORMATION: synthetic construct
<220> FEATURE:
<221> NAME/KEY: MISC_FEATURE
<222> LOCATION: (2)..(9)
<223> OTHER INFORMATION: Cyclization between Lys and Glu

<400> SEQUENCE: 115

Arg Lys Arg Arg Arg Arg Arg Arg Glu
1               5

<210> SEQ ID NO 116
<211> LENGTH: 8
<212> TYPE: PRT
<213> ORGANISM: Artificial Sequence
<220> FEATURE:
<223> OTHER INFORMATION: synthetic construct

<400> SEQUENCE: 116

Cys Arg Cys Arg Cys Arg Cys Arg
1               5

<210> SEQ ID NO 117
<211> LENGTH: 12
<212> TYPE: PRT
<213> ORGANISM: Artificial Sequence
<220> FEATURE:
<223> OTHER INFORMATION: synthetic construct
<220> FEATURE:
<221> NAME/KEY: MISC_FEATURE
<222> LOCATION: (1)..(1)
<223> OTHER INFORMATION: Xaa is L-propargylglycine
<220> FEATURE:
<221> NAME/KEY: MISC_FEATURE
<222> LOCATION: (1)..(12)
<223> OTHER INFORMATION: Cyclization by the click reaction between
      L-propargylglycine and L-6-Azido-2-amino-hexanoic
<220> FEATURE:
<221> NAME/KEY: MISC_FEATURE
<222> LOCATION: (12)..(12)
<223> OTHER INFORMATION: Xaa is L-6-Azido-2-amino-hexanoic

<400> SEQUENCE: 117

Xaa Leu Arg Lys Arg Leu Arg Lys Phe Arg Asn Xaa
1               5                   10

<210> SEQ ID NO 118
<211> LENGTH: 9
<212> TYPE: PRT
<213> ORGANISM: Artificial Sequence
<220> FEATURE:
<223> OTHER INFORMATION: synthetic construct
<220> FEATURE:
<221> NAME/KEY: MISC_FEATURE
<222> LOCATION: (2)..(4)
<223> OTHER INFORMATION: Xaa is L-2,3-diaminopropionic acid
<220> FEATURE:
<221> NAME/KEY: MISC_FEATURE
<222> LOCATION: (5)..(5)
<223> OTHER INFORMATION: Xaa is D-phenylalanine
<220> FEATURE:
<221> NAME/KEY: MISC_FEATURE
<222> LOCATION: (7)..(8)
<223> OTHER INFORMATION: Xaa is L-2,3-diaminopropionic acid

<400> SEQUENCE: 118

Thr Xaa Xaa Xaa Xaa Leu Xaa Xaa Thr
1               5

<210> SEQ ID NO 119

-continued

<211> LENGTH: 9
<212> TYPE: PRT
<213> ORGANISM: Artificial Sequence
<220> FEATURE:
<223> OTHER INFORMATION: synthetic construct
<220> FEATURE:
<221> NAME/KEY: MISC_FEATURE
<222> LOCATION: (2)..(2)
<223> OTHER INFORMATION: Xaa is L-2-amino-3-guanidinylpropionic acid
<220> FEATURE:
<221> NAME/KEY: MISC_FEATURE
<222> LOCATION: (3)..(3)
<223> OTHER INFORMATION: Xaa is L-2,3-diaminopropionic acid
<220> FEATURE:
<221> NAME/KEY: MISC_FEATURE
<222> LOCATION: (4)..(4)
<223> OTHER INFORMATION: Xaa is L-2-amino-3-guanidinylpropionic acid
<220> FEATURE:
<221> NAME/KEY: MISC_FEATURE
<222> LOCATION: (5)..(5)
<223> OTHER INFORMATION: Xaa is D-phenylalanine
<220> FEATURE:
<221> NAME/KEY: MISC_FEATURE
<222> LOCATION: (7)..(8)
<223> OTHER INFORMATION: Xaa is L-2-amino-3-guanidinylpropionic acid

<400> SEQUENCE: 119

Thr Xaa Xaa Xaa Xaa Leu Xaa Xaa Thr
1               5

<210> SEQ ID NO 120
<211> LENGTH: 17
<212> TYPE: PRT
<213> ORGANISM: Artificial Sequence
<220> FEATURE:
<223> OTHER INFORMATION: m-xylene stapled peptidyl inhibitor
<220> FEATURE:
<221> NAME/KEY: MISC_FEATURE
<222> LOCATION: (1)..(1)
<223> OTHER INFORMATION: N-Terminal FAM dye
<220> FEATURE:
<221> NAME/KEY: MOD_RES
<222> LOCATION: (17)..(17)
<223> OTHER INFORMATION: AMIDATION

<400> SEQUENCE: 120

Gly Gly Tyr Pro Glu Cys Ile Leu Asp Cys His Leu Gln Arg Val Ile
1               5                   10                  15

Leu

<210> SEQ ID NO 121
<211> LENGTH: 25
<212> TYPE: PRT
<213> ORGANISM: Artificial Sequence
<220> FEATURE:
<223> OTHER INFORMATION: synthetic construct
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (17)..(18)
<223> OTHER INFORMATION: linked by a polyethylene glycol moiety
      (miniPEG)2
<220> FEATURE:
<221> NAME/KEY: MISC_FEATURE
<222> LOCATION: (18)..(18)
<223> OTHER INFORMATION: Xaa is L-2,3-diaminopropionic acid
<220> FEATURE:
<221> NAME/KEY: MISC_FEATURE
<222> LOCATION: (19)..(25)
<223> OTHER INFORMATION: forms a cyclic peptide
<220> FEATURE:

-continued

```
<221> NAME/KEY: MISC_FEATURE
<222> LOCATION: (19)..(19)
<223> OTHER INFORMATION: Xaa is D-phenylalanine
<220> FEATURE:
<221> NAME/KEY: MISC_FEATURE
<222> LOCATION: (20)..(20)
<223> OTHER INFORMATION: L-napthylalanine
<220> FEATURE:
<221> NAME/KEY: MISC_FEATURE
<222> LOCATION: (22)..(22)
<223> OTHER INFORMATION: Xaa is D-arginine
<220> FEATURE:
<221> NAME/KEY: MISC_FEATURE
<222> LOCATION: (24)..(24)
<223> OTHER INFORMATION: Xaa is D-arginine
<220> FEATURE:
<221> NAME/KEY: MOD_RES
<222> LOCATION: (25)..(25)
<223> OTHER INFORMATION: AMIDATION

<400> SEQUENCE: 121

Gly Gly Tyr Pro Glu Asp Ile Leu Asp Lys His Leu Gln Arg Val Ile
1               5                   10                  15

Leu Xaa Xaa Xaa Arg Xaa Arg Xaa Gln
            20                  25


<210> SEQ ID NO 122
<211> LENGTH: 25
<212> TYPE: PRT
<213> ORGANISM: Artificial Sequence
<220> FEATURE:
<223> OTHER INFORMATION: synthetic construct
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (17)..(18)
<223> OTHER INFORMATION: linked by a polyethylene glycol moiety
      (miniPEG)2
<220> FEATURE:
<221> NAME/KEY: MISC_FEATURE
<222> LOCATION: (18)..(18)
<223> OTHER INFORMATION: Xaa is L-2,3-diaminopropionic acid
<220> FEATURE:
<221> NAME/KEY: MISC_FEATURE
<222> LOCATION: (19)..(25)
<223> OTHER INFORMATION: forms a cyclic peptide
<220> FEATURE:
<221> NAME/KEY: MISC_FEATURE
<222> LOCATION: (19)..(19)
<223> OTHER INFORMATION: Xaa is D-phenylalanine
<220> FEATURE:
<221> NAME/KEY: MISC_FEATURE
<222> LOCATION: (20)..(20)
<223> OTHER INFORMATION: L-napthylalanine
<220> FEATURE:
<221> NAME/KEY: MISC_FEATURE
<222> LOCATION: (22)..(22)
<223> OTHER INFORMATION: Xaa is D-arginine
<220> FEATURE:
<221> NAME/KEY: MISC_FEATURE
<222> LOCATION: (24)..(24)
<223> OTHER INFORMATION: Xaa is D-arginine
<220> FEATURE:
<221> NAME/KEY: MOD_RES
<222> LOCATION: (25)..(25)
<223> OTHER INFORMATION: AMIDATION

<400> SEQUENCE: 122

Gly Gly Tyr Pro Glu Asp Ile Leu His Lys Asp Leu Gln Arg Val Ala
1               5                   10                  15

Leu Xaa Xaa Xaa Arg Xaa Arg Xaa Gln
```

20 25

<210> SEQ ID NO 123
<211> LENGTH: 31
<212> TYPE: PRT
<213> ORGANISM: Artificial Sequence
<220> FEATURE:
<223> OTHER INFORMATION: synthetic construct
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (17)..(18)
<223> OTHER INFORMATION: linked by a polyethylene glycol moiety
(miniPEG)2
<220> FEATURE:
<221> NAME/KEY: MISC_FEATURE
<222> LOCATION: (18)..(18)
<223> OTHER INFORMATION: Xaa is L-2,3-diaminopropionic acid
<220> FEATURE:
<221> NAME/KEY: MOD_RES
<222> LOCATION: (31)..(31)
<223> OTHER INFORMATION: AMIDATION

<400> SEQUENCE: 123

Gly Gly Tyr Pro Glu Asp Ile Leu Asp Lys His Leu Gln Arg Val Ile
1 5 10 15

Leu Xaa Gly Arg Lys Lys Arg Arg Gln Arg Arg Arg Pro Pro Gln
20 25 30

<210> SEQ ID NO 124
<211> LENGTH: 27
<212> TYPE: PRT
<213> ORGANISM: Artificial Sequence
<220> FEATURE:
<223> OTHER INFORMATION: synthetic construct
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (17)..(18)
<223> OTHER INFORMATION: linked by a polyethylene glycol moiety
(miniPEG)2
<220> FEATURE:
<221> NAME/KEY: MISC_FEATURE
<222> LOCATION: (18)..(18)
<223> OTHER INFORMATION: Xaa is L-2,3-diaminopropionic acid
<220> FEATURE:
<221> NAME/KEY: MOD_RES
<222> LOCATION: (27)..(27)
<223> OTHER INFORMATION: AMIDATION

<400> SEQUENCE: 124

Gly Gly Tyr Pro Glu Asp Ile Leu Asp Lys His Leu Gln Arg Val Ile
1 5 10 15

Leu Xaa Arg Arg Arg Arg Arg Arg Arg Arg Arg
20 25

<210> SEQ ID NO 125
<211> LENGTH: 17
<212> TYPE: PRT
<213> ORGANISM: Artificial Sequence
<220> FEATURE:
<223> OTHER INFORMATION: synthetic construct
<220> FEATURE:
<221> NAME/KEY: MOD_RES
<222> LOCATION: (1)..(1)
<223> OTHER INFORMATION: ACETYLATION -continued
<220> FEATURE:
<221> NAME/KEY: MOD_RES
<222> LOCATION: (17)..(17)
<223> OTHER INFORMATION: AMIDATION

<400> SEQUENCE: 125

Gly Gly Tyr Pro Glu Asp Ile Leu Asp Lys His Leu Gln Arg Val Ile
1               5                   10                  15

Leu

<210> SEQ ID NO 126
<211> LENGTH: 20
<212> TYPE: PRT
<213> ORGANISM: Artificial Sequence
<220> FEATURE:
<223> OTHER INFORMATION: synthetic construct
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (20)..(20)
<223> OTHER INFORMATION: Xaa is beta-alanine
<220> FEATURE:
<221> NAME/KEY: MOD_RES
<222> LOCATION: (20)..(20)
<223> OTHER INFORMATION: AMIDATION

<400> SEQUENCE: 126

Gly Gly Tyr Pro Glu Cys Ile Leu Asp Cys Lys His Leu Gln Asp Val
1               5                   10                  15

Ile Leu Lys Xaa
            20

<210> SEQ ID NO 127
<211> LENGTH: 19
<212> TYPE: PRT
<213> ORGANISM: Artificial Sequence
<220> FEATURE:
<223> OTHER INFORMATION: synthetic construct
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (19)..(19)
<223> OTHER INFORMATION: Xaa is beta-alanine
<220> FEATURE:
<221> NAME/KEY: MOD_RES
<222> LOCATION: (19)..(19)
<223> OTHER INFORMATION: AMIDATION

<400> SEQUENCE: 127

Gly Gly Tyr Pro Glu Asp Ile Leu Asp Lys His Leu Gln Cys Val Ile
1               5                   10                  15

Leu Cys Xaa

<210> SEQ ID NO 128
<211> LENGTH: 18
<212> TYPE: PRT
<213> ORGANISM: Artificial Sequence
<220> FEATURE:
<223> OTHER INFORMATION: synthetic construct
<220> FEATURE:
<221> NAME/KEY: MOD_RES
<222> LOCATION: (1)..(1)
<223> OTHER INFORMATION: ACETYLATION
<220> FEATURE:

-continued

<221> NAME/KEY: MISC_FEATURE
<222> LOCATION: (15)..(15)
<223> OTHER INFORMATION: Xaa is tert-leucine
<220> FEATURE:
<221> NAME/KEY: MISC_FEATURE
<222> LOCATION: (18)..(18)
<223> OTHER INFORMATION: Xaa is beta-alanine
<220> FEATURE:
<221> NAME/KEY: MOD_RES
<222> LOCATION: (18)..(18)
<223> OTHER INFORMATION: AMIDATION

<400> SEQUENCE: 128

Gly Gly Tyr Pro Glu Asp Ile Leu Asp Lys His Leu Gln Arg Xaa Ile
1 5 10 15

Leu Xaa

<210> SEQ ID NO 129
<211> LENGTH: 17
<212> TYPE: PRT
<213> ORGANISM: Artificial Sequence
<220> FEATURE:
<223> OTHER INFORMATION: synthetic construct
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (15)..(15)
<223> OTHER INFORMATION: Xaa is tert-leucine
<220> FEATURE:
<221> NAME/KEY: MOD_RES
<222> LOCATION: (17)..(17)
<223> OTHER INFORMATION: AMIDATION

<400> SEQUENCE: 129

Gly Gly Tyr Pro Glu Asp Ile Leu Asp Lys His Leu Gln Arg Xaa Trp
1 5 10 15

Leu

<210> SEQ ID NO 130
<211> LENGTH: 17
<212> TYPE: PRT
<213> ORGANISM: Artificial Sequence
<220> FEATURE:
<223> OTHER INFORMATION: synthetic construct
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (15)..(15)
<223> OTHER INFORMATION: Xaa is tert-leucine
<220> FEATURE:
<221> NAME/KEY: MISC_FEATURE
<222> LOCATION: (16)..(16)
<223> OTHER INFORMATION: Xaa is 3-benzothienyl-l-alanine
<220> FEATURE:
<221> NAME/KEY: MOD_RES
<222> LOCATION: (17)..(17)
<223> OTHER INFORMATION: AMIDATION

<400> SEQUENCE: 130

Gly Gly Tyr Pro Glu Asp Ile Leu Asp Lys His Leu Gln Arg Xaa Xaa
1 5 10 15

Leu

<210> SEQ ID NO 131

<211> LENGTH: 17
<212> TYPE: PRT
<213> ORGANISM: Artificial Sequence
<220> FEATURE:
<223> OTHER INFORMATION: synthetic construct
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (15)..(15)
<223> OTHER INFORMATION: Xaa is tert-leucine
<220> FEATURE:
<221> NAME/KEY: MISC_FEATURE
<222> LOCATION: (16)..(16)
<223> OTHER INFORMATION: Xaa is 1-napthylalanine
<220> FEATURE:
<221> NAME/KEY: MOD_RES
<222> LOCATION: (17)..(17)
<223> OTHER INFORMATION: AMIDATION

<400> SEQUENCE: 131

Gly Gly Tyr Pro Glu Asp Ile Leu Asp Lys His Leu Gln Arg Xaa Xaa
1               5                   10                  15

Leu

<210> SEQ ID NO 132
<211> LENGTH: 17
<212> TYPE: PRT
<213> ORGANISM: Artificial Sequence
<220> FEATURE:
<223> OTHER INFORMATION: synthetic construct
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (15)..(15)
<223> OTHER INFORMATION: Xaa is tert-leucine
<220> FEATURE:
<221> NAME/KEY: MISC_FEATURE
<222> LOCATION: (16)..(16)
<223> OTHER INFORMATION: Xaa is 2-napthylalanine
<220> FEATURE:
<221> NAME/KEY: MOD_RES
<222> LOCATION: (17)..(17)
<223> OTHER INFORMATION: AMIDATION

<400> SEQUENCE: 132

Gly Gly Tyr Pro Glu Asp Ile Leu Asp Lys His Leu Gln Arg Xaa Xaa
1               5                   10                  15

Leu

<210> SEQ ID NO 133
<211> LENGTH: 24
<212> TYPE: PRT
<213> ORGANISM: Artificial Sequence
<220> FEATURE:
<223> OTHER INFORMATION: synthetic construct
<220> FEATURE:
<221> NAME/KEY: MISC_FEATURE
<222> LOCATION: (1)..(1)
<223> OTHER INFORMATION: Xaa is D-phenylalanine
<220> FEATURE:
<221> NAME/KEY: MISC_FEATURE
<222> LOCATION: (2)..(2)
<223> OTHER INFORMATION: L-napthylalanine
<220> FEATURE:
<221> NAME/KEY: MISC_FEATURE
<222> LOCATION: (4)..(4)
<223> OTHER INFORMATION: Xaa is D-arginine
<220> FEATURE:
<221> NAME/KEY: MISC_FEATURE
<222> LOCATION: (6)..(6)
<223> OTHER INFORMATION: Xaa is D-arginine
<220> FEATURE:
<221> NAME/KEY: MISC_FEATURE
<222> LOCATION: (7)..(8)
<223> OTHER INFORMATION: linked by a polyethylene glycol moiety
(miniPEG)2
<220> FEATURE:
<221> NAME/KEY: MISC_FEATURE
<222> LOCATION: (22)..(22)
<223> OTHER INFORMATION: Xaa is tert-leucine
<220> FEATURE:
<221> NAME/KEY: MISC_FEATURE
<222> LOCATION: (23)..(23)
<223> OTHER INFORMATION: Xaa is 3-benzothienyl-l-alanine
<220> FEATURE:
<221> NAME/KEY: MOD_RES
<222> LOCATION: (24)..(24)
<223> OTHER INFORMATION: AMIDATION

<400> SEQUENCE: 133

```
Xaa Xaa Arg Xaa Arg Xaa Gln Gly Gly Tyr Pro Glu Asp Ile Leu Asp
1               5                   10                  15

Lys His Leu Gln Arg Xaa Xaa Leu
            20
```

<210> SEQ ID NO 134
<211> LENGTH: 24
<212> TYPE: PRT
<213> ORGANISM: Artificial Sequence
<220> FEATURE:
<223> OTHER INFORMATION: synthetic construct
<220> FEATURE:
<221> NAME/KEY: MISC_FEATURE
<222> LOCATION: (1)..(1)
<223> OTHER INFORMATION: Xaa is D-phenylalanine
<220> FEATURE:
<221> NAME/KEY: MISC_FEATURE
<222> LOCATION: (2)..(2)
<223> OTHER INFORMATION: L-napthylalanine
<220> FEATURE:
<221> NAME/KEY: MISC_FEATURE
<222> LOCATION: (4)..(4)
<223> OTHER INFORMATION: Xaa is D-arginine
<220> FEATURE:
<221> NAME/KEY: MISC_FEATURE
<222> LOCATION: (6)..(6)
<223> OTHER INFORMATION: Xaa is D-arginine
<220> FEATURE:
<221> NAME/KEY: MISC_FEATURE
<222> LOCATION: (7)..(8)
<223> OTHER INFORMATION: linked by a polyethylene glycol moiety
(miniPEG)2
<220> FEATURE:
<221> NAME/KEY: MISC_FEATURE
<222> LOCATION: (22)..(22)
<223> OTHER INFORMATION: Xaa is tert-leucine
<220> FEATURE:
<221> NAME/KEY: MISC_FEATURE
<222> LOCATION: (23)..(23)
<223> OTHER INFORMATION: Xaa is 2-napthylalanine
<220> FEATURE:
<221> NAME/KEY: MOD_RES
<222> LOCATION: (24)..(24)
<223> OTHER INFORMATION: AMIDATION

<400> SEQUENCE: 134

```
Xaa Xaa Arg Xaa Arg Xaa Gln Gly Gly Tyr Pro Glu Asp Ile Leu Asp
1               5                   10                  15

Lys His Leu Gln Arg Xaa Xaa Leu
            20
```

<210> SEQ ID NO 135
<211> LENGTH: 17
<212> TYPE: PRT
<213> ORGANISM: Artificial Sequence
<220> FEATURE:
<223> OTHER INFORMATION: synthetic construct
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (3)..(3)
<223> OTHER INFORMATION: Xaa is 3-benzothienyl-l-alanine
<220> FEATURE:
<221> NAME/KEY: MISC_FEATURE
<222> LOCATION: (15)..(15)
<223> OTHER INFORMATION: Xaa is tert-leucine
<220> FEATURE:
<221> NAME/KEY: MISC_FEATURE
<222> LOCATION: (16)..(16)
<223> OTHER INFORMATION: Xaa is 3-benzothienyl-l-alanine
<220> FEATURE:
<221> NAME/KEY: MOD_RES
<222> LOCATION: (17)..(17)
<223> OTHER INFORMATION: AMIDATION

<400> SEQUENCE: 135

```
Gly Gly Xaa Pro Glu Asp Ile Leu Asp Lys His Leu Gln Arg Xaa Xaa
1               5                   10                  15

Leu
```

<210> SEQ ID NO 136
<211> LENGTH: 25
<212> TYPE: PRT
<213> ORGANISM: Artificial Sequence
<220> FEATURE:
<223> OTHER INFORMATION: synthetic construct
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (15)..(15)
<223> OTHER INFORMATION: Xaa is tert-leucine
<220> FEATURE:
<221> NAME/KEY: MISC_FEATURE
<222> LOCATION: (17)..(18)
<223> OTHER INFORMATION: linked by a polyethylene glycol moiety
(miniPEG)2
<220> FEATURE:
<221> NAME/KEY: MISC_FEATURE
<222> LOCATION: (18)..(18)
<223> OTHER INFORMATION: Xaa is L-2,3-diaminopropionic acid
<220> FEATURE:
<221> NAME/KEY: MISC_FEATURE
<222> LOCATION: (19)..(25)
<223> OTHER INFORMATION: forms a cyclic peptide
<220> FEATURE:
<221> NAME/KEY: MISC_FEATURE
<222> LOCATION: (19)..(19)
<223> OTHER INFORMATION: Xaa is D-phenylalanine
<220> FEATURE:
<221> NAME/KEY: MISC_FEATURE
<222> LOCATION: (20)..(20)
<223> OTHER INFORMATION: L-napthylalanine
<220> FEATURE:
<221> NAME/KEY: MISC_FEATURE
<222> LOCATION: (22)..(22)
<223> OTHER INFORMATION: Xaa is D-arginine
<220> FEATURE:
<221> NAME/KEY: MISC_FEATURE
<222> LOCATION: (24)..(24)
<223> OTHER INFORMATION: Xaa is D-arginine

<400> SEQUENCE: 136

Gly Gly Tyr Pro Glu Asp Ile Leu Asp Lys His Leu Gln Arg Xaa Ile
1 5 10 15

Leu Xaa Xaa Xaa Arg Xaa Arg Xaa Gln
20 25

<210> SEQ ID NO 137
<211> LENGTH: 25
<212> TYPE: PRT
<213> ORGANISM: Artificial Sequence
<220> FEATURE:
<223> OTHER INFORMATION: synthetic construct
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (15)..(15)
<223> OTHER INFORMATION: Xaa is tert-leucine
<220> FEATURE:
<221> NAME/KEY: MISC_FEATURE
<222> LOCATION: (16)..(16)
<223> OTHER INFORMATION: Xaa is 3-benzothienyl-l-alanine
<220> FEATURE:
<221> NAME/KEY: MISC_FEATURE
<222> LOCATION: (17)..(18)
<223> OTHER INFORMATION: linked by a polyethylene glycol moiety (miniPEG)2
<220> FEATURE:
<221> NAME/KEY: MISC_FEATURE
<222> LOCATION: (18)..(18)
<223> OTHER INFORMATION: Xaa is L-2,3-diaminopropionic acid
<220> FEATURE:
<221> NAME/KEY: MISC_FEATURE
<222> LOCATION: (19)..(25)
<223> OTHER INFORMATION: forms a cyclic peptide
<220> FEATURE:
<221> NAME/KEY: MISC_FEATURE
<222> LOCATION: (19)..(19)
<223> OTHER INFORMATION: Xaa is D-phenylalanine
<220> FEATURE:
<221> NAME/KEY: MISC_FEATURE
<222> LOCATION: (20)..(20)
<223> OTHER INFORMATION: L-napthylalanine
<220> FEATURE:
<221> NAME/KEY: MISC_FEATURE
<222> LOCATION: (22)..(22)
<223> OTHER INFORMATION: Xaa is D-arginine
<220> FEATURE:
<221> NAME/KEY: MISC_FEATURE
<222> LOCATION: (24)..(24)
<223> OTHER INFORMATION: Xaa is D-arginine

<400> SEQUENCE: 137

Gly Gly Tyr Pro Glu Asp Ile Leu Asp Lys His Leu Gln Arg Xaa Xaa
1 5 10 15

Leu Xaa Xaa Xaa Arg Xaa Arg Xaa Gln
20 25

<210> SEQ ID NO 138
<211> LENGTH: 16
<212> TYPE: PRT
<213> ORGANISM: Artificial Sequence
<220> FEATURE:
<223> OTHER INFORMATION: synthetic construct
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (14)..(14)
<223> OTHER INFORMATION: Xaa is 3-benzothienyl-l-alanine
<220> FEATURE:
<221> NAME/KEY: MISC_FEATURE
<222> LOCATION: (15)..(16)
<223> OTHER INFORMATION: linked by a polyethylene glycol moiety
(miniPEG)2
<220> FEATURE:
<221> NAME/KEY: MISC_FEATURE
<222> LOCATION: (16)..(16)
<223> OTHER INFORMATION: Xaa is L-2,3-diaminopropionic acid
<220> FEATURE:
<221> NAME/KEY: MOD_RES
<222> LOCATION: (16)..(16)
<223> OTHER INFORMATION: AMIDATION

<400> SEQUENCE: 138

Tyr Pro Glu Asp Ile Leu Asp Lys His Leu Gln Ser Val Xaa Thr Xaa
1 5 10 15

<210> SEQ ID NO 139
<211> LENGTH: 16
<212> TYPE: PRT
<213> ORGANISM: Artificial Sequence
<220> FEATURE:
<223> OTHER INFORMATION: synthetic construct
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (14)..(14)
<223> OTHER INFORMATION: Xaa is 3-benzothienyl-l-alanine
<220> FEATURE:
<221> NAME/KEY: MISC_FEATURE
<222> LOCATION: (15)..(16)
<223> OTHER INFORMATION: linked by a polyethylene glycol moiety
(miniPEG)2
<220> FEATURE:
<221> NAME/KEY: MISC_FEATURE
<222> LOCATION: (16)..(16)
<223> OTHER INFORMATION: Xaa is L-2,3-diaminopropionic acid
<220> FEATURE:
<221> NAME/KEY: MOD_RES
<222> LOCATION: (16)..(16)
<223> OTHER INFORMATION: AMIDATION

<400> SEQUENCE: 139

Tyr Pro Glu Asp Ile Leu Asp Lys His Leu Gln Glu Val Xaa Thr Xaa
1 5 10 15

<210> SEQ ID NO 140
<211> LENGTH: 16
<212> TYPE: PRT
<213> ORGANISM: Artificial Sequence
<220> FEATURE:
<223> OTHER INFORMATION: synthetic construct
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (14)..(14)
<223> OTHER INFORMATION: Xaa is 3-benzothienyl-l-alanine
<220> FEATURE:
<221> NAME/KEY: MISC_FEATURE
<222> LOCATION: (15)..(16)
<223> OTHER INFORMATION: linked by a polyethylene glycol moiety
(miniPEG)2
<220> FEATURE:
<221> NAME/KEY: MISC_FEATURE
<222> LOCATION: (16)..(16)
<223> OTHER INFORMATION: Xaa is L-2,3-diaminopropionic acid
<220> FEATURE:
<221> NAME/KEY: MOD_RES
<222> LOCATION: (16)..(16)
<223> OTHER INFORMATION: AMIDATION

<400> SEQUENCE: 140

Tyr Pro Glu Asp Ile Leu Asp Lys His Leu Gln Gln Val Xaa Thr Xaa
1 5 10 15

<210> SEQ ID NO 141
<211> LENGTH: 16
<212> TYPE: PRT
<213> ORGANISM: Artificial Sequence
<220> FEATURE:
<223> OTHER INFORMATION: synthetic construct
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (12)..(12)
<223> OTHER INFORMATION: Xaa is D-glutamate
<220> FEATURE:
<221> NAME/KEY: MISC_FEATURE
<222> LOCATION: (14)..(14)
<223> OTHER INFORMATION: Xaa is 3-benzothienyl-l-alanine
<220> FEATURE:
<221> NAME/KEY: MISC_FEATURE
<222> LOCATION: (15)..(16)
<223> OTHER INFORMATION: linked by a polyethylene glycol moiety (miniPEG)2
<220> FEATURE:
<221> NAME/KEY: MISC_FEATURE
<222> LOCATION: (16)..(16)
<223> OTHER INFORMATION: Xaa is L-2,3-diaminopropionic acid
<220> FEATURE:
<221> NAME/KEY: MOD_RES
<222> LOCATION: (16)..(16)
<223> OTHER INFORMATION: AMIDATION

<400> SEQUENCE: 141

Tyr Pro Glu Asp Ile Leu Asp Lys His Leu Gln Xaa Val Xaa Thr Xaa
1 5 10 15

<210> SEQ ID NO 142
<211> LENGTH: 16
<212> TYPE: PRT
<213> ORGANISM: Artificial Sequence
<220> FEATURE:
<223> OTHER INFORMATION: synthetic construct
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (14)..(14)
<223> OTHER INFORMATION: Xaa is 3-benzothienyl-l-alanine
<220> FEATURE:
<221> NAME/KEY: MISC_FEATURE
<222> LOCATION: (15)..(15)
<223> OTHER INFORMATION: Xaa is D-serine
<220> FEATURE:
<221> NAME/KEY: MISC_FEATURE
<222> LOCATION: (15)..(16)
<223> OTHER INFORMATION: linked by a polyethylene glycol moiety (miniPEG)2
<220> FEATURE:
<221> NAME/KEY: MISC_FEATURE
<222> LOCATION: (16)..(16)
<223> OTHER INFORMATION: Xaa L-2,3-diaminopropionic acid
<220> FEATURE:
<221> NAME/KEY: MOD_RES
<222> LOCATION: (16)..(16)

-continued

<223> OTHER INFORMATION: AMIDATION

<400> SEQUENCE: 142

```
Tyr Pro Glu Asp Ile Leu Asp Lys His Leu Gln Ser Val Xaa Xaa Xaa
1               5                   10                  15
```

<210> SEQ ID NO 143
<211> LENGTH: 16
<212> TYPE: PRT
<213> ORGANISM: Artificial Sequence
<220> FEATURE:
<223> OTHER INFORMATION: synthetic construct
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (12)..(12)
<223> OTHER INFORMATION: Xaa is D-arginine
<220> FEATURE:
<221> NAME/KEY: MISC_FEATURE
<222> LOCATION: (15)..(16)
<223> OTHER INFORMATION: linked by a polyethylene glycol moiety
(miniPEG)2
<220> FEATURE:
<221> NAME/KEY: MISC_FEATURE
<222> LOCATION: (16)..(16)
<223> OTHER INFORMATION: Xaa is L-2,3-diaminopropionic acid
<220> FEATURE:
<221> NAME/KEY: MOD_RES
<222> LOCATION: (16)..(16)
<223> OTHER INFORMATION: AMIDATION

<400> SEQUENCE: 143

```
Tyr Pro Glu Asp Ile Leu Asp Lys His Leu Gln Xaa Val Ile Leu Xaa
1               5                   10                  15
```

<210> SEQ ID NO 144
<211> LENGTH: 16
<212> TYPE: PRT
<213> ORGANISM: Artificial Sequence
<220> FEATURE:
<223> OTHER INFORMATION: synthetic construct
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (13)..(13)
<223> OTHER INFORMATION: Xaa is D-alanine
<220> FEATURE:
<221> NAME/KEY: MISC_FEATURE
<222> LOCATION: (15)..(16)
<223> OTHER INFORMATION: linked by a polyethylene glycol moiety
(miniPEG)2
<220> FEATURE:
<221> NAME/KEY: MISC_FEATURE
<222> LOCATION: (16)..(16)
<223> OTHER INFORMATION: Xaa is L-2,3-diaminopropionic acid
<220> FEATURE:
<221> NAME/KEY: MOD_RES
<222> LOCATION: (16)..(16)
<223> OTHER INFORMATION: AMIDATION

<400> SEQUENCE: 144

```
Tyr Pro Glu Asp Ile Leu Asp Lys His Leu Gln Arg Xaa Ile Leu Xaa
1               5                   10                  15
```

<210> SEQ ID NO 145
<211> LENGTH: 16
<212> TYPE: PRT

<213> ORGANISM: Artificial Sequence
<220> FEATURE:
<223> OTHER INFORMATION: synthetic construct
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (13)..(13)
<223> OTHER INFORMATION: Xaa is tert-leucine
<220> FEATURE:
<221> NAME/KEY: MISC_FEATURE
<222> LOCATION: (14)..(14)
<223> OTHER INFORMATION: Xaa is 3-benzothienyl-l-alanine
<220> FEATURE:
<221> NAME/KEY: MISC_FEATURE
<222> LOCATION: (15)..(16)
<223> OTHER INFORMATION: linked by a polyethylene glycol moiety
(miniPEG)2
<220> FEATURE:
<221> NAME/KEY: MISC_FEATURE
<222> LOCATION: (16)..(16)
<223> OTHER INFORMATION: Xaa is L-2,3-diaminopropionic acid
<220> FEATURE:
<221> NAME/KEY: MOD_RES
<222> LOCATION: (16)..(16)
<223> OTHER INFORMATION: AMIDATION

<400> SEQUENCE: 145

Tyr Pro Glu Asp Ile Leu Asp Lys His Leu Gln Arg Xaa Xaa Arg Xaa
1 5 10 15

<210> SEQ ID NO 146
<211> LENGTH: 16
<212> TYPE: PRT
<213> ORGANISM: Artificial Sequence
<220> FEATURE:
<223> OTHER INFORMATION: synthetic construct
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (13)..(13)
<223> OTHER INFORMATION: Xaa is tert-leucine
<220> FEATURE:
<221> NAME/KEY: MISC_FEATURE
<222> LOCATION: (14)..(14)
<223> OTHER INFORMATION: Xaa is 3-benzothienyl-l-alanine
<220> FEATURE:
<221> NAME/KEY: MISC_FEATURE
<222> LOCATION: (15)..(15)
<223> OTHER INFORMATION: Xaa is D-Arg
<220> FEATURE:
<221> NAME/KEY: MISC_FEATURE
<222> LOCATION: (15)..(16)
<223> OTHER INFORMATION: linked by a polyethylene glycol moiety
(miniPEG)2
<220> FEATURE:
<221> NAME/KEY: MISC_FEATURE
<222> LOCATION: (16)..(16)
<223> OTHER INFORMATION: Xaa is L-2,3-diaminopropionic acid
<220> FEATURE:
<221> NAME/KEY: MOD_RES
<222> LOCATION: (16)..(16)
<223> OTHER INFORMATION: AMIDATION

<400> SEQUENCE: 146

Tyr Pro Glu Asp Ile Leu Asp Lys His Leu Gln Arg Xaa Xaa Xaa Xaa
1 5 10 15

<210> SEQ ID NO 147
<211> LENGTH: 16

```
<212> TYPE: PRT
<213> ORGANISM: Artificial Sequence
<220> FEATURE:
<223> OTHER INFORMATION: synthetic construct
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (14)..(14)
<223> OTHER INFORMATION: Xaa can be any naturally occurring amino acid
<220> FEATURE:
<221> NAME/KEY: MISC_FEATURE
<222> LOCATION: (15)..(16)
<223> OTHER INFORMATION: linked by a polyethylene glycol moiety
      (miniPEG)2
<220> FEATURE:
<221> NAME/KEY: MISC_FEATURE
<222> LOCATION: (16)..(16)
<223> OTHER INFORMATION: Xaa is L-2,3-diaminopropionic acid
<220> FEATURE:
<221> NAME/KEY: MOD_RES
<222> LOCATION: (16)..(16)
<223> OTHER INFORMATION: AMIDATION

<400> SEQUENCE: 147

Tyr Pro Glu Asp Ile Leu Asp Lys His Leu Gln Arg Val Xaa Leu Xaa
1               5                   10                  15


<210> SEQ ID NO 148
<211> LENGTH: 16
<212> TYPE: PRT
<213> ORGANISM: Artificial Sequence
<220> FEATURE:
<223> OTHER INFORMATION: synthetic construct
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (13)..(13)
<223> OTHER INFORMATION: Xaa is tert-leucine
<220> FEATURE:
<221> NAME/KEY: MISC_FEATURE
<222> LOCATION: (14)..(14)
<223> OTHER INFORMATION: Xaa is 3-benzothienyl-l-alanine
<220> FEATURE:
<221> NAME/KEY: MISC_FEATURE
<222> LOCATION: (15)..(16)
<223> OTHER INFORMATION: linked by a polyethylene glycol moiety
      (miniPEG)2
<220> FEATURE:
<221> NAME/KEY: MOD_RES
<222> LOCATION: (16)..(16)
<223> OTHER INFORMATION: AMIDATION

<400> SEQUENCE: 148

Tyr Pro Glu Asp Ile Leu Asp Lys His Leu Gln Arg Xaa Xaa Arg Cys
1               5                   10                  15


<210> SEQ ID NO 149
<211> LENGTH: 16
<212> TYPE: PRT
<213> ORGANISM: Artificial Sequence
<220> FEATURE:
<223> OTHER INFORMATION: synthetic construct
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (13)..(13)
```

-continued

```
<223> OTHER INFORMATION: Xaa is tert-leucine
<220> FEATURE:
<221> NAME/KEY: MISC_FEATURE
<222> LOCATION: (14)..(14)
<223> OTHER INFORMATION: Xaa is 3-benzothienyl-l-alanine
<220> FEATURE:
<221> NAME/KEY: MISC_FEATURE
<222> LOCATION: (15)..(15)
<223> OTHER INFORMATION: Xaa is D-arginine
<220> FEATURE:
<221> NAME/KEY: MISC_FEATURE
<222> LOCATION: (15)..(16)
<223> OTHER INFORMATION: linked by a polyethylene glycol moiety
      (miniPEG)2
<220> FEATURE:
<221> NAME/KEY: MOD_RES
<222> LOCATION: (16)..(16)
<223> OTHER INFORMATION: AMIDATION

<400> SEQUENCE: 149

Tyr Pro Glu Asp Ile Leu Asp Lys His Leu Gln Arg Xaa Xaa Xaa Cys
1               5                   10                  15


<210> SEQ ID NO 150
<211> LENGTH: 25
<212> TYPE: PRT
<213> ORGANISM: Artificial Sequence
<220> FEATURE:
<223> OTHER INFORMATION: synthetic construct
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (13)..(13)
<223> OTHER INFORMATION: Xaa is tert-leucine
<220> FEATURE:
<221> NAME/KEY: MISC_FEATURE
<222> LOCATION: (14)..(14)
<223> OTHER INFORMATION: Xaa is 3-benzothienyl-l-alanine
<220> FEATURE:
<221> NAME/KEY: MISC_FEATURE
<222> LOCATION: (15)..(16)
<223> OTHER INFORMATION: linked by a polyethylene glycol moiety
      (miniPEG)2
<220> FEATURE:
<221> NAME/KEY: DISULFID
<222> LOCATION: (16)..(17)
<223> OTHER INFORMATION: joined by a disulfide bond
<220> FEATURE:
<221> NAME/KEY: MISC_FEATURE
<222> LOCATION: (18)..(25)
<223> OTHER INFORMATION: forms a cyclic peptide
<220> FEATURE:
<221> NAME/KEY: MISC_FEATURE
<222> LOCATION: (19)..(19)
<223> OTHER INFORMATION: Xaa is D-phenylalanine
<220> FEATURE:
<221> NAME/KEY: MISC_FEATURE
<222> LOCATION: (20)..(20)
<223> OTHER INFORMATION: L-napthylalanine
<220> FEATURE:
<221> NAME/KEY: MISC_FEATURE
<222> LOCATION: (22)..(22)
<223> OTHER INFORMATION: Xaa is D-arginine
<220> FEATURE:
<221> NAME/KEY: MISC_FEATURE
<222> LOCATION: (24)..(24)
<223> OTHER INFORMATION: Xaa is D-arginine

<400> SEQUENCE: 150

Tyr Pro Glu Asp Ile Leu Asp Lys His Leu Gln Arg Xaa Xaa Arg Cys
1               5                   10                  15

Cys Phe Xaa Xaa Arg Xaa Arg Xaa Gln
```

-continued 20 25

<210> SEQ ID NO 151
<211> LENGTH: 25
<212> TYPE: PRT
<213> ORGANISM: Artificial Sequence
<220> FEATURE:
<223> OTHER INFORMATION: synthetic construct
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (13)..(13)
<223> OTHER INFORMATION: Xaa is tert-leucine
<220> FEATURE:
<221> NAME/KEY: MISC_FEATURE
<222> LOCATION: (14)..(14)
<223> OTHER INFORMATION: Xaa is 3-benzothienyl-l-alanine
<220> FEATURE:
<221> NAME/KEY: MISC_FEATURE
<222> LOCATION: (15)..(15)
<223> OTHER INFORMATION: Xaa is D-arginine
<220> FEATURE:
<221> NAME/KEY: MISC_FEATURE
<222> LOCATION: (15)..(16)
<223> OTHER INFORMATION: linked by a polyethylene glycol moiety
(miniPEG)2
<220> FEATURE:
<221> NAME/KEY: DISULFID
<222> LOCATION: (16)..(17)
<223> OTHER INFORMATION: joined by a disulfide bond
<220> FEATURE:
<221> NAME/KEY: MISC_FEATURE
<222> LOCATION: (18)..(25)
<223> OTHER INFORMATION: forms a cyclic peptide
<220> FEATURE:
<221> NAME/KEY: MISC_FEATURE
<222> LOCATION: (19)..(19)
<223> OTHER INFORMATION: Xaa is D-phenylalanine
<220> FEATURE:
<221> NAME/KEY: MISC_FEATURE
<222> LOCATION: (20)..(20)
<223> OTHER INFORMATION: L-napthylalanine
<220> FEATURE:
<221> NAME/KEY: MISC_FEATURE
<222> LOCATION: (22)..(22)
<223> OTHER INFORMATION: Xaa is D-arginine
<220> FEATURE:
<221> NAME/KEY: MISC_FEATURE
<222> LOCATION: (24)..(24)
<223> OTHER INFORMATION: Xaa is D-arginine

<400> SEQUENCE: 151

Tyr Pro Glu Asp Ile Leu Asp Lys His Leu Gln Arg Xaa Xaa Xaa Cys
1 5 10 15

Cys Phe Xaa Xaa Arg Xaa Arg Xaa Gln
20 25

<210> SEQ ID NO 152
<211> LENGTH: 24
<212> TYPE: PRT
<213> ORGANISM: Artificial Sequence
<220> FEATURE:
<223> OTHER INFORMATION: synthetic construct
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (13)..(13)
<223> OTHER INFORMATION: Xaa is tert-leucine
<220> FEATURE:

<221> NAME/KEY: MISC_FEATURE
<222> LOCATION: (14)..(14)
<223> OTHER INFORMATION: Xaa is 3-benzothienyl-l-alanine
<220> FEATURE:
<221> NAME/KEY: MISC_FEATURE
<222> LOCATION: (15)..(16)
<223> OTHER INFORMATION: linked by a polyethylene glycol moiety
(miniPEG)2
<220> FEATURE:
<221> NAME/KEY: DISULFID
<222> LOCATION: (16)..(17)
<223> OTHER INFORMATION: joined by a disulfide bond
<220> FEATURE:
<221> NAME/KEY: MISC_FEATURE
<222> LOCATION: (18)..(24)
<223> OTHER INFORMATION: forms a cyclic peptide
<220> FEATURE:
<221> NAME/KEY: MISC_FEATURE
<222> LOCATION: (18)..(18)
<223> OTHER INFORMATION: Xaa is D-phenylalanine
<220> FEATURE:
<221> NAME/KEY: MISC_FEATURE
<222> LOCATION: (19)..(19)
<223> OTHER INFORMATION: L-napthylalanine
<220> FEATURE:
<221> NAME/KEY: MISC_FEATURE
<222> LOCATION: (21)..(21)
<223> OTHER INFORMATION: Xaa is D-arginine
<220> FEATURE:
<221> NAME/KEY: MISC_FEATURE
<222> LOCATION: (23)..(23)
<223> OTHER INFORMATION: Xaa is D-arginine

<400> SEQUENCE: 152

```
Tyr Pro Glu Asp Ile Leu Asp Lys His Leu Gln Arg Xaa Xaa Arg Cys
1               5                   10                  15

Cys Xaa Xaa Arg Xaa Arg Xaa Gln
            20
```

<210> SEQ ID NO 153
<211> LENGTH: 24
<212> TYPE: PRT
<213> ORGANISM: Artificial Sequence
<220> FEATURE:
<223> OTHER INFORMATION: synthetic construct
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (13)..(13)
<223> OTHER INFORMATION: Xaa is tert-leucine
<220> FEATURE:
<221> NAME/KEY: MISC_FEATURE
<222> LOCATION: (14)..(14)
<223> OTHER INFORMATION: Xaa is 3-benzothienyl-l-alanine
<220> FEATURE:
<221> NAME/KEY: MISC_FEATURE
<222> LOCATION: (15)..(15)
<223> OTHER INFORMATION: Xaa is D-arginine
<220> FEATURE:
<221> NAME/KEY: MISC_FEATURE
<222> LOCATION: (15)..(16)
<223> OTHER INFORMATION: linked by a polyethylene glycol moiety
(miniPEG)2
<220> FEATURE:
<221> NAME/KEY: DISULFID
<222> LOCATION: (16)..(17)
<223> OTHER INFORMATION: joined by a disulfide bond
<220> FEATURE:
<221> NAME/KEY: MISC_FEATURE
<222> LOCATION: (18)..(24)
<223> OTHER INFORMATION: forms a cyclic peptide
<220> FEATURE:
<221> NAME/KEY: MISC_FEATURE
<222> LOCATION: (18)..(18)
<223> OTHER INFORMATION: Xaa is D-phenylalanine
<220> FEATURE:
<221> NAME/KEY: MISC_FEATURE
<222> LOCATION: (19)..(19)
<223> OTHER INFORMATION: L-napthylalanine
<220> FEATURE:
<221> NAME/KEY: MISC_FEATURE
<222> LOCATION: (21)..(21)
<223> OTHER INFORMATION: Xaa is D-arginine
<220> FEATURE:
<221> NAME/KEY: MISC_FEATURE
<222> LOCATION: (23)..(23)
<223> OTHER INFORMATION: Xaa is D-arginine

<400> SEQUENCE: 153

```
Tyr Pro Glu Asp Ile Leu Asp Lys His Leu Gln Arg Xaa Xaa Xaa Cys
1               5                   10                  15

Cys Xaa Xaa Arg Xaa Arg Xaa Gln
            20
```

<210> SEQ ID NO 154
<211> LENGTH: 25
<212> TYPE: PRT
<213> ORGANISM: Artificial Sequence
<220> FEATURE:
<223> OTHER INFORMATION: synthetic construct
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (13)..(13)
<223> OTHER INFORMATION: Xaa is tert-leucine
<220> FEATURE:
<221> NAME/KEY: MISC_FEATURE
<222> LOCATION: (14)..(14)
<223> OTHER INFORMATION: Xaa is 3-benzothienyl-l-alanine
<220> FEATURE:
<221> NAME/KEY: MISC_FEATURE
<222> LOCATION: (15)..(16)
<223> OTHER INFORMATION: linked by a polyethylene glycol moiety
(miniPEG)2
<220> FEATURE:
<221> NAME/KEY: DISULFID
<222> LOCATION: (16)..(17)
<223> OTHER INFORMATION: joined by a disulfide bond
<220> FEATURE:
<221> NAME/KEY: MISC_FEATURE
<222> LOCATION: (18)..(25)
<223> OTHER INFORMATION: forms a cyclic peptide
<220> FEATURE:
<221> NAME/KEY: MISC_FEATURE
<222> LOCATION: (19)..(19)
<223> OTHER INFORMATION: Xaa is D-phenylalanine
<220> FEATURE:
<221> NAME/KEY: MISC_FEATURE
<222> LOCATION: (20)..(20)
<223> OTHER INFORMATION: L-napthylalanine
<220> FEATURE:
<221> NAME/KEY: MISC_FEATURE
<222> LOCATION: (22)..(22)
<223> OTHER INFORMATION: Xaa is D-arginine
<220> FEATURE:
<221> NAME/KEY: MISC_FEATURE
<222> LOCATION: (24)..(24)
<223> OTHER INFORMATION: Xaa is D-arginine

<400> SEQUENCE: 154

```
Tyr Pro Glu Asp Ile Leu Asp Lys His Leu Gln Arg Xaa Xaa Arg Cys
1               5                   10                  15

Cys Phe Xaa Xaa Arg Xaa Arg Xaa Gln
            20                  25
```

<210> SEQ ID NO 155
<211> LENGTH: 25
<212> TYPE: PRT
<213> ORGANISM: Artificial Sequence
<220> FEATURE:
<223> OTHER INFORMATION: synthetic construct
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (13)..(13)
<223> OTHER INFORMATION: Xaa is tert-leucine
<220> FEATURE:
<221> NAME/KEY: MISC_FEATURE
<222> LOCATION: (14)..(14)
<223> OTHER INFORMATION: Xaa is 3-benzothienyl-l-alanine
<220> FEATURE:
<221> NAME/KEY: MISC_FEATURE
<222> LOCATION: (15)..(15)
<223> OTHER INFORMATION: Xaa is D-arginine
<220> FEATURE:
<221> NAME/KEY: MISC_FEATURE
<222> LOCATION: (15)..(16)
<223> OTHER INFORMATION: linked by a polyethylene glycol moiety
(miniPEG)2
<220> FEATURE:
<221> NAME/KEY: DISULFID
<222> LOCATION: (16)..(17)
<223> OTHER INFORMATION: joined by a disulfide bond
<220> FEATURE:
<221> NAME/KEY: MISC_FEATURE
<222> LOCATION: (18)..(25)
<223> OTHER INFORMATION: forms a cyclic peptide
<220> FEATURE:
<221> NAME/KEY: MISC_FEATURE
<222> LOCATION: (19)..(19)
<223> OTHER INFORMATION: Xaa is D-phenylalanine
<220> FEATURE:
<221> NAME/KEY: MISC_FEATURE
<222> LOCATION: (20)..(20)
<223> OTHER INFORMATION: L-napthylalanine
<220> FEATURE:
<221> NAME/KEY: MISC_FEATURE
<222> LOCATION: (22)..(22)
<223> OTHER INFORMATION: Xaa is D-arginine
<220> FEATURE:
<221> NAME/KEY: MISC_FEATURE
<222> LOCATION: (24)..(24)
<223> OTHER INFORMATION: Xaa is D-arginine

<400> SEQUENCE: 155

```
Tyr Pro Glu Asp Ile Leu Asp Lys His Leu Gln Arg Xaa Xaa Xaa Cys
1               5                   10                  15

Cys Phe Xaa Xaa Arg Xaa Arg Xaa Gln
            20                  25
```

<210> SEQ ID NO 156
<211> LENGTH: 15
<212> TYPE: PRT
<213> ORGANISM: Artificial Sequence
<220> FEATURE:
<223> OTHER INFORMATION: synthetic construct
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (13)..(13)
<223> OTHER INFORMATION: Xaa is beta-hydroxyvaline
<220> FEATURE:
<221> NAME/KEY: MOD_RES

<222> LOCATION: (15)..(15)
<223> OTHER INFORMATION: AMIDATION

<400> SEQUENCE: 156

Tyr Pro Glu Asp Ile Leu Asp Lys His Leu Gln Arg Xaa Ile Leu
1 5 10 15

<210> SEQ ID NO 157
<211> LENGTH: 15
<212> TYPE: PRT
<213> ORGANISM: Artificial Sequence
<220> FEATURE:
<223> OTHER INFORMATION: synthetic construct
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (13)..(13)
<223> OTHER INFORMATION: Xaa is beta-hydroxyvaline
<220> FEATURE:
<221> NAME/KEY: MISC_FEATURE
<222> LOCATION: (15)..(15)
<223> OTHER INFORMATION: Xaa is D-argininine
<220> FEATURE:
<221> NAME/KEY: MOD_RES
<222> LOCATION: (15)..(15)
<223> OTHER INFORMATION: AMIDATION

<400> SEQUENCE: 157

Tyr Pro Glu Asp Ile Leu Asp Lys His Leu Gln Arg Xaa Ile Xaa
1 5 10 15

<210> SEQ ID NO 158
<211> LENGTH: 25
<212> TYPE: PRT
<213> ORGANISM: Artificial Sequence
<220> FEATURE:
<223> OTHER INFORMATION: synthetic construct
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (15)..(15)
<223> OTHER INFORMATION: Xaa is beta-hydroxyvaline
<220> FEATURE:
<221> NAME/KEY: MISC_FEATURE
<222> LOCATION: (17)..(18)
<223> OTHER INFORMATION: linked by a polyethylene glycol moiety
(miniPEG)2
<220> FEATURE:
<221> NAME/KEY: MISC_FEATURE
<222> LOCATION: (18)..(18)
<223> OTHER INFORMATION: Xaa is L-2,3-diaminopropionic acid
<220> FEATURE:
<221> NAME/KEY: MISC_FEATURE
<222> LOCATION: (19)..(25)
<223> OTHER INFORMATION: forms a cyclic peptide
<220> FEATURE:
<221> NAME/KEY: MISC_FEATURE
<222> LOCATION: (19)..(19)
<223> OTHER INFORMATION: Xaa is D-phenylalanine
<220> FEATURE:
<221> NAME/KEY: MISC_FEATURE
<222> LOCATION: (20)..(20)
<223> OTHER INFORMATION: L-napthylalanine
<220> FEATURE:
<221> NAME/KEY: MISC_FEATURE
<222> LOCATION: (22)..(22)
<223> OTHER INFORMATION: Xaa is D-arginine
<220> FEATURE:
<221> NAME/KEY: MISC_FEATURE -continued

```
<222> LOCATION: (24)..(24)
<223> OTHER INFORMATION: Xaa is D-arginine

<400> SEQUENCE: 158

Gly Gly Tyr Pro Glu Asp Ile Leu Asp Lys His Leu Gln Arg Xaa Ile
1               5                   10                  15

Leu Xaa Xaa Xaa Arg Xaa Arg Xaa Gln
            20                  25
```

STAPLED BETA-CATENIN LIGANDS

CROSS REFERENCE TO RELATED APPLICATIONS

This application claims priority to U.S. Provisional Application No. 62/894,195, filed Aug. 30, 2019, which is incorporated by reference in its entirety for all purposes.

STATEMENT CONCERNING GOVERNMENT FUNDING

This invention was made with government support under grant nos. GM122459 and CA234124, each awarded by the National Institute of Health (NIH). The government has certain rights in the invention.

BACKGROUND

The Wnt signaling pathway has emerged as a key regulator for cancer stemness, metastasis, and self-regeneration. β-Catenin is an integral part of the canonical Wnt signaling cascade and is directly responsible for driving expression of Wnt target genes through interaction with transcription factor TCF. In the absence of Wnt, β-Catenin resides in a "destruction complex" and is phosphorylated, ubiquitinated, and degraded. Wnt pathway activation induces dissociation of β-Catenin from the complex, nuclear translocation and downstream gene expression. Mutations in the Wnt pathway lead to aberrant β-Catenin activation in virtually all colorectal cancers, suggesting that inhibitors against the β-Catenin-TCF interaction may provide a novel anticancer treatment. Therapeutic intervention in the periphery of the Wnt signaling pathway has raised concerns for off-target toxicity, while direct small-molecule inhibitors of the β-Catenin-TCF interaction have been met with limited translational success owing to the challenge of targeting a protein-protein interaction (PPI), as PPIs are widely considered undruggable with conventional small-molecule inhibitors.

Stapled peptides have emerged as an exciting class of therapeutic agents for targeting intracellular PPIs, which have been challenging targets for conventional small molecules and biologics. Verdine G. L., et al., *Methods Enzymol.* 503, 3-33 (2012); Walensky, L. D., et al., *J. Med. Chem.* 57, 6275-6288 (2014). Stapled peptides recapitulate the structure and specificity of bioactive α-helices, resist proteolytic degradation in vivo, and, when appropriately designed, gain access to the cytosol and nucleus of mammalian cells. The first cellular application of hydrocarbon-stapled α-helices, which were modeled after the BCL-2 homology 3 (BH3) domain of the pro-apoptotic protein BID, revealed their capacity for cellular uptake by an energy-dependent macropinocytotic mechanism, resulting in activation of the apoptotic signaling cascade. Chu, Q., et al., *Med. Chem. Commun.* 6, 111-119 (2015) (clinicaltrials.gov identifier: NCT02264613).

Despite the remarkable promise of stapled peptides as a novel class of therapeutics for targeting previously intractable proteins, designing stapled peptides with consistent cell-permeability remains a major challenge. Many factors including α-helicity, positive charge, peptide sequence, and staple composition and placement appear to affect cell uptake propensity. Recently, comprehensive analyses of several hundred stapled peptides in the Verdine and Walensky labs suggest that an optimal hydrophobic, positive charge, and helical content and proper staple placement are the key drivers of cellular uptake, whereas excess hydrophobicity and positive charge can trigger membrane lysis at elevated peptide dosing. See Chu, Q., et al., Med. Chem. Commun. 6, 111-119 (2015); *Nature Chemical Biology.* 12, 845-852 (2016). It is clear from these studies that many stapled peptides are either impermeable or poorly permeable to the cell membrane, which limits the application of stapled peptides as therapeutic agents.

The present disclosure addresses these needs.

BRIEF DESCRIPTION

The instant disclosure provides polypeptide conjugates for intracellular delivery of stapled peptidyl ligand of beta-catenin. The instant disclosure demonstrates that cyclic cell-penetrating peptides (cCPPs) can be used to confer consistent cell-permeability to stapled peptidyl ligand of beta-catenin. cCPPs offer superior cytosolic delivery efficiency as well as improved metabolic stability, bioavailability, and biodistribution. As demonstrated herein, the stapled peptidyl ligand inhibits the beta-catenin-TCF interaction, preventing aberrant beta-catenin activation. In addition, the instant disclosure several peptidyl ligands of beta-catenin.

In embodiments, the present disclosure provides for polypeptide conjugates comprising: a peptidyl ligand of beta-catenin and at least one staple which holds the peptidyl ligand of beta-catenin in an α-helical confirmation, and at least one cyclic cell-penetrating peptide (cCPP) conjugated, directly or indirectly, to the stapled peptidyl ligand. In embodiments, the cCPP of the present disclosure is conjugated directly or indirectly, to the staple. In further embodiments, the cCPP is conjugated, directly or indirectly, to the peptidyl ligand. In still further embodiments, the cCPP is conjugated, directly or indirectly, to the N-terminus of the peptide. In other embodiments, the cCPP is conjugated, directly or indirectly, to the C-terminus of the peptide. In further embodiments, the cCPP is conjugated, directly or indirectly, to a side chain of an amino acid of the peptide. In the polypeptide conjugates of the instant invention, the staple may be selected from the group consisting of an amide, alkylene, N-alkylene, alkenylene, alkynylene, aryl, cycloalkyl, cycloalkenyl, cycloalkynyl, heterocyclyl, and heteroaryl, each of which are optionally substituted.

The polypeptide conjugates of the instant invention may further comprise a linker, which is covalently bound to an amino acid on the cCPP and either an amino acid on the peptide or the staple. In some embodiments, the linker is covalently bound to the stapled peptide through a disulfide bond. In further embodiments, the linker may be selected from the group consisting of at least one amino acid, alkylene, alkenylene, alkynylene, aryl, cycloalkyl, cycloalkenyl, cycloalkynyl, heterocyclyl, heteroaryl, ether, and combinations thereof, each of which are optionally substituted. In embodiments, the linker is capable of releasing the stapled peptide from the cCPP after the polypeptide conjugate enters the cytosol of a cell.

The polypeptide conjugates of the instant invention may have a structure according to Formula IA, IB, or IC:

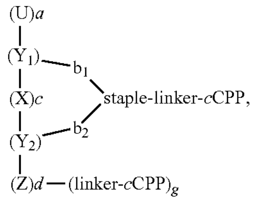

IA

-continued

IB

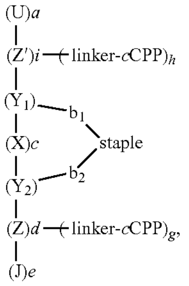

or

IC

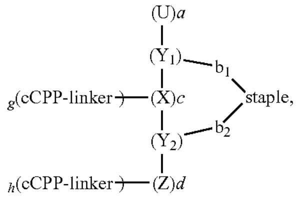

wherein:

- each of X and Z, at each instance, are independently selected from an amino acid;
- U, at each instance and when present, is independently selected from an amino acid;
- J, at each instance and when present, is independently selected from an amino acid;
- Z', at each instance and when present, is independent selected from an amino acid;
- a is a number in the range of from 0 to 500;
- c is at least 3;
- d is a number in the range of from 1 to 500;
- e is a number in the range of from 0 to 500;
- each of g and h are independently and at each instance 0 or 1, provided in at least one instance g is 1;
- i is a number in the range of from 0 to 100;
- $Y_1$ is an amino acid with a side chain that forms either a first bonding group ($b_1$) or the staple, and $Y_2$ is an amino acid with a side chain that forms either a second bonding group ($b_2$) or the staple.
- $b_1$ and $b_2$ are independently absent or present,
  - when $b_1$ is present, $b_1$ is a first bonding group formed between the side chain of $Y_1$,
  - when $b_1$ is absent, the side chain of $Y_1$ forms part of the staple,
  - when $b_2$ is present, $b_2$ is a second bonding group formed between the side chain of $Y_2$, and
  - when $b_2$ is absent, the side chain of $Y_2$ forms part of the staple.

In some embodiments, c is a number in the range of from 3 to 30. In some embodiments, c is 3, 6, or 10. In further embodiments, each of $b_1$ and $b_2$ are independently selected from a bond, aryl, thioether, disulfide, amide, ester, and ether.

In embodiments, J is absent, and Z may be either the N-terminus or the C-terminus of the peptide. In embodiments, J is present, e is 1, and J may be either the N-terminus or the C-terminus of the peptide. In further embodiments, J is present, e is 2 or more, and the terminal J is either the N-terminus or the C-terminus of the peptide. In other embodiments, U is absent, and Z' is either the N-terminus or the C-terminus of the peptide. In embodiments, U is present, a is 1, and U is either the N-terminus or the C-terminus of the peptide. In embodiments, U is present, a is 2 or more, and the terminal U is either the N-terminus or the C-terminus of the peptide.

In embodiments, the polypeptide conjugate of Formula IB may have the following structure:

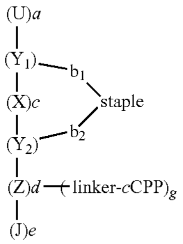

In embodiments, the polypeptide conjugate of Formula IC may have the following structure:

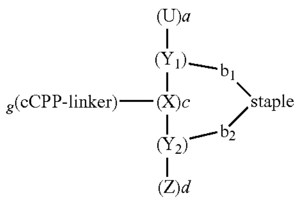

In the above formulae, the beta-catenin binding sequence is represented by $(U)_a$—$(Y_1)$—$(X)_c$—$(Y_2)$—$(Z)_d$ or $(U)_a$—$(Z')_i$—$(Y_1)$—$(X)_c$—$(Y_2)$—$(Z)_d$-$(J)_e$ In some embodiments, the stapled peptidyl beta-catenin ligand comprises at least one histidine. In some embodiments, the stapled peptidyl beta-catenin ligand comprises at least one aspartic acid. In some embodiments, the stapled peptidyl beta-catenin ligand comprises at least one isoleucine. In some embodiments, the stapled peptidyl beta-catenin ligand comprises two or more amino acids selected from the group consisting of: histidine, aspartic acid, and isoleucine. In some embodiments, the stapled peptidyl beta-catenin ligand comprises histidine, aspartic acid, and isoleucine.

In some embodiments, the stapled peptidyl beta-catenin ligand comprises an amino acid sequence that is at least 90%, at least 91%, at least 92%, at least 93%, at least 94%, at least 95%, at least 96%, at least 97%, at least 98%, or at least 99% identical to GGYPEDILDKHLQRVIL (SEQ ID NO: 1). In some embodiments, the stapled peptidyl beta-catenin ligand is GGYPEDILDKHLQRVIL (SEQ ID NO: 1).

In embodiments, the cCPP may have a sequence comprising Formula II:

$$(AA_u)_m\text{-}AA_1\text{-}AA_2\text{-}AA_3\text{-}AA_4\text{-}(AA_z)_n \quad \text{II}$$

wherein:

- each of $AA_1$, $AA_2$, $AA_3$, and $AA_4$, are independently selected from a D or L amino acid,
- each of $AA_u$ and $AA_z$, at each instance and when present, are independently selected from a D or L amino acid, and
- m and n are independently selected from a number from 0 to 6; and wherein:

- at least two amino acids selected from the group consisting of $AA_u$, at each instance and when present, $AA_1$, $AA_2$, $AA_3$, $AA_4$, and $AA_z$, at each instance and when present, are independently arginine, and at least two of amino acids selected from the group consisting $AA_u$, at each instance and when present, $AA_1$, $AA_2$, $AA_3$, $AA_4$, and $AA_z$, at each instance and when present, are independently a hydrophobic amino acid.

In some embodiments, the cCPP has a sequence comprising any of Formula IIIA-D:

$$(AAu)m—AA_{H2}—AA_{H1}—R\text{-}r\text{-}(AA_z)_n, \qquad \text{III-A}$$

$$(AAu)m\text{-}r\text{-}R—AA_{H1}—AA_{H2}—(AAz)n \qquad \text{III-B}$$

$$(AAu)m—AA_{H2}—AA_{H1}\text{-}r\text{-}R—(AAz)n, \text{ and} \qquad \text{III-C}$$

$$(AAu)m—R\text{-}r\text{-}AA_{H1}—AA_{H2}—(AAz)n; \qquad \text{III-D}$$

wherein:

each of $AA_{H1}$ and $AA_{H2}$ are independently a D or L hydrophobic amino acid;

at each instance and when present, each of $AA_U$ and $AA_Z$ are independently a D or L amino acid; and m and n are independently selected from a number from 0 to 6.

The present disclosure also provides for a cell comprising the polypeptide conjugates disclosed herein.

The present disclosure additionally provides for a method for cellular delivery of a stapled peptide, the method comprising contacting a cell with the polypeptide conjugates disclosed herein.

Further, the present disclosure provides for a method for treating a patient in need thereof, comprising administering the polypeptide conjugates disclosed herein to the patient.

Additionally, the present disclosure provides for a method for making the polypeptide conjugates disclosed herein, the method comprising conjugating a stapled peptide and a cCPP. In other embodiments, the present disclosure provides for a method for making a polypeptide conjugates disclosed herein, the method comprising conjugating a peptide to at least one cCPP, and stapling the peptide.

The present disclosure also provides for a pharmaceutical composition comprising the polypeptide conjugates disclosed herein.

DETAILED DESCRIPTION OF THE INVENTION

Figure 1:
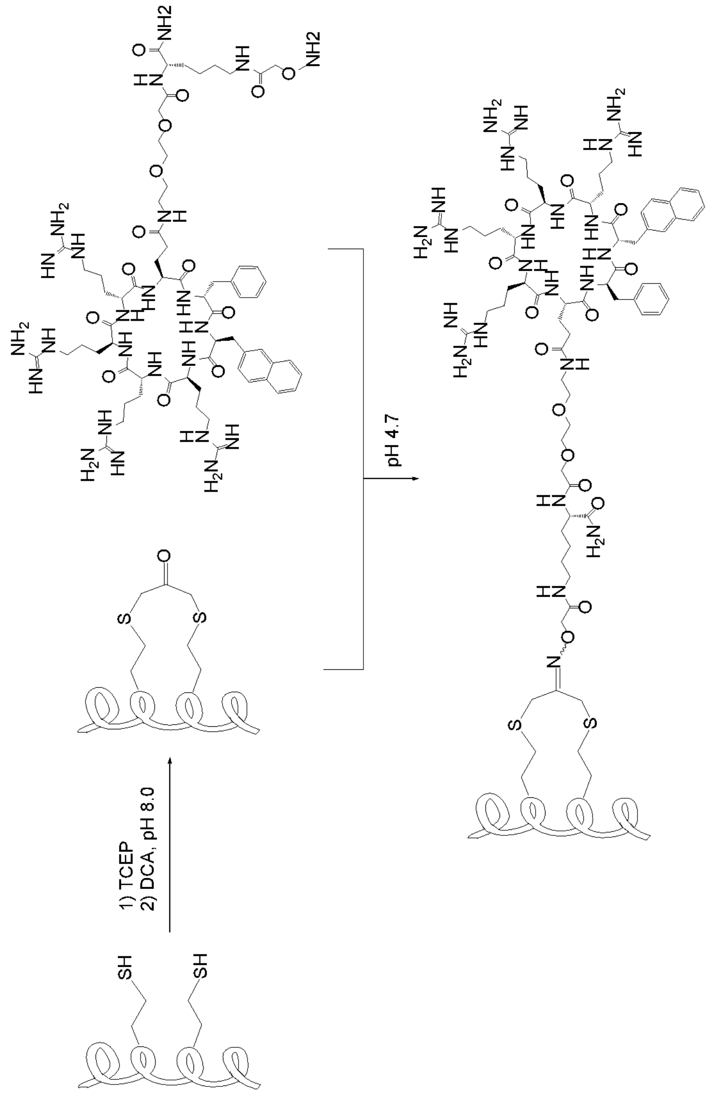
FIG. 1 is a schematic showing a strategy for synthesizing cCPP-stapled peptide conjugates with DCA as the staple.
Figure 2:
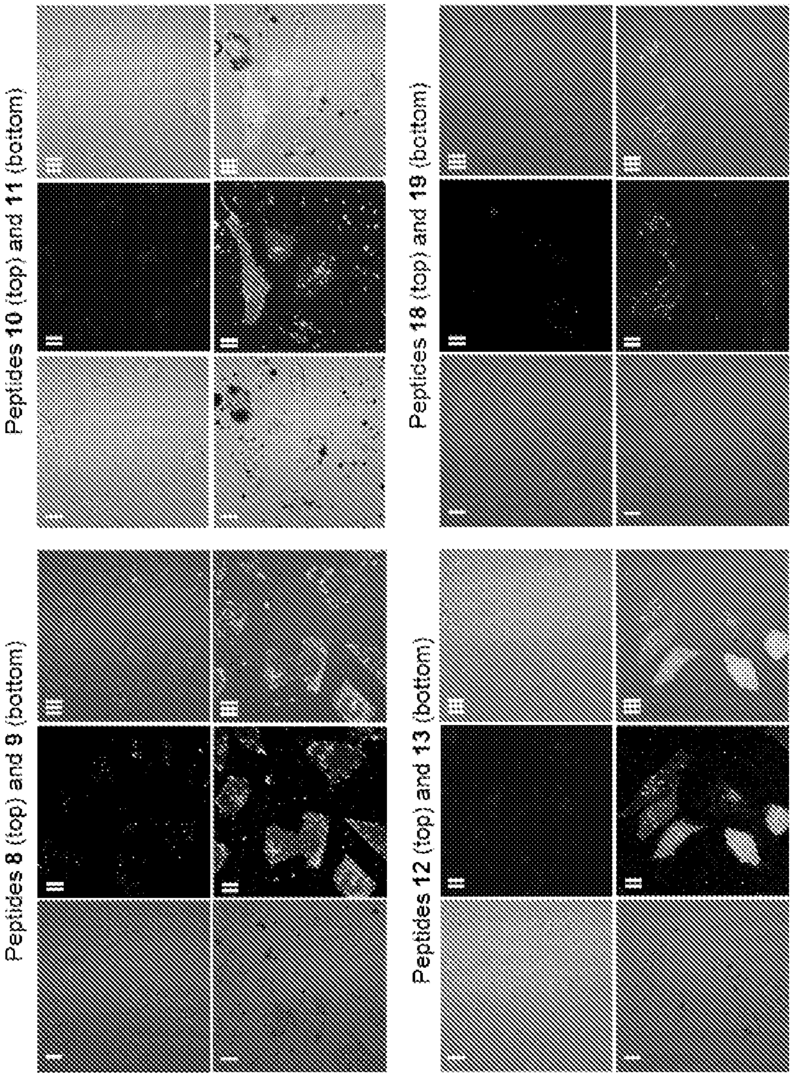
FIG. 2 shows a comparison of the cellular entry efficiency of stapled peptides with and without CPP9 conjugation.

When describing the present invention, all terms not defined herein have their common art-recognized meanings. Any term or expression not expressly defined herein shall have its commonly accepted definition understood by those skilled in the art. To the extent that the following description is of a specific embodiment or a particular use of the invention, it is intended to be illustrative only, and not limiting of the claimed invention. The following description is intended to cover all alternatives, modifications and equivalents that are included in the spirit and scope of the invention, as defined in the appended claims.

Definitions

"Amino acid" as used herein refers to the moiety that is present in the stapled peptide conjugates of the present disclosure. As used herein "hydrophobic amino acid" refers to an amino acid that has a hydrophobic group (e.g., an alkyl chain) on the side chain. Similarly, an "aromatic amino acid" refers to an amino acid having an aromatic group (e.g., a phenyl) on the side chain.

"Alkylene" or "alkylene chain" refers to a fully saturated, straight or branched divalent hydrocarbon chain radical, having from one to forty carbon atoms. Non-limiting examples of $C_2$-$C_{40}$ alkylene include ethylene, propylene, n-butylene, ethenylene, propenylene, n-butenylene, propynylene, n-butynylene, and the like. In some embodiments, the alkylene chain is attached, directly or indirectly, to the CPP through a single bond and, directly or indirectly, to the staple or the peptide through a single bond. In some embodiments, the alkylene chain is independently attached, directly or indirectly, to side chain of a first amino acid of the peptide and a second amino acid of a peptide. Unless stated otherwise specifically in the specification, an alkylene chain can be optionally substituted as described herein.

"Alkenylene" or "alkenylene chain" refers to a straight or branched divalent hydrocarbon chain radical, having from two to forty carbon atoms, and having one or more carbon-carbon double bonds. Non-limiting examples of $C_2$-$C_{40}$ alkenylene include ethene, propene, butene, and the like. In some embodiments, the alkenylene chain is attached, directly or indirectly, to the cCPP through a single bond and, directly or indirectly, to the staple or the peptide through a single bond. In some embodiments, the alkenylene chain is independently attached, directly or indirectly, to side chain of a first amino acid of the peptide and a second amino acid of a peptide. Unless stated otherwise specifically in the specification, an alkenylene chain can be optionally substituted.

"Alkynylene" or "alkynylene chain" refers to a straight or branched divalent hydrocarbon chain radical, having from two to forty carbon atoms, and having one or more carbon-carbon triple bonds. Non-limiting examples of $C_2$-$C_{40}$ alkynylene include ethynylene, propargylene and the like. In some embodiments, the alkynylene chain is attached, directly or indirectly, to the cCPP through a single bond and, directly or indirectly, to the staple or the peptide through a single bond. In some embodiments, the alkynylene chain is independently attached, directly or indirectly, to side chain of a first amino acid of the peptide and, directly or indirectly, to a second amino acid of a peptide. Unless stated otherwise specifically in the specification, an alkynylene chain can be optionally substituted.

"Aryl" refers to a hydrocarbon ring system divalent radical comprising hydrogen, 6 to 40 carbon atoms and at least one aromatic ring. For purposes of this invention, the aryl divalent radical can be a monocyclic, bicyclic, tricyclic or tetracyclic ring system, which can include fused or bridged ring systems. Aryl divalent radicals include, but are not limited to, aryl divalent radicals derived from aceanthrylene, acenaphthylene, acephenanthrylene, anthracene, azulene, benzene, chrysene, fluoranthene, fluorene, as-indacene, s-indacene, indane, indene, naphthalene, phenalene, phenanthrene, pleiadene, pyrene, and triphenylene. In some embodiments, the aryl divalent radical is attached, directly or indirectly, to the cCPP through a single bond and, directly or indirectly, to the staple or the peptide through a single bond. In some embodiments, the aryl is independently attached, directly or indirectly, to side chain of a first amino acid of the peptide and, directly or indirectly, to either the staple or a second amino acid of a peptide. Unless stated otherwise specifically in the specification, an aryl group can be optionally substituted.

"Cycloalkyl" refers to a stable non-aromatic monocyclic or polycyclic fully saturated hydrocarbon divalent radical having from 3 to 40 carbon atoms and at least one ring, wherein the ring consists solely of carbon and hydrogen atoms, which can include fused or bridged ring systems. Monocyclic cycloalkyl divalent radicals include, for example, cyclopropyl, cyclobutyl, cyclopentyl, cyclohexyl, cycloheptyl, and cyclooctyl. Polycyclic cycloalkyl divalent radicals include, for example, adamantyl, norbornyl, decalinyl, 7,7-dimethyl-bicyclo[2.2.1]heptanyl, and the like. In some embodiments, the cycloalkyl divalent radical is attached, directly or indirectly, to the cCPP through a single bond and, directly or indirectly, to the staple or the peptide through a single bond. In some embodiments, the cycloalkyl is independently attached, directly or indirectly, to side chain of a first amino acid of the peptide and, directly or indirectly, to either the staple or a second amino acid of a peptide. Unless otherwise stated specifically in the specification, a cycloalkyl group can be optionally substituted.

"Cycloalkenyl" refers to a stable non-aromatic monocyclic or polycyclic hydrocarbon divalent radical having from 3 to 40 carbon atoms, at least one ring having, and one or more carbon-carbon double bonds, wherein the ring consists solely of carbon and hydrogen atoms, which can include fused or bridged ring systems. Monocyclic cycloalkenyl radicals include, for example, cyclopentenyl, cyclohexenyl, cycloheptenyl, cycloctenyl, and the like. Polycyclic cycloalkenyl radicals include, for example, bicyclo[2.2.1]hept-2-enyl and the like. In some embodiments, the cycloalkenyl divalent radical is attached, directly or indirectly, to the CPP through a single bond and, directly or indirectly, to the staple or the peptide through a single bond. In some embodiments, the cycloalkenyl is independently attached, directly or indirectly, to side chain of a first amino acid of the peptide and, directly or indirectly, to either the staple or a second amino acid of a peptide. Unless otherwise stated specifically in the specification, a cycloalkenyl group can be optionally substituted.

"Cycloalkynyl" refers to a stable non-aromatic monocyclic or polycyclic hydrocarbon divalent radical having from 3 to 40 carbon atoms, at least one ring having, and one or more carbon-carbon triple bonds, wherein the ring consists solely of carbon and hydrogen atoms, which can include fused or bridged ring systems. Monocyclic cycloalkynyl radicals include, for example, cycloheptynyl, cyclooctynyl, and the like. In some embodiments, the cycloalkynyl divalent radical is attached, directly or indirectly, to the CPP through a single bond and, directly or indirectly, to the staple or the peptide through a single bond. In some embodiments, the cycloalkynyl is independently attached, directly or indirectly, to side chain of a first amino acid of the peptide and, directly or indirectly, to either the staple or a second amino acid of a peptide. Unless otherwise stated specifically in the specification, a cycloalkynyl group can be optionally substituted.

"Heterocyclyl," "heterocyclic ring" or "heterocycle" refers to a stable 3- to 20-membered aromatic or non-aromatic ring divalent radical which consists of two to twelve carbon atoms and from one to six heteroatoms selected from the group consisting of nitrogen, oxygen and sulfur. Heterocycycl or heterocyclic rings include heteroaryls as defined below. Unless stated otherwise specifically in the specification, the heterocyclyl radical can be a monocyclic, bicyclic, tricyclic or tetracyclic ring system, which can include fused or bridged ring systems; and the nitrogen, carbon or sulfur atoms in the heterocyclyl radical can be optionally oxidized; the nitrogen atom can be optionally quaternized; and the heterocyclyl radical can be partially or fully saturated. Examples of such heterocyclyl radicals include, but are not limited to, dioxolanyl, thienyl[1,3] dithianyl, decahydroisoquinolyl, imidazolinyl, imidazolidinyl, isothiazolidinyl, isoxazolidinyl, morpholinyl, octahydroindolyl, octahydroisoindolyl, 2-oxopiperazinyl, 2-oxopiperidinyl, 2-oxopyrrolidinyl, oxazolidinyl, piperidinyl, piperazinyl, 4-piperidonyl, pyrrolidinyl, pyrazolidinyl, quinuclidinyl, thiazolidinyl, tetrahydrofuryl, trithianyl, tetrahydropyranyl, thiomorpholinyl, thiamorpholinyl, 1-oxo-thiomorpholinyl, and 1,1-dioxo-thiomorpholinyl. In some embodiments, the heterocyclyl divalent radical is attached, directly or indirectly, to the CPP through a single bond and, directly or indirectly, to the staple or the peptide through a single bond. In some embodiments, the heterocyclyl is independently attached, directly or indirectly, to side chain of a first amino acid of the peptide and, directly or indirectly, to either the staple or a second amino acid of a peptide. Unless stated otherwise specifically in the specification, a heterocyclyl group can be optionally substituted.

"Heteroaryl" refers to a 5- to 20-membered ring system radical comprising hydrogen atoms, one to thirteen carbon atoms, one to six heteroatoms selected from the group consisting of nitrogen, oxygen and sulfur, and at least one aromatic ring. For purposes of this invention, the heteroaryl radical can be a monocyclic, bicyclic, tricyclic or tetracyclic ring system, which can include fused or bridged ring systems; and the nitrogen, carbon or sulfur atoms in the heteroaryl radical can be optionally oxidized; the nitrogen atom can be optionally quaternized. Examples include, but are not limited to, azepinyl, acridinyl, benzimidazolyl, benzothiazolyl, benzindolyl, benzodioxolyl, benzofuranyl, benzooxazolyl, benzothiazolyl, benzothiadiazolyl, benzo[b][1,4]dioxepinyl, 1,4-benzodioxanyl, benzonaphthofuranyl, benzoxazolyl, benzodioxolyl, benzodioxinyl, benzopyranyl, benzopyranonyl, benzofuranyl, benzofuranonyl, benzothienyl (benzothiophenyl), benzotriazolyl, benzo[4,6]imidazo[1,2-a]pyridinyl, carbazolyl, cinnolinyl, dibenzofuranyl, dibenzothiophenyl, furanyl, furanonyl, isothiazolyl, imidazolyl, indazolyl, indolyl, indazolyl, isoindolyl, indolinyl, isoindolinyl, isoquinolyl, indolizinyl, isoxazolyl, naphthyridinyl, oxadiazolyl, 2-oxoazepinyl, oxazolyl, oxiranyl, 1-oxidopyridinyl, 1-oxidopyrim idinyl, 1-oxidopyrazinyl, 1-oxidopyridazinyl, 1-phenyl-1H-pyrrolyl, phenazinyl, phenothiazinyl, phenoxazinyl, phthalazinyl, pteridinyl, purinyl, pyrrolyl, pyrazolyl, pyridinyl, pyrazinyl, pyrimidinyl, pyridazinyl, quinazolinyl, quinoxalinyl, quinolinyl, quinuclidinyl, isoquinolinyl, tetrahydroquinolinyl, thiazolyl, thiadiazolyl, triazolyl, tetrazolyl, triazinyl, and thiophenyl (i.e. thienyl). In some embodiments, the heteroaryl divalent radical is attached, directly or indirectly, to the CPP through a single bond and, directly or indirectly, to the staple or the peptide through a single bond. In some embodiments, the heteroaryl is independently attached, directly or indirectly, to side chain of a first amino acid of the peptide and, directly or indirectly, to either the staple or a second amino acid of a peptide. Unless stated otherwise specifically in the specification, a heteroaryl group can be optionally substituted.

The term "ether" used herein refers to a divalent radical moiety having a formula $—[(R_1)_m—O—(R_2)_n]_z—$ wherein each of m, n, and z are independently selected from 1 to 40, and each of $R_1$ and $R_2$ are independently an alkylene, alkenylene, alkynylene, aryl, heteroaryl, cycloalkyl, cycloalkenyl, cycloalkynyl, or heterocyclyl group. In some embodiments, each of $R_1$ and $R_2$ are independently straight or branched alkylene groups. In particular embodiments, the ether has the formula $—[(CH_2)_m—O—(CH_2)_n]_z—$ wherein each of m, n, and z are independently selected from 1 to 40. Examples include polyethylene glycol. The ether is attached, directly or indirectly, to the CPP through a single bond and, directly or indirectly, to the staple or the peptide through a single bond. Unless stated otherwise specifically in the specification, the ether can be optionally substituted.

The term "N-alkylene" used herein refers to an alkylene divalent radical as defined above containing at least one nitrogen atom and where a point of attachment of the alkylene radical to the rest of the molecule is through the alkylene radical. In some embodiments, the point of attachment may optionally be the nitrogen atom. Unless stated otherwise specifically in the specification, a N-alkylene group can be optionally substituted.

As used herein, a "peptide" or "polypeptide" comprises a polymer of amino acid residues linked together by peptide (amide) bonds. The term(s), as used herein, refer to proteins, polypeptides, and peptide of any size, structure, or function. Typically, a peptide or polypeptide will be at least three amino acids long. A peptide or polypeptide may refer to an individual protein or a collection of proteins. The peptides of the instant invention may contain natural amino acids and/or non-natural amino acids (i.e., compounds that do not occur in nature but that can be incorporated into a polypeptide chain). Amino acid analogs as are known in the art may alternatively be employed. One or more of the amino acids in a peptide or polypeptide may be modified, for example, by the addition of a chemical entity such as a carbohydrate group, a hydroxyl group, a phosphate group, a farnesyl group, an isofarnesyl group, a fatty acid group, a linker for conjugation, functionalization, or other modification. A peptide or polypeptide may also be a single molecule or may be a multi-molecular complex, such as a protein. A peptide or polypeptide may be just a fragment of a naturally occurring protein or peptide. A peptide or polypeptide may be naturally occurring, recombinant, or synthetic, or any combination thereof.

"Stapling" or "peptide stapling" is a strategy for constraining peptides typically in an alpha-helical conformation. Stapling is carried out by covalently linking the side-chains of two amino acids on a peptide, thereby forming a peptide macrocycle. Stapling generally involves introducing into a peptide at least two moieties capable of undergoing reaction to generate at least one cross-linker between the at least two moieties. The moieties may be two amino acids with appropriate side chains that are introduced into peptide sequence or the moieties may refer to chemical modifications of side chains. Stapling provides a constraint on a secondary structure, such as an alpha-helical structure. The length and geometry of the cross-linker can be optimized to improve the yield of the desired secondary structure content. The constraint provided can, for example, prevent the secondary structure from unfolding and/or can reinforce the shape of the secondary structure. A secondary structure that is prevented from unfolding is, for example, more stable.

A "stapled peptide" or "stapled peptidyl ligand" is a peptide comprising a staple (as described in detail herein). More specifically, a stapled peptide is a peptide in which one or more amino acids on the peptide are cross-linked to hold the peptide in a particular secondary structure, such as an alpha-helical conformation. The peptide of a stapled peptide comprises a selected number of natural or non-natural amino acids, and further comprises at least two moieties which undergo a reaction to generate at least one cross-linker between the at least two moieties, which modulates, for example, peptide stability.

A "stitched" peptide, is a stapled peptide comprising more than one (e.g., two, three, four, five, six, etc.) staple.

The term "substituted" used herein means any of the above groups (i.e., alkylene, alkenylene, alkynylene, aryl, carbocyclyl, cycloalkyl, cycloalkenyl, cycloalkynyl, heterocyclyl, heteroaryl, and/or ether) wherein at least one hydrogen atom is replaced by at least one non-hydrogen atom such as, but not limited to: a halogen atom such as F, CI, Br, and I; an oxygen atom in groups such as hydroxyl groups, alkoxy groups, and ester groups; a sulfur atom in groups such as thiol groups, thioalkyl groups, sulfone groups, sulfonyl groups, and sulfoxide groups; a nitrogen atom in groups such as amines, amides, alkylamines, dialkylamines, arylamines, alkylarylamines, diarylamines, N-oxides, imides, and enamines; a silicon atom in groups such as trialkylsilyl groups, dialkylarylsilyl groups, alkyldiarylsilyl groups, and triarylsilyl groups; and other heteroatoms in various other groups. "Substituted" also means any of the above groups in which one or more hydrogen atoms are replaced by a higher-order bond (e.g., a double- or triple-bond) to a heteroatom such as oxygen in oxo, carbonyl, carboxyl, and ester groups; and nitrogen in groups such as imines, oximes, hydrazones, and nitriles. For example, "substituted" includes any of the above groups in which one or more hydrogen atoms are replaced with $—NR_gR_h$, $—NR_gC(=O)R_h$, $—NR_gC(=O)NR_gR_h$, $—NR_gC(=O)OR_h$, $—NR_gSO_2R_h$, $—OC(=O)NR_gR_h$, $—OR_g$, $—SR_g$, $—SOR_g$, $—SO_2R_g$, $—OSO_2R_g$, $—SO_2OR_g$, $=NSO_2R_g$, and $—SO_2NR_gR_h$. "Substituted also means any of the above groups in which one or more hydrogen atoms are replaced with $—C(=O)R_g$, $—C(=O)OR_g$, $—C(=O)NR_gR_h$, $—CH_2SO_2R_g$, $—CH_2SO_2NR_gR_h$. In the foregoing, $R_g$ and $R_h$ are the same or different and independently hydrogen, alkyl, alkenyl, alkynyl, alkoxy, alkylamino, thioalkyl, aryl, aralkyl, cycloalkyl, cycloalkenyl, cycloalkynyl, cycloalkylalkyl, haloalkyl, haloalkenyl, haloalkynyl, heterocyclyl, N-heterocyclyl, heterocyclylalkyl, heteroaryl, N-heteroaryl and/or heteroarylalkyl. "Substituted" further means any of the above groups in which one or more hydrogen atoms are replaced by a bond to an amino, cyano, hydroxyl, imino, nitro, oxo, thioxo, halo, alkyl, alkenyl, alkynyl, alkoxy, alkylamino, thioalkyl, aryl, aralkyl, cycloalkyl, cycloalkenyl, cycloalkynyl, cycloalkylalkyl, haloalkyl, haloalkenyl, haloalkynyl, heterocyclyl, N-heterocyclyl, heterocyclylalkyl, heteroaryl, N-heteroaryl and/or heteroarylalkyl group. In addition, each of the foregoing substituents can also be optionally substituted with one or more of the above substituents. Further, those skilled in the art will recognize that "substituted" also encompasses instances in which one or more hydrogen atoms on any of the groups described herein are replaced by a functional group, and the functional group undergoes a reaction to form a covalent bond with the CPP, the staple or the peptide. The reaction product is also considered a substituent. For example, in embodiments where the linker is conjugated to the staple, the staple may be appropriately substituted with a group that is capable of forming a bond to the linker. In some embodiments, said sample may be substituted with a carbonyl group (e.g., ketone or aldehyde), which forms an oxime upon coupling with the linker having a nucleophilic hydroxylamine (e.g., FIG. 1). In another example, any of the above groups can be substituted at a first position with a carboxylic acid (i.e., $—C(=O)OH$) which forms an amide bond with an appropriate amino acid CPP (e.g., lysine). Alternatively, or in addition, any of the above groups can be substituted with either an electrophilic group (e.g., $—C(=O)H$, $—CO_2R_g$, -halide, etc. where $R_g$ is a leaving group) which forms a bond with the N-terminus of the peptide or a nucleophilic group ($—NH_2$, $—NHR_g$, —OH, etc.) which forms a bond with the C-terminus of the peptide. In other embodiments, the group is substituted with a thiol group which forms a disulfide bond with a cysteine (or amino acid analog having a thiol group) in the peptide.

The term "radical" as used herein in reference to the above groups refer to an electron that participates in forming a bond to the moiety to which it is attached. For example, when the polypeptide conjugates disclosed herein comprise an ether linker which conjugates the CCP to the stapled peptide. Prior to conjugation, the either linker is defined as a divalent radical. To form the polypeptide conjugate one electron of the divalent radical is shared in a single bond to the CPP, and the other electron is shared in a single bond with the stapled peptide.

The term "indirectly" when used in conjunction with attached or conjugated refers to a connection between groups (e.g., a cCPP and a stapled peptide), which is achieved using a linker. For example, a linker can be used to indirectly attach a cCPP to a staple, according to some embodiments.

As used herein, the term "sequence identity" refers to the percentage of amino acids between two polypeptide sequences that are the same and in the same relative position. As such one polypeptide sequence has a certain percentage of sequence identity compared to another polypeptide sequence. For sequence comparison, typically one sequence acts as a reference sequence, to which test sequences are compared. Those of ordinary skill in the art will appreciate that two sequences are generally considered to be "substantially identical" if they contain identical residues in corresponding positions. In some embodiments, the sequence identity between two amino acid sequences may be determined using the Needleman-Wunsch algorithm (Needleman and Wunsch, 1970, J. Mol. Biol. 48: 443-453) as implemented in the Needle program of the EMBOSS package (EMBOSS: The European Molecular Biology Open Software Suite, Rice et al., 2000, Trends Genet. 16: 276-277), in the version that exists as of the date of filing. The parameters used are gap open penalty of 10, gap extension penalty of 0.5, and the EBLOSUM62 (EMBOSS version of BLOSUM62) substitution matrix. The output of Needle labeled "longest identity" (obtained using the –nobrief option) is used as the percent identity and is calculated as follows: (Identical Residues×100)/(Length of Alignment-Total Number of Gaps in Alignment)

In other embodiments, sequence identity may be determined using the Smith-Waterman algorithm, in the version that exists as of the date of filing.

As used herein, "sequence homology" refers to the percentage of amino acids between two polypeptide sequences that are homologous and in the same relative position. As such one polypeptide sequence has a certain percentage of sequence homology compared to another polypeptide sequence. As will be appreciated by those of ordinary skill in the art, two sequences are generally considered to be "substantially homologous" if they contain homologous residues in corresponding positions. Homologous residues may be identical residues. Alternatively, homologous residues may be non-identical residues with appropriately similar structural and/or functional characteristics. For example, as is well known by those of ordinary skill in the art, certain amino acids are typically classified as "hydrophobic" or "hydrophilic" amino acids, and/or as having "polar" or "non-polar" side chains, and substitution of one amino acid for another of the same type may often be considered a "homologous" substitution.

As is well known in this art, amino acid sequences may be compared using any of a variety of algorithms, including those available in commercial computer programs such as BLASTP, gapped BLAST, and PSI-BLAST, in existence as of the date of filing. Exemplary such programs are described in Altschul, et al., Basic local alignment search tool, J. Mol. Biol., 215(3): 403-410, 1990; Altschul, et al., *Methods in Enzymology*; Altschul, et al., "Gapped BLAST and PSI-BLAST: a new generation of protein database search programs", *Nucleic Acids Res.* 25:3389-3402, 1997; Baxevanis, et al., *Bioinformatics A Practical Guide to the Analysis of Genes and Proteins*, Wiley, 1998; and Misener, et al., (eds.), *Bioinformatics Methods and Protocols* (Methods in Molecular Biology, Vol. 132), Humana Press, 1999. In addition to identifying homologous sequences, the programs mentioned above typically provide an indication of the degree of homology.

The terms "hydrophilic" and polar" in reference to an amino acid refer to amino acids that are soluble in water.

The terms "hydrophobic" and "nonpolar" in reference to an amino acid refer to amino acids that are insoluble in water.

Polypeptide Conjugates

The present disclosure, in various embodiments, provides for polypeptide conjugates comprising: a stapled peptide comprising a peptide and at least one staple which holds the peptide in an α-helical confirmation, and at least one cell-penetrating peptide (CPP) conjugated, directly or indirectly, to the stapled peptidyl beta-catenin ligand. The CPP can be conjugated to the stapled peptidyl beta-catenin ligand at any suitable location. In some embodiments, the CPP may be conjugated directly or indirectly, to the staple. In other embodiments, the CPP may be conjugated, directly or indirectly, to the peptide at any appropriate position, including to a side chain of an amino acid in the peptide or to the N- or C-terminus of the peptide. Thus, in some embodiments, the CPP may be conjugated, directly or indirectly, to the N-terminus of the peptide. In other embodiments, the CPP may be conjugated, directly or indirectly, to the C-terminus of the peptide. In still other embodiments, the CPP may be conjugated, directly or indirectly, to a side chain of an amino acid of the peptide. The CPP may be linear or cyclic.

In some embodiments, the CPP is a linear cell penetrating sequence.

In some embodiments, the CPP is a cyclic cell-penetrating sequence, which is referred to herein as cCPP.

The polypeptide conjugates of the instant invention may have a structure according to Formula IA, IB, or IC:

IA

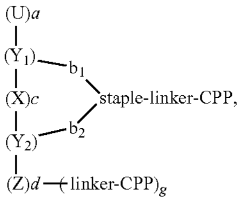

-continued

IB

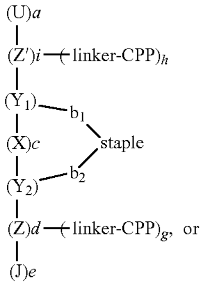

IC

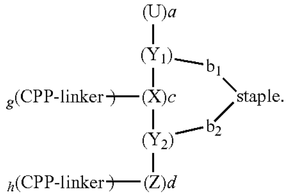

In some embodiments, each of X and Z, at each instance, are independently selected from an amino acid. In some embodiments, U, at each instance and when present, is independently selected from an amino acid. In some embodiments, J, at each instance and when present, is independently selected from an amino acid. In some embodiments, Z', at each instance and when present, is independent selected from an amino acid.

In some embodiments, d is a number in the range of from 1 to 500. In some embodiments, e is a number in the range of from 0 to 500. In some embodiments, i is a number in the range of from 0 to 100.

In some embodiments, each of g and h are independently and at each instance 0 or 1, provided in at least instance g is 1. Thus, in some embodiments, the peptide conjugates may comprise one CPP-linker moiety (e.g., when d=1, g=1, and h=0 in Formula IB) or more than one CPP-linker moiety (e.g., when d=2, g=2, and h=0 in Formula IB; or when d=10, g=2, and h=0 in Formula IB). In some embodiments, Z' is absent, i.e. i=0.

In some embodiments, a is a number in the range of from 0 to 500. In some embodiments, c is at least 3. In some embodiments, c may be any number, 3 or greater, such that the staple (as described herein) is the same face of the alpha helix. In some embodiments, c is 3, 6, or 10. In further embodiments, each of $b_1$ and $b_2$ are independently selected from a bond, aryl, thioether, disulfide, amide, ester, and ether.

In some embodiments, $Y_1$ is an amino acid which has a side chain which forms a first bonding group ($b_1$) that connects the peptidyl ligand to the staple, and $Y_2$ is an amino acid which has a side chain which forms a second bonding group ($b_2$) that connects the peptidyl ligand to the staple.

In some embodiments, $b_1$ and $b_2$ are independently absent. When $b_1$ is absent, the side chain of $Y_1$ forms part of the staple. When $b_2$ is absent, the side chain of $Y_2$ forms part of the staple.

The present disclosure envisions that the structures of Formula IA, IB, or IC can be interpreted as having an N to C or C to N orientation. That is, the top of the structure can be either the N-terminus or the C-terminus. Similarly, the bottom of the structure can be either the C-terminus or the N-terminus. In embodiments, J is absent, Z' is absent (i.e. i=0) and Z may be either the N-terminus or the C-terminus of the peptide. In embodiments, is present, e is 1, and J may be either the N-terminus or the C-terminus of the peptide. In further embodiments, J is present, e is 2 or more, and the terminal J is either the N-terminus or the C-terminus of the peptide. In other embodiments, U is absent, and Z' is either the N-terminus or the C-terminus of the peptide. In embodiments, U is present, a is 1, and U is either the N-terminus or the C-terminus of the peptide. In embodiments, U is present, a is 2 or more, and the terminal U is either the N-terminus or the C-terminus of the peptide.

In embodiments, the polypeptide conjugate of Formula IB may have the following structure Formula IB1:

IB1

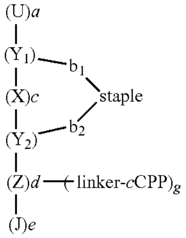

In embodiments, the polypeptide conjugate of Formula IB may have the following structure Formula IB2, in which J is absent (i.e. e=0), d=0-20, c=0-20, and a=0-20.

IB2

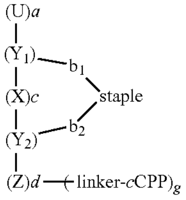

In embodiments, the polypeptide conjugate of Formula IB2 comprises a structure in which d=1-10, c=3-10, g=1-10, and a=0-10.

In embodiments, the polypeptide conjugate of Formula IB2 comprises a structure in which d=1-5, g=1-5, c=3-4, and a=1-5.

In embodiments, the polypeptide conjugate of Formula IB2 comprises a structure in which d=1-8, g=1-5, c=3-8, and a=0-8.

In embodiments, the beta-catenin binding sequence (e.g. $(U)_a$—$Y_1$—$(X)_c$—$Y_2$—$(Z)_d$) of Formula IB2 comprises a structure comprising between about 10 amino acids and about 30 amino acids, for example, about 10, about 11, about 12, about 13, about 14, about 15, about 16, about 17, about 18, about 19, about 20, about 21, about 22, about 23, about 24, about 25, about 26, about 27, about 28, about 29, or about 30 amino acids. In embodiments, the beta-catenin binding sequence (e.g. $(U)_a$—$Y_1$—$(X)_c$—$Y_2$—$(Z)_d$) of Formula IB2 comprises a structure comprising between about 10 amino acids and about 20 amino acids, for example, about 10, about 11, about 12, about 13, about 14, about 15, about 16, about 17, about 18, about 19, or about 20 amino acids. In embodiments, the beta-catenin binding sequence (e.g. $(U)_a$—$Y_1$—$(X)_c$—$Y_2$—$(Z)_d$) of Formula IB2 comprises a structure comprising about 15 amino acids. In embodiments, the beta-catenin binding sequence (e.g. $(U)_a$—$Y_1$—$(X)_c$—$Y_2$—$(Z)_d$) of Formula IB2 comprises a structure comprising about 17 amino acids. In embodiments, the beta-catenin binding sequence (e.g. $(U)_a$—$Y_1$—$(X)_c$—$Y_2$—$(Z)_d$) of Formula IB2 comprises at least two glycines. In embodiments, the beta-catenin binding sequence (e.g. $(U)_a$—$Y_1$—$(X)_c$—$Y_2$—$(Z)_d$) of Formula IB2 comprises at least two leucines. In embodiments, the beta-catenin binding sequence (e.g. $(U)_a$—$Y_1$— $(X)_c$—$Y_2$—$(Z)_d$) of Formula IB2 comprises at least three leucines. In embodiments, $(X)_{c3}$=Asp. In embodiments, $(Z)_{d1}$=His. In embodiments, $(Z)_{d6}$=Ile. In embodiments $(Z)_{d5}$=Val. In embodiments, $(Z)_{d5}$=tert-leucine. In embodiments $(Z)_{d5}$=Hvl.

In embodiments, position $Y_1$ of Formula IB2 is aspartic acid, and position $Y_2$ of Formula IB2 is lysine.

In embodiments, $Y_1$ of Formula IB2 is lysine and $Y_2$ is aspartic acid.

In embodiments, $(U)_a$ is represented by a contiguous amino acid sequence. For example, when a=20, $(U)_a$ is $(U)_{a1}$—$(U)_{a2}$—$(U)_{a3}$—$(U)_{a4}$—$(U)_{a5}$—$(U)_{a6}$—$(U)_{a7}$—$(U)_{a8}$—$(U)_{a9}$—$(U)_{a10}$—$(U)_{a11}$—$(U)_{a12}$—$(U)_{a13}$—$(U)_{a14}$—$(U)_{a15}$—$(U)_{a16}$—$(U)_{a17}$—$(U)_{a18}$—$(U)_{a19}$—$(U)_{a20}$. $(U)_a$ is a terminal amino acid. In further embodiments, $(U)_{a1}$ is the N-terminal or C-terminal amino acid. If a=5, $(U)_5$ is represented by the sequence $(U)_{a1}$—$(U)_{a2}$—$(U)_{a3}$—$(U)_{a4}$—$(U)_{a5}$ In embodiments, $(X)_c$ is represented by the linear amino acid sequence. For example, when c=3 (e.g., when $Y_1$ is at position i and $Y_2$ is at position i+4), $(X)_c$ is $(X)_{c1}$—$(X)_{c2}$—$(X)_{c3}$. If c=6 (e.g., when $Y_1$ is at position i and $Y_2$ is at position i+7), $(X)_5$ is represented by the sequence $(X)_{c1}$—$(X)_{c2}$—$(X)_{c3}$—$(X)_{c4}$—$(X)_{c5}$.

In embodiments, $(Z)_d$ is represented by a linear amino acid sequence. For example, when d=20, $(Z)_d$ is $(Z)_{d1}$—$(Z)_{d2}$—$(Z)_{d3}$—$(Z)_{d4}$—$(Z)_{d5}$—$(Z)_{d6}$—$(Z)_{d7}$—$(Z)_{d8}$—$(Z)_{d9}$—$(Z)_{d10}$—$(Z)_{d11}$—$(Z)_{d12}$—$(Z)_{d13}$—$(Z)_{d14}$—$(Z)_{d15}$—$(Z)_{d16}$—$(Z)_{d17}$—$(Z)_{d18}$—$(Z)_{d19}$—$(Z)_{d20}$. If d=5, $(Z)_5$ is represented by the sequence $(Z)_{d1}$—$(Z)_{d2}$—$(Z)_{d3}$—$(Z)_{d4}$—$(Z)_{d5}$.

$(Z)_d$ is a terminal amino acid. In further embodiments, $(Z)_{d1}$ is the N-terminal or C-terminal amino acid.

In embodiments, c=3.

In embodiments, a=5, c=3, and d=7. In embodiments, the peptide sequence of Formula IB2 is $(U)_5$—$Y_1$—$(X)_3$—$Y_2$—$(Z)_6$. In such embodiments, Formula IB2 can be represented as $(U)_{a1}$—$(U)_{a2}$—$(U)_{a3}$—$(U)_{a4}$—$(U)_{a5}$—$Y_1$—$(X)_{c1}$—$(X)_{c2}$—$(X)_{c3}$—$Y_2$—$(Z)_{d1}$— $(Z)_{d2}$—$(Z)_{d3}$—$(Z)_{d4}$—$(Z)_{d5}$—$(Z)_{d6}$—$(Z)_{d7}$. In embodiments, a=3, c=3, and d=7. In embodiments, the peptide sequence of Formula IB2 is (U)3—Y1—(X)3—Y2—(Z)6. In such embodiments, Formula IB2 can be represented as (U)a1—(U)a2—(U)a3—Y1—(X)c1—(X)c2—(X)c3—Y2—(Z)d1—(Z)d2—(Z)d3—(Z)d4—(Z)d5—(Z)d6—(Z)d7.

In embodiments, $(X)_{c3}$=Asp.

In embodiments, $(Z)_{d1}$=His.

In embodiments, $(Z)_{d6}$=Ile.

In embodiments $(Z)_{d5}$=Val. In embodiments, $(Z)_{d5}$=tert-leucine. In embodiments $(Z)_{d5}$=Hvl.

In embodiments, the polypeptide conjugate of Formula IC may have the following structure:

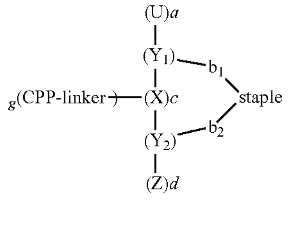

Stapled Peptidyl Beta-Catenin Ligand

The beta-catenin ligand for use in the polypeptide conjugates disclosed herein may be any peptide which contains at least one region having alpha-helical structure and which inhibits the beta-catenin-TCF interaction. In some embodiments, the beta-catenin ligand has a $K_D \leq 1$ μM. In some embodiments, the inhibitor has a $K_D \leq 0.1$ μM. In some embodiments, the inhibitor has a $K_D \leq 0.010$ μM. In some embodiments, the inhibitor has a $K_D \leq 0.0010$ μM. In some embodiments, the inhibitor has a $K_D \leq 0.00010$ μM. In some embodiments, the inhibitor has a $K_D \leq 0.000010$ μM. In some embodiments, the inhibitor has a $K_D \leq 0.0000010$ μM.

The alpha-helix is a common secondary structure motif and plays an important functional role in many proteins. In some embodiments, the peptide may be mostly in alpha-helical conformation, or the peptide may be part of a larger protein that includes one or more alpha-helical regions. As discussed above, the staple is appropriately located to substantially maintain the alpha-helical conformation.

The peptide may be naturally occurring, or it may be specifically designed to interact with a target (e.g., to inhibit protein-protein interactions). In some embodiments, the peptide may be derived from a naturally occurring peptide, in which appropriate modifications to facilitate conjugation with the staple, linker, and/or cCPP, or combinations thereof can be made. Thus, the amino acids in the peptide (each of X, Z, U, J, $Y_1$, $Y_2$, and Z', at each instance and when present) are independently selected from any natural or non-natural amino acid, and may independently refer to amino acids that naturally occur in the peptide or are introduced into the peptide. The term "non-natural amino acid" refers to an organic compound that is analog of a natural amino acid in that it has a structure similar to a natural amino acid so that it mimics the structure and reactivity of a natural amino acid. The non-natural amino acid can be a modified amino acid, and/or amino acid analog, that is not one of the 20 common naturally occurring amino acids or the rare natural amino acids selenocysteine or pyrrolysine. Non-natural amino acids can also be the D-isomer of the natural amino acids. Examples of suitable amino acids include, but are not limited to, alanine, allosoleucine, arginine, asparagine, aspartic acid, cysteine, glutamine, glutamic acid, glycine, histidine, isoleucine, leucine, lysine, methionine, napthylalanine, phenylalanine, proline, pyroglutamic acid, serine, threonine, tryptophan, tyrosine, valine, 2,3-diaminopropionic acid, tert-leucine, 1-napthylalanine (1-Nal), 2-napthylalanine (2-Nap), β-hydroxyvaline (Hvl), 3-benzothienyl-1-alanine (3-Bta), and derivatives or combinations thereof. These, and others, are listed in the Table 1 along with their abbreviations used herein.

TABLE 1

Amino Acid Abbreviations

| Amino Acid | Abbreviations* L-amino acid | Abbreviations* D-amino acid |
|---|---|---|
| Alanine | Ala (A) | ala (a) |
| Allosoleucine | Aile | aile |
| Arginine | Arg (R) | arg (r) |
| Asparagine | Asn (N) | asn (n) |
| aspartic acid | Asp (D) | asp (d) |
| Cysteine | Cys (C) | cys (c) |
| Cyclohexylalanine | Cha | cha |
| 2,3-diaminopropionic acid | Dap | dap |
| 4-fluorophenylalanine | Fpa (Σ) | pfa |
| glutamic acid | Glu (E) | glu (e) |
| glutamine | Gln (Q) | gln (q) |
| glycine | Gly (G) | gly (g) |
| histidine | His (H) | his (h) |
| Homoproline (aka pipecolic acid) | Pip (Θ) | Pip (θ) |
| isoleucine | Ile (I) | ile (i) |
| leucine | Leu (L) | leu (l) |
| lysine | Lys (K) | lys (k) |
| methionine | Met (M) | met (m) |
| napthylalanine | Nal (Φ) | nal (φ) |
| norleucine | Nle (Ω) | nle |
| phenylalanine | Phe (F) | phe (f) |
| phenylglycine | Phg (Ψ) | phg |
| 4-(phosphonodifluoromethyl)phenylalanine | $F_2$Pmp (/\) | $f_2$pmp |
| proline | Pro (P) | pro (p) |
| sarcosine | Sar (Ξ) | sar |
| Selenocysteine | Sec (U) | sec (u) |
| Serine | Ser (S) | ser (s) |
| Threonine | Thr (T) | thr (y) |
| Tyrosine | Tyr (Y) | tyr (y) |
| Tryptophan | Trp (W) | trp (w) |
| Valine | Val (V) | val (v) |
| 2,3-diaminopropionic acid | Dap | Dap |
| Tert-leucine | Tle | tle |
| Ornithine | Orn | orn |

*single letter abbreviations: when shown in capital letters herein it indicates the L-amino acid form, when shown in lower case herein it indicates the D-amino acid.

One example of a ligand of the β-Catenin protein is Ac-GGYPEDILDKHLQRVIL (SEQ ID NO: 2). This ligand is capable of binding to the β-Catenin protein and therefore disrupting the interaction of TCF with β-Catenin. The β-Catenin/TCF interaction leads to aberrant Wnt signaling, resulting in cancer development and growth.

In some embodiments, the polypeptide conjugate comprises a beta-catenin ligand that is at least 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% identical to GGYPEDILDKHLQRVIL (SEQ ID NO: 1). In some embodiments, the beta-catenin ligand comprises one or more amino-acid substitutions, insertions, or deletions as described herein. Persons skilled in the art can, using routine recombinant genetic techniques, generate and screen libraries of peptides comprising such amino-acid substitutions, insertions, or deletions. Skilled persons can use molecular modeling to select mutations that are likely to be structurally tolerated, e.g. deletion in loops, insertion in loops, deletion of domains, C-terminal truncations, and N-terminal truncations.

In some embodiments, one or more amino acids in the sequence Ac-GGYPEDILDKHLQRVIL (SEQ ID NO: 2) be substituted. The substitutions may be conservative or non-conservative.

Examples of conservative amino acid substitutions include substitution of one amino acid for another amino acid within one from one of the following groups: basic amino acids (arginine, lysine and histidine), acidic amino acids (glutamic acid and aspartic acid), polar amino acids (glutamine and asparagine), hydrophobic amino acids (leucine, isoleucine and valine), aromatic amino acids (phenylalanine, tryptophan and tyrosine), and small amino acids (glycine, alanine, serine, threonine and methionine). In some embodiments, structurally similar amino acids are substituted to reverse the charge of a residue (e.g., glutamine for glutamic acid or vice-versa, aspartic acid for asparagine or vice-versa). In some embodiments, tyrosine is substituted for phenylalanine or vice-versa. Other non-limiting examples of amino acid substitutions are described, for example, by H. Neurath and R. L. Hill, 1979, *In, The Proteins*, Academic Press, New York. Common substitutions are Ala/Ser, Val/Ile, Asp/Glu, Thr/Ser, Ala/Gly, Ala/Thr, Ser/Asn, Ala/Val, Ser/Gly, Tyr/Phe, Ala/Pro, Lys/Arg, Asp/Asn, Leu/Ile, Leu/Val, Ala/Glu, and Asp/Gly. Such substitutions may (in addition or in the alternative) include non-conservative substitutions, e.g., where an amino acid that does not participate in binding to β-catenin is replaced by an amino acid which interacts favorably with β-catenin.

In some embodiments, the amino acid sequence of the beta-catenin ligand comprises at least one histidine. In some embodiments, the amino acid sequence of the beta-catenin ligand comprises at least one aspartate. In some embodiments, the amino acid sequence of the beta-catenin ligand comprises at least one isoleucine. In some embodiments, the amino acid sequence of the beta-catenin ligand comprises two or more amino acids selected from the consisting of histidine, aspartate, and isoleucine. In some embodiments, the amino acid sequence of the beta-catenin ligand comprises histidine, aspartate, and lysine. In some embodiments, the beta-catenin ligand contains one or more of (e.g., any two of or all three of) the histidine, aspartate, and isoleucine in the sequence Ac-GGYPEDILDKHLQRVIL (SEQ ID NO: 2), and one or more of the remaining amino acids are substituted with any other amino acid (i.e., either conservatively or non-conservatively).

In some embodiments, the beta-catenin ligand comprises the amino acid sequence of Formula IB2, wherein the amino acids at each position are selected from Table 2A.

TABLE 2A

| Non-limiting examples of amino acids that may be present in the beta-catenin ligand of Formula IB2 | | |
|---|---|---|
| Position | Properties of amino acids | Non-limiting Examples of Amino Acids * |
| $(U)_{a1}$ | Non-polar side chain | Ala, Gly, Ile, Leu, Met, Phe, Pro, Trp, Val, Tle, Trp, 3-Bta, 1-Nal, 2-Nal, Hvl |
| $(U)_{a2}$ | Non-polar side chain | Ala, Gly, Ile, Leu, Met, Phe, Pro, Trp, Val, Tle, Trp, 3-Bta, 1-Nal, 2-Nal, Hvl |
| $(U)_{a3}$ | Polar side chain | Asn, Cys, Gin, Ser, Thr, Tyr |
| $(U)_{a4}$ | Non-polar side chain | Ala, Gly, Ile, Leu, Met, Phe, Pro, Trp, Val, Tle, Trp, 3-Bta, 1-Nal, 2-Nal, Hvl |
| $(U)_{a5}$ | Acidic side chain | Asp, Glu |
| $Y_1$ | Any amino acid that can be used to create a staple | Asp, Lys, Glu, Arg, Orn, Cys |
| $(X)c_1$ | Non-polar side chain | Ala, Gly, Ile, Leu, Met, Phe, Pro, Trp, Val, Tle, Trp, 3-Bta, 1-Nal, 2-Nal, Hvl |
| $(X)c_2$ | Non-polar side chain | Ala, Gly, Ile, Leu, Met, Phe, Pro, Trp, Val, Tle, Trp, 3-Bta, 1-Nal, 2-Nal, Hvl |
| $(X)c_3$ | Negatively charged amino acid or hydrogen bond acceptor | Asp, Glu |
| $Y_2$ | Any amino acid that can be used to create a staple | Lys, Asp, Glu, Arg, Orn, Cys |
| $(Z)_{d1}$ | Positively charged amino acid or hydrogen bond donor | His |
| $(Z)_{d2}$ | Non-polar side chain | Ala, Gly, Ile, Leu, Met, Phe, Pro, Trp, Val, Tle, Trp, 3-Bta, 1-Nal, 2-Nal, Hvl |
| $(Z)_{d3}$ | Polar side chain | Asn, Cys, Gln, Ser, Thr, Tyr, |
| $(Z)_{d4}$ | Positively charged side chain | Arg, His, Lys |
| $(Z)_{d5}$ | Non-polar side chain | Ala, Gly, Ile, Leu, Met, Phe, Pro, Trp, Val, Tle, Trp, 3-Bta, 1-Nal, 2-Nal, Hvl |
| $(Z)_{d6}$ | Hydrophobic amino acid | Ile, Leu, Met, Phe, Pro, Trp, Val, Tle, Trp, 3-Bta, 1-Nal, 2-Nal, Hvl |
| $(Z)_{d7}$ | Non-polar side chain | Ala, Gly, Ile, Leu, Met, Phe, Pro, Trp, Val, Tle, Trp, 3-Bta, 1-Nal, 2-Nal, Hvl |

* Amino acids can be in the L-configuration or the D-configuration.

In some embodiments, the beta-catenin ligand comprises the amino acid sequence of Formula IB2, wherein the amino acids at each position are selected from Table 2B.

TABLE 2B

| Non-limiting examples of amino acids that may be present in the beta-catenin ligand of Formula IB2 | | |
|---|---|---|
| Position | Properties of amino acids | Non-limiting Examples of Amino Acids * |
| $(U)_{a1}$ | Non-polar side chain or absent | Gly |
| $(U)_{a2}$ | Non-polar side chain or absent | Gly |
| $(U)_{a3}$ | Aromatic Side Chain | Tyr |
| $(U)_{a4}$ | Non-polar side chain | Pro |
| $(U)_{a5}$ | Acidic side chain | Glu |
| $Y_1$ | Any amino acid that can be used to create a staple | Asp, Lys, Glu, Arg, Orn, Cys |
| $(X)_{c1}$ | Non-polar side chain | Ile |
| $(X)_{c2}$ | Non-polar side chain | Leu |
| $(X)_{c3}$ | Negatively charged amino acid or hydrogen bond acceptor | Asp, Glu |

TABLE 2B-continued

Non-limiting examples of amino acids that may be present in the beta-catenin ligand of Formula IB2

| Position | Properties of amino acids | Non-limiting Examples of Amino Acids * |
|---|---|---|
| $Y_2$ | Any amino acid that can be used to create a staple | Lys, Asp, Glu, Arg, Orn, Cys |
| $(Z)_{d1}$ | Positively charged amino acid or hydrogen bond donor | His |
| $(Z)_{d2}$ | Non-polar side chain | Leu |
| $(Z)_{d3}$ | Polar side chain | Gln |
| $(Z)_{d4}$ | Polar Side Chain | Arg, His, Lys, Ser, Gln, Asn, Thr, Glu, Asp |
| $(Z)_{d5}$ | Non-polar side chain | Val, Hvl, Tle |
| $(Z)_{d6}$ | Hydrophobic amino acid | Ile, Trp, 3-Bta, 1-Nal, 2-Nal |
| $(Z)_{d7}$ | Various | Leu, Thr, Ser, Arg |

* Amino acids can be in the L-configuration or the D-configuration. "Absent" refers to an amino acid that may not be included in Formula IB2. In some embodiments, Formula IB2 does not contain amino acids at positions $(U)_{a1}$ or $(U)_{a2}$.

In other embodiments, the beta-catenin ligand for use in the present disclosure comprises E-cadherin, Lef-1, phosphorylated adenomatous polyposis *coli* (APC), APC, and axin. See J Biol Chem. 2006 Jan. 13; 281(2):1027-38. Epub 2005 Nov. 17.

In some embodiments, the disclosed polypeptide conjugate comprises a beta-catenin ligand comprising f LSQEQLEHRERSLQTLRIDQRMLF (SEQ ID NO: 3). In some embodiments, the polypeptide conjugate comprises beta-catenin ligand that is at least 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% identical to LSQEQLEHRERSLQTLRIDQRMLF (SEQ ID NO: 3). Any two of the amino acids of LSQEQLEHRERSLQTLRIDQRMLF (SEQ ID NO: 3) can be replaced with amino acids suitable for forming a staple. For example, in some embodiments, the beta-catenin ligand comprises LSQEQLEHRXRSLXTLRDIQRMLF (SEQ ID NO: 4), where X is any amino acid which can be utilized to form a staple. In some embodiments, the beta-catenin ligand comprises f LSQEQLEHRERSLQTLRDIQRLLF (SEQ ID NO: 5). In some embodiments, the beta-catenin ligand comprising an amino acid sequence that is at least 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% identical to LSQEQLEHRERSLQTLRDIQRLLF (SEQ ID NO: 5). Any two of the amino acids of LSQEQLEHRERSLQTLRIDQRMLF (SEQ ID NO: 3) can be replaced with amino acids suitable for forming a staple. In some embodiments, the beta-catenin ligand comprises StAx or StAx-35R (RRWPRXILDXHVRRVWR (SEQ ID NO: 6)), wherein X is two amino acids, which can be stapled. For example, hydrophobic amino acids are mutated to hydrophobic amino acids. Hydrophilic amino acids are mutated to amino acids which contain hydrogen bonding groups and/or ionic side chains.

In some embodiments, the peptides for use in the present disclosure are acetylated, acylated, methylated, propionylated, myristoylated, or palmitoylated on the N-terminus. See Proteomics. 2015 July; 15(14): 2385-2401.

In other embodiments, the peptides for use in the present disclosure are amidated on the C-terminus.

The protein β-Catenin comprises a N-terminal region, a central armadillo arm repeat domain, and a C-terminal tail. See The Journal of Biological Chemistry, Vol. 281, No. 2, pp. 1027-1038, Jan. 13, 2006

In some embodiments, the peptides of the present disclosure bind to the N-terminal region of β-Catenin.

In other embodiments, the peptides of the present disclosure bind to the C-terminal tail of β-Catenin.

In other embodiments, the peptides of the present disclosure bind to the central armadillo arm repeat domain of β-Catenin.

In some embodiments, the peptides of the present disclosure bind to the N-terminal region and C-terminal tail of β-Catenin.

In some embodiments, the peptides of the present disclosure bind to the N-terminal region and central armadillo arm repeat domain of β-Catenin.

In some embodiments, the peptides of the present disclosure bind to the C-terminal tail and central armadillo arm repeat domain of β-Catenin.

In some embodiments, the peptides of the present disclosure bind to the C-terminal tail, central armadillo arm repeat domain, and N-terminal region of β-Catenin.

In some embodiments, the beta-catenin ligand has a Kd of 500 nM or less, e.g., about 500 nM, about 400 nM, about 300 nM, about 200 nM, about 100 nM, about 75 nM, about 50 nM, about 25 nM, about 1 nM, 0.1 nM, about 0.01 nM, about 0.001, or less, inclusive of all values and ranges therebetween.

In some embodiments, the beta-catenin ligand has an IC50 of 500 nM or less, e.g., about 500 nM, about 400 nM, about 300 nM, about 200 nM, about 100 nM, about 75 nM, about 50 nM, about 25 nM, about 1 nM, 0.1 nM, about 0.01 nM, about 0.001, or less, inclusive of all values and ranges therebetween.

Staple

The staple described herein stabilizes the bioactive, alpha-helical structure of the peptide, conferring, for example, protease resistance, cellular penetrance, and biological activity. The staple may be any synthetic brace capable of holding the peptide in an alpha-helical conformation. In embodiments, the staple reinforces the native alpha-helical conformation of the peptide, thereby maintaining binding affinity towards its protein targets.

Methods for peptide stapling are known to those of skill in the art. In some embodiments, peptide stapling may require generation of a polypeptide comprising two natural or non-natural amino acids (i.e., precursors of $Y_1$ and $Y_2$) bearing side chains with functional groups that are suitable for stapling. In certain embodiments, the sides of the precursors of $Y_1$ and $Y_2$ can react to form the staple. In other embodiments, the side precursors of $Y_1$ and $Y_2$ have side chains suitable for conjugating a staple (i.e., side chains with appropriate functional groups to bind the staple by forming of bonding groups, $b_1$ or $b_2$). In still other embodiments, the staple is formed by replacing an intramolecular hydrogen bond with a covalent bond, for example by replacing the hydrogen atom and carbonyl group on the opposing amino acids that participate in the intramolecular hydrogen bonding interaction with a group that crosslinks said opposing amino acids. Examples of such modifications are described in Joy, S. T. et al., *Chem. Commun* (*Camb.*) 52 (33), 5738-5741), and Zhao, H. et al. *Angew. Chem. Int. Ed.* 2016, 55, 12088-12093, each of which are herein incorporated by reference in its entirety.

The amino acids which form or are bound to the staple are typically spaced apart in the peptide chain such that their side chains are on substantially the same face of the folded peptide. Thus, for an alpha-helical peptide, the amino acid side chains are typically located on substantially the same face of the alpha helix. The distance between opposing amino acids on the same face of the peptide per turn of the helix is about 5.4 Å. Accordingly, in various embodiments, the staple is any appropriate moiety which holds these opposing amino acids at a distance of about 5.4 Å, thereby maintaining the alpha helical conformation. Thus, in embodiments, the staple may have a size in the range of from about 5 Å to about 6 Å, of from about 10 Å to about 12 Å, of from about 15 Å to about 17 Å, of from about 21 Å to about 23 Å, of from about 26 Å to about 28 Å, and of from about 31 Å to about 34 Å, inclusive of all values and subranges therebetween. In other embodiments, the staple may have a size of about 5 Å, about 5.5 Å, about 6 Å, about 10.5, about 11 Å, about 11.5 Å, about 12 Å, about 16.5 Å, about 17 Å, about 17.5 Å, about 22 Å, about 22.5 Å, about 23 Å, about 23.5 Å, about 25.5 Å, about 26 Å, about 26.5 Å, about 27 Å, about 27.5 Å, about 28 Å, about 28.5 Å, about 30.5 Å, about 31 Å, about 31.5 Å, about 32 Å, about 32.5 Å, about 33 Å, about 33.5 Å, about 34 Å, or about 34.5 Å.

For single turn stapling in an alpha helix, the amino acids to which the staple is conjugated are generally located at the i, i+4 positions. For double turn stapling in an alpha helix, the amino acids are generally located at the i, i+7 positions. For triple turn stapling in an alpha helix, the amino acids are generally located at the i, i+11 positions. In other embodiments, the polypeptide conjugates disclosed herein can comprise two or more staples (also referred to as stitched peptides). For example, the staple can be located at the i, i+4 positions and at the i+7, i+11.

In various embodiments, the number of amino acids between $Y_1$ and $Y_2$— i.e., "c" in Formula IA-IC— is an appropriate number of amino acids such that the staple is located on substantially the same face of the alpha helix. In embodiments, c is at least 3. In other embodiments, c is a number from 3 to 30. In still other embodiments, c is 3, 6, or 10.

In some embodiments, the staple is selected from the group consisting of alkylene, N-alkylene, alkenylene, alkynylene, aryl, cycloalkyl, cycloalkenyl, cycloalkynyl, heterocyclyl, and heteroaryl, each of which are optionally substituted. Non-limiting examples of staples include a lactam staple, a hydrocarbon staple, a CuAAC staple, a bis-thioether staple, a perfluorobenzene staple, 1,3-bis[(methylthio)methyl]-benzene, m-xylene, m-xylene alkylated cysteine, and a thioether staple.

In some embodiments, $Y_1$ is an amino acid which has a side chain that forms a first bonding group ($b_1$) to the staple, and $Y_2$ is an amino acid which has a side chain that forms a second bonding group ($b_2$) to the staple. Thus, precursors of each of $Y_1$ and $Y_2$ may independently be any amino acid having a side chain which is suitable, or can be modified to be suitable, to covalently bind the staple. Non-limiting examples of such amino acids include cysteine, glutamine, asparagine, and lysine, and analogs thereof (e.g., having additional hydrocarbons in the side chain, such as homocysteine). In some embodiments, cysteine is alkylated.

Further examples of amino acid analogs which can be introduced to the peptides disclosed herein include those having an alkene side chain, an alkyne side chain or a nitrile side chain, as these side chains may be used to form the staple (e.g., during olefin or ring closing metathesis between two alkene-containing side chains) or to conjugate the staple. In still other embodiments, the precursor of $Y_1$ may be an amino acid having a side chain which is suitable for covalently bonding (e.g., forming an amide bond) to a side chain of the precursor of $Y_2$. In such embodiments, the "reaction product" between side chains of these amino acid analogs is the staple. For example, in certain embodiments, the precursor to $Y_1$ is lysine and the precursor to $Y_2$ is aspartate, and the amino group on the side chain of the $Y_1$ precursor reacts with the carboxyl group on the side chain of the $Y_2$ precursor to form an amide, which is the staple. Such a staple is referred to herein as a "DK staple". As another example, the precursor to $Y_1$ may be an amino acid analog having a alkyne on the side chain and the precursor to $Y_2$ may be an amino acid having an azide on the side chain, and these groups react to form a triazole.

In particular, embodiments, the peptide can comprise one or more amino acids having a side chain comprising a thiol group (i.e., prior to conjugation to the linker, CPP, and/or staple). The thiol group may be used to conjugate the CPP, linker, and/or staple, by forming thioether, thioester, or disulfide. Non-limiting examples of amino acid analogs having a thiol group include cysteine, homocysteine, and any of the following amino acid analogs:

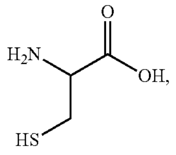 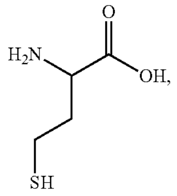

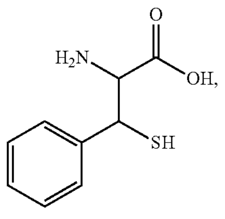 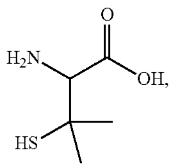

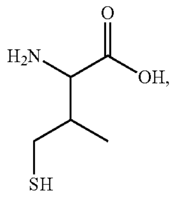 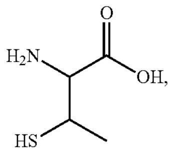

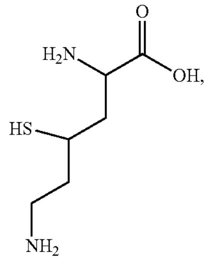 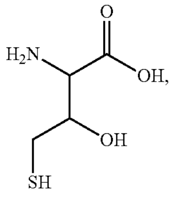

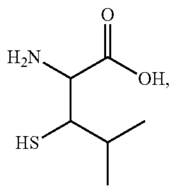 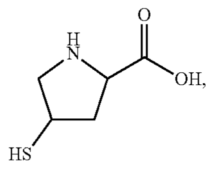 or

-continued

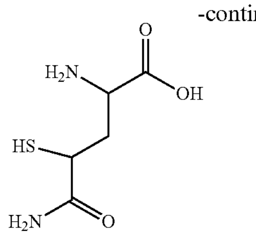

As previously stated, the above groups are precursors which allow for conjugation of a staple, linker, and/or a CPP. Specifically, in order to conjugate the staple, linker, and/or a CPP to the peptide, the hydrogen of the thiol in the above group is replaced by a bond to the staple, linker, or the CPP.

A number of alternative stapling methods are known to those in the art, each using a different form of macrocyclization chemistry and giving rise to stapled peptides with different bioactive properties. For example, the stapling may be one-component stapling. One-component stapling involves a direct bond-forming reaction between the side-chains of two amino acids. In some embodiments, the one-component stapling technique may comprise formation of an amide bond between to side chains of amino acids in the peptide. In some embodiments, the one-component stapling technique may comprise, for example, a ring-closing metathesis, a lactamization, a cycloaddition (such as the Cu(I)-catalyzed azide-alkyne cycloaddition (CuAAC, "click reaction")), a reversible reaction (such as formation of a disulfide bridge or an oxime linkage), or thioether formation. The stapling technique may alternatively be two-component stapling. Two-component stapling involves a bifunctional linker compound which forms a staple by reacting with two complementary native or non-native amino acids in the peptide of interest. Two-component stapling may employ, for example, a photoswitchable linker or a functionalized "double click" linker. When the staple is conjugated via click reaction, each of $b_1$ and $b_2$ are a triazole, which may be optionally substituted. That is, in some embodiments, the precursors to $Y_1$ and $Y_2$ may independently be an amino acid analog having an alkyne group on the side chain or an amino acid having an azide group on the side chain, and these groups react with a precursor to the staple having complementary alkyne and/or azide groups to form a triazole. The click reaction may also be used to produce a staple by two-component stapling, in which case the staple is the triazole and $b_1$ and $b_2$ are absent. Thus, $b_1$ and $b_2$ may independently be the bonding group formed when any of the above techniques are used to conjugate to staple to the peptide. In some embodiments, each of $b_1$ and $b_2$ are independently absent or selected from aryl (e.g., triazole), thioether, disulfide, amide, ester, and ether.

Additional examples of staples and stapling methods appropriate for use in the stapled peptides of the instant invention are described in Walensky, L. D., et al., *J. Med. Chem.,* 57, 6275-6288 (2014), Lau, Y. H., et al., *Chem. Soc. Rev.,* 00, 1-12 (2014), Joy, S. T. et al., *Chem. Commun* (*Camb.*) 52 (33), 5738-5741), and Zhao, H. et al. *Angew. Chem. Int. Ed.* 2016, 55, 12088-12093, each of which are incorporated herein by reference in their entireties.

Cell-Penetrating Peptide (CPP)

Cell-penetrating peptides allows for delivery of otherwise impermeable stapled peptides to be efficiently delivered to the cytosol and nucleus of cells. The CPP of the polypeptide conjugates disclosed herein may be or include any amino sequence which facilitates cellular uptake of the polypeptide conjugates disclosed herein.

In some embodiments, the CPP is a linear CPP. Non-limiting examples of linear CPPs include Polyarginine (e.g., $R_9$ or $R_{11}$), Antennapedia sequences, HIV-TAT, Penetratin, Antp-3A (Antp mutant), Buforin II. Transportan, MAP (model amphipathic peptide), K-FGF, Ku70, Prion, pVEC, Pep-1, SynB1, Pep-7, HN-1, BGSC (Bis-Guanidinium-Spermidine-Cholesterol, and BGTC (Bis-Guanidinium-Tren-Cholesterol).

Suitable CPPs for use in the polypeptide conjugates and methods described herein can include naturally occurring sequences, modified sequences, and synthetic sequences. In embodiments, the total number of amino acids in the CPP may be in the range of from 4 to about 20 amino acids, e.g., about 5, about 6, about 7, about 8, about 9, about 10, about 11, about 12, about 13, about 14, about 15, about 16, about 17, about 18, and about 19 amino acids, inclusive of all ranges and subranges therebetween. In some embodiments, the CPPs disclosed herein comprise about 4 to about to about 13 amino acids. In particular embodiments, the CPPs disclosed herein comprise about 6 to about 10 amino acids, or about 6 to about 8 amino acids.

Each amino acid in the CPP may independently be a natural or non-natural amino acid.

In some embodiments, the CPPs may include any combination of at least two arginines and at least two hydrophobic amino acids. In some embodiments, the CPPs may include any combination of two to three arginines and at least two hydrophobic amino acids.

In some embodiments, the CPP used in polypeptide conjugates described herein has a structure comprising Formula 3:

$$(AA_u)_m\text{-}AA_1\text{-}AA_2\text{-}AA_3\text{-}AA_4\text{-}(AA_z)_n$$

wherein each of $AA_1$, $AA_2$, $AA_3$, and $AA_4$, are independently selected from a D or L amino acid, each of $AA_u$ and $AA_z$, at each instance and when present, are independently selected from a D or L amino acid, and m and n are independently selected from a number from 0 to 6; and wherein:

at least two of $AA_u$, when present, $AA_1$, $AA_2$, $AA_3$, $AA_4$, and $AA_z$, when present, are independently arginine, and at least two of $AA_u$, when present, $AA_1$, $AA_2$, $AA_3$, $AA_4$, and $AA_z$, when present, are independently a hydrophobic amino acid.

In some embodiments, each hydrophobic amino acid is independently selected from glycine, alanine, valine, leucine, isoleucine, methionine, phenylalanine, tryptophan, proline, naphthylalanine, phenylglycine, homophenylalanine, tyrosine, cyclohexylalanine, piperidine-2-carboxylic acid, cyclohexylalanine, norleucine, 3-(3-benzothienyl)-alanine, 3-(2-quinolyl)-alanine, O-benzylserine, 3-(4-(benzyloxy)phenyl)-alanine, S-(4-methylbenzyl)cysteine, N-(naphthalen-2-yl)glutamine, 3-(1,1'-biphenyl-4-yl)-alanine, tert-leucine, or nicotinoyl lysine, each of which is optionally substituted with one or more substituents. The structures of a few of these non-natural aromatic hydrophobic amino acids (prior to incorporation into the peptides disclosed herein) are provided below. In particular embodiments, each hydrophobic amino acid is independently a hydrophobic aromatic amino acid. In some embodiments, the aromatic hydrophobic amino acid is naphthylalanine, phenylglycine, homophenylalanine, phenylalanine, tryptophan, or tyrosine, each of which is optionally substituted with one or more substituents. In particular embodiments, the hydrophobic amino acid is piperidine-2-carboxylic acid, naphthylalanine, tryptophan, or phenylalanine, each of which is optionally substituted with one or more substituents.

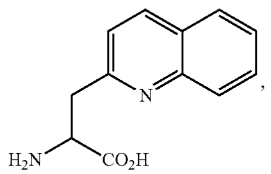

3-(2-quinolyl)-alanine

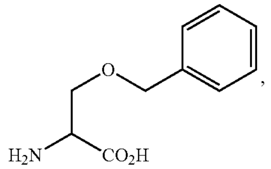

O-benzylserine

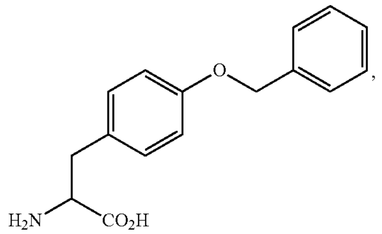

3-(4-(benzyloxy)phenyl)-alanine

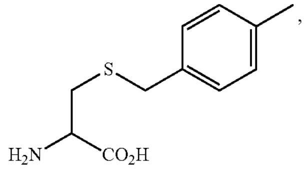

S-(4-methylbenzyl)cysteine

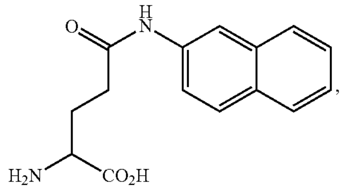

N5-(naphthalen-2-yl)glutamine

-continued

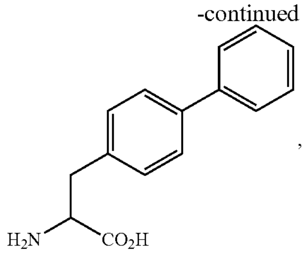

3-(1,1'-biphenyl-4-yl)-alanine

,

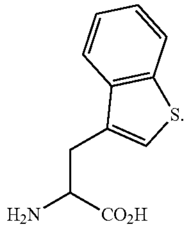

3-(3-benzothienyl)-alanine

The optional substituent can be any atom or group which does not significantly reduce the cytosolic delivery efficiency of the CPP, e.g., a substituent that does not reduce relative cytosolic delivery efficiency to less than that of c(FϕRRRRQ) (SEQ ID NO: 15). In some embodiments, the optional substituent can be a hydrophobic substituent or a hydrophilic substituent. In certain embodiments, the optional substituent is a hydrophobic substituent. In some embodiments, the substituent increases the solvent-accessible surface area (as defined herein) of the hydrophobic amino acid. In some embodiments, the substituent can be a halogen, alkyl, alkenyl, alkynyl, cycloalkyl, cycloalkenyl, cycloalkynyl, heterocyclyl, aryl, heteroaryl, alkoxy, aryloxy, acyl, alkylcarbamoyl, alkylcarboxamidyl, alkoxycarbonyl, alkylthio, or arylthio. In some embodiments, the substituent is one or more halogen atoms.

Amino acids having higher hydrophobicity values can be selected to improve cytosolic delivery efficiency of a CPP relative to amino acids having a lower hydrophobicity value. In some embodiments, each hydrophobic amino acid independently has a hydrophobicity value which is greater than that of glycine. In other embodiments, each hydrophobic amino acid independently is a hydrophobic amino acid having a hydrophobicity value which is greater than that of alanine. In still other embodiments, each hydrophobic amino acid independently has a hydrophobicity value which is greater or equal to phenylalanine. Hydrophobicity may be measured using hydrophobicity scales known in the art. Table 3 below lists hydrophobicity values for various amino acids as reported by Eisenberg and Weiss (Proc. Natl. Acad. Sci. U.S.A. 1984; 81(1):140-144), Engleman, et al. (Ann. Rev. of Biophys. Biophys. Chem. 1986; 1986(15):321-53), Kyte and Doolittle (J. Mol. Biol. 1982; 157(1):105-132), Hoop and Woods (Proc. Natl. Acad. Sci. U.S.A 1981; 78(6):3824-3828), and Janin (Nature. 1979; 277(5696):491-492), the entirety of each of which is herein incorporated by reference in its entirety. In particular embodiments, hydrophobicity is measured using the hydrophobicity scale reported in Engleman, et al.

TABLE 3

| Amino Acid | Group | Eisenberg and Weiss | Engleman et al. | Kyrie and Doolittle | Hoop and Woods | Janin |
|---|---|---|---|---|---|---|
| Ile | Nonpolar | 0.73 | 3.1 | 4.5 | −1.8 | 0.7 |
| Phe | Nonpolar | 0.61 | 3.7 | 2.8 | −2.5 | 0.5 |
| Val | Nonpolar | 0.54 | 2.6 | 4.2 | −1.5 | 0.6 |
| Leu | Nonpolar | 0.53 | 2.8 | 3.8 | −1.8 | 0.5 |
| Trp | Nonpolar | 0.37 | 1.9 | −0.9 | −3.4 | 0.3 |
| Met | Nonpolar | 0.26 | 3.4 | 1.9 | −1.3 | 0.4 |
| Ala | Nonpolar | 0.25 | 1.6 | 1.8 | −0.5 | 0.3 |
| Gly | Nonpolar | 0.16 | 1.0 | −0.4 | 0.0 | 0.3 |
| Cys | Unch/Polar | 0.04 | 2.0 | 2.5 | −1.0 | 0.9 |
| Tyr | Unch/Polar | 0.02 | −0.7 | −1.3 | −2.3 | −0.4 |
| Pro | Nonpolar | −0.07 | −0.2 | −1.6 | 0.0 | −0.3 |

TABLE 3-continued

| Amino Acid | Group | Eisenberg and Weiss | Engleman et al. | Kyrie and Doolittle | Hoop and Woods | Janin |
|---|---|---|---|---|---|---|
| Thr | Unch/Polar | −0.18 | 1.2 | −0.7 | −0.4 | −0.2 |
| Ser | Unch/Polar | −0.26 | 0.6 | −0.8 | 0.3 | −0.1 |
| His | Charged | −0.40 | −3.0 | −3.2 | −0.5 | −0.1 |
| Glu | Charged | −0.62 | −8.2 | −3.5 | 3.0 | −0.7 |
| Asn | Unch/Polar | −0.64 | −4.8 | −3.5 | 0.2 | −0.5 |
| Gln | Unch/Polar | −0.69 | −4.1 | −3.5 | 0.2 | −0.7 |
| Asp | Charged | −0.72 | −9.2 | −3.5 | 3.0 | −0.6 |
| Lys | Charged | −1.10 | −8.8 | −3.9 | 3.0 | −1.8 |
| Arg | Charged | −1.80 | −12.3 | −4.5 | 3.0 | −1.4 |

The chirality of the amino acids can be selected to improve cytosolic uptake efficiency. In some embodiments, at least two of the amino acids have the opposite chirality. In some embodiments, the at least two amino acids having the opposite chirality can be adjacent to each other. In some embodiments, at least three amino acids have alternating stereochemistry relative to each other. In some embodiments, the at least three amino acids having the alternating chirality relative to each other can be adjacent to each other. In some embodiments, at least two of the amino acids have the same chirality. In some embodiments, the at least two amino acids having the same chirality can be adjacent to each other. In some embodiments, at least two amino acids have the same chirality and at least two amino acids have the opposite chirality. In some embodiments, the at least two amino acids having the opposite chirality can be adjacent to the at least two amino acids having the same chirality. Accordingly, in some embodiments, adjacent amino acids in the cCPP can have any of the following sequences: D-L; L-D; D-L-L-D; L-D-D-L; L-D-L-L-D; D-L-D-D-L; D-L-L-D-L; or L-D-D-L-D.

In some embodiments, an arginine is adjacent to a hydrophobic amino acid. In some embodiments, the arginine has the same chirality as the hydrophobic amino acid. In some embodiments, at least two arginines are adjacent to each other. In still other embodiments, three arginines are adjacent to each other. In some embodiments, at least two hydrophobic amino acids are adjacent to each other. In other embodiments, at least three hydrophobic amino acids are adjacent to each other. In other embodiments, the CPPs described herein comprise at least two consecutive hydrophobic amino acids and at least two consecutive arginines. In further embodiments, one hydrophobic amino acid is adjacent to one of the arginines. In still other embodiments, the CPPs described herein comprise at least three consecutive hydrophobic amino acids and there consecutive arginines. In further embodiments, one hydrophobic amino acid is adjacent to one of the arginines. These various combinations of amino acids can have any arrangement of D and L amino acids, e.g., the sequences described above.

In some embodiments, any four adjacent amino acids in the CPPs described herein (e.g., the CPPs according to Formula 2) can have one of the following sequences: $AA_{H2}$-$AA_{H1}$-R-r, $AA_{H2}$-$AA_{H1}$-r-R, R-r-$AA_{H1}$-$AA_{H2}$, or r-R-$AA_{H1}$-$AA_{H2}$, wherein each of $AA_{H1}$ and $AA_{H2}$ are independently a hydrophobic amino acid. Accordingly, in some embodiments, the cCPPs used in the polypeptide conjugates described herein have a structure according any of Formula 4A-D:

$$(AAu)m\text{—}AA_{H2}\text{—}AA_{H1}\text{—}R\text{-}r\text{-}(AA_z)_n, \quad \text{4-A}$$

-continued $$(AAu)m\text{-}r\text{-}R\text{—}AA_{H1}\text{—}AA_{H2}\text{—}(AAz)n \quad \text{4-B}$$

$$(AAu)m\text{—}AA_{H2}\text{—}AA_{H1}\text{-}r\text{-}R\text{—}(AA_z)_n, \text{ and} \quad \text{4-C}$$

$$(AAu)m\text{—}R\text{-}r\text{-}AA_{H1}\text{—}AA_{H2}\text{—}(AAz)n; \quad \text{4-D}$$

wherein:

each of $AA_{H1}$ and $AA_{H2}$ are independently a hydrophobic amino acid;

at each instance and when present, each of $AA_u$ and $AA_z$ are independently any amino acid; and m and n are independently selected from a number from 0 to 6.

In some embodiments, the total number of amino acids (including r, R, $AA_{H1}$, $AA_{H2}$), in the CPPs of Formula 4-A to 4-D are in the range of 6 to 10. In some embodiments, the total number of amino acids is 6. In some embodiments, the total number of amino acids is 7. In some embodiments, the total number of amino acids is 8. In some embodiments, the total number of amino acids is 9. In some embodiments, the total number of amino acids is 10.

In some embodiments, the sum of m and n is from 2 to 6. In some embodiments, the sum of m and n is 2. In some embodiments, the sum of m and n is 3. In some embodiments, the sum of m and n is 4. In some embodiments, the sum of m and n is 5. In some embodiments, the sum of m and n is 6. In some embodiments, m is 0. In some embodiments, m is 1. In some embodiments, m is 2. In some embodiments, m is 3. In some embodiments, m is 4. In some embodiments, m is 5. In some embodiments, m is 6. In some embodiments, n is 0. In some embodiments, n is 1. In some embodiments, n is 2. In some embodiments, n is 3. In some embodiments, n is 4. In some embodiments, n is 5. In some embodiments, n is 6.

In some embodiments, each hydrophobic amino acid is independently selected from independently selected from glycine, alanine, valine, leucine, isoleucine, methionine, phenylalanine, tryptophan, proline, naphthylalanine, phenylglycine, homophenylalanine, tyrosine, cyclohexylalanine, piperidine-2-carboxylic acid, cyclohexylalanine, norleucine, 3-(3-benzothienyl)-alanine, 3-(2-quinolyl)-alanine, O-benzylserine, 3-(4-(benzyloxy)phenyl)-alanine, S-(4-methylbenzyl)cysteine, N-(naphthalen-2-yl)glutamine, 3-(1, 1'-biphenyl-4-yl)-alanine, tert-leucine, or nicotinoyl lysine, each of which is optionally substituted with one or more substituents, each of which is optionally substituted with one or more substituents. In particular embodiments, each hydrophobic amino acid is independently a hydrophobic aromatic amino acid. In some embodiments, the aromatic hydrophobic amino acid is naphthylalanine, phenylglycine, homophenylalanine, phenylalanine, tryptophan, or tyrosine, each of which is optionally substituted with one or more substituents. In particular embodiments, the hydrophobic amino acid is piperidine-2-carboxylic acid, naphthylalanine, tryptophan, or phenylalanine, each of which is optionally substituted with one or more substituents.

In some embodiments, each of $AA_{H1}$ and $AA_{H2}$ are independently a hydrophobic amino acid having a hydrophobicity value that is greater than that of glycine. In other embodiments, each of $AA_{H1}$ and $AA_{H2}$ are independently a hydrophobic amino acid having a hydrophobicity value that is greater than that of alanine. In still other embodiments, each of $AA_{H1}$ and $AA_{H2}$ are independently an hydrophobic amino acid having a hydrophobicity value which is greater than that of phenylalanine, e.g., as measured using the hydrophobicity scales described above, including Eisenberg and Weiss (Proc. Natl. Acad. Sci. U.S.A 1984; 81(1):140-144), Engleman, et al. (Ann. Rev. of Biophys. Biophys. Chem. 1986; 1986(15):321-53), Kyte and Doolittle (J. Mol. Biol. 1982; 157(1):105-132), Hoop and Woods (Proc. Natl. Acad. Sci. U.S.A. 1981; 78(6):3824-3828), and Janin (Nature. 1979; 277(5696):491-492), (see Table 3 above). In particular embodiments, hydrophobicity is measured using the hydrophobicity scale reported in Engleman, et al.

The presence of a hydrophobic amino acid on the N- or C-terminal of a D-Arg or L-Arg, or a combination thereof, has also found to improve the cytosolic uptake of the CPP (and the attached cargo). For example, in some embodiments, the CPPs disclosed herein may include $AA_{H1}$-D-Arg or D-Arg-$AA_{H1}$. In other embodiments, the CPPs disclosed herein may include $AA_{H1}$-L-Arg or L-Arg-$AA_{H1}$.

The size of the hydrophobic amino acid on the N- or C-terminal of the D-Arg or an L-Arg, or a combination thereof (i.e., $AA_{H1}$), may be selected to improve cytosolic delivery efficiency of the CPP. For example, a larger hydrophobic amino acid on the N- or C-terminal of a D-Arg or L-Arg, or a combination thereof, improves cytosolic delivery efficiency compared to an otherwise identical sequence having a smaller hydrophobic amino acid. The size of the hydrophobic amino acid can be measured in terms of molecular weight of the hydrophobic amino acid, the steric effects of the hydrophobic amino acid, the solvent-accessible surface area (SASA) of the side chain, or combinations thereof. In some embodiments, the size of the hydrophobic amino acid is measured in terms of the molecular weight of the hydrophobic amino acid, and the larger hydrophobic amino acid has a side chain with a molecular weight of at least about 90 g/mol, or at least about 130 g/mol, or at least about 141 g/mol. In other embodiments, the size of the amino acid is measured in terms of the SASA of the hydrophobic side chain, and the larger hydrophobic amino acid has a side chain with a SASA greater than alanine, or greater than glycine. In other embodiments, $AA_{H1}$ has a hydrophobic side chain with a SASA greater than or equal to about piperidine-2-carboxylic acid, greater than or equal to about tryptophan, greater than or equal to about phenylalanine, or equal to or greater than about naphthylalanine. In some embodiments, $AA_{H1}$ has a side chain side with a SASA of at least about 200 Å$^2$, at least about 210 Å$^2$, at least about 220 Å$^2$, at least about 240 Å$^2$, at least about 250 Å$^2$, at least about 260 Å$^2$, at least about 270 Å$^2$, at least about 280 Å$^2$, at least about 290 Å$^2$, at least about 300 Å$^2$, at least about 310 Å$^2$, at least about 320 Å$^2$, or at least about 330 Å$^2$. In some embodiments, $AA_{H2}$ has a side chain side with a SASA of at least about 200 Å$^2$, at least about 210 Å$^2$, at least about 220 Å$^2$, at least about 240 Å$^2$, at least about 250 Å$^2$, at least about 260 Å$^2$, at least about 270 Å$^2$, at least about 280 Å$^2$, at least about 290 Å$^2$, at least about 300 Å$^2$, at least about 310 Å$^2$, at least about 320 Å$^2$, or at least about 330 Å$^2$. In some embodiments, the side chains of $AA_{H1}$ and $AA_{H2}$ have a combined SASA of at least about 350 Å$^2$, at least about 360 Å$^2$, at least about 370 Å$^2$, at least about 380 Å$^2$, at least about 390 Å$^2$, at least about 400 Å$^2$, at least about 410 Å$^2$, at least about 420 Å$^2$, at least about 430 Å$^2$, at least about 440 Å$^2$, at least about 450 Å$^2$, at least about 460 Å$^2$, at least about 470 Å$^2$, at least about 480 Å$^2$, at least about 490 Å$^2$, greater than about 500 Å$^2$, at least about 510 Å$^2$, at least about 520 Å$^2$, at least about 530 Å$^2$, at least about 540 Å$^2$, at least about 550 Å$^2$, at least about 560 Å$^2$, at least about 570 Å$^2$, at least about 580 Å$^2$, at least about 590 Å$^2$, at least about 600 Å$^2$, at least about 610 Å$^2$, at least about 620 Å$^2$, at least about 630 Å$^2$, at least about 640 Å$^2$, greater than about 650 Å$^2$, at least about 660 Å$^2$, at least about 670 Å$^2$, at least about 680 Å$^2$, at least about 690 Å$^2$, or at least about 700 Å$^2$. In some embodiments, $AA_{H2}$ is a hydrophobic amino acid with a side chain having a SASA that is less than or equal to the SASA of the hydrophobic side chain of $AA_{H1}$. By way of example, and not by limitation, a CPP having a Nal-Arg motif exhibits improved cytosolic delivery efficiency compared to an otherwise identical CPP having a Phe-Arg motif; a cCPP having a Phe-Nal-Arg motif exhibits improved cytosolic delivery efficiency compared to an otherwise identical CPP having a Nal-Phe-Arg motif; and a phe-Nal-Arg motif exhibits improved cytosolic delivery efficiency compared to an otherwise identical CPP having a nal-Phe-Arg motif.

As used herein, "hydrophobic surface area" or "SASA" refers to the surface area (reported as square Angstroms; Å$^2$) of an amino acid side chain that is accessible to a solvent. In particular embodiments, SASA is calculated using the 'rolling ball' algorithm developed by Shrake & Rupley (*J Mol Biol.* 79 (2): 351-71), which is herein incorporated by reference in its entirety for all purposes. This algorithm uses a "sphere" of solvent of a particular radius to probe the surface of the molecule. A typical value of the sphere is 1.4 Å, which approximates to the radius of a water molecule.

SASA values for certain side chains are shown below in Table 5. In certain embodiments, the SASA values described herein are based on the theoretical values listed in Table 5 below, as reported by Tien, et al. (PLOS ONE 8(11): e80635., which is herein incorporated by reference in its entirety for all purposes.

TABLE 5

SASA values for amino acid side chains.

| Residue | Theoretical | Empirical | Miller et al. (1987) | Rose et al. (1985) |
|---|---|---|---|---|
| Alanine | 129.0 | 121.0 | 113.0 | 118.1 |
| Arginine | 274.0 | 265.0 | 241.0 | 256.0 |
| Asparagine | 195.0 | 187.0 | 158.0 | 165.5 |
| Aspartate | 193.0 | 187.0 | 151.0 | 158.7 |
| Cysteine | 167.0 | 148.0 | 140.0 | 146.1 |
| Glutamate | 223.0 | 214.0 | 183.0 | 186.2 |
| Glutamine | 225.0 | 214.0 | 189.0 | 193.2 |
| Glycine | 104.0 | 97.0 | 85.0 | 88.1 |
| Histidine | 224.0 | 216.0 | 194.0 | 202.5 |
| Isoleucine | 197.0 | 195.0 | 182.0 | 181.0 |
| Leucine | 201.0 | 191.0 | 180.0 | 193.1 |
| Lysine | 236.0 | 230.0 | 211.0 | 225.8 |
| Methionine | 224.0 | 203.0 | 204.0 | 203.4 |

TABLE 5-continued

| SASA values for amino acid side chains. | | | | |
|---|---|---|---|---|
| Residue | Theoretical | Empirical | Miller et al. (1987) | Rose et al. (1985) |
| Phenylalanine | 240.0 | 228.0 | 218.0 | 222.8 |
| Proline | 159.0 | 154.0 | 143.0 | 146.8 |
| Serine | 155.0 | 143.0 | 122.0 | 129.8 |
| Threonine | 172.0 | 163.0 | 146.0 | 152.5 |
| Tryptophan | 285.0 | 264.0 | 259.0 | 266.3 |
| Tyrosine | 263.0 | 255.0 | 229.0 | 236.8 |
| Valine | 174.0 | 165.0 | 160.0 | 164.5 |

In some embodiments, the CPP does not include a hydrophobic amino acid on the N- and/or C-terminal of $AA_{H2}$-$AA_{H1}$-R-r, $AA_{H2}$-$AA_{H1}$-r-R, R-r-$AA_{H1}$-$AA_{H2}$, or r-R-$AA_{H1}$-$AA_{H2}$. In alternative embodiments, the CPP does not include a hydrophobic amino acid having a side chain which is larger (as described herein) than at least one of $AA_{H1}$ or $AA_{H2}$. In further embodiments, the CPP does not include a hydrophobic amino acid with a side chain having a surface area greater than $AA_{H1}$. For example, in embodiments in which at least one of $AA_{H1}$ or $AA_{H2}$ is phenylalanine, the CPP does not further include a naphthylalanine (although the CPP include at least one hydrophobic amino acid which is smaller than $AA_{H1}$ and $AA_{H2}$, e.g., leucine). In still other embodiments, the CPP does not include a naphthylalanine in addition to the hydrophobic amino acids in $AA_{H2}$-$AA_{H1}$-R-r, $AA_{H2}$-$AA_{H1}$-r-R, R-r-$AA_{H1}$-$AA_{H2}$, or r-R-$AA_{H1}$-$AA_{H2}$.

The chirality of the amino acids (i.e., D or L amino acids) can be selected to improve cytosolic delivery efficiency of the CPP (and the attached cargo as described below). In some embodiments, the hydrophobic amino acid on the N- or C-terminal of an arginine (e.g., $AA_{H1}$) has the same or opposite chirality as the adjacent arginine. In some embodiments, $AA_{H1}$ has the opposite chirality as the adjacent arginine. For example, when the arginine is D-arg (i.e. "r"), $AA_{H1}$ is a D-$AA_{H1}$, and when the arginine is L-Arg (i.e., "R"), $AA_{H1}$ is a L-$AA_{H1}$. Accordingly, in some embodiments, the CPPs disclosed herein may include at least one of the following motifs: D-$AA_{H1}$-D-arg, D-arg-D-$AA_{H1}$, L-$AA_{H1}$-L-Arg, or L-Arg-L$AA_{H1}$. In particular embodiments, when arginine is D-arg, $AA_H$ can be D-nal, D-trp, or D-phe. In another non-limiting example, when arginine is L-Arg, $AA_H$ can be L-Nal, L-Trp, or L-Phe.

In some embodiments, the CPPs described herein include three arginines. Accordingly, in some embodiments, the CPPs described herein include one of the following sequences: $AA_{H2}$-$AA_{H1}$-R-r-R, $AA_{H2}$-$AA_{H1}$-R-r-r, $AA_{H2}$-$AA_{H1}$-r-R—R, $AA_{H2}$-$AA_{H1}$-r-R-r, R—R-r-$AA_{H1}$-$AA_{H2}$, r-R-r-$AA_{H1}$-$AA_{H2}$, r-r-R-$AA_{H1}$-$AA_{H2}$, or, R-r-R-$AA_{H1}$-$AA_{H2}$. In particular embodiments, the CPPS have one of the following sequences $AA_{H2}$-$AA_{H1}$-R-r-R, $AA_{H2}$-$AA_{H1}$-r-R-r, r-R-r-$AA_{H1}$-$AA_{H2}$, or R-r-R-$AA_{H1}$-$AA_{H2}$. In some embodiments, the chirality of $AA_{H1}$ and $AA_{H2}$ can be selected to improve cytosolic uptake efficiency, e.g., as described above, where $AA_{H1}$ has the same chirality as the adjacent arginine, and $AA_{H1}$ and $AA_{H2}$ have the opposite chirality.

In some embodiments, the CPPs described herein include three hydrophobic amino acids. Accordingly, in some embodiments, the CPPs described herein include one of the following sequences: $AA_{H3}$-$AA_{H2}$-$AA_{H1}$-R-r, $AA_{H3}$-$AA_{H2}$-$AA_{H1}$-R-r, $AA_{H3}$-$AA_{H2}$-$AA_{H1}$-r-R, $AA_{H3}$-$AA_{H2}$-$AA_{H1}$-r-R, R-r-$AA_{H1}$-$AA_{H2}$-$AA_{H3}$, R-r-$AA_{H1}$-$AA_{H2}$-$AA_{H3}$, r-R-$AA_{H1}$-$AA_{H2}$-$AA_{H3}$, or, r-R-$AA_{H1}$-$AA_{H2}$-$AA_{H3}$, wherein $AA_{H3}$ is any hydrophobic amino acid described above, e.g., piperidine-2-carboxylic acid, naphthylalanine, tryptophan, or phenylalanine. In some embodiments, the chirality of $AA_{H1}$, $AA_{H2}$, and $AA_{H3}$ can be selected to improve cytosolic uptake efficiency, e.g., as described above, where $AA_{H1}$ has the same chirality as the adjacent arginine, and $AA_{H1}$ and $AA_{H2}$ have the opposite chirality. In other embodiments, the size of $AA_{H1}$, $AA_{H2}$, and $AA_{H3}$ can be selected to improve cytosolic uptake efficiency, e.g., as described above, where $AA_{H3}$ has a SAS of less than or equal to $AA_{H1}$ and/or $AA_{H2}$.

In some embodiments, $AA_{H1}$ and $AA_{H2}$ have the same or opposite chirality. In certain embodiments, $AA_{H1}$ and $AA_{H2}$ have the opposite chirality. Accordingly, in some embodiments, the CPPs disclosed herein include at least one of the following sequences: D-$AA_{H2}$-L-$AA_{H1}$-R-r; L-$AA_{H2}$-D-$AA_{H1}$-r-R; R-r-D-$AA_{H1}$-L-$AA_{H2}$; or r-R— wherein each of D-$AA_{H1}$ and D-$AA_{H2}$ is a hydrophobic amino acid having a D configuration, and each of L-$AA_{H1}$ and L-$AA_{H2}$ is a hydrophobic amino acid having an L configuration. In some embodiments, each of D-$AA_{H1}$ and D-$AA_{H2}$ is independently selected from the group consisting of D-pip, D-nal, D-trp, and D-phe. In particular embodiments, D-$AA_{H1}$ or D-$AA_{H2}$ is D-nal. In other particular embodiments, D-$AA_{H1}$ is D-nal. In some embodiments, each of L-$AA_{H1}$ and L-$AA_{H2}$ is independently selected from the group consisting of L-Pip, L-Nal, L-Trp, and L-Phe. In particular embodiments, each of L-$AA_{H1}$ and L-$AA_{H2}$ is L-Nal.

As discussed above, the disclosure provides for various modifications to a cyclic peptide sequence, which may improve cytosolic delivery efficiency. In some embodiments, improved cytosolic uptake efficiency can be measured by comparing the cytosolic delivery efficiency of the CPP having the modified sequence to a proper control sequence. In some embodiments, the control sequence does not include a particular modification (e.g., matching chirality of R and $AA_{H1}$) but is otherwise identical to the modified sequence. In other embodiments, the control has the following sequence: cyclic(FϕRRRRQ) (SEQ ID NO: 15).

As used herein cytosolic delivery efficiency refers to the ability of a CPP to traverse a cell membrane and enter the cytosol. In embodiments, cytosolic delivery efficiency of the CPP is not dependent on a receptor or a cell type. Cytosolic delivery efficiency can refer to absolute cytosolic delivery efficiency or relative cytosolic delivery efficiency.

Absolute cytosolic delivery efficiency is the ratio of cytosolic concentration of a CPP (or a polypeptide conjugate) over the concentration of the CPP (or the polypeptide conjugate) in the growth medium. Relative cytosolic delivery efficiency refers to the concentration of a CPP in the cytosol compared to the concentration of a control CPP in the cytosol. Quantification can be achieved by fluorescently labeling the CPP (e.g., with a FITC dye) and measuring the fluorescence intensity using techniques well-known in the art.

In particular embodiments, relative cytosolic delivery efficiency is determined by comparing (i) the amount of a CPP of the invention internalized by a cell type (e.g., HeLa cells) to (ii) the amount of the control CPP internalized by the same cell type. To measure relative cytosolic delivery efficiency, the cell type may be incubated in the presence of a cell-penetrating peptide of the invention for a specified period of time (e.g., 30 minutes, 1 hour, 2 hours, etc.) after which the amount of the CPP internalized by the cell is quantified using methods known in the art, e.g., fluorescence microscopy. Separately, the same concentration of the control CPP is incubated in the presence of the cell type over the same period of time, and the amount of the control CPP internalized by the cell is quantified.

In other embodiments, relative cytosolic delivery efficiency can be determined by measuring the $IC_{50}$ of a CPP having a modified sequence for an intracellular target, and comparing the $IC_{50}$ of the CPP having the modified sequence to a proper control sequence (as described herein).

In other embodiments, the absolute cytosolic delivery efficacy of from about 40% to about 100%, e.g., about 45%, about 50%, about 55%, about 60%, about 65%, about 70%, about 75%, about 80%, about 85%, about 90%, about 91%, about 92%, about 93%, about 94%, about 95%, about 96%, about 97%, about 98%, about 99%, inclusive of all values and subranges therebetween.

Non-limiting examples of suitable cyclic cell penetrating peptides are provided in Table 6.

TABLE 6

Examples of cyclic cell penetrating peptides (cCPPs).

| ID | cCPP Sequence | SEQ ID NO: |
|---|---|---|
| PCT 1 | cyclo(FϕRRRQ) | 7 |
| PCT 2 | cyclo(FϕRRRC) | 8 |
| PCT 3 | cyclo(FϕRRRU) | 9 |
| PCT 4 | cyclo(RRRϕFQ) | 10 |
| PCT 5 | cyclo(RRRRϕF) | 11 |
| PCT 6 | cyclo(FϕRRRR) | 12 |
| PCT 7 | cyclo(FϕrRrRq) | 13 |
| PCT 8 | cyclo(FϕrRrRQ) | 14 |
| PCT 9 | cyclo(FϕRRRRQ) | 15 |
| PCT 10 | cyclo(fϕRrRrQ) | 16 |
| PCT 11 | cyclo(RRFRϕRQ) | 17 |
| PCT 12 | cyclo(FRRRRϕQ) | 18 |
| PCT 13 | cyclo(rRFRϕRQ) | 19 |
| PCT 14 | cyclo(RRϕFRRQ) | 20 |
| PCT 15 | cyclo(CRRRRFWQ) | 21 |
| PCT 16 | cyclo(FfϕRrRrQ) | 22 |
| PCT 17 | cyclo(FFϕRRRRQ) | 23 |
| PCT 18 | cyclo(RFRFRϕRQ) | 24 |
| PCT 19 | cyclo(URRRRFWQ) | 25 |
| PCT 20 | cyclo(CRRRRFWQ) | 21 |
| PCT 21 | cyclo(FϕRRRRQK) | 26 |
| PCT 22 | cyclo(FϕRRRRQC) | 27 |
| PCT 23 | cyclo(fϕRrRrRQ) | 28 |
| PCT 24 | cyclo(FϕRRRRRQ) | 29 |
| PCT 25 | cyclo(RRRRϕFDΩC) | 30 |
| PCT 26 | cyclo(FϕRRR) | 31 |
| PCT 27 | cyclo(FWRRR) | 32 |
| PCT 28 | cyclo(RRRϕF) | 33 |
| PCT 29 | cyclo(RRRWF) | 34 |
| SAR 1 | cyclo(FϕRRRRQ) | 15 |
| SAR 19 | cyclo(FFRRRQ) | 35 |
| SAR 20 | cyclo(FFrRrQ) | 36 |
| SAR 21 | cyclo(FFRrRQ) | 37 |
| SAR 22 | cyclo(FRFRRQ) | 38 |
| SAR 23 | cyclo(FRRFRQ) | 39 |
| SAR 24 | cyclo(FRRRFQ) | 40 |
| SAR 25 | cyclo(GϕRRRQ) | 41 |
| SAR 26 | cyclo(FFFRAQ) | 42 |
| SAR 27 | cyclo(FFFRRQ) | 43 |
| SAR 28 | cyclo(FFRRRRQ) | 44 |
| SAR 29 | cyclo(FRRFRRQ) | 45 |
| SAR 30 | cyclo(FRRRFRQ) | 46 |
| SAR 31 | cyclo(RFFRRRQ) | 47 |
| SAR 32 | cyclo(RFRRFRQ) | 48 |
| SAR 33 | cyclo(FRFRRRQ) | 49 |
| SAR 34 | cyclo(FFFRRRQ) | 50 |
| SAR 35 | cyclo(FFRRRFQ) | 51 |
| SAR 36 | cyclo(FRFFRRQ) | 52 |
| SAR 37 | cyclo(RRFFFRQ) | 53 |
| SAR 38 | cyclo(FFRFRRQ) | 54 |
| SAR 39 | cyclo(FFRRFRQ) | 55 |
| SAR 40 | cyclo(FRRFFRQ) | 56 |
| SAR 41 | cyclo(FRRFRFQ) | 57 |

TABLE 6-continued

Examples of cyclic cell penetrating peptides (cCPPs).

| ID | cCPP Sequence | SEQ ID NO: |
|---|---|---|
| SAR 42 | cyclo(FRFRFRQ) | 58 |
| SAR 43 | cyclo(RFFRFRQ) | 59 |
| SAR 44 | cyclo(GϕRRRRQ) | 60 |
| SAR 45 | cyclo(FFFRRRRQ) | 61 |
| SAR 46 | cyclo(RFFRRRRQ) | 62 |
| SAR 47 | cyclo(RRFFRRRQ) | 63 |
| SAR 48 | cyclo(RFFFRRRQ) | 64 |
| SAR 49 | cyclo(RRFFFRRQ) | 65 |
| SAR 50 | cyclo(FFRRFRRQ) | 66 |
| SAR 51 | cyclo(FFRRRRFQ) | 67 |
| SAR 52 | cyclo(FRRFFRRQ) | 68 |
| SAR 53 | cyclo(FFFFRRRRQ) | 69 |
| SAR 54 | cyclo(FFFRRRRRRQ) | 70 |
| SAR 55 | cyclo(FϕRrRrQ) | 71 |
| SAR 56 | cyclo(XXRRRRQ) | 72 |
| SAR 57 | cyclo(FfFRrRQ) | 73 |
| SAR 58 | cyclo(fFfrRrQ) | 74 |
| SAR 59 | cyclo(fFfRrRQ) | 75 |
| SAR 60 | cyclo(FfFrRrQ) | 76 |
| SAR 61 | cyclo(fFϕrRrQ) | 77 |
| SAR 62 | cyclo(fϕfrRrQ) | 78 |
| SAR 63 | cyclo(ϕFfrRrQ) | 79 |
| SAR 64 | cyclo(FϕrRrQ) | 80 |
| SAR 65 | cyclo(fϕrRrQ) | 81 |
| SAR 66 | Ac-(Lys-fFRrRrD) | 82 |
| SAR 67 | Ac-(Dap-fFRrRrD) | 83 |
| SAR 68 | CWWRRRRC (S—S) | 84 |
| SAR 69 | CWWWRRRRC (S—S) | 85 |
| SAR 70 | CFWRRRRC (S—S) | 86 |
| SAR 71 | CWWWRRRC (S—S) | 87 |
| Pin1 15 | cyclo(Pip-Nal-Arg-Glu-arg-arg-glu) | 88 |
| Pin1 16 | cyclo(Pip-Nal-Arg-Arg-arg-arg-glu) | 89 |
| Pin1 17 | cyclo(Pip-Nal-Nal-Arg-arg-arg-glu) | 90 |
| Pin1 18 | cyclo(Pip-Nal-Nal-Arg-arg-arg-Glu) | 91 |
| Pin1 19 | cyclo(Pip-Nal-Phe-Arg-arg-arg-glu) | 92 |
| Pin1 20 | cyclo(Pip-Nal-Phe-Arg-arg-arg-Glu) | 93 |
| Pin1 21 | cyclo(Pip-Nal-phe-Arg-arg-arg-glu) | 94 |
| Pin1 22 | cyclo(Pip-Nal-phe-Arg-arg-arg-Glu) | 95 |
| Pin1 23 | cyclo(Pip-Nal-nal-Arg-arg-arg-Glu) | 96 |
| Pin1 24 | cyclo(Pip-Nal-nal-Arg-arg-arg-glu) | 97 |
| Rev-13 | [Pim-RQRR-Nlys]GRRR[b] | 98 |
| hLF | KCFQWQRNMRKVRGPPVSC | 99 |
| cTat | [KrRrGrKkRrE][c] | 100 |
| cR10 | [KrRrRrRrRrE][c] | 101 |
| L-50 | [RVRTRGKRRIRRpP] | 102 |
| L-51 | [RTRTRGKRRIRVpP] | 103 |
| $[WR]_4$ | [WRWRWRWR] | 104 |
| MCoTI-II | [GGVCPKILKKCRRDSDCPGACICRGNGYCGSGSD] | 105 |

TABLE 6-continued

| Examples of cyclic cell penetrating peptides (cCPPs). | | |
|---|---|---|
| ID | cCPP Sequence | SEQ ID NO: |
| Rotstein et al. Chem. Eur. J. 2011 | [P-Cha-r-Cha-r-Cha-r-Cha-r-G][d] | 106 |
| Lian et al. J. Am. Chem. Soc. 2014 | Tm(SvP-$F_2$Pmp-H)-Dap-(FϕRRRR-Dap)][f] | 107 |
| Lian et al. J. Am. Chem. Soc. 2014 | [Tm(a-Sar-D-pThr-Pip-ϕRAa)-Dap-(FϕRRRR-Dap)][f] | 108 |
| IA8b | [CRRSRRGCGRRSRRCG][g] | 109 |
| Dod-[$R_5$] | [K(Dod)RRRR] | 110 |
| LK-3 | LKKLCKLLKKLCKLAG<br>LKKLCKLLKKLCKLAG | 111 |
| | RRRR-[KRRRE][c] | 112 |
| | RRR-[KRRRRE][c] | 113 |
| | RR-[KRRRRRE][c] | 114 |
| | R-[KRRRRRRE][c] | 115 |
| $[CR]_4$ | [CRCRCRCR] | 116 |
| cyc3 | [Pra-LRKRLRKFRN-AzK][h] | 117 |
| PMB | T-Dap-[Dap-Dap-f-L-Dap-Dap-T] | 118 |
| GPMB | T-Agp-[Dap-Agp-f-L-Agp-Agp-T] | 119 |
| cCPP1 | cyclo(FϕRRRRQ) | 15 |
| cCPP12 | cyclo(FfϕRrRrQ) | 22 |
| cCPP9 | cyclo(fϕRrRrQ) | 16 |
| cCPP11 | cyclo(fϕRrRrRQ) | 28 |
| cCPP18 | cyclo(FϕrRrRq) | 13 |
| cCPP13 | cyclo(FϕrRrRQ) | 14 |
| cCPP6 | cyclo(FϕRRRRRQ) | 29 |
| cCPP3 | cyclo(RRFRϕRQ) | 17 |
| cCPP7 | cyclo(FFϕRRRRQ) | 23 |
| cCPP8 | cyclo(RFRFRϕRQ) | 24 |
| cCPP5 | cyclo(FϕRRRQ) | 7 |
| cCPP4 | cyclo(FRRRRϕQ) | 18 |
| cCPP10 | cyclo(rRFRϕRQ) | 19 |
| cCPP2 | cyclo(RRϕFRRQ) | 20 |

ϕ, L-2-naphthylalanine; Pim, pimelic acid; Nlys, lysine peptoid residue; D-pThr, D-phosphothreonine; Pip, L-piperidine-2-carboxylic acid; Cha, L-3-cyclohexyl-alanine; Tm, trimesic acid; Dap, L-2,3-diaminopropionic acid; Sar, sarcosine; $F_2$Pmp, L-difluorophosphonomethyl phenylalanine; Dod, dodecanoyl; Pra, L-propargylglycine; AzK, L-6-Azido-2-amino-hexanoic; Agp, L-2-amino-3-guanidinyl-propionic acid; [b]Cyclization between Pim and Nlys; [c]Cyclization between Lys and Glu; [d]Macrocyclization by multicomponent reaction with aziridine aldehyde and isocyanide; [e]Cyclization between the main-chain of Gln residue; [f]N-terminal amine and side chains of two Dap residues bicyclized with Tm; [g]Three Cys side chains bicyclized with tris(bromomethyl)benzene; [h]Cyclization by the click reaction between Pra and Azk.

Additionally, the cCPP used in the polypeptide conjugates and methods described herein can include any sequence disclosed in: U.S. application Ser. No. 15/312,878 (US Pub. No. US 2017/0190743 A1); U.S. application Ser. No. 15/360,719 (US Pub. No. US 2017/0355730); PCT/US2017/060881 (and the resulting US publication); and PCT/US2017/062951 (and the resulting US publication), each of which is incorporated by reference in its entirety for all purposes.

In some embodiments, the cCPP improves the cytosolic delivery efficiency by about 1.1 fold to about 30 fold, compared to a linear cell-penetrating peptide sequence (such as HIV-TAT, polyarginine and the like), e.g., about 1.2, about 1.3, about 1.4, about 1.5, about 1.6, about 1.7, about 1.8, about 1.9, about 2.0, about 2.5, about 3.0, about 3.5, about 4.0, about 4.5, about 5.0, about 5.5, about 6.0, about 6.5, about 7.0, about 7.5, about 8.0, about 8.5, about 9.0, about 10, about 10.5, about 11.0, about 11.5, about 12.0, about 12.5, about 13.0, about 13.5, about 14.0, about 14.5, about 15.0, about 15.5, about 16.0, about 16.5, about 17.0, about 17.5, about 18.0, about 18.5, about 19.0, about 19.5, about 20, about 20.5, about 21.0, about 21.5, about 22.0, about 22.5, about 23.0, about 23.5, about 24.0, about 24.5, about 25.0, about 25.5, about 26.0, about 26.5, about 27.0, about 27.5, about 28.0, about 28.5, about 29.0, or about 29.5 fold, inclusive of all values and subranges therebetween.

Linker

As discussed above, the CPP may be directly conjugated to the stapled peptide (e.g., by a covalent bond between a side chain of an amino acid on the CPP and an appropriate group on the stapled peptide) or a linker may be used to conjugate the CPP to the stapled peptide. As used herein, "linker" refers to a moiety that forms a covalent bond between the two or more components of the polypeptide conjugates disclosed herein (e.g., a CPP and a stapled peptide via the staple or the peptide).

In various embodiments, the linker is covalently bound to an amino acid on the CPP and either an amino acid on the peptide or the staple. The linker may be any moiety which conjugates two or more of the CPP moiety, the peptide, and the staple. In some embodiments, the linker can be an amino acid. In other embodiments, the precursor to the linker can be any appropriate molecule which is capable of forming two or more bonds with amino acids in the CPP, the peptide, the staple, and combinations thereof. Thus, in various embodiments, the precursor of the linker has two or more functional groups, each of which are capable of forming a covalent bond to at least two of the CPP moiety, the peptide, and the staple. For example, the linker can be covalently bound to the N-terminus, C-terminus, or side chain, or combinations thereof, of any amino acid in the CPP moiety, the peptide, or the staple. In particular embodiments, the linker forms a covalent bond between the CPP and peptide.

In various embodiments of the present disclosure, the linker comprises (i) one or more D or L amino acids, each of which is optionally substituted; (ii) alkylene, alkenylene, alkynylene, carbocyclyl, or heterocyclyl, each of which is optionally substituted; or (iii) $—(R_1—X—R_2)_z—$, wherein each of $R_1$ and $R_2$, at each instance, are independently selected from alkylene, alkenylene, alkynylene, carbocyclyl, and heterocyclyl, each X is independently $NR_3$, $—NR_3C(O)—$, S, and O, wherein $R_3$ is H, alkyl, alkenyl, alkynyl, carbocyclyl, or heterocyclyl, each of which is optionally substituted, and z is an integer from 1 to 50; or (iv) combinations thereof.

In some embodiments, the linker comprises one or more D or L amino acids, each of which is optionally substituted. For example, the linker may comprise one or more glycine (e.g., gly-Gly, Gly-Gly, or Gly-gly).

In other embodiments, L comprises alkylene, alkenylene, alkynylene, carbocyclyl, or heterocyclyl, each of which is optionally substituted.

In still other embodiments, L comprises $(R_1—X—R_2)z$-, wherein each of $R_1$ and $R_2$, at each instance, are independently selected from alkylene, alkenylene, alkynylene, carbocyclyl, and heterocyclyl, each X is independently $NR_3$, $—NR_3C(O)—$, S, and O, wherein $R_3$ is H, alkyl, alkenyl, alkynyl, carbocyclyl, or heterocyclyl, each of which is optionally substituted, and z is an integer from 1 to 50; or combinations thereof.

In certain embodiments, the linker is an ether, which is optionally substituted.

In more specific embodiments, the linker comprises $—(CH_2—O—CH_2)_z—$, wherein Z is an integer from 1-50.

In more specific embodiments, the linker comprises $—(CH_2—O—CH_2)_z—$, wherein Z is an integer from 1-25 (e.g., 12), and one or more D or L amino acids, such as and lysine. For example, in various embodiments, the linker comprises a polyethylene glycol moiety, having from 1 to 50 ethylene glycol units, and a lysine residue. In embodiments, L comprises -(miniPEG)$_z$- wherein Z is an integer from 1-50.

In embodiments, the linker comprises -(miniPEG)$_z$-Lys, wherein Z is an integer from 1-50.

In other specific embodiments, the linker comprises $—(CH_2—S—CH_2)_z—$, wherein Z is an integer from 1-50.

In still other specific embodiments, the linker comprises $—(CH_2—NR_3—CH_2)_z—$, wherein $R_3$ is H, —C(O), alkyl, alkenyl, alkynyl, carbocyclyl, or heterocyclyl, each of which is optionally substituted, and z is an integer from 1-50, e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, and 50, inclusive of all subranges therebetween. In some embodiments, z is an integer from 1-5.

In some embodiments, the linker is covalently bound to the N or C-terminus of an amino acid on the stapled peptide, or to a side chain of glutamine, asparagine, or lysine, or a modified side chain of glutamine or asparagine (e.g., a reduced side chain having an amino group), on the CPP, peptide, or staple. In particular embodiments, the linker forms a bond with the side chain of glutamine on the CPP. In other particular embodiments, the linker described herein has a structure of L-1 or L-2:

L-1

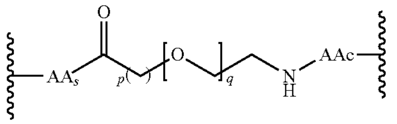

L-2

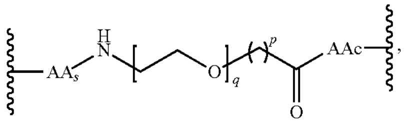

wherein $AA_s$ is a side chain or terminus of an amino acid on the peptide or staple;

$AA_c$ is a side chain or terminus of an amino acid of the CPP;

p is an integer from 0 to 10; and q is an integer from 1 to 50.

In some embodiments, the linker is capable of releasing the stapled peptide from the CPP after the polypeptide conjugate enters the cytosol of the cell. In some embodiments, the linker contains a group, or forms a group after binding to CPP, peptide, staple, or a combination thereof, that is cleaved after cytosolic uptake of the polypeptide conjugate to thereby release the peptide. Non-limiting examples of physiologically cleavable linking group include carbonate, thiocarbonate, thioester, disulfide, sulfoxide, hydrazine, protease-cleavable dipeptide linker, and the like.

For example, in embodiments, the linker is covalently bound to the stapled peptide through a disulfide bond e.g., with the side chain of cysteine or cysteine analog located in the stapled peptide or the CPP. In some embodiments, the disulfide bond is formed between a thiol group on a precursor of the linker, and the side chain of cysteine or an amino acid analog having a thiol group on the peptide, wherein the bond to hydrogen on each of the thiol groups is replaced by a bond to a sulfur atom. Non-limiting examples of amino acid analogs having a thiol group which can be used with the polypeptide conjugates disclosed herein are discussed above.

In some embodiments, the polypeptide conjugates have one of the following structures:

Peptide 1

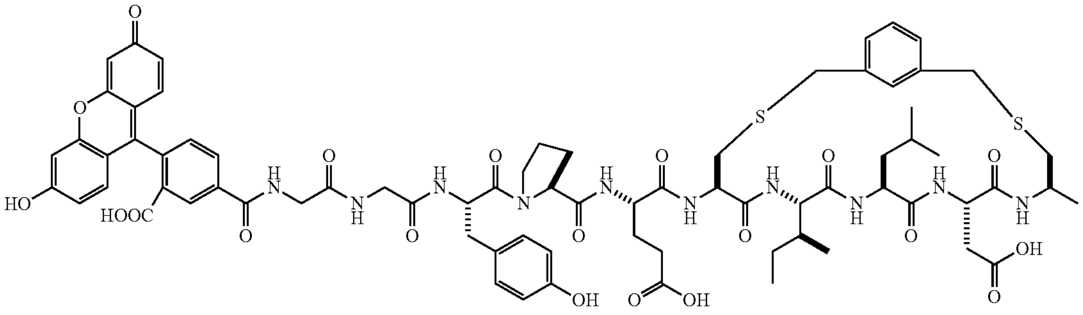

-continued
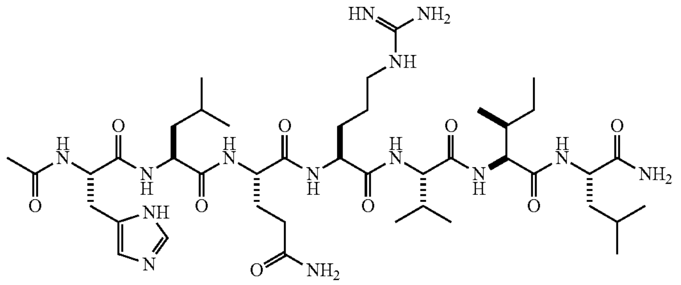
Peptide 2
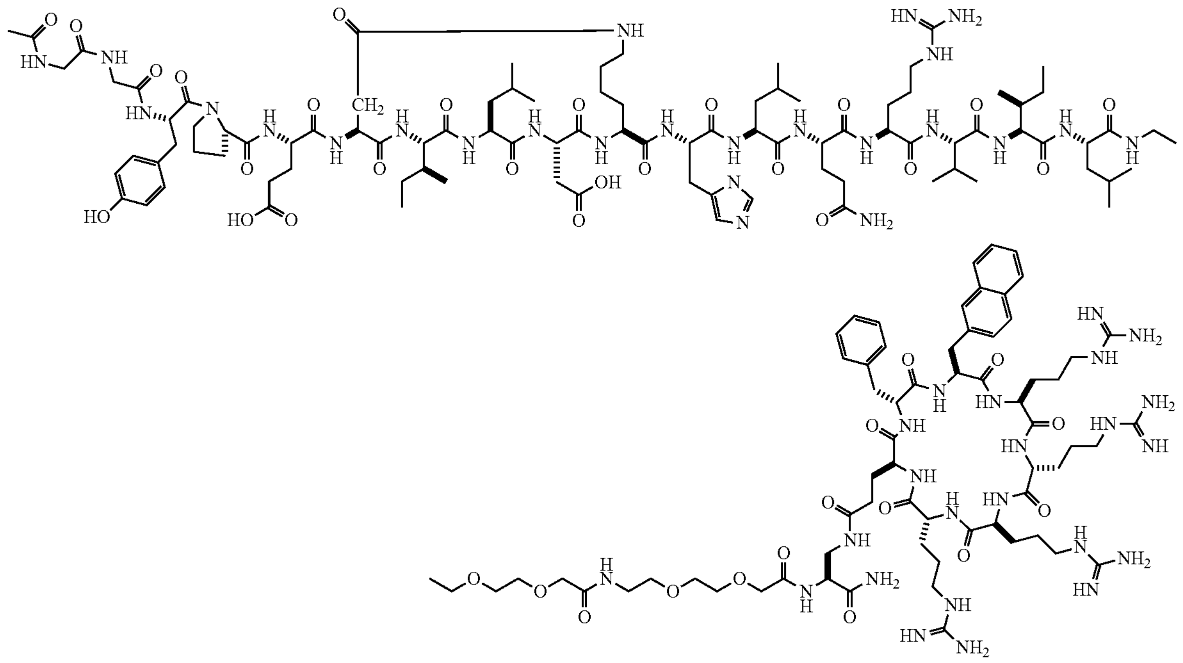
Peptide 3
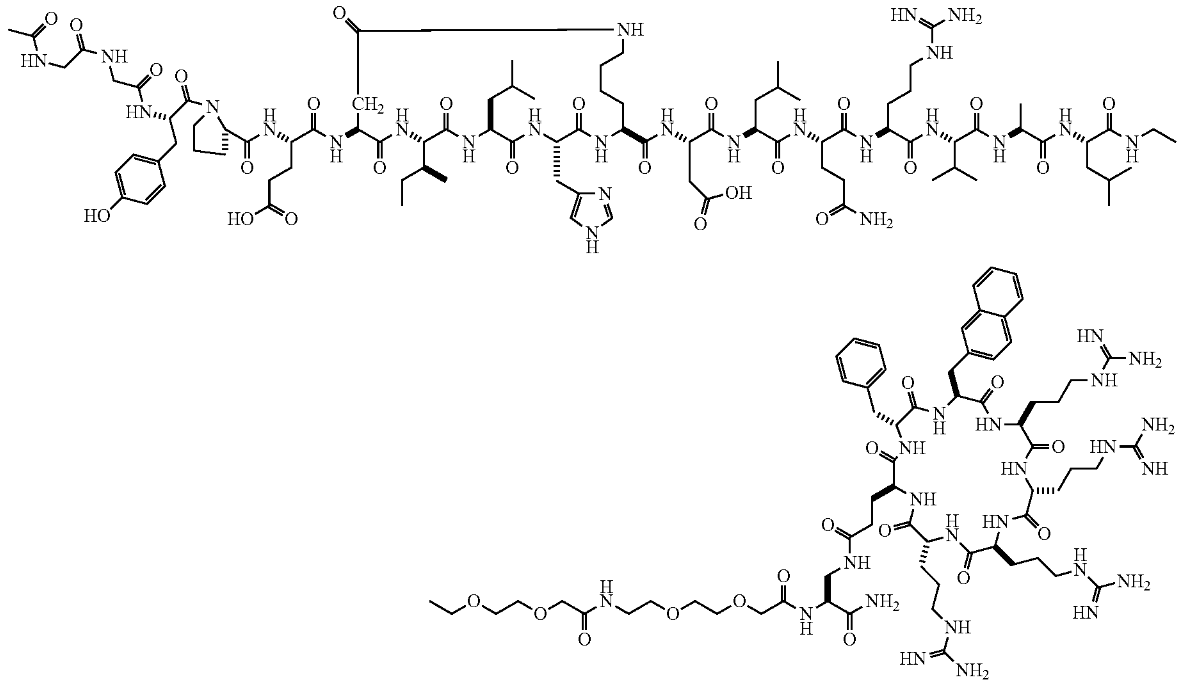

-continued

Peptide 4

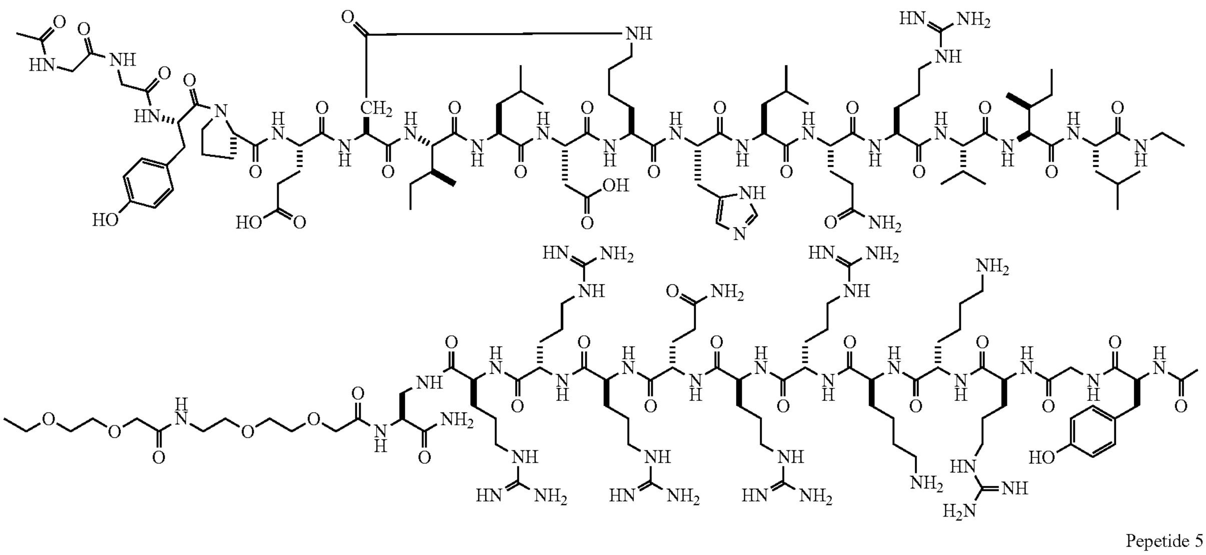

Pepetide 5

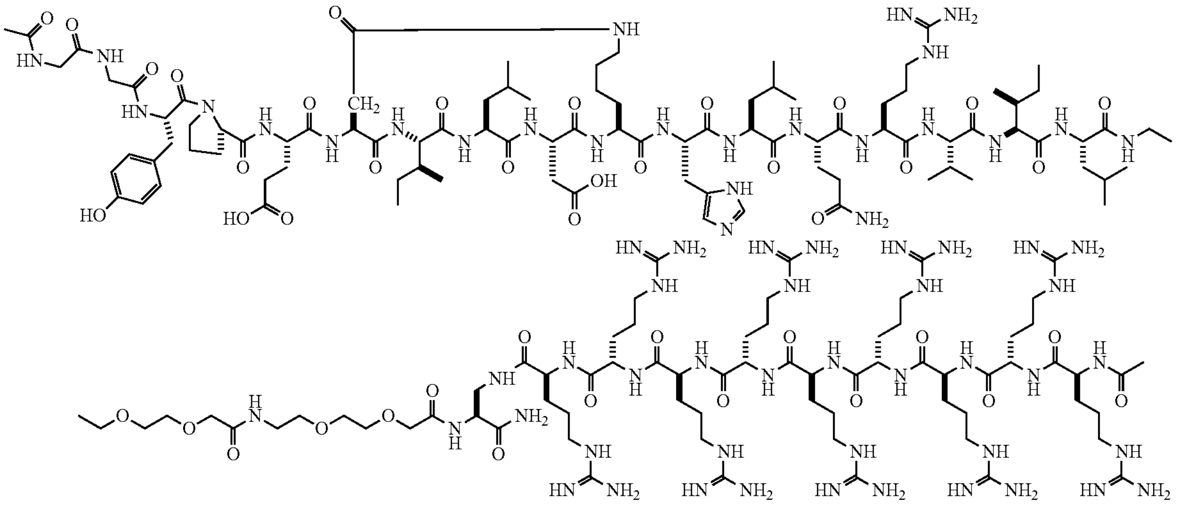

Methods of Treatment

As discussed above, the polypeptide conjugates described herein can be used to treat or prevent a disease, disorder, or condition in a patient in need thereof. In some embodiments, treatment refers to partial or complete alleviation, amelioration, relief, inhibition, delaying onset, reducing severity and/or incidence of the disease, disorder, or condition in the patient.

The terms, "improve," "increase," "reduce," "decrease," and the like, as used herein, indicate values that are relative to a control. In some embodiments, a suitable control is a baseline measurement, such as a measurement in the same individual prior to initiation of the treatment described herein, or a measurement in a control individual (or multiple control individuals) in the absence of the treatment described herein.

The individual (also referred to as "patient") being treated is an individual (fetus, infant, child, adolescent, or adult human) having a disease, disorder, or condition, or having the potential to develop a disease, disorder, or condition.

In some embodiments, the individual is an individual who has been recently diagnosed with a disease, disorder or condition. Typically, early treatment (treatment commencing as soon as possible after diagnosis) is important to minimize the effects of the disease, disorder or condition and to maximize the benefits of treatment.

In some embodiments, the peptide conjugates disclosed herein can be used to inhibit β-Catenin/TCF interaction. In some embodiments, the peptide conjugates disclosed herein can be used to treat a disease characterized by aberrant β-Catenin activation. In some embodiments, the peptide conjugates disclosed herein can be used to treat a disease characterized by deregulated Wnt signaling, such as cancer, aortic valve calcification, and disorders of the bone. See Rev Endocr Metab Disord. 2006 June; 7(0): 41-49.

In some embodiments, the polypeptide conjugates may be used to treat an individual diagnosed with a cancer. The polypeptide conjugates of the instant invention may be used to treat, for example, the following cancers: brain tumors such as for example acoustic neurinoma, astrocytomas such as fibrillary, protoplasmic, gemistocytary, anaplastic, pilocytic astrocytomas, glioblastoma, gliosarcoma, pleomorphic xanthoastrocytoma, subependymal large-cell giant cell astrocytoma and desmoplastic infantile astrocytoma; brain lymphomas, brain metastases, hypophyseal tumor such as prolactinoma, hypophyseal incidentaloma, HGH (human growth hormone) producing adenoma and corticotrophic adenoma, craniopharyngiomas, medulloblastoma, meningeoma and oligodendroglioma; nerve tumors such as for example tumors of the vegetative nervous system such as neuroblastoma, ganglioneuroma, paraganglioma (pheochromocytoma, chromaffinoma) and glomus-caroticum tumor, tumors on the peripheral nervous system such as amputation neuroma, neurofibroma, neurinoma (neurilemmoma, Schwannoma) and malignant Schwannoma, as well as tumors of the central nervous system such as brain and bone marrow tumors; intestinal cancer such as for example carcinoma of the rectum, colon, anus and duodenum; eyelid tumors (basalioma or adenocarcinoma of the eyelid apparatus); retinoblastoma; carcinoma of the pancreas; carcinoma of the bladder; lung tumors (bronchial carcinoma—small-cell lung cancer (SCLC), non-small-cell lung cancer (NSCLC) such as for example spindle-cell plate epithelial carcinomas, adenocarcinomas (acinary, papillary, bronchiolo-alveolar) and large-cell bronchial carcinoma (giant cell carcinoma, clear-cell carcinoma)); breast cancer such as ductal, lobular, mucinous or tubular carcinoma, Paget's carcinoma; non-Hodgkin's lymphomas (B-lymphatic or T-lymphatic NHL) such as for example hair cell leukemia, Burkitt's lymphoma or mucosis fungoides; Hodgkin's disease; uterine cancer (corpus carcinoma or endometrial carcinoma); CUP syndrome (Cancer of Unknown Primary); ovarian cancer (ovarian carcinoma—mucinous or serous cystoma, endometriodal tumors, clear cell tumor, Brenner's tumor); gall bladder cancer; bile duct cancer such as for example Klatskin tumor; testicular cancer (germinal or non-germinal germ cell tumors); laryngeal cancer such as for example supra-glottal, glottal and subglottal tumors of the vocal cords; bone cancer such as for example osteochondroma, chondroma, chondroblastoma, chondromyxoid fibroma, chondrosarcoma, osteoma, osteoid osteoma, osteoblastoma, osteosarcoma, non-ossifying bone fibroma, osteofibroma, desmoplastic bone fibroma, bone fibrosarcoma, malignant fibrous histiocyoma, osteoclastoma or giant cell tumor, Ewing's sarcoma, and plasmocytoma, head and neck tumors (HNO tumors) such as for example tumors of the lips, and oral cavity (carcinoma of the lips, tongue, oral cavity), nasopharyngeal carcinoma (tumors of the nose, lymphoepithelioma), pharyngeal carcinoma, oropharyngeal carcinomas, carcinomas of the tonsils (tonsil malignoma) and (base of the) tongue, hypopharyngeal carcinoma, laryngeal carcinoma (cancer of the larynx), tumors of the paranasal sinuses and nasal cavity, tumors of the salivary glands and ears; liver cell carcinoma (hepatocellular carcinoma (HCC); leukemias, such as for example acute leukemias such as acute lymphatic/lymphoblastic leukemia (ALL), acute myeloid leukemia (AML); chronic lymphatic leukemia (CLL), chronic myeloid leukemia (CML); stomach cancer (papillary, tubular or mucinous adenocarcinoma, adenosquamous, squamous or undifferentiated carcinoma; malignant melanomas such as for example superficially spreading (SSM), nodular (NMM), lentigo-maligna (LMM), acral-lentiginous (ALM) or amelanotic melanoma (AMM); renal cancer such as for example kidney cell carcinoma (hypernephroma or Grawitz's tumor); oesophageal cancer; penile cancer; prostate cancer; vaginal cancer or vaginal carcinoma; thyroid carcinomas such as for example papillary, follicular, medullary or anaplastic thyroid carcinoma; thymus carcinoma (thymoma); cancer of the urethra (carcinoma of the urethra, urothelial carcinoma) and cancer of the vulva. In some embodiments, the cancer is soft tissue sarcomas, leukemia, melanoma, breast cancer, colorectal cancer, and pancreatic ductal adenocarcinoma (PDAC).

Combination Therapies

In some embodiments, the polypeptide conjugates disclosed herein can be administered in combination with other therapies. The polypeptide conjugates can be administered simultaneous, sequentially, or at distinct time points as part of the same therapeutic regimen.

In some embodiments, the polypeptide conjugates disclosed herein are administered in combination with one or more chemotherapeutic agents. Chemotherapeutic agents which may be administered in combination with the compounds according to the invention include, without being restricted thereto, hormones, hormone analogues and antihormones (e.g. tamoxifen, toremifene, raloxifene, fulvestrant, megestrol acetate, flutamide, nilutamide, bicalutamide, aminoglutethimide, cyproterone acetate, finasteride, buserelin acetate, fludrocortisone, fluoxymesterone, medroxyprogesterone, octreotide), aromatase inhibitors (e.g. anastrozole, letrozole, liarozole, vorozole, exemestane, atamestane), LHRH agonists and antagonists (e.g. goserelin acetate, luprolide), inhibitors of growth factors (growth factors such as for example "platelet derived growth factor" and "hepatocyte growth factor", inhibitors are for example "growth factor" antibodies, "growth factor receptor" antibodies and tyrosinekinase inhibitors, such as for example gefitinib, lapatinib and trastuzumab); signal transduction inhibitors (e.g. imatinib and sorafenib); antimetabolites (e.g. antifolates such as methotrexate, premetrexed and raltitrexed, pyrimidine analogues such as 5-fluorouracil, capecitabin and gemcitabin, purine and adenosine analogues such as mercaptopurine, thioguanine, cladribine and pentostatin, cytarabine, fludarabine); antitumour antibiotics (e.g. anthracyclins such as doxorubicin, daunorubicin, epirubicin and idarubicin, mitomycin-C, bleomycin, dactinomycin, plicamycin, streptozocin); platinum derivatives (e.g. cisplatin, oxaliplatin, carboplatin); alkylation agents (e.g. estramustin, meclorethamine, melphalan, chlorambucil, busulphan, dacarbazin, cyclophosphamide, ifosfamide, temozolomide, nitrosoureas such as for example carmustin and lomustin, thiotepa); antimitotic agents (e.g. *Vinca* alkaloids such as for example vinblastine, vindesin, vinorelbin and vincristine; and taxanes such as paclitaxel, docetaxel); topoisomerase inhibitors (e.g. epipodophyllotoxins such as for example etoposide and etopophos, teniposide, amsacrin, topotecan, irinotecan, mitoxantron) and various chemotherapeutic agents such as amifostin, anagrelid, clodronat, filgrastin, interferon alpha, leucovorin, rituximab, procarbazine, levamisole, mesna, mitotane, pamidronate and porfimer.

Methods of Making

The polypeptide conjugates described herein can be prepared in a variety of ways known to one skilled in the art of organic synthesis or variations thereon as appreciated by those skilled in the art. The compounds described herein can be prepared from readily available starting materials. Optimum reaction conditions can vary with the particular reactants or solvents used, but such conditions can be determined by one skilled in the art.

Variations on the compounds described herein include the addition, subtraction, or movement of the various constituents as described for each compound. Similarly, when one or more chiral centers are present in a molecule, the chirality of the molecule can be changed. Additionally, compound synthesis can involve the protection and deprotection of various chemical groups. The use of protection and deprotection, and the selection of appropriate protecting groups can be determined by one skilled in the art. The chemistry of protecting groups can be found, for example, in Wuts and Greene, Protective Groups in Organic Synthesis, 4th Ed., Wiley & Sons, 2006, which is incorporated herein by reference in its entirety.

The starting materials and reagents used in preparing the disclosed compounds and compositions are either available from commercial suppliers such as Aldrich Chemical Co., (Milwaukee, Wis.), Acros Organics (Morris Plains, N.J.), Fisher Scientific (Pittsburgh, Pa.), Sigma (St. Louis, Mo.), Pfizer (New York, N.Y.), GlaxoSmithKline (Raleigh, N.C.), Merck (Whitehouse Station, N.J.), Johnson & Johnson (New Brunswick, N.J.), Aventis (Bridgewater, N.J.), AstraZeneca (Wilmington, Del.), Novartis (Basel, Switzerland), Wyeth (Madison, N.J.), Bristol-Myers-Squibb (New York, N.Y.), Roche (Basel, Switzerland), Lilly (Indianapolis, Ind.), Abbott (Abbott Park, Ill.), Schering Plough (Kenilworth, N.J.), or Boehringer Ingelheim (Ingelheim, Germany), or are prepared by methods known to those skilled in the art following procedures set forth in references such as Fieser and Fieser's Reagents for Organic Synthesis, Volumes 1-17 (John Wiley and Sons, 1991); Rodd's Chemistry of Carbon Compounds, Volumes 1-5 and Supplementals (Elsevier Science Publishers, 1989); Organic Reactions, Volumes 1-40 (John Wiley and Sons, 1991); March's Advanced Organic Chemistry, (John Wiley and Sons, 4th Edition); and Larock's Comprehensive Organic Transformations (VCH Publishers Inc., 1989). Other materials, such as the pharmaceutical carriers disclosed herein can be obtained from commercial sources.

Reactions to produce the compounds described herein can be carried out in solvents, which can be selected by one of skill in the art of organic synthesis. Solvents can be substantially nonreactive with the starting materials (reactants), the intermediates, or products under the conditions at which the reactions are carried out, i.e., temperature and pressure. Reactions can be carried out in one solvent or a mixture of more than one solvent. Product or intermediate formation can be monitored according to any suitable method known in the art. For example, product formation can be monitored by spectroscopic means, such as nuclear magnetic resonance spectroscopy (e.g., $^{1}H$ or $^{13}C$) infrared spectroscopy, spectrophotometry (e.g., UV-visible), or mass spectrometry, or by chromatography such as high performance liquid chromatography (HPLC) or thin layer chromatography.

The disclosed compounds can be prepared by solid phase peptide synthesis wherein the amino acid α-N-terminal is protected by an acid or base protecting group. Such protecting groups should have the properties of being stable to the conditions of peptide linkage formation while being readily removable without destruction of the growing peptide chain or racemization of any of the chiral centers contained therein. Suitable protecting groups are 9-fluorenylmethyloxycarbonyl (Fmoc), t-butyloxycarbonyl (Boc), benzyloxycarbonyl (Cbz), biphenylisopropyloxycarbonyl, t-amyloxycarbonyl, isobornyloxycarbonyl, α,α-dimethyl-3,5-dimethoxybenzyloxycarbonyl, o-nitrophenylsulfenyl, 2-cyano-t-butyloxycarbonyl, and the like. The 9-fluorenylmethyloxycarbonyl (Fmoc) protecting group is particularly preferred for the synthesis of the disclosed compounds. Other preferred side chain protecting groups are, for side chain amino groups like lysine and arginine, 2,2,5,7,8-pentamethylchroman-6-sulfonyl (pmc), nitro, p-toluenesulfonyl, 4-methoxybenzene-sulfonyl, Cbz, Boc, and adamantyloxycarbonyl; for tyrosine, benzyl, o-bromobenzyloxy-carbonyl, 2,6-dichlorobenzyl, isopropyl, t-butyl (t-Bu), cyclohexyl, cyclopenyl and acetyl (Ac); for serine, t-butyl, benzyl and tetrahydropyranyl; for histidine, trityl, benzyl, Cbz, p-toluenesulfonyl and 2,4-dinitrophenyl; for tryptophan, formyl; for aspartic acid and glutamic acid, benzyl and t-butyl and for cysteine, triphenylmethyl (trityl).

In the solid phase peptide synthesis method, the α-C-terminal amino acid is attached to a suitable solid support or resin. Suitable solid supports useful for the above synthesis are those materials which are inert to the reagents and reaction conditions of the stepwise condensation-deprotection reactions, as well as being insoluble in the media used. Solid supports for synthesis of α-C-terminal carboxy peptides is 4-hydroxymethylphenoxymethyl-copoly(styrene-1% divinylbenzene) or 4-(2',4'-dimethoxyphenyl-Fmoc-aminomethyl)phenoxyacetamidoethyl resin available from Applied Biosystems (Foster City, Calif.). The α-C-terminal amino acid is coupled to the resin by means of N,N'-dicyclohexylcarbodiimide (DCC), N,N'-diisopropylcarbodiimide (DIC) or O-benzotriazol-1-yl-N,N,N',N'-tetramethyluroniumhexafluorophosphate (HBTU), with or without 4-dimethylaminopyridine (DMAP), 1-hydroxybenzotriazole (HOBT), benzotriazol-1-yloxy-tris(dimethylamino)phosphoniumhexafluorophosphate (BOP) or bis(2-oxo-3-oxazolidinyl)phosphine chloride (BOPCl), mediated coupling for from about 1 to about 24 hours at a temperature of between 10° C. and 50° C. in a solvent such as dichloromethane or DMF. When the solid support is 4-(2',4'-dimethoxyphenyl-Fmoc-aminomethyl)phenoxy-acetamidoethyl resin, the Fmoc group is cleaved with a secondary amine, preferably piperidine, prior to coupling with the α-C-terminal amino acid as described above. One method for coupling to the deprotected 4 (2',4'-dimethoxyphenyl-Fmoc-aminomethyl) phenoxy-acetamidoethyl resin is O-benzotriazol-1-yl-N,N,N',N'-tetramethyluroniumhexafluorophosphate (HBTU, 1 equiv.) and 1-hydroxybenzotriazole (HOBT, 1 equiv.) in DMF. The coupling of successive protected amino acids can be carried out in an automatic polypeptide synthesizer. In one example, the α-N-terminal in the amino acids of the growing peptide chain are protected with Fmoc. The removal of the Fmoc protecting group from the α-N-terminal side of the growing peptide is accomplished by treatment with a secondary amine, preferably piperidine. Each protected amino acid is then introduced in about 3-fold molar excess, and the coupling is preferably carried out in DMF. The coupling agent can be O-benzotriazol-1-yl-N,N,N',N'-tetramethyluroniumhexafluorophosphate (HBTU, 1 equiv.) and 1-hydroxybenzotriazole (HOBT, 1 equiv.). At the end of the solid phase synthesis, the polypeptide is removed from the resin and deprotected, either in successively or in a single operation. Removal of the polypeptide and deprotection can be accomplished in a single operation by treating the resin-bound polypeptide with a cleavage reagent comprising thianisole, water, ethanedithiol and trifluoroacetic acid. In cases wherein the α-C-terminal of the polypeptide is an alkylamide, the resin is cleaved by aminolysis with an alkylamine. Alternatively, the peptide can be removed by transesterification, e.g. with methanol, followed by aminolysis or by direct transamidation. The protected peptide can be purified at this point or taken to the next step directly. The removal of the side chain protecting groups can be accomplished using the cleavage cocktail described above. The fully deprotected peptide can be purified by a sequence of chromatographic steps employing any or all of the following types: ion exchange on a weakly basic resin (acetate form); hydrophobic adsorption chromatography on underivatized polystyrene-divinylbenzene (for example, Amberlite XAD); silica gel adsorption chromatography; ion exchange chromatography on carboxymethylcellulose; partition chromatography, e.g. on Sephadex G-25, LH-20 or countercurrent distribution; high performance liquid chromatography (HPLC), especially reverse-phase HPLC on octyl- or octadecylsilyl-silica bonded phase column packing.

Methods of Administration

In vivo application of the disclosed polypeptide conjugates, and compositions containing them, can be accomplished by any suitable method and technique presently or prospectively known to those skilled in the art. For example, the disclosed compounds can be formulated in a physiologically- or pharmaceutically-acceptable form and administered by any suitable route known in the art including, for example, oral and parenteral routes of administration. As used herein, the term parenteral includes subcutaneous, intradermal, intravenous, intramuscular, intraperitoneal, and intrasternal administration, such as by injection. Administration of the disclosed compounds or compositions can be a single administration, or at continuous or distinct intervals as can be readily determined by a person skilled in the art.

The compounds disclosed herein, and compositions comprising them, can also be administered utilizing liposome technology, slow release capsules, implantable pumps, and biodegradable containers. These delivery methods can, advantageously, provide a uniform dosage over an extended period of time. The compounds can also be administered in their salt derivative forms or crystalline forms.

The compounds disclosed herein can be formulated according to known methods for preparing pharmaceutically acceptable compositions. Formulations are described in detail in a number of sources which are well known and readily available to those skilled in the art. For example, *Remington's Pharmaceutical Science* by E. W. Martin (1995) describes formulations that can be used in connection with the disclosed methods. In general, the compounds disclosed herein can be formulated such that an effective amount of the compound is combined with a suitable carrier in order to facilitate effective administration of the compound. The compositions used can also be in a variety of forms. These include, for example, solid, semi-solid, and liquid dosage forms, such as tablets, pills, powders, liquid solutions or suspension, suppositories, injectable and infusible solutions, and sprays. The preferred form depends on the intended mode of administration and therapeutic application. The compositions also preferably include conventional pharmaceutically-acceptable carriers and diluents which are known to those skilled in the art. Examples of carriers or diluents for use with the compounds include ethanol, dimethyl sulfoxide, glycerol, alumina, starch, saline, and equivalent carriers and diluents. To provide for the administration of such dosages for the desired therapeutic treatment, compositions disclosed herein can advantageously comprise between about 0.1% and 100% by weight of the total of one or more of the subject compounds based on the weight of the total composition including carrier or diluent.

Formulations suitable for administration include, for example, aqueous sterile injection solutions, which can contain antioxidants, buffers, bacteriostats, and solutes that render the formulation isotonic with the blood of the intended recipient; and aqueous and nonaqueous sterile suspensions, which can include suspending agents and thickening agents. The formulations can be presented in unit-dose or multi-dose containers, for example sealed ampoules and vials, and can be stored in a freeze dried (lyophilized) condition requiring only the condition of the sterile liquid carrier, for example, water for injections, prior to use. Extemporaneous injection solutions and suspensions can be prepared from sterile powder, granules, tablets, etc. It should be understood that in addition to the ingredients particularly mentioned above, the compositions disclosed herein can include other agents conventional in the art having regard to the type of formulation in question.

Compounds and compositions disclosed herein, including pharmaceutically acceptable salts thereof, can be administered intravenously, intramuscularly, or intraperitoneally by infusion or injection. Solutions of the active agent or its salts can be prepared in water, optionally mixed with a nontoxic surfactant. Dispersions can also be prepared in glycerol, liquid polyethylene glycols, triacetin, and mixtures thereof and in oils. Under ordinary conditions of storage and use, these preparations can contain a preservative to prevent the growth of microorganisms.

The pharmaceutical dosage forms suitable for injection or infusion can include sterile aqueous solutions or dispersions or sterile powders comprising the active ingredient, which are adapted for the extemporaneous preparation of sterile injectable or infusible solutions or dispersions, optionally encapsulated in liposomes. The ultimate dosage form should be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions or by the use of surfactants. Optionally, the prevention of the action of microorganisms can be brought about by various other antibacterial and antifungal agents, for example, parabens, chlorobutanol, phenol, sorbic acid, thimerosal, and the like. In many cases, it will be preferable to include isotonic agents, for example, sugars, buffers or sodium chloride. Prolonged absorption of the injectable compositions can be brought about by the inclusion of agents that delay absorption, for example, aluminum monostearate and gelatin.

Sterile injectable solutions are prepared by incorporating a compound and/or agent disclosed herein in the required amount in the appropriate solvent with various other ingredients enumerated above, as required, followed by filter sterilization. In the case of sterile powders for the preparation of sterile injectable solutions, the preferred methods of preparation are vacuum drying and the freeze drying techniques, which yield a powder of the active ingredient plus any additional desired ingredient present in the previously sterile-filtered solutions.

Useful dosages of the compounds and agents and pharmaceutical compositions disclosed herein can be determined by comparing their in vitro activity, and in vivo activity in animal models. Methods for the extrapolation of effective dosages in mice, and other animals, to humans are known to the art.

The dosage ranges for the administration of the compositions are those large enough to produce the desired effect in which the symptoms or disorder are affected. The dosage should not be so large as to cause adverse side effects, such as unwanted cross-reactions, anaphylactic reactions, and the like. Generally, the dosage will vary with the age, condition, sex and extent of the disease in the patient and can be determined by one of skill in the art. The dosage can be adjusted by the individual physician in the event of any counterindications. Dosage can vary, and can be administered in one or more dose administrations daily, for one or several days.

Also disclosed are pharmaceutical compositions that comprise a compound disclosed herein in combination with a pharmaceutically acceptable carrier. Pharmaceutical compositions adapted for oral, topical or parenteral administration, comprising an amount of a compound constitute a preferred aspect. The dose administered to a patient, particularly a human, should be sufficient to achieve a therapeutic response in the patient over a reasonable time frame, without lethal toxicity, and preferably causing no more than an acceptable level of side effects or morbidity. One skilled in the art will recognize that dosage will depend upon a variety of factors including the condition (health) of the subject, the body weight of the subject, kind of concurrent treatment, if any, frequency of treatment, therapeutic ratio, as well as the severity and stage of the pathological condition.

Also disclosed are kits that comprise a compound disclosed herein in one or more containers. The disclosed kits can optionally include pharmaceutically acceptable carriers and/or diluents. In one embodiment, a kit includes one or more other components, adjuncts, or adjuvants as described herein. In another embodiment, a kit includes one or more anti-cancer agents, such as those agents described herein. In one embodiment, a kit includes instructions or packaging materials that describe how to administer a compound or composition of the kit. Containers of the kit can be of any suitable material, e.g., glass, plastic, metal, etc., and of any suitable size, shape, or configuration. In one embodiment, a compound and/or agent disclosed herein is provided in the kit as a solid, such as a tablet, pill, or powder form. In another embodiment, a compound and/or agent disclosed herein is provided in the kit as a liquid or solution. In one embodiment, the kit comprises an ampoule or syringe containing a compound and/or agent disclosed herein in liquid or solution form.

A number of embodiments of the invention have been described. Nevertheless, it will be understood that various modifications may be made without departing from the spirit and scope of the invention. Accordingly, other embodiments are within the scope of the following claims.

A number of publications, patents, and patent applications have been cited herein. Each of the cited publications, patents, and patent applications is hereby incorporated by reference in their entireties to the same extent as if each individual publication, patent or patent application was specifically and individually indicated as incorporated by reference in its entirety.

EXAMPLES

Example 1: Design Strategy and Synthesis of Cyclic CPP-Stapled Peptide Conjugates We prepared CPP-stapled peptide conjugates by using a convergent synthesis method (FIG. 1). First, the cargo peptide was synthesized by standard solid-phase peptide synthesis (SPPS) with two homocysteine residues incorporated at the i and i+4 positions. After cleavage from the resin and side-chain deprotection, the peptide was treated with 1.5 equivalents of 1,3-dichloroacetone (DCA) to staple the peptide into an alpha-helical conformation. This stapling procedure also incorporates a ketone group into the stapled peptide for subsequent bioorthogonal conjugation with a cCPP. Next, a cCPP [e.g., cCPP9] was synthesized by SPPS with a miniPEG-Lys(Mtt) linker attached to the Gln side chain. While still on resin, the Mtt group on the Lys side chain was selectively removed by treatment with 5% trifluoroacetic acid (TFA) and the exposed amine was acylated with a Boc-aminoxyacetyl moiety. Cleavage from resin and side chain deprotection with TFA gave cCPP9 derivatized with a nucleophilic hydroxylamine group (aminoxy-CPP9; FIG. 1). Finally, the DCA-stapled peptide and aminoxy-cCPP9 were conjugated in an aqueous solution (pH 4.7) through the formation of an oxime linkage. Note that the oxime formation results in two different stereoisomers (Z and E isomers).

Figure 3A:
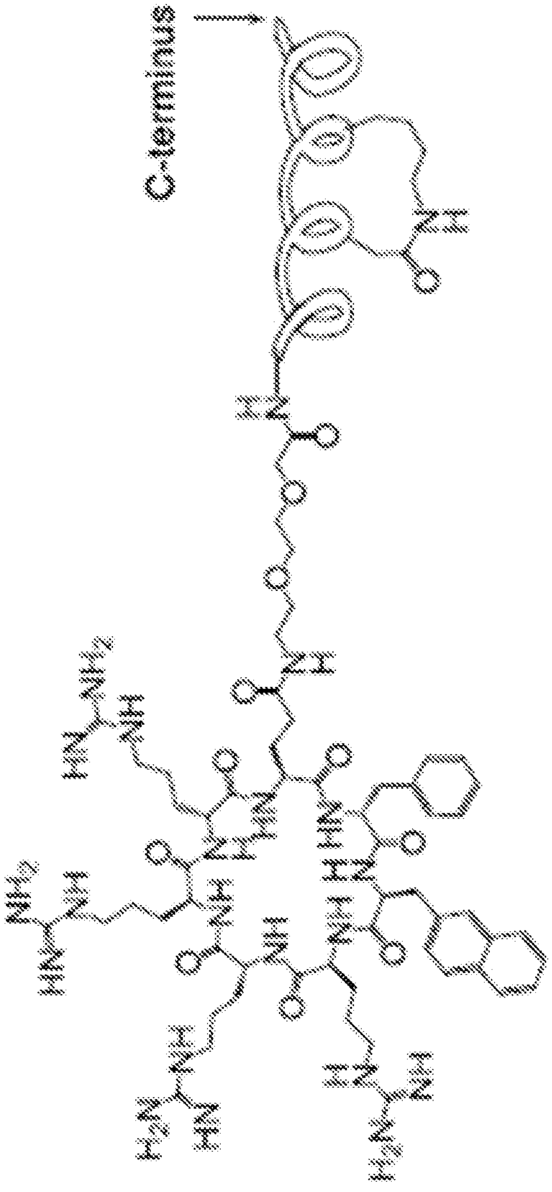
FIG. 3A reveals cyclic CPP-stapled peptide conjugates with a DK staple and conjugation to the CPP at its C-terminus.
Figure 3B:
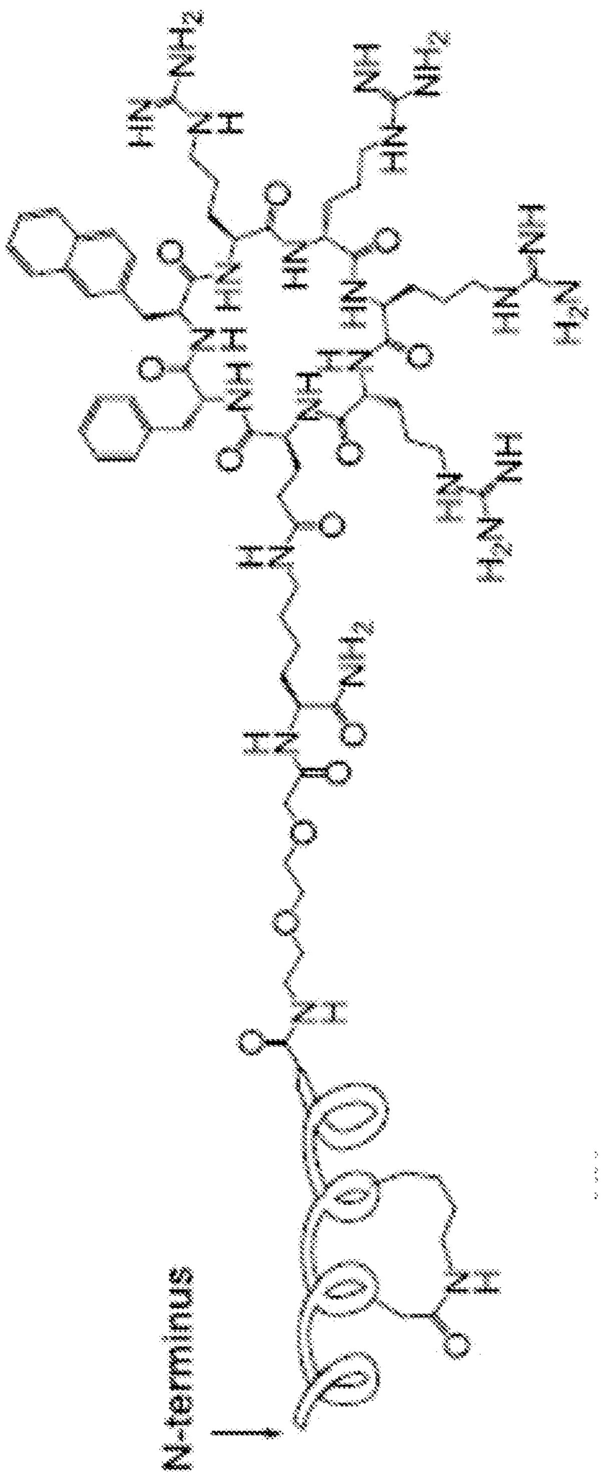
FIG. 3B reveals cyclic CPP-stapled peptide conjugates with a DK staple and conjugation to the CPP at its N-terminus.
Figure 3C:
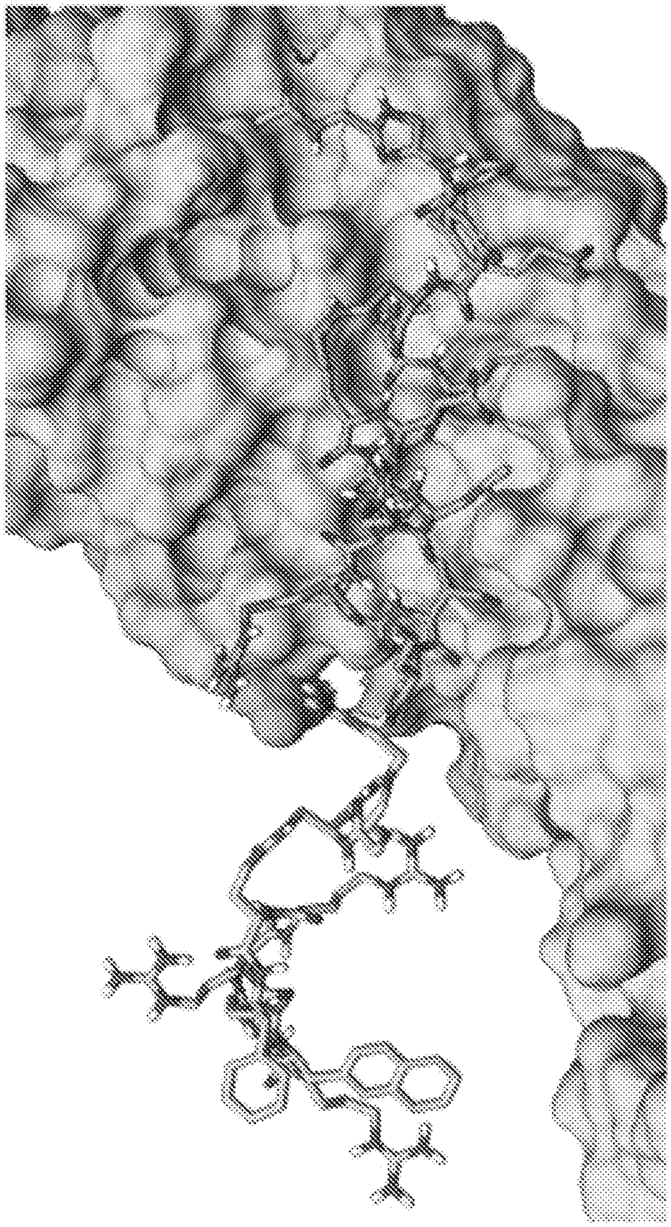
FIG. 3C reveals the binding mode of peptide 2 in complex with 13-catenin derived from PDB ID: 1 QZ7.
Figure 7:
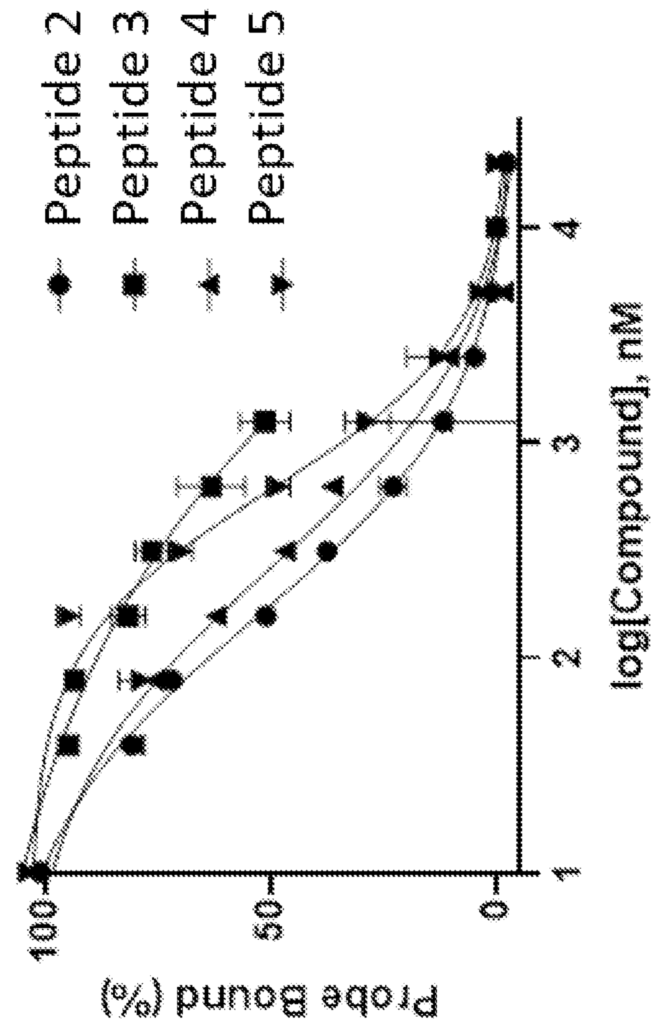
FIG. 7 show competition for binding to β-catenin by peptides 2-5. Data shown represent the mean±SD of three independent experiments. A reliable $IC_{50}$ value could not be determined for peptide 3 due to peptide precipitation at higher peptide concentrations under the buffer conditions.
Figure 8A:
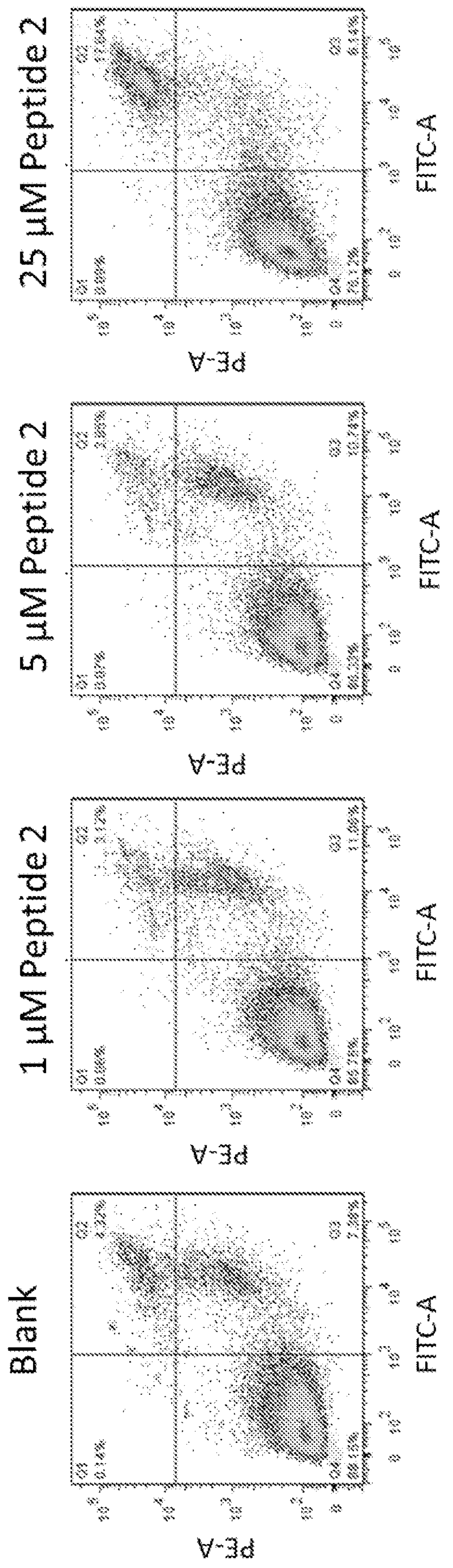
FIG. 8A shows annexin V/PI staining of SW480 cells after treatment with increasing concentrations of peptide 2.
Figure 8B:
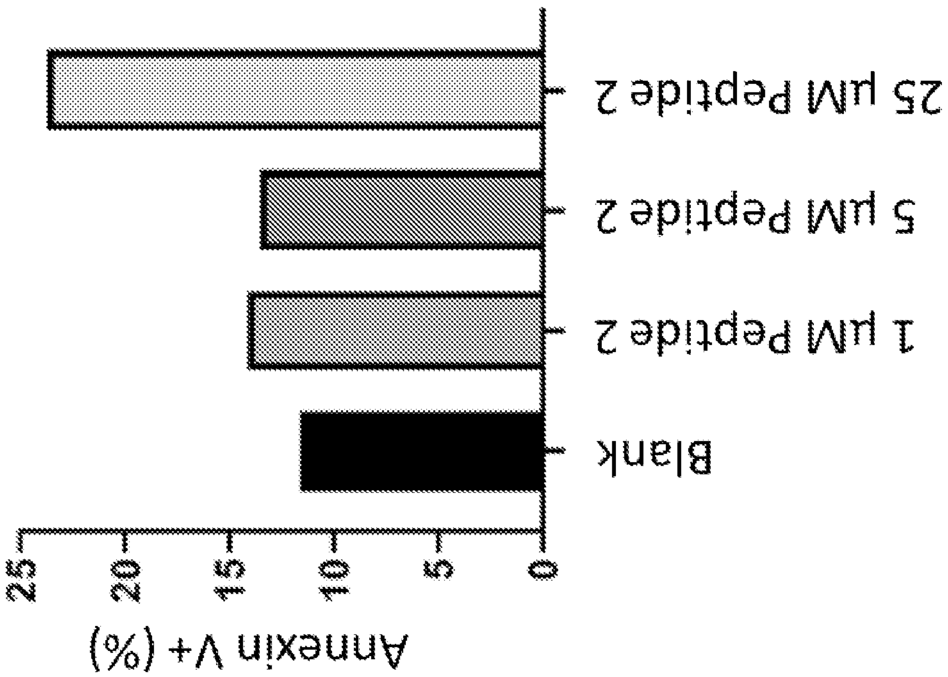
FIG. 8B shows the percentage of apoptotic cells (populations in Q2 and Q3) with and without compound treatment from FIG. 8A.
Figure 9A:
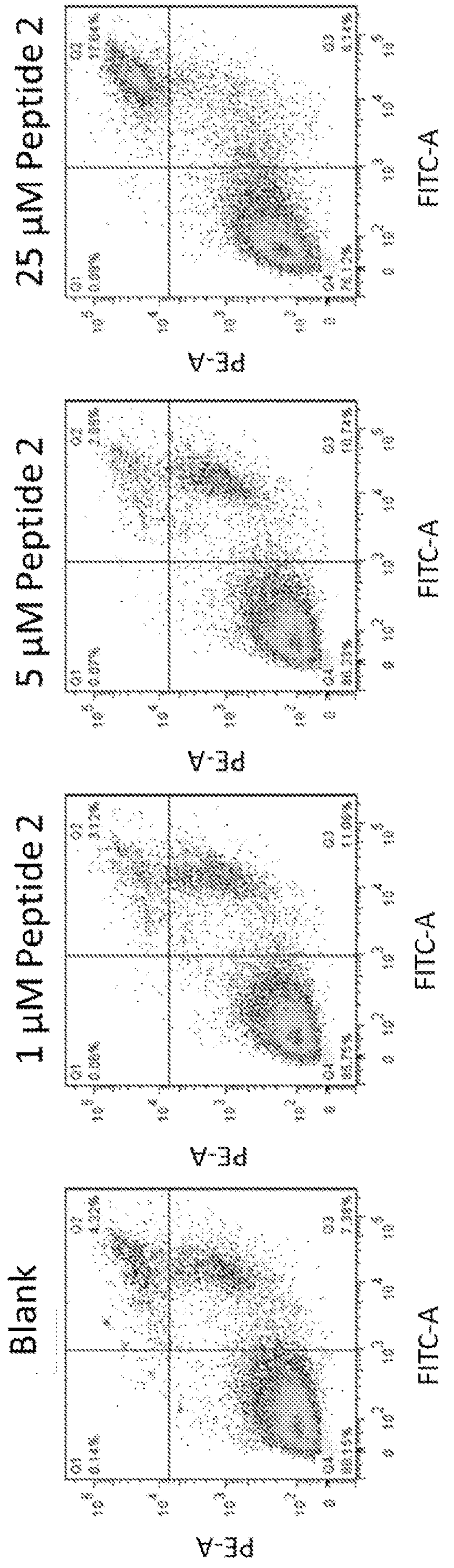
FIG. 9A shows annexin V/PI staining of DLD-1 cells after treatment with increasing concentrations of peptide 2.
Figure 9B:
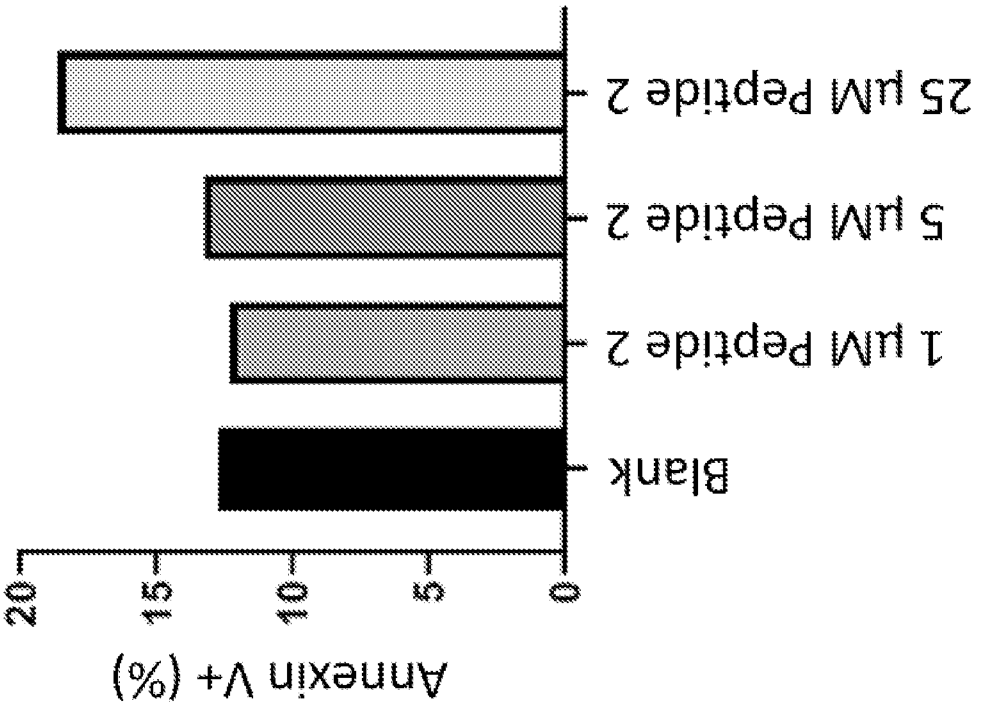
FIG. 9B shows the percentage of apoptotic cells (populations in Q2 and Q3) with and without compound treatment from FIG. 9A.

Example 2: Cell-Permeable Stapled Peptides Against β-Catenin-TCF Interaction A cell permeable stapled peptide against the β-Catenin-TCF interaction was synthesized. An m-xylene stapled peptidyl inhibitor, FAM-GGYPECILDCHLQRVIL-$NH_2$ (SEQ ID NO: 120), which has high affinity for β-Catenin ($K_D$=18 nM) was chosen (peptide 1, Table 7) and further modified. The two cysteine residues were replaced with aspartic acid and lysine and the m-xylene staple with a DK staple. The N-terminal FAM dye was also removed to increase the aqueous solubility and the resulting peptide, i.e. peptide 2 (Table 7), was conjugated to cyclic cCPP9 at its C-terminus via a $(miniPEG)_2$ linker. Analysis of the binding mode through molecular dynamics indicated that C-terminal conjugation resulted in minimal disruption of the productive binding conformation with cCPP9 extended into the solvent (FIG. 3C). In an FP-based competition assay, peptide 2 bound to β-Catenin with an $IC_{50}$ value of 152±8 nM (FIG. 7). A negative control peptide (peptide 3, Table 7) was generated by swapping two binding residues (Asp and His) and replacement of a C— terminal isoleucine with alanine. Peptide 3 bound to β-catenin with ~10-fold lower affinity than peptide 2 (FIG. 7). The cCPP9 moiety of peptide 2 was also replaced with Tat and R9, to give peptides 4 and 5 (Table 7), respectively.

Figure 4A:
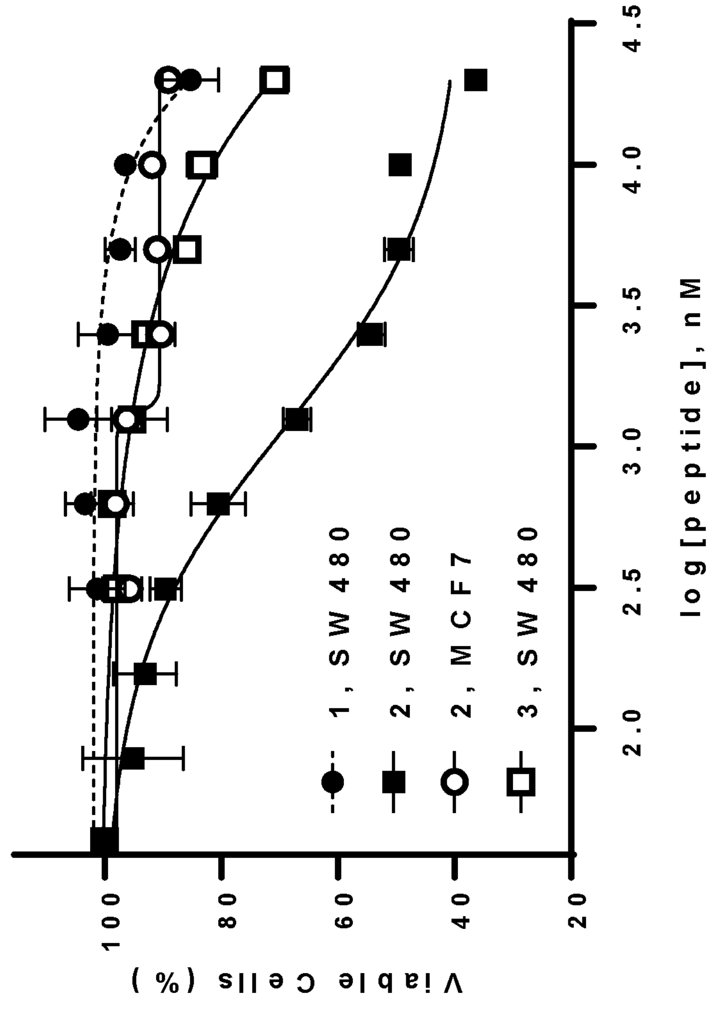
FIG. 4A shows the effect of β-catenin-TCF inhibitors, peptide 1, peptide 2, and peptide 3, on the viability of SW480 (Wnt-addicted) and MCF7 (Wnt-independent) cells as determined by the MTT assay. Data reported represent the mean±SD of 3 independent experiments.
Figure 4B:
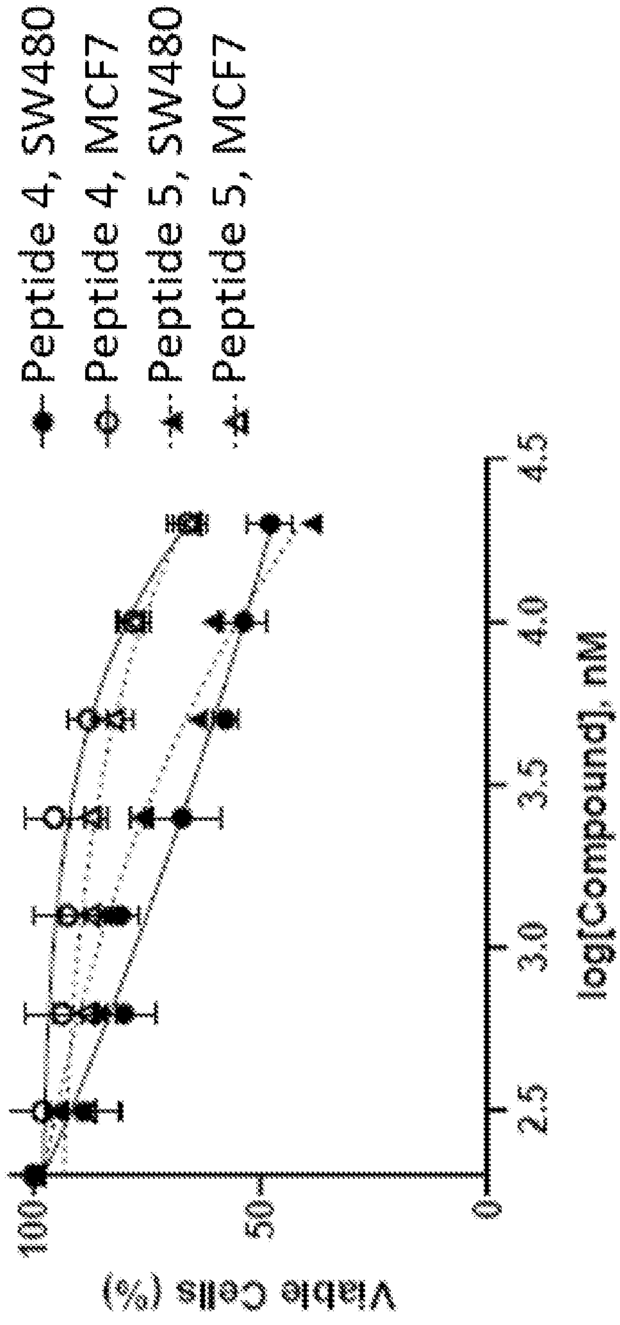
FIG. 4B shows the effect of β-catenin-TCF inhibitors, peptide 4 and peptide 5, on the viability of SW480 (Wnt-addicted) and MCF7 (Wnt-independent) cells as determined by the MTT assay.
Figure 5:
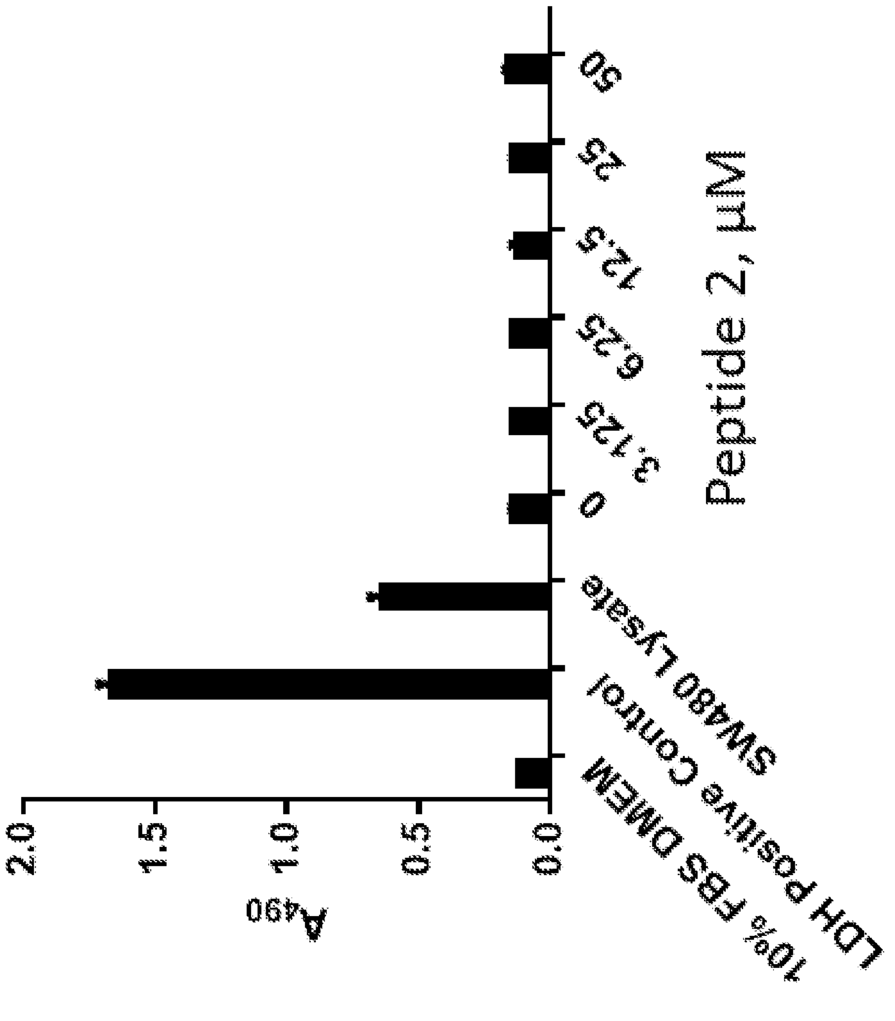
FIG. 5 shows lactate dehydrogenase (LDH) release caused by membrane disruption. SW480 cells treated with 0-50 μM peptide 2. Growth medium without cells (10% FBS RPMI) was used as negative control, whereas enzymatically active LDH was used as positive control. Data shown represent the mean±SD of three independent experiments.

Peptides 1-5 (Table 7) were tested for anti-proliferative activity against SW480 cells, a colorectal cancer cell line which has elevated levels of β-catenin due to an APC mutation and requires the Wnt signaling pathway for proliferation. Peptide 2 potently and dose-dependently reduced the viability of SW480 cells, with an EC50 value of 3.7 μM (FIG. 4A). In comparison, peptides 1 and 3 resulted in only slight decreases in the viability of SW480 cells at the highest concentration tested (20 μM). Peptides 4 and 5 showed weak activities with EC50 values exceeding 20 μM (FIG. 4B). To test whether the peptides exerted anti-proliferative effects through specific inhibition of Wnt-independent signaling or as a result of general cytotoxicity, we tested the same set of peptides against Wnt-independent breast cancer MCF7 cells. Peptide 2 up to 20 μM showed negligible effect on MCF7 cell viability (FIG. 4A), consistent with the notion that peptide 2 inhibits SW480 cell proliferation through inhibition of β-Catenin. On the other hand, peptides 4 and 5 also reduced the viability of MCF7 cells, albeit to a lesser extent compared to SW480 cells, indicating that peptides 4 and 5 cause cytotoxicity due to as yet unidentified off-target effects (FIG. 4B). Annexin V and PI staining revealed that peptide 2 did not induce apoptosis or necrosis of SW480 cells or another Wnt-addicted colorectal cancer cell line, DLD-1 cells, until 25 μM concentration, when ~10% cells underwent apoptotic cell death (FIGS. 8, 8B, 9A, and 9B). Further, treatment of SW480 cells with up to 50 μM peptide 2 did not cause significant LDH release (FIG. 5).

Figure 6:
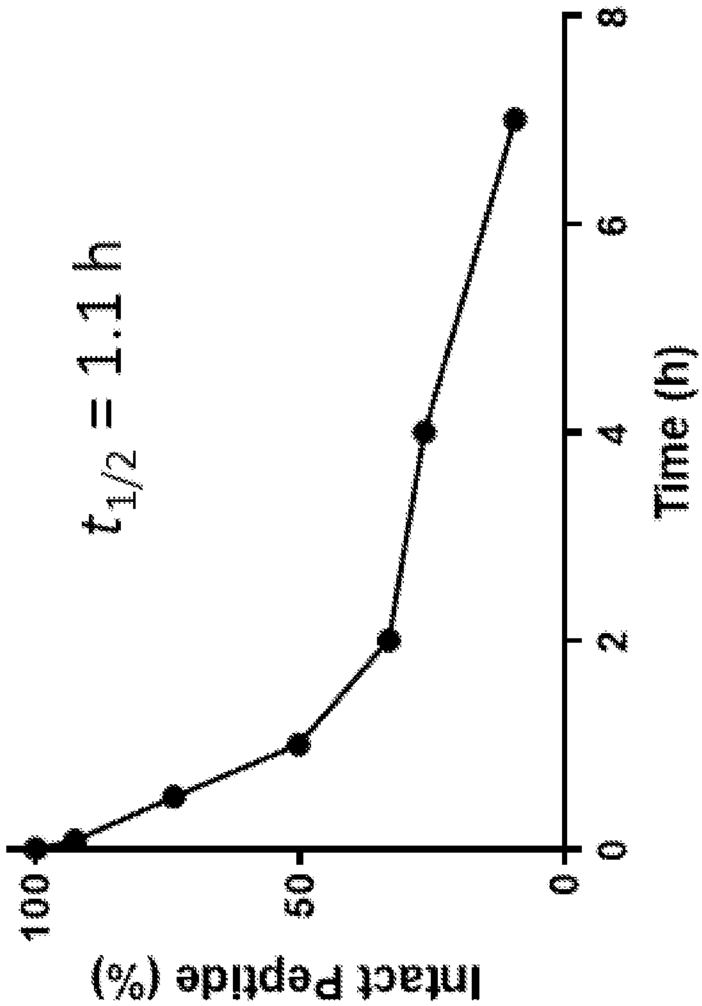
FIG. 6 shows the stability of peptide 9 in human serum. Data is from a single set of experiment.

Our results confirm that knockdown of β-catenin results in activation of apoptosis among ~20% of the cell population, indicating that peptide 2 reduces the viability of SW480 and DLD-1 cells primarily by inhibiting their rate of proliferation. A relatively large difference between the in vitro IC50 and cellular EC50 values (8-fold) was observed. Without being limited by theory, factors contributing to this difference likely include the rapid degradation of peptide 2 (which has a serum $t_{1/2}$ of 1.1 h; FIG. 6), by proteases in the growth medium and/or the intracellular compartments.
Peptide 1
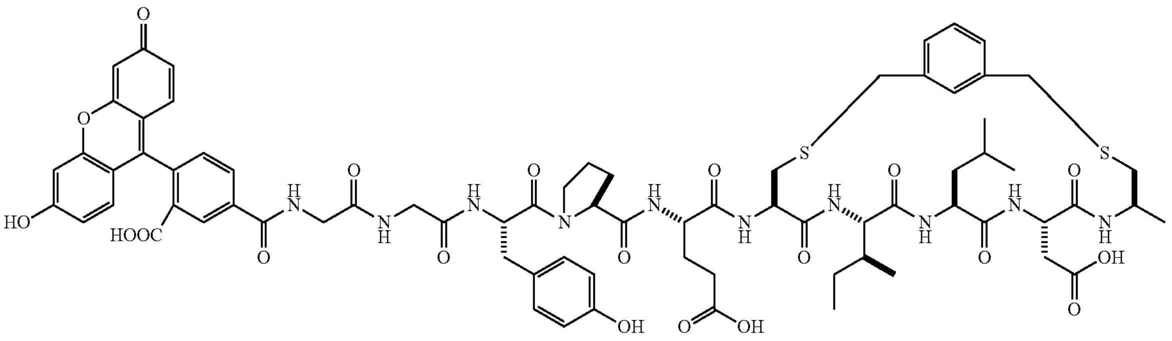
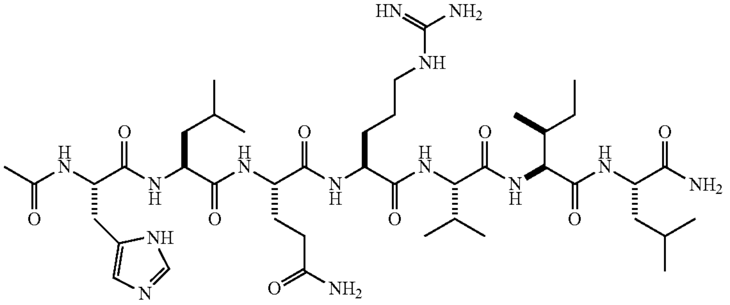
Peptide 2
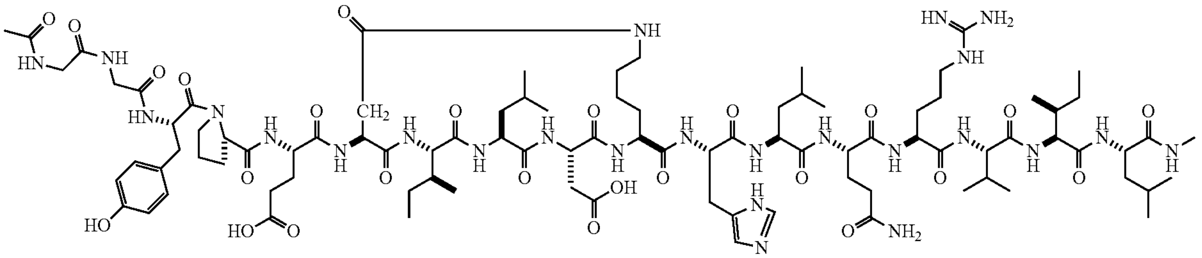
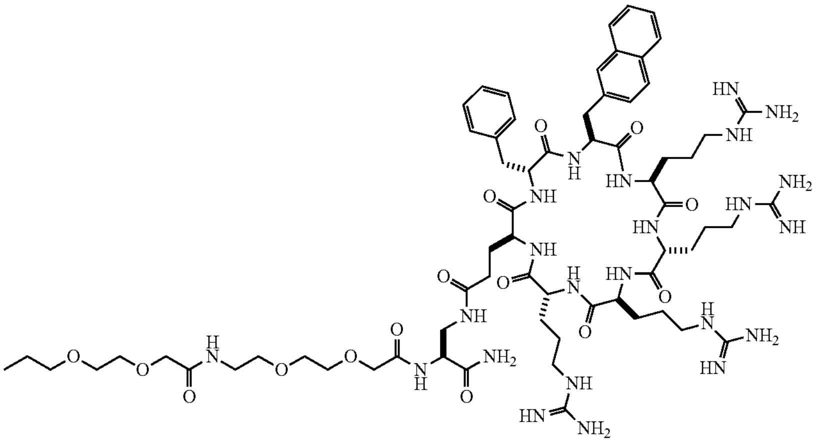

-continued
Peptide 3
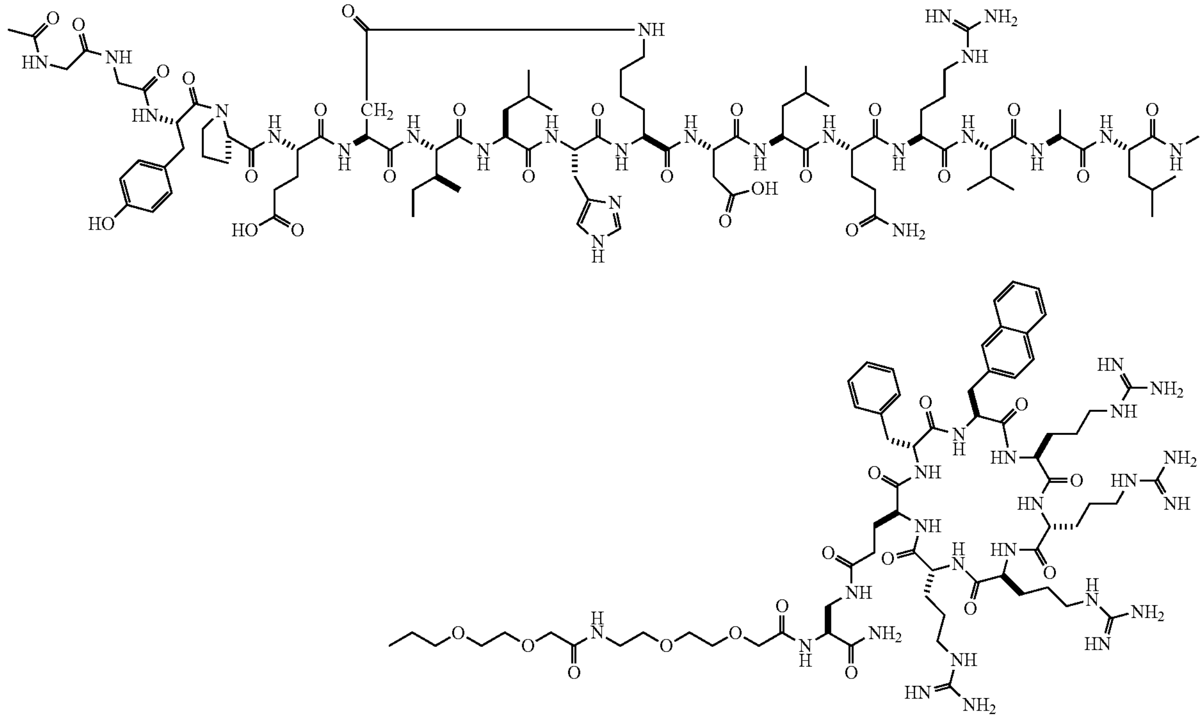
Peptide 4
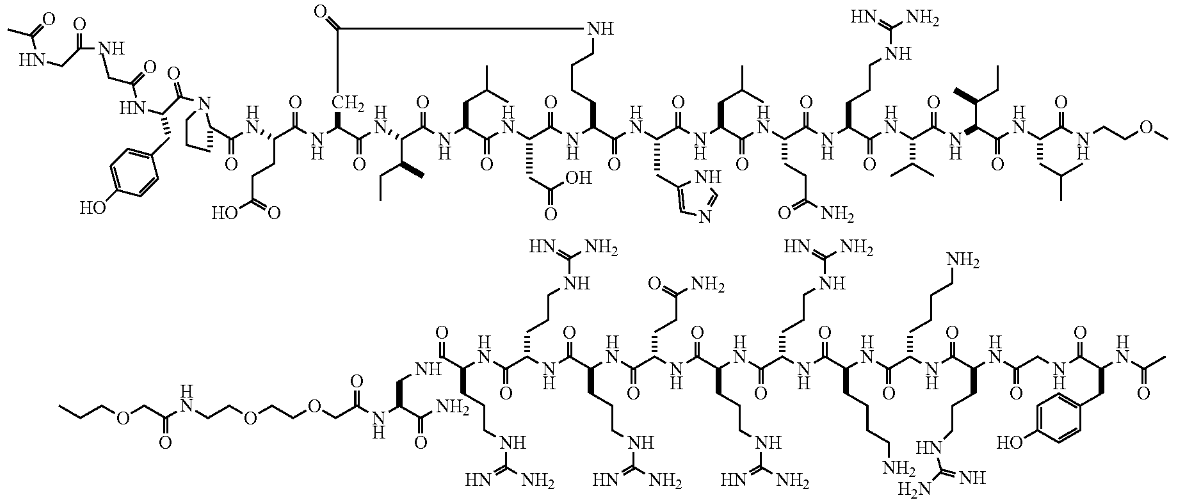
Peptide 5
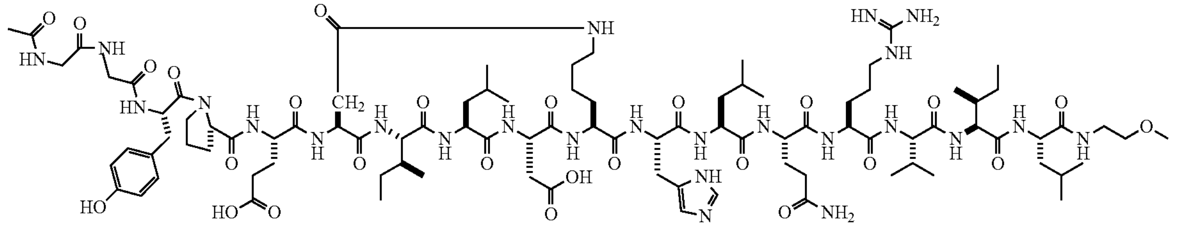

-continued
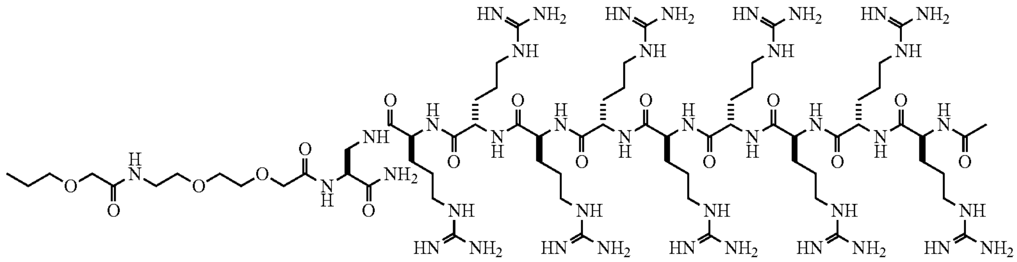
Peptide 7
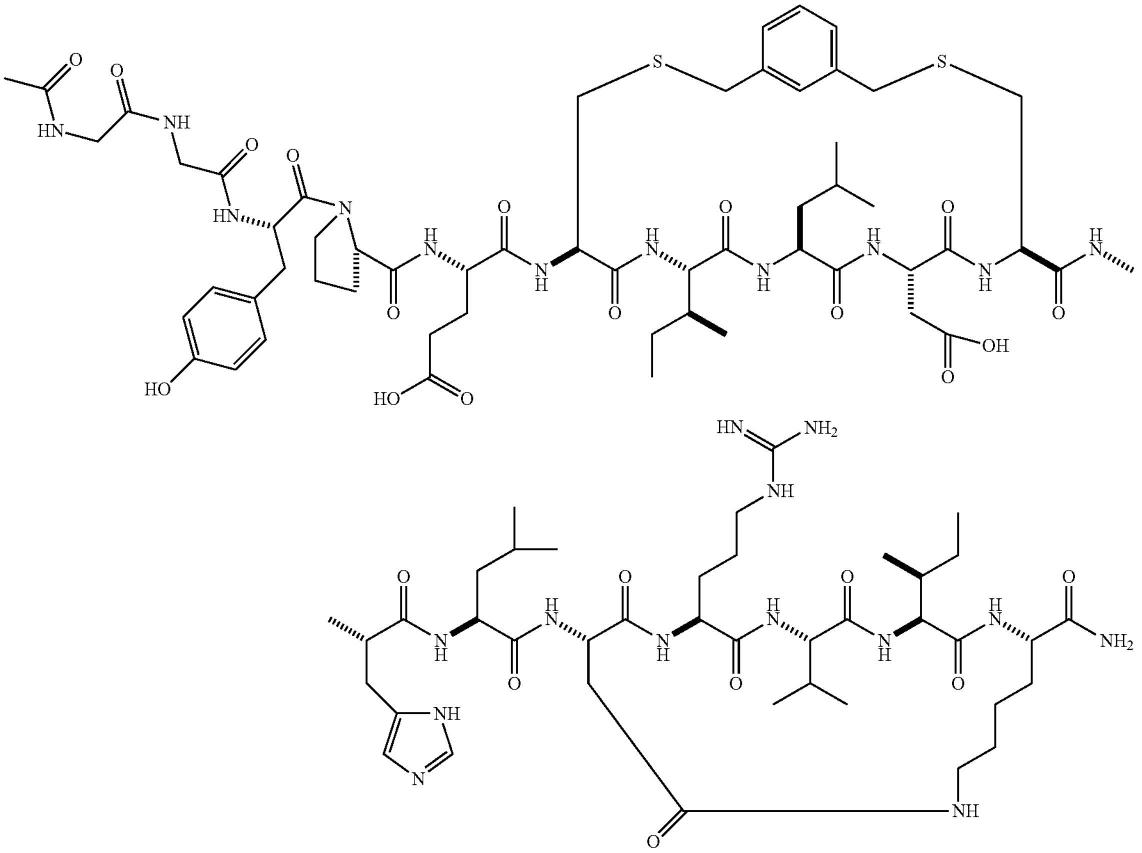
Peptide 8
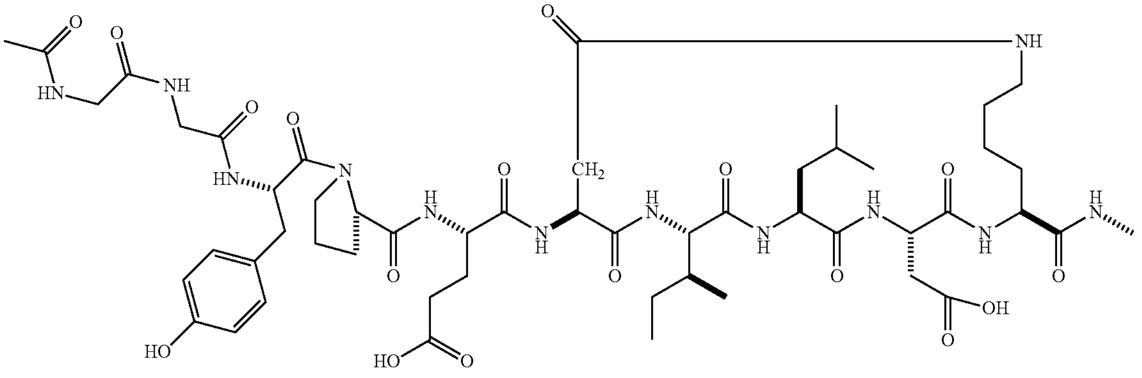

-continued

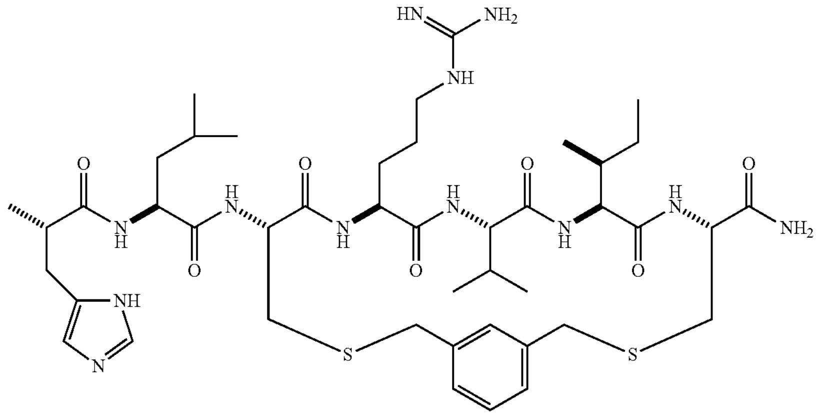

TABLE 7

Sequences and Potency of Peptidyl p-Catenin Ligands. Amino acids are represented by their one letter codes. Z is the amino acid tert-leucine. 1-Nal is 1-napthylalanine. 2-Nal is 2-napthylalanine. Hvl is β-hydroxyvaline. 3-Bta is 3-benzothienyl-1-alanine.

| Structure/ Peptide ID | Amino Acid Sequence (N-terminus to C-terminus) | Staple | $K_D$ or IC50 (nM) | | SEQ ID NO. |
|---|---|---|---|---|---|
| peptide 1 | FAM-GGYPECILDCHLQRVIL-NH$_2$ | xylene | 18 | | 120 |
| peptide 2 | Ac-GGYPEDILDKHLQRVIL-(miniPEG)$_2$-Dap(cCPP9)-NH$_2$ | Asp-Lys | 152 ± 7.6 | | 121 |
| peptide 3 | Ac-GGYPEDILHKDLQRVAL-(miniPEG)$_2$-Dap(cCPP9)-NH$_2$ | Asp-Lys | >1250 | | 122 |
| peptide 4 | Ac-GGYPEDILDKHLQRVIL-(miniPEG)$_2$-Dap(Tat)-NH$_2$ | Asp-Lys | 265 ± 9.3 | | 123 |
| peptide 5 | Ac-GGYPEDILDKHLQRVIL-(miniPEG)$_2$-Dap(R9)-NH$_2$ | Asp-Lys | 602 ± 3.6 | | 124 |
| Peptide 6 | Ac-GGYPEDILDKHLQRVIL-NH$_2$ | Asp-Lys | 245 ± 35 | nM | 125 |
| Peptide 7 | Ac-GGYPECILD**C**KHLQ**D**V IL**K**(β-Ala)-NH$_2$ | Asp-Lys; 1,3bis [(methylthio) Methyl]-benzene | 3.2* | μM | 126 |
| Peptide 8 | Ac-GGYPEDILDKHLQ**C**VIL**C**(β-**Ala**)-NH$_2$ | Asp-Lys; 1,3-bis+(methylthio) methyl+-benzene | 525* | μM | 127 |
| Peptide 9 | Ac-GGYPEDILDKHLQR**Z**IL(β-**Ala**)-NH$_2$ | Asp-Lys | 305 ± 19 | nM | 128 |
| Peptide 10 | Ac-GGYPEDILDKHLQR**ZW**L-NH$_2$ | Asp-Lys | 71 ± 5.3 | nM | 129 |
| Peptide 11 | Ac-GGYPEDILDKHLQR**Z**(**3-Bta**)L-NH$_2$ | Asp-Lys | 65 ± 23 | nM | 130 |
| Peptide 12 | Ac-GGYPEDILDKHLQR**Z**(**1-Nal**)L-NH$_2$ | Asp-Lys | 175 ± 16 | nM | 131 |
| Peptide 13 | Ac-GGYPEDILDKHLQR**Z**(**2-Nal**)L-NH$_2$ | Asp-Lys | 86 ± 33 | nM | 132 |
| Peptide 14 | CPP9-(miniPEG)$_2$-GGYPEDILDKHLQR**Z**(**3-Bta**)L-NH$_2$ | Asp-Lys | 63.5* | nM | 133 |

TABLE 7-continued

Sequences and Potency of Peptidyl p-Catenin Ligands. Amino acids are represented by their one letter codes. Z is the amino acid tert-leucine. 1-Nal is 1-napthylalanine. 2-Nal is 2-napthylalanine. Hvl is β-hydroxyvaline. 3-Bta is 3-benzothienyl-1-alanine.

| Structure/ Peptide ID | Amino Acid Sequence (N-terminus to C-terminus) | Staple | $K_D$ or IC50 (nM) | | SEQ ID NO. |
|---|---|---|---|---|---|
| Peptide 15 | CPP9-(miniPEG)$_2$-GGYPEDILDKHLQR**Z**(**2-Nal**)L-$NH_2$ | Asp-Lys | 79.4* | nM | 134 |
| Peptide 16 | Ac-GG(3-Bta)PEDILDKHLQR**Z**(**3-Bta**)L-$NH_2$ | Asp-Lys | 97.9* | nM | 135 |
| Peptide 17 | Ac-GGYPEDILDKHLQR**Z**IL-(miniPEG)$_2$-Dap(CPP9) | Asp-Lys | 100.4* | nM | 136 |
| Peptide 18 | Ac-GGYPEDILDKHLQR**Z**(**3-Bta**)L-(miniPEG)$_2$-Dap(CPP9) | Asp-Lys | 104.4* | nM | 137 |
| Peptide 19 | Ac-YPEDILDKHLQSV(**3-Bta**)**T**-(miniPEG)$_2$-Dap-$NH_2$ | Asp-Lys | 382 ± 13 | nM | 138 |
| Peptide 20 | Ac-YPEDILDKHLQEV(**3-Bta**)**T**-(miniPEG)$_2$-Dap-$NH_2$ | Asp-Lys | 1.8* | µM | 139 |
| Peptide 21 | Ac-YPEDILDKHLQQV(**3-Bta**)**T**-(miniPEG)$_2$-Dap-$NH_2$ | Asp-Lys | 328 ± 12 | nM | 140 |
| Peptide 22 | Ac-YPEDILDKHLQ(dE)V(**3-Bta**)**T**-(miniPEG)$_2$-Dap-$NH_2$ | Asp-Lys | 3.5* | µM | 141 |
| Peptide 23 | Ac-YPEDILDKHLQ**S**V(**3-Bta**)(**dS**)-(miniPEG)$_2$-Dap-$NH_2$ | Asp-Lys | 565 ± 40 | nM | 142 |
| Peptide 24 | Ac-YPEDILDKHLQ(**dR**)VIL-(miniPEG)$_2$-Dap-$NH_2$ | Asp-Lys | 10.7* | µM | 143 |
| Peptide 25 | Ac-YPEDILDKHLQR(**dA**)IL-(miniPEG)$_2$-Dap-$NH_2$ | Asp-Lys | 5.3* | µM | 144 |
| Peptide 26 | Ac-YPEDILDKHLQR**Z**(**3-Bta**)R-(miniPEG)$_2$-Dap-$NH_2$ | Asp-Lys | 37 ± 18 | nM | 145 |
| Peptide 27 | Ac-YPEDILDKHLQR**Z**(**3-Bta**)(**dR**)-(miniPEG)$_2$-Dap-$NH_2$ | Asp-Lys | 41 ± 8.2 | nM | 146 |
| Peptide 28 | Ac-YPEDILDKHLQRV**Z**L-(miniPEG)$_2$-Dap-$NH_2$ | Asp-Lys | 306 ± 58 | nM | 147 |
| Peptide 29 | Ac-YPEDILDKHLQR**Z**(**3-Bta**)**R**-(miniPEG)$_2$-C—$NH_2$ | Asp-Lys | | | 148 |
| Peptide 30 | Ac-YPEDILDKHLQR**Z**(**3-Bta**)(**dR**)-(miniPEG)$_2$-C—$NH_2$ | Asp-Lys | | | 149 |
| Peptide 31* | Ac-YPEDILDKHLQR**Z**(**3-Bta**)**R**-(miniPEG)$_2$—C—C-CPP12 | Asp-Lys | | | 150 |
| Peptide 32* | Ac-YPEDILDKHLQR**Z**(**3-Bta**)(dR)-(miniPEG)$_2$—C—C-CPP12 | Asp-Lys | | | 151 |
| Peptide 33* | Ac-YPEDILDKHLQR**Z**(**3-Bta**)R-(miniPEG)$_2$—C—C-CPP9 | Asp-Lys | | | 152 |
| Peptide 34* | Ac-YPEDILDKHLQR**Z**(**3-Bta**)(**dR**)-(miniPEG)$_2$—C—C-CPP9 | Asp-Lys | | | 153 |
| Peptide 35* | Ac-YPEDILDKHLQR**Z**(**3-Bta**)**R**-(miniPEG)$_2$—C—C-CPP12 | Asp-Lys | | | 154 |
| Peptide 36* | Ac-YPEDILDKHLQR**Z**(**3-Bta**)(**dR**)-(miniPEG)$_2$—C—C-CPP12 | Asp-Lys | | | 155 |

TABLE 7-continued

Sequences and Potency of Peptidyl p-Catenin Ligands. Amino acids are represented by their one letter codes. Z is the amino acid tert-leucine. 1-Nal is 1-napthylalanine. 2-Nal is 2-napthylalanine. Hvl is β-hydroxyvaline. 3-Bta is 3-benzothienyl-1-alanine.

| Structure/ Peptide ID | Amino Acid Sequence (N-terminus to C-terminus) | Staple | $K_D$ or IC50 (nM) | | SEQ ID NO. |
|---|---|---|---|---|---|
| Peptide 37* | Ac-YPEDILDKHLQR(**Hvl**)IL-$NH_2$ | Asp-Lys | 154* | nM | 156 |
| Peptide 38 | Ac-YPEDILDKHLQR(**Hvl**)**ldR**-$NH_2$ | Asp-Lys | 1.3* | µM | 157 |
| Peptide 39 | Ac-GGYPEDILDKHLQR(**Hvl**)IL-(miniPEG)$_2$-Dap(CPP9) | Asp-Lys | | | 158 |

*the "—C—C-" in the above-indicated peptides represents two cysteine residues joined by a disulfide bond.

Figure 11A:
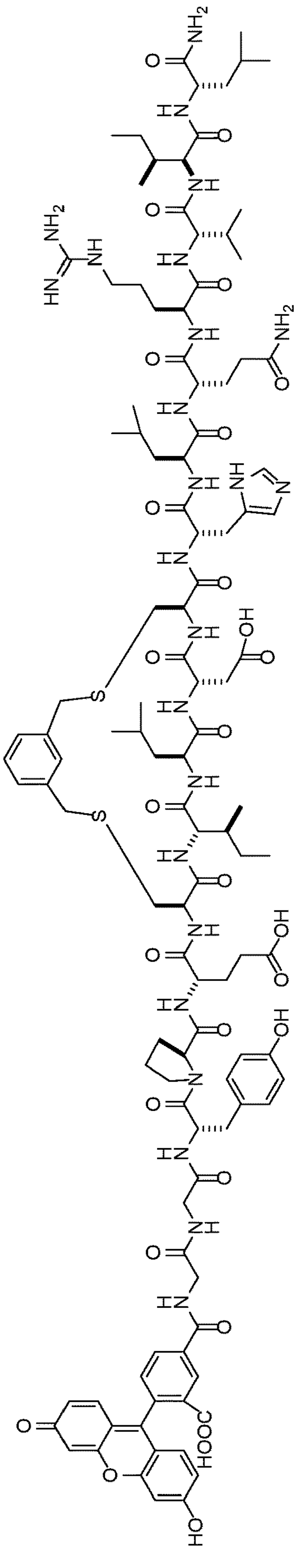
FIGS. 11A-C shows the structure (FIG. 11A), analytical high performance liquid chromatography (HPLC) trace (FIG. 11C), and high resolution mass spectrometry spectrum (FIG. 11B) for Peptide 1.
Figure 11B:
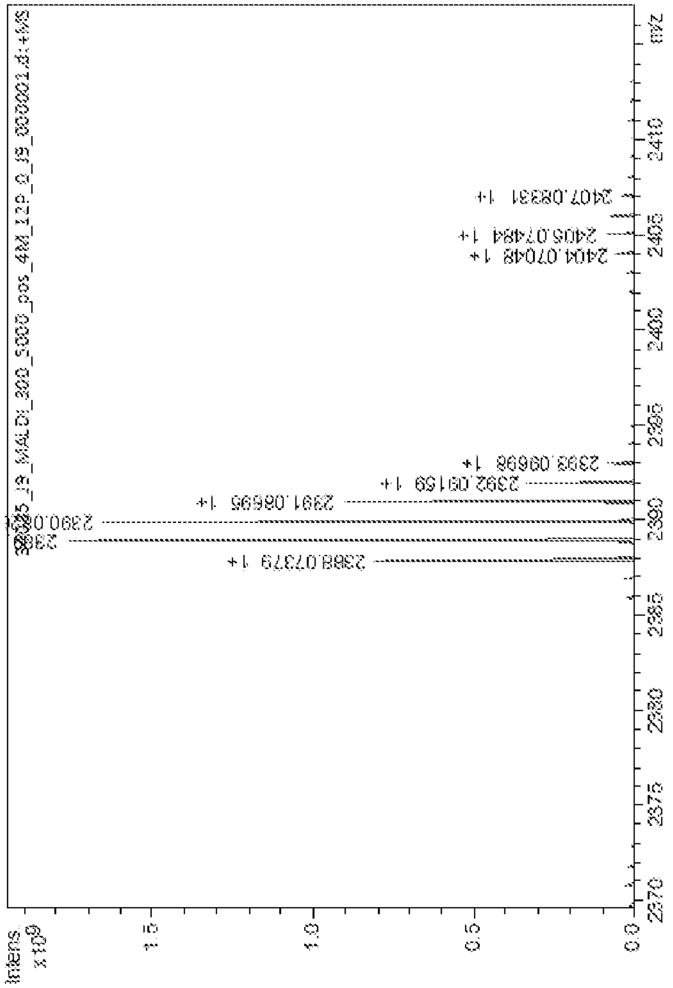
Figure 11C:
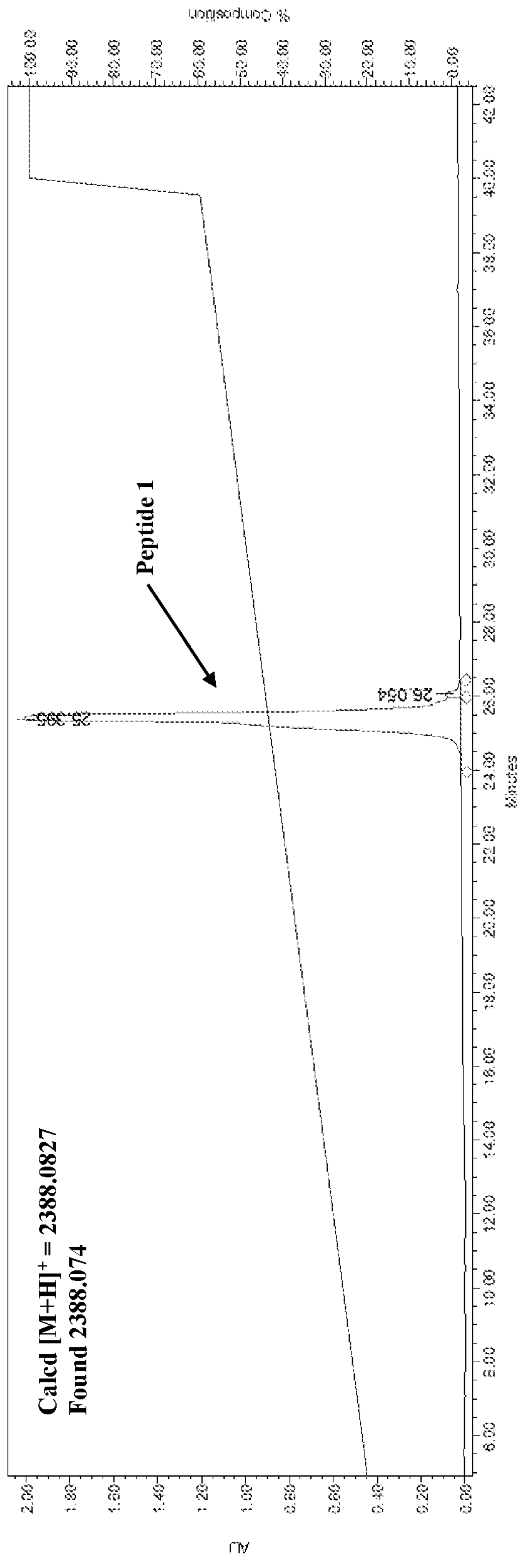
Figure 12A:
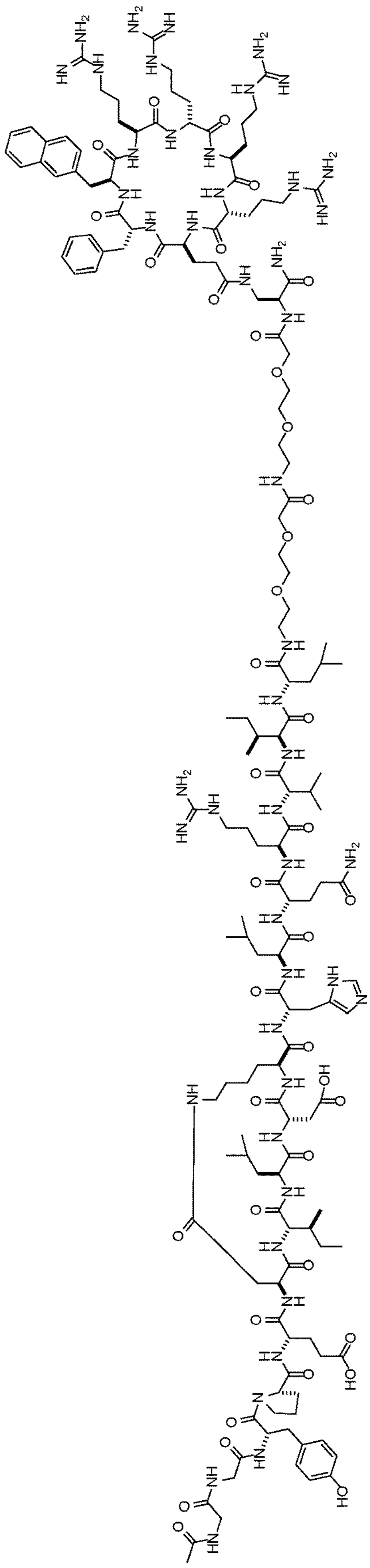
FIG. 12 shows the structure (FIG. 12A), analytical high performance liquid chromatography (HPLC) trace (FIG. 12C), and high resolution mass spectrometry spectrum (FIG. 12B) for Peptide 2.
Figure 12B:
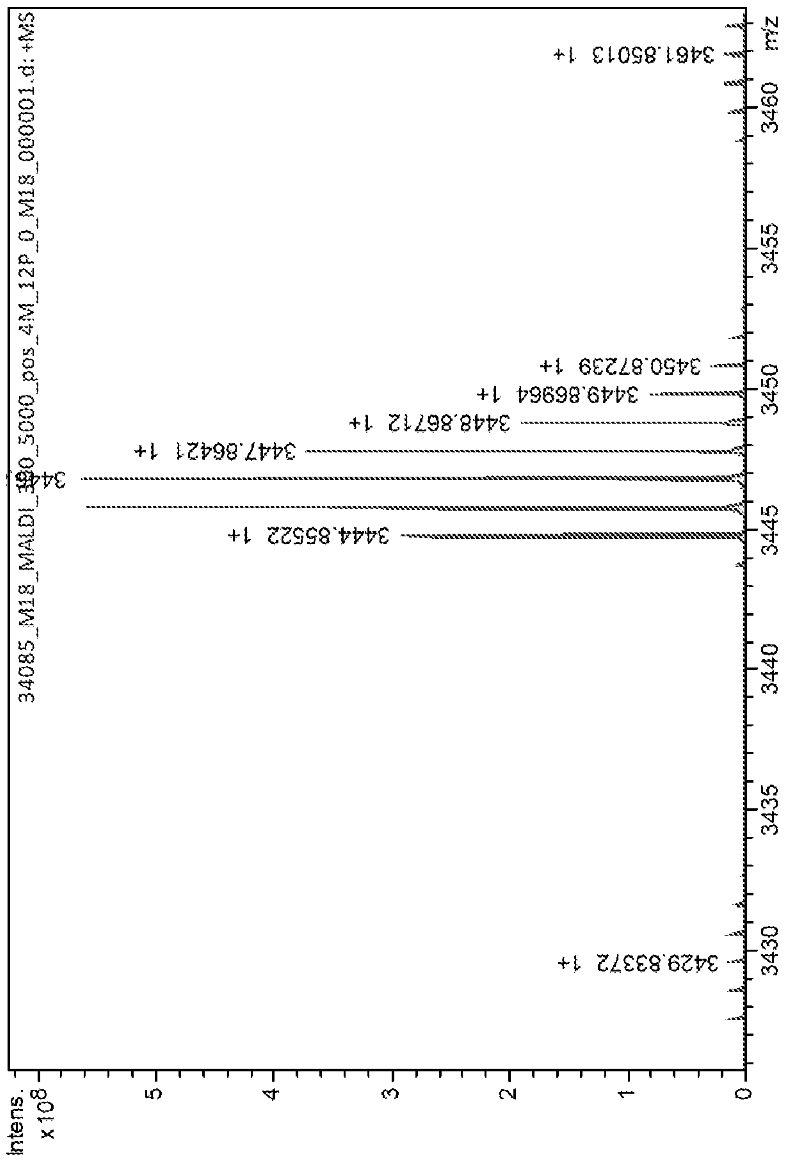
Figure 12C:
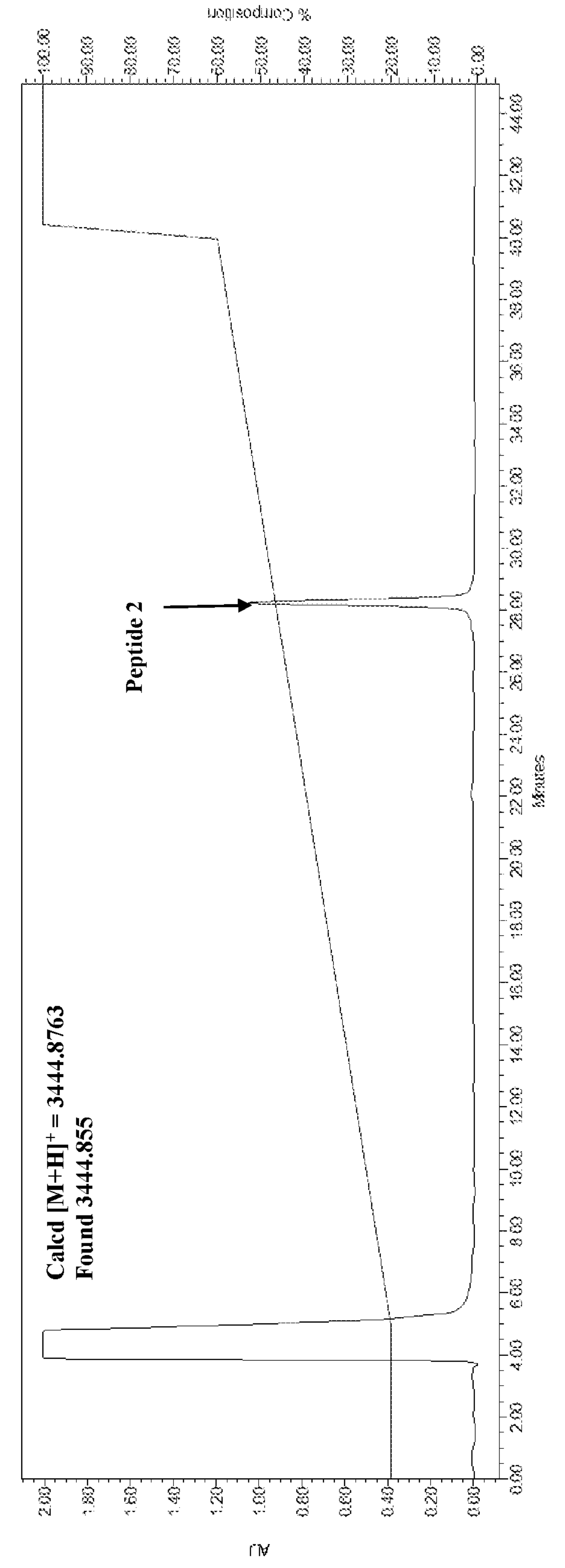
Figure 13A:
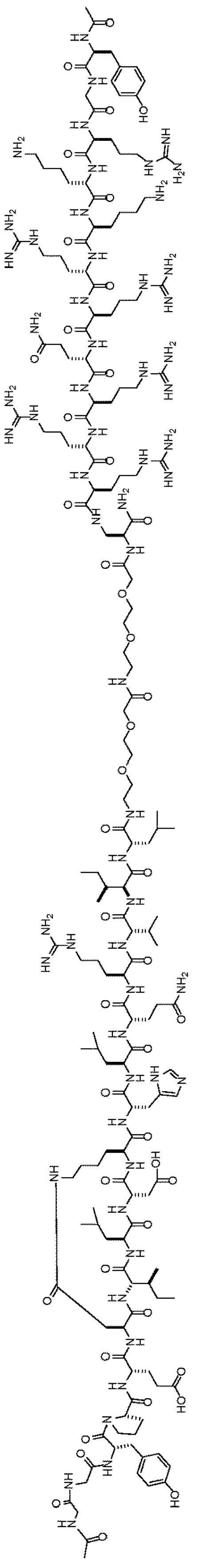
FIG. 13 shows the structure (FIG. 13A), analytical high performance liquid chromatography (HPLC) trace (FIG. 13C), and high resolution mass spectrometry spectrum (FIG. 13B) for Peptide 4.
Figure 13B:
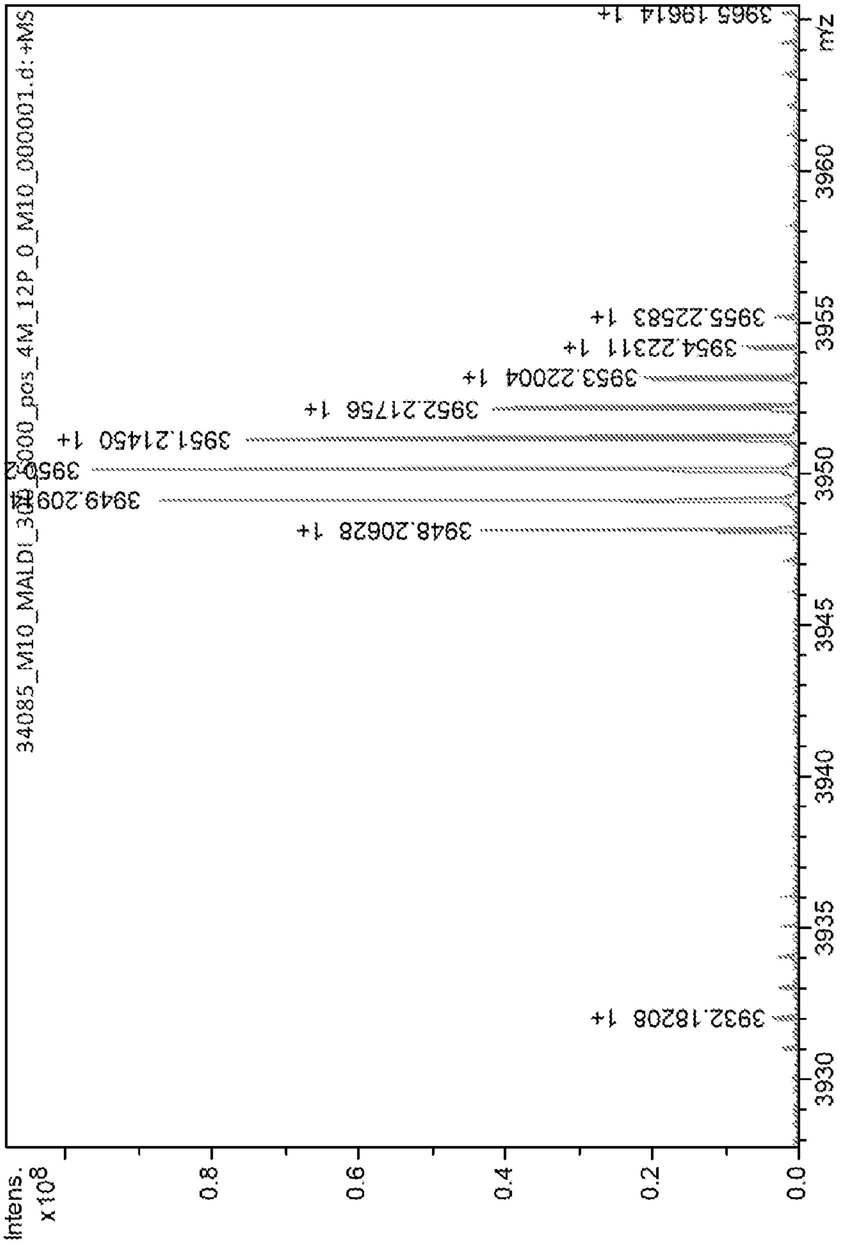
Figure 13C:
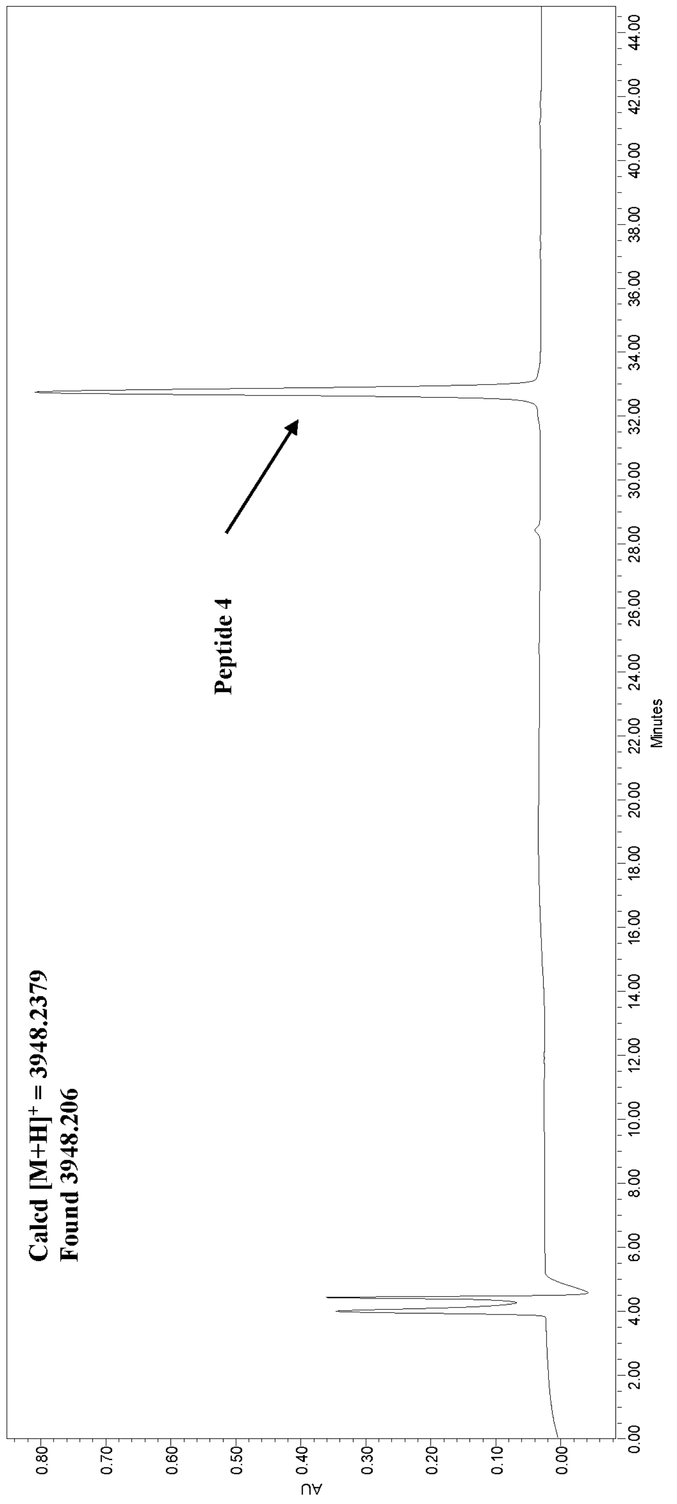

FIGS. 11, 12, and 13, show the structure, analytical high performance liquid chromatography (HPLC) trace, and high resolution mass spectrometry spectrum for Peptide 1, Peptide 2, and Peptide 4, respectively.

Figure 14:
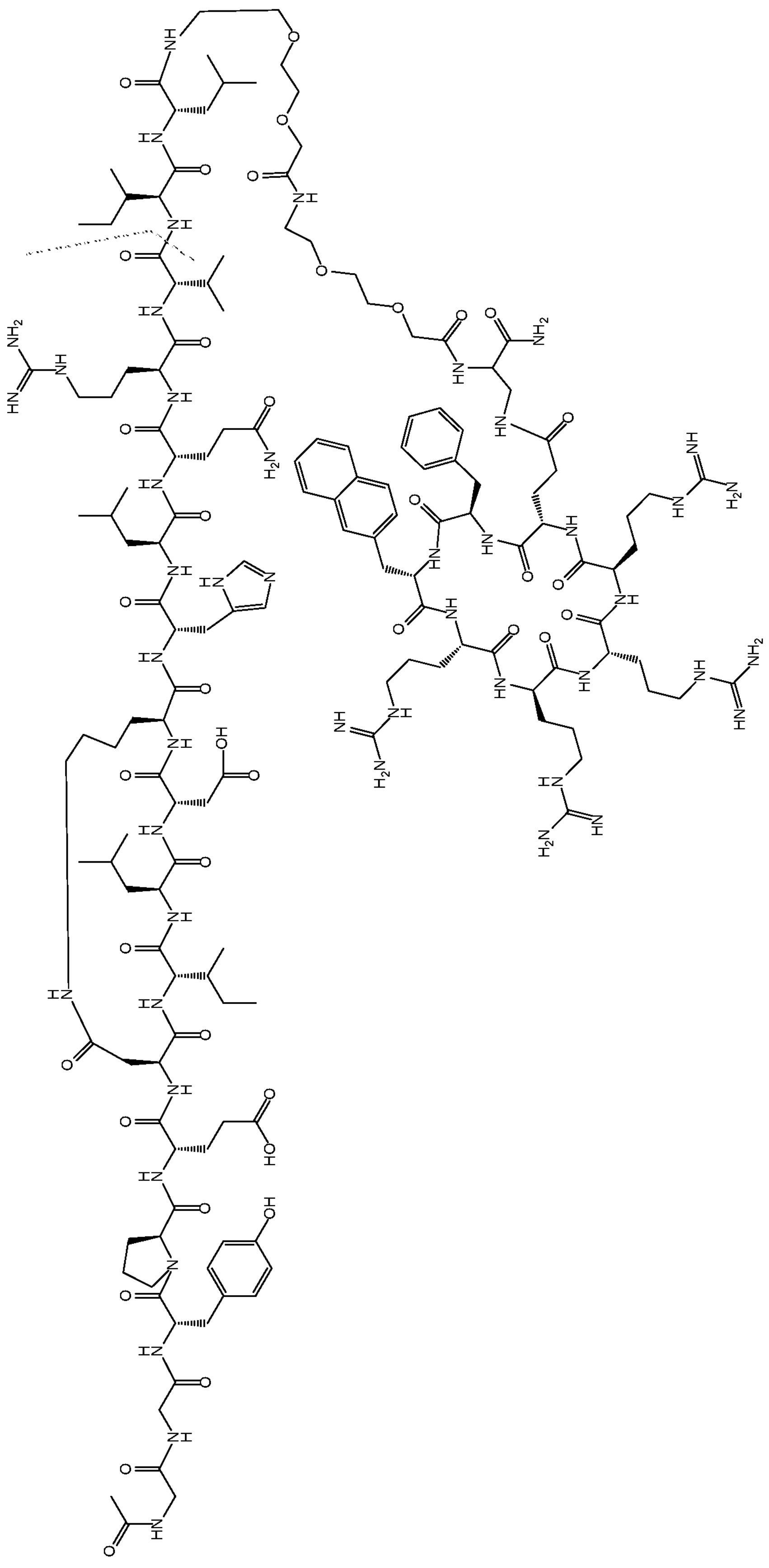
FIG. 14 shows the structure of Peptide 2 and the location of the exopeptidase cleavage site.

The ability of peptide 2 to withstand proteolytic degradation was evaluated. Our starting point was a previously reported β-catenin peptide inhibitor conjugated at the C-terminus with CPP9 (peptide 2, FIG. 14). Peptide 2 inhibits β-catenin-TCF interaction with an $IC_{50}$=152±8 nM and the proliferation of SW480 cells with an $EC_{50}$ value of 1.2±0.4 µM (J. Med. Chem. 2019, 62, 10098). In human serum, the $t_{1/2}$ was ~2 h. Mass spectrometric analysis of the degradation products indicates that degradation of peptide 2 begins at the Val-Ile bond and is followed by exopeptidase action at the newly exposed free N- and C-termini.

To improve the proteolytic stability, we first placed a second staple to peptide 2 to generate peptides 7 and 8. The double stapled peptides binding affinities to β-catenin was determined by their $IC_{50}$ values of 3.2 µM and 525 µM, respectively (Table 7). We next replaced Val-15 with a tert-leucine (Z), whose bulky side chain was expected to block the initial endopeptidase cleavage and stabilize the peptide overall. Indeed, the resulting peptide (peptide 9 in Table 7) has much improved serum stability ($t_{1/2}$~12 h in human serum). The β-catenin binding affinity was 305±19 nM.

To improve the peptide potency, we replaced Ile-16 with different aromatic residues (Trp, 3-Bta, 1- and 2-Nal). Substitution of a large aromatic hydrophobic residue increased the binding affinity by 2- to 5-fold, with Bta and Trp being most effective (peptides 10-13). Bta offers additional benefits for being more metabolically stable than Trp (e.g., against oxidation). However, to our surprise, when the improved peptides (9 and 11) were conjugated to CPP9, they (peptides 14, 15, 17, and 18) did not exhibit significant anti-proliferative activity against SW480 cells ($EC_{50}$>100 µM). We hypothesized that these peptides, while having improved binding to β-catenin, might also have stronger binding to off-targets, because of their greater hydrophobicity. Binding to abundant intracellular proteins (e.g., actin, which is present inside the cytosol at ~100 M concentration) would sequester the peptides and prevent them from binding to the intended target.

To reduce the peptide hydrophobicity and off-target binding, we reverted tert-leucine back to Val and replaced various other residues with hydrophilic residues, especially D-amino acids, anticipating that D-amino acids would increase the proteolytic stability (peptides 19-25). β-catenin affinity for these peptides is reported in Table 7.

Next, we modified peptide 11 by replacing the C-terminal Leu with Arg or D-arginine to give peptides 26 and 27, respectively. Peptides 26 and 27 had excellent binding affinities for β-catenin ($IC_{50}$=37 and 41 nM). Peptides 26 and 27 were conjugated to CPP9, CPP12, and a CPP9 analog through a reversible disulfide linker (peptides 31-36). $EC_{50}$ values for peptides 31-36 are reported in Table 7.

Finally, we replaced the tert-leucine of peptide 9 with β-hydroxyvaline (Hvl) to give peptide 37, which has identical binding affinity for β-catenin and serum stability to peptide 9. $EC_{50}$ values for peptides 1-35 are reported in Table 7.

Example 3: Peptide Stapling and Conjugation with a KD Staple

The main limitation of the oxime-based conjugation method is the formation of two different stereoisomers, which complicates product isolation and further clinical development. To overcome this limitation, a lactam linker formed by the side chains of a lysine/aspartate pair at the i and i+4 positions (KD staple) was employed. Previous studies have shown that the KD staple results in consistently higher α-helicity for stapled peptides than other commonly used staples. The staple is also more hydrophilic than other staples (e.g., all hydrocarbon staple), improving the aqueous solubility of the stapled peptides. See Shepherd, N. E.; Hoang, H. N.; Abbenante, G.; Fairlie, D. P. Single Turn Peptide Alpha Helices with Exceptional Stability in Water. J. Am. Chem. Soc. 2005, 127, 2974-2983. Peptides containing the KD staple were synthesized by solid-phase peptide synthesis. Peptides containing the KD staple can be conjugated to the CPP at its N-terminus, C-terminus, or within the peptide chain (FIG. 3A and FIG. 3B).

Example 4: Intracellular Delivery of Other Stapled Peptides by Cyclic cCPP9

Figure 10:
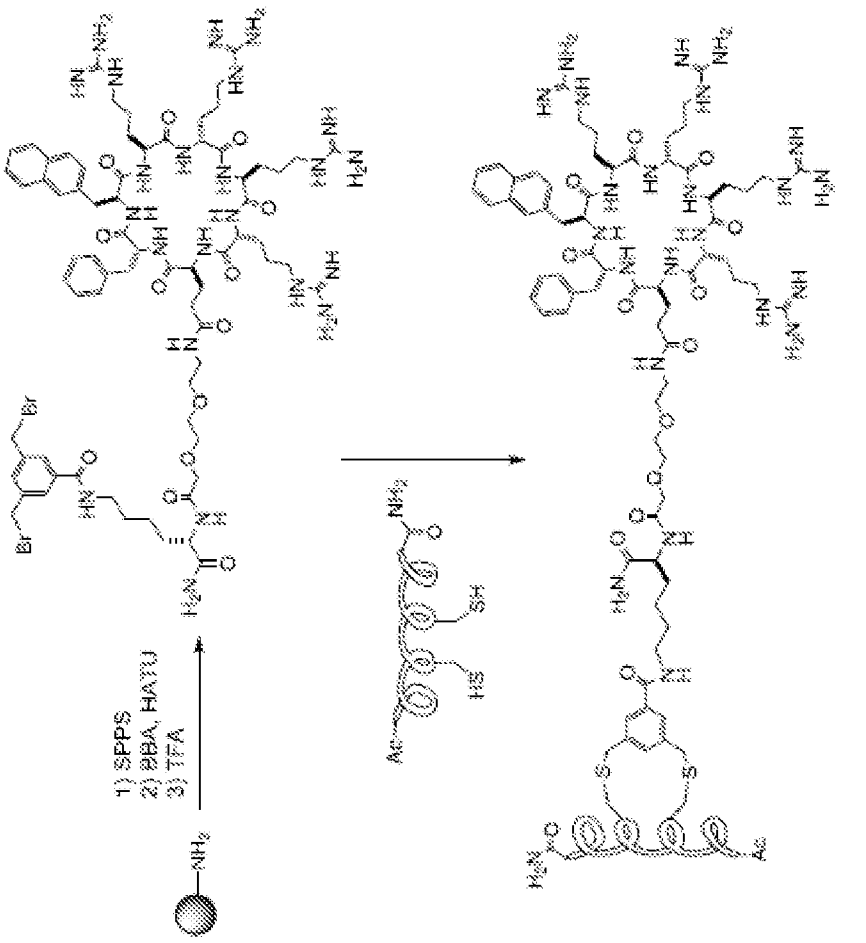
FIG. 10. Simultaneous stapling and conjugation of Cys-con-taining peptides to a cyclic CPP. SPPS, solid-phase peptide synthesis; BBA, 3,5-bis(bromomethyl)benzoic acid; HATU, O-Benzotriazole-N,N,N',N'-tetramethyluronium hexafluoro-phosphate; TFA, trifluoroacetic acid.

An alternative stapling and conjugation was explored in which 3,5-bis(bromomethyl)benzoic acid (BBA) was used as the stapling agent, and can be used to concomitantly conjugate the CPP (FIG. 10). A cCPP9 containing a mini-PEG-Lys(Mtt) linker was synthesized by standard solid-phase peptide chemistry (FIG. 10). While still on resin, the methyltrityl (Mtt) group on the lysine side chain was selectively removed with 2% trifluoroacetic acid (TFA) and the ex-posed amine was acylated with BBA. The cCPP9-BBA adduct was released from the resin and side-chain deprotected by treatment with TFA and purified by HPLC. For stapling, a linear peptide of interest is modified to contain two cysteine residues at i and i+4 positions and mixed with cCPP9-BBA to generate cCPP9-stapled Experimental Details Peptide Synthesis and Labeling. Peptides were manually synthesized by SPPS on Rink amide resin by using Fmoc chemistry and 2-(7-aza-1H-benzotriazole-1-yl)-1,1,3,3-tetramethyluronium hexafluorophosphate (HATU) as the coupling agent. Coupling reactions typically involved 5 equiv of Fmoc-amino acids, 5 equiv of HATU, and 10 equiv of diisopropylethylamine (DIPEA) and were carried out at R.T. for 45 min. The peptides were cleaved off the resin and deprotected by treatment with 92.5% TFA, 2.5% water, 2.5% triisopropylsilane, and 2.5% 1,3-dimethoxybenzene for 3 h at R.T. The solvents were removed by flowing a stream of $N_2$ over the solution and the residue was triturated with cold diethylether. The crude peptides were purified by reversed-phase HPLC equipped with a $C_{18}$ column, which was eluted with linear gradients of acetonitrile (containing 0.05% TFA) in $ddH_2O$ (containing 0.05% TFA). Fluorescent labeling of the peptides were conducted in solution-phase. Lyophilized peptides were incubated with 5 equiv. of an activated fluorescent labelling reagent (e.g., fluorescein isothiocyanate or 5(6)-carboxynaphthofluorescein succinimidyl ester) and 5 equivalents of DIPEA in DMF for 2 h. The reaction was quenched by TFA and the labelled peptides were purified again by HPLC and their authenticity was confirmed by MALDI-TOF mass spectrometry.

For peptides containing a side-chain lactam crosslink, Lys(Mtt) and Asp(O-2-PhiPr) were incorporated at their designated positions during manual SPPS using the previously indicated coupling reagents. Following completion of the linear sequence, the N-terminal Fmoc group was removed and acylated with $Ac_2O$ (10 equiv), DIPEA (10 equiv) in DCM for 10 min twice. Acid-labile side-chain protecting groups were removed by incubating the resin with 2% TFA, 1% TIPS in DCM, three times for 5 min. Lactam formation was performed using PyBOP (5 equiv), DIPEA (5 equiv) in 1:1 (v/v) DMF/DCM for 2 h, followed by overnight incubation. Peptides were washed and any remaining amine was acylated using $Ac_2O$ (10 equiv) and DIPEA (10 equiv) in DCM 2×10 min. Peptides were cleaved from the resin by the addition of 92.5% TFA, 2.5% water, 2.5% TIPS, and 2.5% 1,3-dimethoxybenzene for 3 h at RT, triturated with diethyl ether, and purified by HPLC as described above.

For peptides containing a C-terminal cell-penetrating peptide, the linear precursor peptides were synthesized via manual SPPS containing a C-terminal allyloxycarbonyl (Alloc)-protected Lys or Dap residue. Following general synthesis and side-chain cyclization as mentioned previously, the C-terminal Alloc group was removed using $Pd(PPH_3)_4$ (0.3 equiv) and PhSiH3 (15 equiv) in dry DCM (3×15 min). Following deprotection, the resin was incubated in 10% sodium dimethyldithiocarbamate (SDDC) in DMF (w/v) and washed thoroughly with DMF/DCM. Cell-penetrating sequences were then synthesized by manual SPPS as mentioned previously.

For BBA- or xylene-stapled peptides, linear peptides were first synthesized as previously described and purified. After lyophilization, 2 mg of each peptide was dissolved in 3 mL of DMF and 7 mL of 100 mM $NH_4HCO_3$ (pH 8.1) to a final concentration of 0.1 mM peptide. To this mixture, tris (carboxyethyl)phosphine (TCEP; 1.1 equiv) was added and mixed for 1 h at RT. cCPP9-BBA (2 equiv) or m-xylene dibromide was freshly prepared in DMF and added to the reduced peptide solution and mixed for 3 h at RT. Reaction progress was monitored by MALDI-TOF mass spectrometry. Upon completion, the reaction mixture was quenched with TFA and purified by RP-HPLC to obtain the cross-linked peptides.

For peptides containing a fluorescent label, precursor peptides were first synthesized and purified as previously described. Approximately 1 mg of lyophilized peptide was incubated with 5 equiv. of an activated fluorescent labeling reagent [e.g., FITC, 5(6)-carboxyfluorescein succinimidyl ester, or 5(6)-carboxynaphthofluorescein succinimidyl ester) and 5 equiv. of DIPEA in 150 μL of 1:1 (v/v) DMF/150 mM sodium bicarbonate (pH 8.5) for 2 h. The reaction was quenched by TFA and the labeled peptides were purified again by HPLC and their authenticity was confirmed by MALDI-TOF mass spectrometry. To generate TMR-labeled pep-tides, an NE-4-methyltrityl-L-lysine was added to the C-terminus. The lysine side chain was selectively deprotected using 2% (v/v) TFA in DCM. The resin was incubated with 5(6)-carboxy-tetra-methylrhodamine (5 equiv), DIC (5 equiv) and DIPEA (5 equiv) in DMF overnight. The resin was washed and subjected to deprotection by 92.5% TFA, 2.5% water, 2.5% TIPS, and 2.5% 1,3-di-methoxybenzene for 3 h at RT, triturated with diethyl ether, and purified by HPLC as described above.

The purity of each peptide was assessed by reversed-phase HPLC equipped with a Waters XBridge C18 analytical column and its authenticity was confirmed by high-resolution mass spectrome-try using a custom Bruker 15-Tesla MALDI-FT-ICR instrument. The detailed structures of peptides used in this study and their analytical data are provided in FIGS. 5-9.

MTT Assay. SW480 (Wnt-addicted) and MCF7 (Wnt-independent) cells were seeded in 96-well plate with $3\times10^3$ cells per well, and allowed to grow overnight. Different concentrations of peptides (0-25 μM) were added to the cells in McCoy's 5A medium supplemented with 10% FBS and 1% penicillin/streptomycin and incubated at 37° C. for 48 h in the presence of 5% $CO_2$. After that, 10 μL of an MTT stock solution (5 mg/mL) was added into each well and the plate was incubated at 37° C. for 4 h. 100 μL of SDS-HCl solubilizing solution was added and the plate was incubated at 37° C. overnight. The absorbance of the formazan product formed was measured at 570 nm on a Tecan microtiter plate reader. Cells were incubated with serially diluted compounds for 72 hours in the presence of 10% FBS. Data reported represent the mean±SD of 3 independent experiments.

Cell Viability Assay. Cell viability was determined using the MTT assay. SW480 and MCF7 cells were maintained in RPMI-1640 supplemented with 10% FBS and 1% penicillin/streptomycin in an atmosphere of 5% CO2 at 37° C. The cells were harvested by first washing with DPBS, then trypsinized using 0.025% trypsin-EDTA for 5 min at 37° C. Trypsin was neutralized with the addition of warm DPBS and cells were pelleted down at 200 g for 5 min at 4° C. Cell density was determined using a hemocytometer and cells were resuspended in fresh RPMI-1640 or MEM supplemented with 10% FBS and 1% penicillin/streptomycin, pipetted into clear culture-treated 96-well plates (Sigma-Aldrich) at a final density of 5.0×103 cells/well, and incubated for 24 h at 37° C., 5% CO2. Com-pounds were serially diluted in DPBS with standardized DMSO concentration (0.5% v/v) and added to each well. Treated cells were incubated at 37° C. for 72 h. After that, 10 µL of MTT solution was added to each well, followed by incubation for 4 h at 37° C., 5% CO2. The formazan crystals formed were solubilized through the addition of 100 µL of a solubilization buffer and allowed to stand overnight at 37° C. The next day, $A_{565}$ was determined using a Tecan M1000 Infinite plate reader and absorbance values were standardized against cell-free wells and normalized to untreated control cells. Data was analyzed using GraphPad Prism v. 8.0. Values reported are the mean±SD of three independent experiments.

Flow Cytometry. HeLa cells were seeded in 12-well plates at $1.5\times10^5$ cells per well for 24 h. The next day, naphthofluorescein-labelled peptide (5 µM) was added to the cells in DMEM medium supplemented with 10% fetal bovine serum (FBS) and 1% penicillin/streptomycin and the cells were incubated at 37° C. for 2 h in the presence of 5% $CO_2$. The medium containing the peptide was removed and the cells were washed with DPBS twice. The cells were detached from the plate with 0.25% trypsin, pelleted by centrifugation at 250 g for 5 min, washed twice with DPBS, resuspended in DPBS, and analyzed on a BD FACS LSR II or Aria III flow cytometer. For NF-labelled peptides, a 633-nm laser was used for excitation and the fluorescence emission was analyzed in the APC channel. Data were analyzed using the Flowjo software (Tree Star).

Annexin V/PI Staining. For SW480 and MCF7 cells, cells were maintained in RPMI-1640 or MEM supplemented with 10% FBS and 1% penicillin/streptomycin in an atmosphere of 5% CO2 at 37° C. Cells were harvested by first washing with DPBS, then trypsinized using 0.025% trypsin-EDTA for 5 min at 37° C. Trypsin was neutralized with the addition of warm DPBS and cells were pelleted down at 200 g for 5 min at 4° C. Cell density was determined using a hemocytometer and cells were resuspended in RPMI-1640 or MEM supplemented with 10% FBS and 1% penicillin/streptomycin, pipetted into clear culture-treated 12-well plates (Sigma-Aldrich) at a final concentration of $1.0\times10^5$ cells/well, and incubated for 24 h at 37° C. in the presence of 5% $CO_2$. Compounds were prepared in warm Dulbecco's Phosphate Buffered Saline (DPBS) and treated with 0-25 µM peptide in fresh RPMI-1640 supplemented with 10% FBS and 1% penicillin/streptomycin for 48 hours. Subsequently, cells were washed with cold DPBS and harvested as mentioned previously. The cell pellet was resuspended and washed with cold DPBS twice, followed by resuspension in 100 µL of Annexin V binding buffer containing 5 µL of Annexin V-Alexa 488 and 1 µL of 100 µg/mL propidium iodide and incubated at RT for 15 min. After incubation, 400 µL of Annexin V binding buffer was added to each sample, mixed gently on ice and immediately analyzed on a BD Fortessa flow cytometer. Data was analyzed using FlowJo.

Protein-Ligand Binding Assays. Peptide 1: Binding affinity was determined using FP. Peptide 1 (10 nM) was added to serial dilutions of GST-β-catenin in 20 mM Tris, 300 mM NaCl, pH 8.8, 0.01% Triton-X100 as reported previously. 34 After 1 h, aliquots were transferred from the reaction mixtures into black-on-black 384-well non-binding plates (Greiner) and FP was measured using a Tecan Infinite M1000 Pro plate reader. The $K_D$ value was calculated using KaleidaGraph v. 3.6 using the equation below.

$$FP = \frac{\left(A_{min} + \left(A_{max} \times \frac{Q_b}{Q_f} - A_{min}\right)\left(\frac{(L + x + K_d) - \sqrt{((L + x + K_d)^2 - 4Lx)}}{2L}\right)\right)}{\left(1 + \left(\frac{Q_b}{Q_f} - 1\right)\left(\frac{(L + x + K_d) - \sqrt{((L + x + K_d)^2 - 4Lx)}}{2L}\right)\right)}$$

Peptides 2-5: Binding affinity was determined using a FP-based competition assay. FAM-labeled peptide 1 (10 nM) was incubated with 50 nM GST-β-catenin in 20 mM Tris, 300 mM NaCl, pH 8.8, 0.01% Triton-X100 for 1 hour. 34 serial dilutions of a competitor peptide (peptides 2-5) were prepared in 20 mM Tris, 300 mM NaCl, pH 8.8, 0.01% Triton-X100. After 1 h, aliquots of the equilibrated peptide 1-β-catenin solution were added to serially diluted peptide solutions and incubated for 1 hour at RT. Samples were transferred into black-on-black 384-well non-binding microplates (Greiner) and FP was measured using a Tecan M1000 Infinite plate reader. The data were analyzed using GraphPad Prism v. 8.0 and normalized to FP values corresponding to fully bound/unbound probe. All binding values reported are the mean±SD of independent experiments. Values were normalized to fully bound/unbound FP values for peptide 2-FITC.

Human Serum Stability. Whole human serum was diluted 1:4 in sterile DPBS and equilibrated at 37° C. for 15 min. The peptide was added to the diluted serum to a final concentration of 100 µM and incubated at 37° C. with gentle mixing. At varying time points, 100-µL aliquots were withdrawn and combined with 100 µL of 15% trichloroacetic acid in MeOH (w/v), 100 µL of MeCN and stored at 4° C. for 24 h. After protein precipitation was complete, each aliquot was centrifuged (15000 g, 5 min, 4° C.) and analyzed by RP-HPLC. The percentage of remaining peptide at a given time point was determined by integrating the peak area and compared it to that of the untreated control (100%).

Confocal Microscopy. HeLa cells (1 mL, $5\times10^3$ cells/mL) suspended in DMEM supplemented with 10% FBS and 1% penicillin/streptomycin were seeded into glass-bottomed culture dishes (MatTek) and cultured overnight at 37° C., 5% $CO_2$. The next day, cells were washed with DPBS (3×) and then peptides which are labeled with FITC were added in fresh DMEM supplemented with 1% FBS and 1% penicillin/streptomycin and incubated at 37° C. for 2 h. After 2 h, cells were washed with phenol red-free DMEM containing 1% FBS before imaging in the same media using a Nikon AIR live-cell confocal microscope equipped with a 100× oil objective. Images were processed using NIS-Elements AR. The channels are represented by (I)=differential interference contrast (DIC), (ID=green fluorescent protein (GFP), and (III)=overlap of DIC and GFP. The FITC-labeled peptides can be visualized in the green fluorescent protein channel.

Molecular Dynamics. For peptide 2 in complex with β-catenin, the system was prepared from a previously reported crystal structure of β-catenin in complex with Axin (PDBID: 1QZ7).51 First, a cubic (10 Å×10 Å×10 Å) protein grid for docking was produced using the Grid Gener-ation tool in Maestro v. 10.2 centered on the geometric center of the existing ligand. Docking for Ax4 was carried out using Glide XP with the OPLS3 forcefield, with settings applied for enhanced planarity of conjugated π systems, 100,000 poses generated per ligand and 5,000 poses carried forward for energy minimization. The final docked pose of Ax4 with the lactam staple installed was then subjected to a 50 ns production MD run using Desmond in an octahedral box, solvated with TIP3P water containing 0.15 M NaCl in addition to ions necessary to neutralize the system, and using the OPLS3 forcefield as configured in the Schrodinger Suite. From this final pose, the C-terminal transporter sequence was constructed in Maestro, appended and an additional 50 ns MD run using Desmond was performed using the previously mentioned conditions.

Protein Purification. For β-catenin, *E. coli* BL21 (DE3) cells harboring plasmid pGEX-β-catenin(133-665)52 were grown in LB medium supplemented with 50 mg/L ampicillin at 37° C. to an OD600 of 0.6 before induction with 0.2 mM IPTG overnight at 30° C. Cells were harvested by centrifugation and lysed in lysis buffer (20 mM Tris, pH 8.0, 150 mM NaCl, 2 mM DTT, 1% Triton-X100, 200 mM EDTA, 10 mg/mL PMSF, and 0.2 mg/mL lysozyme) on ice for 20 min, followed by sonication (8 s off, 2 s on, 1 min total, performed twice at 70% amplitude). The homogenate was centrifuged (13,000 g for 30 min at 4° C. and the clear supernatant was loaded onto an equilibrated glutathione-agarose column. After exhaustive washing with wash buffer (20 mM Tris, pH 7.4, 150 mM NaCl, 2 mM DTT), the bound GST-β-catenin was eluted with wash buffer supplemented with 10 mM glutathione, concentrated, and stored at −80° C. in 30% glycerol.

LDH Release. SW480 cells were maintained as described above. Cells were harvested and seeded into clear 96-well plates at a final density of $5\times10^3$ cells/well in complete growth media and incubated overnight at 37° C., 5% $CO_2$. The next day, peptides serially diluted in DPBS were added to each well at a peptide concentration of 0-50 μM to give a constant final concentration of 0.5% DMSO (v/v), with control wells containing 10 μL of lysis buffer, cell-free complete growth media, or positive LDH control. The plates were incubated for 45 min to 4 h at 37° C., 5% $CO_2$. After that, 50 μL of growth medium was withdrawn from each well, transferred to a clear 96-well plate, mixed with 50 μL of LDH substrate mix, and incubated at RT for 30 min with gentle mixing. Finally, 50 μL of 1 N HCl was added to each well and the absorbances at 490 and 680 nm were immediately measured on a TECAN Infinite M1000 plate reader. The absorbance values, after subtraction of background signal at 680 nm, were plotted by using GraphPad PRISM v. 8.0. Values represent the mean±SD of three replicates from two independent experiments (n=6). Growth medium without cells (10% FBS RPMI) was used as negative control, whereas enzymatically active LDH was used as positive control. Data shown represent the mean±SD of three independent experiments.

INCORPORATION BY REFERENCE

All references, articles, publications, patents, patent publications, and patent applications cited herein are incorporated by reference in their entireties for all purposes. However, mention of any reference, article, publication, patent, patent publication, and patent application cited herein is not, and should not be taken as, an acknowledgment or any form of suggestion that they constitute valid prior art or form part of the common general knowledge in any country in the world. Further, International Application No. PCT/US2018/057894, published on Feb. 5, 2010, and entitled: Polypeptide Conjugates for Intracellular Delivery of Stapled Peptides, is hereby incorporated by reference.

What is claimed is:

1. A peptide-having a comprising the sequence selected from:

GGYPEDILDKHLQRVIL(SEQ ID NO: 125),

GGYPEDILDKHLQRZWL(SEQ ID NO: 129),

GGYPEDILDKHLQRZ(1-Nal)L (SEQ ID NO: 131),

GGYPEDILDKHLQRZ(2-Nal)L (SEQ ID NO: 132),

GGYPECILDCKHLQDVILK(β-Ala) (SEQ ID NO: 126),

GGYPEDILDKHLQCVILC(β-Ala) (SEQ ID NO: 127),

GGYPEDILDKHLQRZIL(β-Ala) (SEQ ID NO: 128),

GGYPEDILDKHLQRZ(3-Bta) (SEQ ID NO: 130),

GG(3-Bta)PEDILDKHLQRZ(3-Bta)L (SEQ ID NO: 135), and

YPEDILDKHLQR(Hvl)IL (SEQ ID NO: 156), wherein Z is tert-leucine, 1-Nal is 1-napthylalanine, 2-Nal is 2-napthylalanine, Hvl is β-hydroxyvaline, β-Ala is beta-alanine, and 3-Bta is 3-benzothienyl-I-alanine.

* * * * *